United States Patent
Takabe et al.

(10) Patent No.: US 8,334,236 B2
(45) Date of Patent: Dec. 18, 2012

(54) RING-FUSED 2-PYRIDONE DERIVATIVES AND HERBICIDES

(75) Inventors: Fumiaki Takabe, Shizuoka (JP); Yuuki Hirano, Shizuoka (JP); Akira Funyu, Shizuoka (JP); Masami Kobayashi, Tokyo (JP); Takashi Mitsunari, Tokyo (JP)

(73) Assignees: Kumiai Chemical Industry Co., Ltd., Tokyo (JP); Ihara Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 13/147,341

(22) PCT Filed: Feb. 2, 2010

(86) PCT No.: PCT/JP2010/000607
§ 371 (c)(1),
(2), (4) Date: Aug. 1, 2011

(87) PCT Pub. No.: WO2010/089993
PCT Pub. Date: Aug. 12, 2010

(65) Prior Publication Data
US 2011/0287937 A1    Nov. 24, 2011

(30) Foreign Application Priority Data
Feb. 3, 2009  (JP) .................. 2009-023115

(51) Int. Cl.
| | |
|---|---|
| *A01N 43/90* | (2006.01) |
| *A01N 43/42* | (2006.01) |
| *A01N 43/54* | (2006.01) |
| *A01N 43/80* | (2006.01) |
| *A01N 43/84* | (2006.01) |
| *A01P 13/00* | (2006.01) |
| *C07D 413/04* | (2006.01) |
| *C07D 401/04* | (2006.01) |
| *C07D 405/10* | (2006.01) |
| *C07D 417/04* | (2006.01) |
| *C07D 471/04* | (2006.01) |
| *C07D 491/056* | (2006.01) |

(52) U.S. Cl. ........ 504/225; 504/239; 504/241; 504/247; 544/58.2; 544/58.6; 544/127; 544/279; 544/331; 546/115; 546/123; 546/156

(58) Field of Classification Search ................. None
See application file for complete search history.

(56) References Cited

U.S. PATENT DOCUMENTS
2010/0197674 A1 * 8/2010 Tamai et al. ............... 514/228.5

FOREIGN PATENT DOCUMENTS
| | | |
|---|---|---|
| JP | 01006256 A | 1/1989 |
| JP | 08301870 A | 11/1996 |
| JP | 2000016982 A | 1/2000 |
| WO | 9812180 A1 | 3/1998 |
| WO | 0014069 A1 | 3/2000 |
| WO | 0014087 A1 | 3/2000 |
| WO | 2009016841 A1 | 2/2009 |
| WO | 2009115788 A1 | 9/2009 |

* cited by examiner

*Primary Examiner* — Janet Andres
*Assistant Examiner* — Timothy R Rozof
(74) *Attorney, Agent, or Firm* — Edwards Wildman Palmer LLP; Peter F. Corless; Christine C. O'Day

(57) ABSTRACT

Provided are 2-pyridone derivatives which have excellent herbicidal activity and exhibit high safety to useful crops and so on; salts thereof; and herbicides containing same. In more detail, 2-pyridone derivatives represented by general formula [I] or agrochemically acceptable salts thereof, and herbicides containing these compounds are provided. In general formula [I], $X^1$ is an oxygen atom or a sulfur atom; $X^2$, $X^3$, and $X^4$ are to each CH or $N(O)_m$; m is an integer of 0 or 1; $R^1$ is a hydrogen atom, a $C_{1-12}$ alkyl group, or the like; $R^2$ is a halogen atom, a cyano group, or the like; n is an integer of 0 to 4; $R^3$ is a hydroxyl group, a halogen atom, or the like; $A^1$ is $C(R^{11}R^{12})$; $A^2$ is $C(R^{13}R^{14})$ or C=O; $A^3$ is $C(R^{15}R^{16})$; and $R^{11}$, $R^{12}$, $R^{13}$, $R^{14}$, $R^{15}$, and $R^{16}$ are each independently a hydrogen atom or a $C_{1-6}$ alkyl group.

3 Claims, No Drawings

US 8,334,236 B2

RING-FUSED 2-PYRIDONE DERIVATIVES AND HERBICIDES

CROSS-REFERENCES TO RELATED APPLICATIONS

This application is a 35 U.S.C. §371 U.S. national entry of International Application PCT/JP2010/000607 (WO 2010/089993) having an International filing date of Feb. 2, 2010, which claims under 35 U.S.C. §119(a) the benefit of Japanese Application No. 2009-023115, filed Feb. 3, 2009, the entire contents of which are incorporated herein by reference.

TECHNICAL FIELD

The present invention relates to a novel ring-fused 2-pyridone derivative or a salt thereof, a herbicide containing these compounds as active ingredients, and a method for use of the herbicide.

BACKGROUND ART

Several compounds among the 1,3-cyclohexanedione derivatives which are acylated at the 2-position with an arylcarbonyl group, have already been commercially available as agrochemicals. For example, mesotrione has attracted public attention as a foliar treatment type herbicide for maize. A 1,3-cyclohexanedione ring is tautomeric and exists also as 1-hydroxycyclohexen-3-one, which is an enol form thereof, and this derivative has been developed into various compounds for agrochemical use.

There have been reports on, for example, derivatives in which the aryl group of the arylcarbonyl group substituted at the 2-position has been changed to heteroaryl such as thiophene (see Patent Document 1), derivatives having the 1,3-cyclohexanedione ring fused at the 4- and 5-positions with a cyclopropane ring (see Patent Document 2), derivatives having the arylcarbonyl group at the 2-position changed to a pyrimidin-5-ylcarbonyl group derivative (see Patent Document 3), derivatives having the aryl carbonyl group at the 2-position changed to a pyrazin-2-ylcarbonyl group derivative (see Patent Document 4), derivatives having the arylcarbonyl group at the 2-position changed to a 1,2,3-thiadiazol-5-ylcarbonyl group derivative (see Patent Document 5), derivatives having the arylcarbonyl group at the 2-position changed to a pyridinecarbonyl group derivative (see Patent Documents 2, 6, 7, 8, 9 and 10), derivatives having the arylcarbonyl group at the 2-position changed to a quinolinecarbonyl group derivative (see Patent Documents 11 and 12), derivatives having the arylcarbonyl group at the 2-position changed to a heteroarylcarbonyl group derivative formed from a benzazole compound (see Patent Document 13), derivatives having the arylcarbonyl group at the 2-position changed to an azolecarbonyl group derivative formed from a 1,2-azole compound (see Patent Document 14), and derivatives having the arylcarbonyl group at the 2-position changed to a pyridonecarbonyl group derivative (see Patent Document 15). Furthermore, derivatives in which the 4-position and the 6-position of the 1,3-cyclohexanedione ring are crosslinked with an alkylene group such as an ethylene group, have also been reported (see Patent Documents 8, 11, 12, 13, 14, 16 and 17). There have been also reported derivatives in which the 1,3-cyclohexanedione ring has a substituted thiol group introduced at the 5-position (see Patent Document 18).

As such, a large number of cyclohexanedione-based compounds having a herbicidal activity have been reported, but there is no known cyclohexanedione-based compound having a dihydropyrazine ring substituted with an oxo group or a thioxo group (in the present specification, these groups may be collectively referred to as (thio)oxo), such as the compound of the present invention represented by formula [I] which will be shown below.

PRIOR ART DOCUMENTS

Patent Documents

Patent Document 1: European Patent Publication (EP) No. EP-283261 A1
Patent Document 2: WO 91/00260
Patent Document 3: U.S. Pat. No. 4,708,732
Patent Document 4: EP No. DE-3902818 A1
Patent Document 5: EP No. EP-338525 A1
Patent Document 6: Japanese Patent Application Laid-Open (JP-A) No. 2-78662
Patent Document 7: JP-A No. 3-52862
Patent Document 8: JP-A No. 4-29973
Patent Document 9: WO 96/14285
Patent Document 10: WO 2000/39094
Patent Document 11: JP-A No. 2000-16982
Patent Document 12: WO 2000/14069
Patent Document 13: WO 2000/68210
Patent Document 14: JP-A No. 2005-200401
Patent Document 15: WO 2007/088876
Patent Document 16: WO 2005/058831
Patent Document 17: WO 2006/066871
Patent Document 18: DE 10256354

SUMMARY OF THE INVENTION

Problems to be Solved by the Invention

As such, 1,3-cyclohexanedione-based compounds substituted with specific heteroarylcarbonyl groups are known to have a herbicidal activity. However, since these compounds need to be applied in high doses, the compounds are not satisfactory as herbicides. Thus, there has been a demand for the development of a herbicide capable of exhibiting excellent characteristics at lower doses.

The present invention was made under such circumstances, and an object of the invention is to provide a compound having a herbicidal activity, which causes no drug-induced damage to useful plants and useful crops, and is capable of controlling various weeds growing in farmlands, orchards, paddy fields, and non-agricultural lands at low doses, and a herbicide containing the compound.

Means for Solving the Problems

In order to achieve the object described above, the inventors of the present invention have conducted a thorough investigation on the chemical structure and the herbicidal activity of cyclohexanedione-based compounds. As a result, they found that a cyclohexanedione-based compound having a 2-pyridone ring substituted with an oxo group or a thioxo group is capable of controlling various weeds growing in farmlands, orchards, paddy fields and non-agricultural lands for a long time, and exhibits high safety to useful plants, useful crops and the like. Thus, the inventors completed the present invention.

That is, the present invention is characterized by using a 2-(thio)oxo-quinolin-3-yl group which may be substituted, a 2-(thio)oxo-1,8-naphthyridin-3-yl group which may be substituted, a 2-(thio)oxo-1,5-naphthyridin-3-yl group which may be substituted, or a 7-(thio)oxo-pyrido[2,3-d]-pyrimidin-6-yl group which may be substituted, as a heteroaryl group for a 2-heteroarylcarbonyl-1,3-cyclohexanedione-based compound having a herbicidal activity.

More particularly, the present invention relates to the following item (1).

(1) A 2-pyridone derivative represented by formula [I], or an agrochemically acceptable salt thereof:

[Chemical Formula 1]

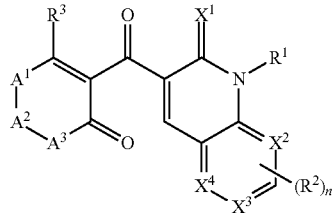

[I]

wherein $X^1$ represents an oxygen atom or a sulfur atom;

$X^2$, $X^3$ and $X^4$ each represent CH (the carbon atom may be substituted with $R^2$), or $N(O)_m$;

m represents an integer of 0 or 1;

$R^1$ represents a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; an amino-$C_1$-$C_6$ alkyl group; a nitro-$C_1$-$C_6$ alkyl group; a mono($C_1$-$C_6$ alkyl)amino-$C_1$-$C_6$ alkyl group; a di($C_1$-$C_6$ alkyl)amino-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a $C_1$-$C_6$ alkoxy-$C_1$-$C_6$ alkyl group; a hydroxy-$C_1$-$C_6$ alkyl group; a phenyl-$C_1$-$C_6$ alkoxy-$C_1$-$C_6$ alkyl group (the phenyl moiety of this group may be substituted with one $R^4$ or two to five identical or different $R^4$); a $C_1$-$C_6$ alkoxy-$C_1$-$C_6$ alkoxy-$C_1$-$C_6$ alkyl group; a $C_3$-$C_8$ cycloalkyloxy-$C_1$-$C_6$ alkyl group; a $C_3$-$C_8$ cycloalkyl-$C_1$-$C_6$ alkoxy-$C_1$-$C_6$ alkyl group; a phenyloxy-$C_1$-$C_6$ alkyl group (the phenyl moiety of this group may be substituted with one $R^4$ or two to five identical or different $R^4$); a heterocyclic-oxy-$C_1$-$C_6$ alkyl group in which the heterocyclic moiety has 2 to 10 carbon atoms and 1 to 5 heteroatoms selected from an oxygen atom, a sulfur atom, and a nitrogen atom (the heterocyclic moiety having 2 to 10 carbon atoms and having one to five heteroatoms selected from an oxygen atom, a sulfur atom, and a nitrogen atom in the group, may be substituted with one $R^5$ or two to five identical or different $R^5$); a phenylthio-$C_1$-$C_6$ alkyl group (the phenyl moiety of this group may be substituted with one $R^4$ or two to five identical or different $R^4$); a phenylsulfinyl-$C_1$-$C_6$ alkyl group (the phenyl moiety of this group may be substituted with one $R^4$ or two to five identical or different $R^4$), a phenylsulfonyl-$C_1$-$C_6$ alkyl group (the phenyl moiety of this group may be substituted with one $R^4$ or two to five identical or different $R^4$); a $C_1$-$C_6$ haloalkoxy-$C_1$-$C_6$ alkyl group; a heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom, and a nitrogen atom (the heterocyclic moiety having 2 to 10 carbon atoms and having 1 to 5 heteroatoms selected from an oxygen atom, a sulfur atom, and a nitrogen atom in this group, may be substituted with one $R^5$ or two to five identical or different $R^5$); a $C_1$-$C_6$ alkylthio-$C_1$-$C_6$ alkoxy-$C_1$-$C_6$ alkyl group; a $C_1$-$C_6$ alkylsulfinyl-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a di($C_1$-$C_6$ alkoxy)-$C_1$-$C_6$ alkyl group; a $C_1$-$C_6$ alkoxycarbonyl-$C_1$-$C_6$ alkyl group; a $C_1$-$C_6$ alkoxyimino-$C_1$-$C_6$ alkyl group; a $C_1$-$C_6$ alkylideneaminooxy-$C_1$-$C_6$ alkyl group; a ($R^6R^7N$—C=O)—$C_1$-$C_6$ alkyl group; a $C_6$-$C_{10}$ aryl-$C_1$-$C_6$ alkyl group (the aryl moiety of this group may be substituted with one $R^4$ or two to five identical or different $R^4$); a heterocyclic-$C_1$-$C_6$ alkyl group in which the heterocyclic moiety has 2 to 10 carbon atoms and 1 to 5 heteroatoms selected from an oxygen atom, a sulfur atom, and a nitrogen atom (the heterocyclic moiety having 2 to 10 carbon atoms and 1 to 5 heteroatoms selected from an oxygen atom, a sulfur atom, and a nitrogen atom in this group, may be substituted with one $R^5$ or two to five identical or different $R^5$); an $NR^8R^9$ group; a $C_1$-$C_6$ alkoxy group; a $C_6$-$C_{10}$ aryl group (this group may be substituted with one $R^4$ or two to five identical or different $R^4$); or a heterocyclic group having 2 to 10 carbon atoms and 1 to 5 heteroatoms selected from an oxygen atom, a sulfur atom, and a nitrogen atom (this group may be substituted with one $R^5$ or two to five identical or different $R^5$);

$R^2$ represents a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_3$-$C_8$ cycloalkyl-$C_1$-$C_6$ alkyloxy group; a $C_2$-$C_6$ alkenyloxy group; a $C_2$-$C_6$ alkynyloxy group; a $C_1$-$C_6$ haloalkoxy group; a $C_1$-$C_6$ alkoxy-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl)amino group; a $C_1$-$C_6$ acylamino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; or a heterocyclic group having 2 to 10 carbon atoms and 1 to 5 heteroatoms selected from an oxygen atom, a sulfur atom, and a nitrogen atom (the heterocyclic moiety having 2 to 10 carbon atoms and 1 to 5 heteroatoms selected from an oxygen atom, a sulfur atom, and a nitrogen atom in this group, may be substituted with one $R^{10}$ or two to five identical or different $R^{10}$);

furthermore, two adjacent $R^2$ may be joined to form, together with the respective carbon atoms to which $R^2$ are directly bound, a 4- to 8-membered carbocyclic ring or a 4- to 8-membered heterocyclic ring having 1 to 4 heteroatoms selected from an oxygen atom, a sulfur atom, and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group, or an oxo group;

n represents an integer from 0 to 4 when $X^2$, $X^3$, and $X^4$ each represent CH (the relevant carbon atom may be substituted with $R^2$), that is, when $X^2$, $X^3$, and $X^4$ each represent CH which may be substituted with substituent $R^2$;

$R^3$ represents a hydroxyl group; $O^-M^+$ (wherein $M^+$ represents an alkali metal cation or an ammonium cation); an amino group; a halogen atom; a $C_1$-$C_6$ alkylsulfonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a $C_1$-$C_6$ alkylcarbonyloxy group; a $C_2$-$C_6$ alkenylcarbonyloxy group; a $C_2$-$C_6$ alkynylcarbonyloxy group; a phenoxy group (this group may be substituted with one $R^{10}$ or two to five identical or different $R^{10}$; a phenylthio group (this group may be substituted with one $R^{10}$ or two to five identical or different $R^{10}$); a phenylsulfinyl group (this group may be substituted with one $R^{10}$ or two to five identical or different) $R^{10}$; a phenylsulfonyl group (this group may be substituted with one $R^{10}$ or two to five identical or different $R^{10}$; a phenylsulfonyloxy group (this group may be substituted with one $R^{10}$ or two to five identical or different $R^{10}$; a phenylcarbonyloxy group (this group may be substituted with one $R^{10}$ or two to five identical or different $R^{10}$; a 1,2,4-triazol-1-yl group; a 1,2,3-triazol-1-yl group; a 1,2,3-triazol-2-yl group; an imidazol-1-yl group; a pyrazol-1-yl group; a tetrazol-1-yl group; or a tetrazol-2-yl group;

$R^4$ represents a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ acylamino group; a mono($C_1$-$C_6$ alkyl)amino group; a di($C_1$-$C_6$ alkyl)amino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ alkoxy-$C_1$-$C_6$ alkoxy group; a $C_3$-$C_8$ cycloalkyl-$C_1$-$C_6$ alkyloxy group; a $C_1$-$C_6$ haloalkoxy-$C_1$-$C_6$ alkoxy group; a cyano-$C_1$-$C_6$ alkoxy group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a heterocyclic group having 2 to 10 carbon atoms and 1 to 5 heteroatoms selected from an oxygen atom, a sulfur atom, and a nitrogen atom (the heterocyclic moiety in this group, may be substituted with one $R^{10}$ or two to five identical or different $R^{10}$); or a heterocyclic-oxy group having 2 to 10 carbon atoms and 1 to 5 heteroatoms arbitrarily selected from an oxygen atom, a sulfur atom, and a nitrogen atom (the heterocyclic moiety having 2 to 10 carbon atoms and 1 to 5 heteroatoms selected from an oxygen atom, a sulfur atom, and a nitrogen atom in this group, may be substituted with one $R^{10}$ or two to five identical or different $R^{10}$;

furthermore, two adjacent $R^4$ may be joined to form, together with the respective carbon atoms to which $R^4$ are directly bound, a 4- to 8-membered carbocyclic ring or a 4- to 8-membered heterocyclic ring having 1 to 4 heteroatoms selected from an oxygen atom, a sulfur atom, and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group, or an oxo group;

$R^5$ represents an oxo group; a thioxo group; a hydroxyl group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_2$-$C_6$ alkenyloxy group; a $C_2$-$C_6$ alkynyloxy group; a $C_3$-$C_8$ cycloalkyloxy group; a $C_3$-$C_8$ cycloalkyl-$C_1$-$C_6$ alkyloxy group; a $C_1$-$C_6$ haloalkoxy group; a $C_1$-$C_6$ alkoxy-$C_1$-$C_6$ alkoxy group; a $C_1$-$C_6$ haloalkoxy-$C_1$-$C_6$ alkoxy group; a cyano-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl) amino group; a $C_1$-$C_6$ acylamino group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a $C_1$-$C_6$ acyl group; a $C_1$-$C_6$ alkoxyimino-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; or a cyano-$C_1$-$C_6$ alkyl group;

furthermore, two adjacent $R^5$ may be joined to form, together with the respective carbon atoms to which $R^5$ are directly bound, a 4- to 8-membered carbocyclic ring or a 4- to 8-membered heterocyclic ring having 1 to 4 heteroatoms selected from an oxygen atom, a sulfur atom, and a nitrogen atom, and the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group, or an oxo group;

$R^6$ and $R^7$ each independently represent a $C_1$-$C_6$ alkyl group; or a phenyl-$C_1$-$C_6$ alkyloxycarbonyl group;

furthermore, $R^6$ and $R^7$ may be joined to form, together with the nitrogen atom to which these are bound, a 5- to 6-membered ring, while the ring thus formed may be interrupted by an oxygen atom in addition to the nitrogen atom to which $R^6$ and $R^7$ are bound;

$R^8$ and $R^9$ each independently represent a hydrogen atom; a $C_1$-$C_6$ alkyl group; a $NR^6R^7$ group; or a $C_1$-$C_6$ alkoxycarbonyl group;

furthermore, $R^8$ and $R^9$ may be joined to form, together with the nitrogen atom to which these are bound, a 5- to 6-membered ring, while the ring thus formed may be interrupted by a sulfur atom and/or an oxygen atom in addition to the nitrogen atom to which $R^8$ and $R^9$ are bound;

$R^{10}$ represents a halogen atom; a nitro group; a cyano group; a $C_2$-$C_6$ alkyl group; a $C_2$-$C_6$ haloalkyl group; a $C_2$-$C_6$ alkoxy group; or a $C_2$-$C_6$ haloalkoxy group;

$A^1$ represents $C(R^{11}R^{12})$;

$A^2$ represents $C(R^{13}R^{14})$, or $C=O$;

$A^3$ represents $C(R^{15}R^{16})$;

$R^{11}$, $R^{12}$, $R^{13}$, $R^{14}$, $R^{15}$, and $R^{16}$ each independently represent a hydrogen atom; or a $C_1$-$C_6$ alkyl group; and $R^{11}$ and $R^{16}$ may be joined to form a $C_2$-$C_5$ alkylene chain, which may constitute a ring together with adjacent carbon atoms.

(2) A herbicide comprising the 2-pyridone derivative or a salt thereof described in the above item (1), as an active ingredient.

(3) Use of a herbicide, comprising treating soil and/or a plant with an effective amount of the herbicide described in the above item (2).

(4) A method for weeding, including treating soil and/or plants with an effective amount of the herbicide described in the above item (2).

Effects of the Invention

The 2-pyridone derivative represented by formula [I] of the present invention or an agrochemically acceptable salt thereof has excellent operating effects as an agrochemical, such as being capable of controlling various weeds growing in farmlands, orchards, paddy fields, and non-agricultural lands, and exhibiting high safety to useful plants, useful crops and the like.

MODES FOR CARRYING OUT THE INVENTION

The symbols and terms described in the present specification will be described.

A halogen atom refers to a fluorine atom, a chlorine atom, a bromine atom, or an iodine atom.

A notation showing elemental symbols and subscript numbers, such as in $C_1$-$C_3$, indicates that the number of elements of the group described subsequently to the notation is in the range indicated by the subscript numbers. For example, in this case, it is indicated that the carbon number is 1 to 3. The notation of $C_1$-$C_6$ indicates that the carbon number is 1 to 6, while the notation of $C_1$-$C_{12}$ indicates that the carbon number is 1 to 12.

Furthermore, in regard to the naming of a group based on a carbon chain such as an alkyl group or an alkenyl group, unless particularly stated otherwise, the group is meant to be a normal (n-) carbon chain.

The $C_1$-$C_6$ alkyl group represents, unless particularly limited, a linear or branched alkyl group having 1 to 6 carbon atoms, and examples thereof include groups such as methyl, ethyl, n-propyl, isopropyl, n-butyl, sec-butyl, isobutyl, tert-butyl, n-pentyl, 1-methylbutyl, 2-methylbutyl, 3-methylbutyl, 1-ethylpropyl, 1,1-dimethylpropyl, 1,2-dimethylpropyl, neopentyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, and 1-ethyl-2-methylpropyl. A preferred example of an alkyl group having 1 to 6 carbon atoms may be a linear or branched alkyl group having 1 to 4, or 1 to 3, carbon atoms.

The $C_1$-$C_{12}$ alkyl group represents, unless particularly limited, a linear or branched alkyl group having 1 to 12 carbon atoms, and examples thereof include, in addition to the examples of the $C_1$-$C_6$ alkyl group listed above, groups such as n-heptyl, 1-methylhexyl, 5-methylhexyl, 1,1-dimethylpentyl, 2,2-dimethylpentyl, 4,4-dimethylpentyl, 1-ethylpentyl, 2-ethylpentyl, 1,1,3-trimethylbutyl, 1,2,2-trimethylbutyl, 1,3,3-trimethylbutyl, 2,2,3-trimethylbutyl, 2,3,3-trimethylbutyl, 1-propylbutyl, 1,1,2,2-tetramethylpropyl, n-octyl, 1-methylheptyl, 3-methylheptyl, 6-methylheptyl, 2-ethylhexyl, 5,5-dimethylhexyl, 2,4,4-trimethylpentyl, 1-ethyl-1-methylpentyl, nonyl, 1-methyloctyl, 2-methyloctyl, 3-methyloctyl, 7-methyloctyl, a 1-ethylheptyl group, 1,1-dimethylheptyl, 6,6-dimethylheptyl, decyl, 1-methylnonyl, 2-methylnonyl, 6-methylnonyl, 1-ethyloctyl, 1-propylheptyl, n-nonyl, n-decyl, n-undecyl, and n-dodecyl. A preferred example of an alkyl group having 1 to 12 carbon atoms may be a linear or branched alkyl group having 1 to 8, 1 to 6, or 1 to 3, carbon atoms.

The $C_3$-$C_8$ cycloalkyl group represents, unless particularly limited, a cycloalkyl group having 3 to 8 carbon atoms, and examples thereof include groups such as cyclopropyl, cyclobutyl, cyclopentyl, or cyclohexyl. A preferred example of a cycloalkyl group having 3 to 8 carbon atoms may be a cycloalkyl group having 3 to 6, or 4 to 6, carbon atoms.

The $C_3$-$C_8$ cycloalkyl-$C_1$-$C_6$ alkyl group represents, unless particularly limited, an alkyl group having 1 to 6 carbon atoms substituted with a cycloalkyl group having 3 to 8 carbon atoms, in which the cycloalkyl moiety and the alkyl moiety respectively have the same meanings as defined above. Examples thereof include groups such as cyclopropylmethyl, 1-cyclopropylethyl, 2-cyclopropylethyl, 1-cyclopropylpropyl, 2-cyclopropylpropyl, 3-cyclopropylpropyl, cyclobutylmethyl, cyclopentylmethyl, and cyclohexylmethyl.

The $C_1$-$C_6$ haloalkyl group represents a linear or branched alkyl group having 1 to 6 carbon atoms substituted with one or more, preferably 1 to 10, and more preferably 1 to 5, halogen atoms. Examples thereof include groups such as fluoromethyl, chloromethyl, bromomethyl, difluoromethyl, dichloromethyl, trifluoromethyl, trichloromethyl, chlorodifluoromethyl, bromodifluoromethyl, 2-fluoroethyl, 1-chloroethyl, 2-chloroethyl, 1-bromoethyl, 2-bromoethyl, 2,2-difluoroethyl, 1,2-dichloroethyl, 2,2-dichloroethyl, 2,2,2-trifluoroethyl, 2,2,2-trichloroethyl, 1,1,2,2-tetrafluoroethyl, pentafluoroethyl, 2-bromo-2-chloroethyl, 2-chloro-1,1,2,2-tetrafluoroethyl, 1-chloro-1,2,2,2-tetrafluoroethyl, 1-chloropropyl, 2-chloropropyl, 3-chloropropyl, 2-bromopropyl, 3-bromopropyl, 2-bromo-1-methylethyl, 3-iodopropyl, 2,3-dichloropropyl, 2,3-dibromopropyl, 3,3,3-trifluoropropyl, 3,3,3-trichloropropyl, 3-bromo-3,3-difluoropropyl, 3,3-dichloro-3-fluoropropyl, 2,2,3,3-tetrafluoropropyl, 1-bromo-3,3,3-trifluoropropyl, 2,2,3,3,3-pentafluoropropyl, 2,2,2-trifluoro-1-trifluoromethylethyl, heptafluoropropyl, 1,2,2,2-tetrafluoro-1-trifluoromethylethyl, 2,3-dichloro-1,1,2,3,3-pentafluoropropyl, 2-chlorobutyl, 3-chlorobutyl, 4-chlorobutyl, 2-chloro-1,1-dimethylethyl, 4-bromobutyl, 3-bromo-2-methylpropyl, 2-bromo-1,1-dimethylethyl, 2,2-dichloro-1,1-dimethylethyl, 2-chloro-1-chloromethyl-2-methylethyl, 4,4,4-trifluorobutyl, 3,3,3-trifluoro-1-methylpropyl, 3,3,3-trifluoro-2-methylpropyl, 2,3,4-trichlorobutyl, 2,2,2-trichloro-1,1-dimethylethyl, 4-chloro-4,4-difluorobutyl, 4,4-dichloro-4-fluorobutyl, 4-bromo-4,4-difluorobutyl, 2,4-dibromo-4,4-difluorobutyl, 3,4-dichloro-3,4,4-trifluorobutyl, 3,3-dichloro-4,4,4-trifluorobutyl, 4-bromo-3,3,4,4-tetrafluorobutyl, 4-bromo-3-chloro-3,4,4-trifluorobutyl, 2,2,3,3,4,4-hexafluorobutyl, 2,2,3,4,4,4-hexafluorobutyl, 2,2,2-trifluoro-1-methyl-1-trifluoromethylethyl, 3,3,3-trifluoro-2-trifluoromethylpropyl, 2,2,3,3,4,4,4-heptafluorobutyl, 2,3,3,3-tetrafluoro-2-trifluoromethylpropyl, 1,1,2,2,3,3,4,4-octafluorobutyl, nonafluorobutyl, 4-chloro-1,1,2,2,3,3,4,4-octafluorobutyl, 5-fluoropentyl, 5-chloropentyl, 5,5-difluoropentyl, 5,5-dichloropentyl, 5,5,5-trifluoropentyl, 6,6,6-trifluorohexyl group, and 5,5,6,6,6-pentafluorohexyl group.

The $C_2$-$C_6$ alkenyl group represents, unless particularly limited, a linear or branched alkenyl group having 2 to 6 carbon atoms, and examples thereof include groups such as vinyl, 1-propenyl, isopropenyl, 2-propenyl, 1-butenyl, 1-methyl-1-propenyl, 2-butenyl, 1-methyl-2-propenyl, 3-butenyl, 2-methyl-1-propenyl, 2-methyl-2-propenyl, 1,3-butadienyl, 1-pentenyl, 1-ethyl-2-propenyl, 2-pentenyl, 1-methyl-1-butenyl, 3-pentenyl, 1-methyl-2-butenyl, 4-pentenyl, 1-methyl-3-butenyl, 3-methyl-1-butenyl, 1,2-dimethyl-2-propenyl, 1,1-dimethyl-2-propenyl, 2-methyl-2-butenyl, 3-methyl-2-butenyl, 1,2-dimethyl-1-propenyl, 2-methyl-3-butenyl, 3-methyl-3-butenyl, 1,3-pentadienyl, 1-vinyl-2-propenyl, 1-hexenyl, 1-propyl-2-propenyl, 2-hexenyl, 1-methyl-1-pentenyl, 1-ethyl-2-butenyl, 3-hexenyl, 4-hexenyl, 5-hexenyl, 1-methyl-4-pentenyl, 1-ethyl-3-butenyl, 1-(isobutyl)vinyl, 1-ethyl-1-methyl-2-propenyl, 1-ethyl-2-methyl-2-propenyl, 1-(isopropyl)-2-propenyl, 2-methyl-2-pentenyl, 3-methyl-3-pentenyl, 4-methyl-3-pentenyl, 1,3-dimethyl-2-butenyl, 1,1-dimethyl-3-butenyl, 3-methyl-4-pentenyl, 4-methyl-4-pentenyl, 1,2-dimethyl-3-butenyl, 1,3-dimethyl-3-butenyl, 1,1,2-trimethyl-2-propenyl, 1,5-hexadienyl, 1-vinyl-3-butenyl, and 2,4-hexadienyl. A preferred example of an alkenyl group having 2 to 6 carbon atoms may be a linear or branched alkenyl group having 2 to 4 carbon atoms.

The $C_2$-$C_6$ alkynyl group represents, unless particularly limited, a linear or branched alkynyl group having 2 to 6 carbon atoms, and examples thereof include groups such as ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 1-(n-propyl)-2-propynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, 1-ethyl-3-butynyl, 1-ethyl-1-methyl-2-propynyl, 1-(isopropyl)-2-propynyl, 1,1-dimethyl-2-butynyl, and 2,2-dimethyl-3-butynyl. A preferred example of an alkynyl group having 2 to 6 carbon atoms may be a linear or branched alkynyl group having 2 to 4 carbon atoms.

The $C_1$-$C_6$ alkoxy group represents, unless particularly limited, a linear or branched alkoxy group having 1 to 6 carbon atoms, and examples thereof include groups such as methoxy, ethoxy, propoxy, isopropoxy, butoxy, pentyloxy, and hexyloxy. A preferred example of an alkoxy group having 1 to 6 carbon atoms may be a linear or branched alkoxy group having 1 to 4, or 1 to 3, carbon atoms.

The $C_1$-$C_6$ alkoxy-$C_1$-$C_6$ alkyl group represents an alkyl group having 1 to 6 carbon atoms substituted with an alkoxy group having 1 to 6 carbon atoms, in which the alkyl moiety and the alkoxy moiety respectively have the same meanings as defined above. Examples thereof include groups such as methoxymethyl, ethoxymethyl, isopropoxymethyl, pentyloxymethyl, 2-methoxyethyl, and 2-butoxyethyl.

The $C_1$-$C_6$ alkoxy-$C_1$-$C_6$ alkoxy group represents an alkoxy group having 1 to 6 carbon atoms substituted with an alkoxy group having 1 to 6 carbon atoms, in which the alkoxy moiety has the same meaning as defined above. Examples thereof include groups such as methoxymethoxy, ethoxymethoxy, 2-methoxyethoxy, and 2-ethoxyethoxy.

The $C_3$-$C_8$ cycloalkyl-$C_1$-$C_6$ alkyloxy group represents an (alkyl)-O— group having 1 to 6 carbon atoms substituted with a cycloalkyl group having 3 to 8 carbon atoms, in which the cycloalkyl moiety and the alkyl moiety respectively have the same meanings as defined above. Examples thereof include groups such as cyclopropylmethyloxy, 2-(cyclopropyl)ethyloxy, and cyclopentylmethyloxy. A preferred example of a cycloalkyl group having 3 to 8 carbon atoms may be a cycloalkyl group having 3 to 6 carbon atoms.

The cyano-$C_1$-$C_6$ alkoxy group represents an alkoxy group having 1 to 6 carbon atoms substituted with a cyano group, in which the alkoxy moiety has the same meaning as defined above. Examples thereof include groups such as 2-cyanoethoxy and 3-cyanopropoxy.

The $C_3$-$C_8$ cycloalkyloxy group represents, unless particularly limited, a (cycloalkyl)-O— group having 3 to 8 carbon atoms, in which the cycloalkyl moiety has the same meaning as defined above. Examples thereof include groups such as cyclopropyloxy, cyclobutyloxy, cyclopentyloxy, and cyclohexyloxy.

The $C_2$-$C_6$ alkenyloxy group represents, unless particularly limited, an (alkenyl)-O— group having 2 to 6 carbon atoms, in which the alkenyl moiety has the same meaning as defined above. Examples thereof include groups such as 2-propenyloxy.

The $C_2$-$C_6$ alkynyloxy group represents, unless particularly limited, an (alkynyl)-O— group having 2 to 6 carbon atoms, in which the alkynyl moiety has the same meaning as defined above. Examples thereof include groups such as 2-propynyloxy.

The $C_1$-$C_6$ alkylthio group represents an (alkyl)-S— group having 1 to 6 carbon atoms, in which the alkyl moiety has the same meaning as defined above. Examples thereof include groups such as methylthio, ethylthio, n-propylthio, and isopropylthio.

The $C_1$-$C_6$ alkylsulfinyl group represents an (alkyl)-SO— group having 1 to 6 carbon atoms, in which the alkyl moiety has the same meaning as defined above. Examples thereof include groups such as methylsulfinyl, ethylsulfinyl, n-propylsulfinyl, and isopropylsulfinyl.

The $C_1$-$C_6$ alkylsulfonyl group represents an (alkyl)-$SO_2$— group having 1 to 6 carbon atoms, in which the alkyl moiety has the same meaning as defined above. Examples thereof include groups such as methylsulfonyl, ethylsulfonyl, n-propylsulfonyl, and isopropylsulfonyl.

The $C_1$-$C_6$ alkylsulfonyloxy group represents an (alkyl)$SO_2$—O— group having 1 to 6 carbon atoms, in which the alkyl moiety has the same meaning as defined above. Examples thereof include groups such as methylsulfonyloxy and ethylsulfonyloxy.

The mono($C_1$-$C_6$ alkyl)amino group represents an (alkyl)-NH— group having 1 to 6 carbon atoms in the alkyl moiety, in which the alkyl moiety has the same meaning as defined above. Examples thereof include groups such as methylamino and ethylamino.

The di($C_1$-$C_6$ alkyl)amino group represents an $(alkyl)_2$N— group having 1 to 6 carbon atoms in the alkyl moiety, in which the alkyl moiety has the same meaning as defined above. Examples thereof include groups such as dimethylamino, diethylamino, methylethylamino, dipropylamino, and dibutylamino.

The mono($C_1$-$C_6$ alkyl)aminocarbonyl group represents an (alkyl)-NH—C(=O)— group having 1 to 6 carbon atoms in the alkyl moiety, in which the alkyl moiety has the same meaning as defined above. Examples thereof include groups such as methylaminocarbonyl and ethylaminocarbonyl.

The di($C_1$-$C_6$ alkyl)aminocarbonyl group represents an $(alkyl)_2$N—C(=O)— group having 1 to 6 carbon atoms in the alkyl moiety, in which the alkyl moiety has the same meaning as defined above. Examples thereof include groups such as dimethylaminocarbonyl, diethylaminocarbonyl, methylethylaminocarbonyl, dipropylaminocarbonyl, and dibutylaminocarbonyl.

The $C_1$-$C_6$ alkoxycarbonyl group represents an (alkyl)-OC(=O)— group having 1 to 6 carbon atoms in the alkyl moiety, in which the alkyl moiety has the same meaning as defined above. Examples thereof include groups such as methoxycarbonyl, ethoxycarbonyl, n-propoxycarbonyl, and isopropoxycarbonyl.

The $C_1$-$C_6$ acyl group represents an acyl group derived from a linear or branched aliphatic carboxylic acid having 1 to 6 carbon atoms, and when the aliphatic group is an alkyl group, the acyl group may be regarded as an alkylcarbonyl group. Examples thereof include groups such as formyl, acetyl, propionyl, isopropionyl, butyryl, and pivaloyl.

The $C_1$-$C_6$ alkylcarbonyloxy group represents an (alkyl)-C(=O)O— group having 1 to 6 carbon atoms in the alkyl moiety, in which the alkyl moiety has the same meaning as defined above. Examples thereof include groups such as acetoxy, propionyloxy, isopropionyloxy, and pivaloyloxy.

The $C_2$-$C_6$ alkenylcarbonyloxy group represents an (alkenyl)-C(=O)—O— group having 2 to 6 carbon atoms in the alkenyl moiety, in which the alkenyl moiety has the same meaning as defined above. Examples thereof include groups such as 1-propenylcarbonyloxy, 2-propenylcarbonyloxy, 1-butenylcarbonyloxy, and 1-methyl-1-propenylcarbonyloxy.

The $C_2$-$C_6$ alkynylcarbonyloxy group represents an (alkynyl)-C(=O)—O— group having 2 to 6 carbon atoms in the alkynyl moiety, in which the alkynyl moiety has the same meaning as defined above. Examples thereof include groups such as 1-propynylcarbonyloxy and 2-propynylcarbonyloxy.

The $C_1$-$C_6$ haloalkylthio group represents a (haloalkyl)-S— group having 1 to 6 carbon atoms, in which the haloalkyl moiety has the same meaning as defined above. Examples thereof include groups such as difluoromethylthio and trifluoromethylthio.

The $C_1$-$C_6$ haloalkylsulfinyl group represents a (haloalkyl)-SO— group having 1 to 6 carbon atoms, in which the haloalkyl moiety has the same meaning as defined above. Examples thereof include groups such as chloromethylsulfinyl, difluoromethylsulfinyl, and trifluoromethylsulfinyl.

The $C_1$-$C_6$ haloalkylsulfonyl group represents a (haloalkyl)-SO$_2$— group having 1 to 6 carbon atoms, in which the haloalkyl moiety has the same meaning as defined above. Examples thereof include groups such as chloromethylsulfonyl, difluoromethylsulfonyl, and trifluoromethylsulfonyl.

The mono($C_1$-$C_6$ alkyl)aminocarbonyl group represents an (alkyl)NH—C(=O)— group having 1 to 6 carbon atoms in the alkyl moiety, in which the alkyl moiety has the same meaning as defined above. Examples thereof include groups such as methylaminocarbonyl or ethylaminocarbonyl.

The di($C_1$-$C_6$ alkyl)aminocarbonyl group represents an (alkyl)$_2$N—C(=O)— group in which the alkyl moiety has the same meaning as defined above. Examples thereof include groups such as dimethylaminocarbonyl, diethylaminocarbonyl, methylethylaminocarbonyl, dipropylaminocarbonyl, and dibutylaminocarbonyl.

The $C_2$-$C_6$ alkenylthio group represents an (alkenyl)-S— group having 2 to 6 carbon atoms, in which the alkenyl moiety has the same meaning as defined above. Examples thereof include groups such as allylthio.

The $C_2$-$C_6$ alkenylsulfinyl group represents an (alkenyl)-SO— group having 2 to 6 carbon atoms, in which the alkenyl moiety has the same meaning as defined above. Examples thereof include groups such as allylsulfinyl.

The $C_2$-$C_6$ alkenylsulfonyl group represents an (alkenyl)-SO$_2$— group having 2 to 6 carbon atoms, in which the alkenyl moiety has the same meaning as defined above. Examples thereof include groups such as allylsulfonyl.

The $C_2$-$C_6$ alkynylthio group represents an (alkynyl)-S— group having 2 to 6 carbon atoms, in which the alkynyl moiety has the same meaning as defined above. Examples thereof include groups such as 2-propynylthio.

The $C_2$-$C_6$ alkynylsulfinyl group represents an (alkynyl)-SO— group having 2 to 6 carbon atoms, in which the alkynyl moiety has the same meaning as defined above. Examples thereof include groups such as 2-propynylsulfinyl.

The $C_2$-$C_6$ alkynylsulfonyl group represents an (alkynyl)-SO$_2$— group having 2 to 6 carbon atoms, in which the alkynyl moiety has the same meaning as defined above. Examples thereof include groups such as 2-propynylsulfonyl.

The heterocyclic group having 2 to 10 carbon atoms and 1 to 5 heteroatoms selected from an oxygen atom, a sulfur atom, and a nitrogen atom, represents, unless particularly limited, a monovalent group formed from a 3- to 8-membered, and preferably 5- to 7-membered, monocyclic, polycyclic or fused-ring heterocyclic ring having 1 to 5, and preferably 1 to 3, heteroatoms selected from the group consisting of an oxygen atom, a sulfur atom, and a nitrogen atom. Examples thereof include groups such as oxirane, tetrahydrofuran, pyrrolidine, tetrahydrothiophene, tetrahydrothiophene dioxide, tetrahydrothiopyrane, tetrahydrothiopyrane dioxide, 4,5-dihydroisoxazole, piperidine, piperazine, morpholine, furan, thiophene, pyrrole, pyrazole, imidazole, oxazole, isoxazole, triazole, isothiazole, 1,3,4-oxadiazole, 1,3,4-thiadiazole, 1,3,4-triazole, 1,2,4-oxadiazole, 1,2,4-thiadiazole, 1,2,4-triazole, 1,2,3-oxadiazole, 1,2,3-thiadiazole, 1,2,3-triazole, tetrazole, pyridine, pyrimidine, pyrazine, pyridazine, 1,3,5-triazine, 1,2,4-triazine, benzothiophene, benzofuran, indole, benzoxazole, benzothiazole, benzimidazole, benzisoxazole, benzisothiazole, indazole, 1,3-benzodioxole, benzo-1,4-dioxane, and 2,3-dihydrobenzofuran.

The heterocyclic-$C_1$-$C_6$ alkyl group in which the heterocyclic moiety has 2 to 10 carbon atoms and 1 to 5 heteroatoms selected from an oxygen atom, a sulfur atom, and a nitrogen atom, represents, unless particularly limited, an alkyl group having 1 to 6 carbon atoms substituted with a heterocyclic group, in which the alkyl moiety has the same meaning as defined above. Examples thereof include groups such as (tetrahydrofuran-2-yl)methyl, (4,5-dihydroisoxazol-5-yl)methyl, (isoxazol-5-yl)methyl, and a (thiophen-2-yl)methyl group.

The heterocyclic-oxy group in which the heterocyclic moiety has 2 to 10 carbon atoms and 1 to 5 heteroatoms arbitrarily selected from an oxygen atom, a sulfur atom, and a nitrogen atom, represents, unless particularly limited, a group substituted at an oxygen atom with a heterocyclic group having the same meaning as defined above. Examples thereof include groups such as (tetrahydrofuran-2-yl)oxy, (4,5-dihydroisoxazol-5-yl)oxy, (isoxazol-5-yl)oxy, and a (thiophen-2-yl)oxy group.

The heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom, and a nitrogen atom, represents an alkyl group having 1 to 6 carbon atoms substituted with an alkoxy group having 1 to 6 carbon atoms which is further substituted with a heterocyclic group having 2 to 10 carbon atoms and 1 to 5 heteroatoms selected from an oxygen atom, a sulfur atom, and a nitrogen atom, in which the heterocyclic moiety having 2 to 10 carbon atoms and 1 to 5 heteroatoms selected from an oxygen atom, a sulfur atom, and a nitrogen atom, the alkoxy moiety, and the alkyl moiety respectively have the same meanings as defined above. Examples thereof include groups such as (tetrahydrofuran-2-yl)methoxymethyl and (tetrahydrofuran-3-yl)methoxymethyl.

The $C_2$-$C_6$ haloalkenyl group represents, unless particularly limited, a linear or branched alkenyl group having 2 to 6 carbon atoms substituted with 1 to 11, and preferably 1 to 5, identical or different halogen atoms. Examples thereof include groups such as 2-chlorovinyl, 2-bromovinyl, 2-iodovinyl, 3-chloro-2-propenyl, 3-bromo-2-propenyl, 1-chloromethylvinyl, 2-bromo-1-methylvinyl, 1-trifluoromethylvinyl, 3,3,3-trichloro-1-propenyl, 3-bromo-3,3-difluoro-1-propenyl, 2,3,3,3-tetrachloro-1-propenyl, 1-trifluoromethyl-2,2-difluorovinyl, 2-chloro-2-propenyl, 3,3-difluoro-2-propenyl, 2,3,3-trichloro-2-propenyl, 4-bromo-3-chloro-3,4,4-trifluoro-1-butenyl, 1-bromomethyl-2-propenyl, 3-chloro-2-butenyl, 4,4,4-trifluoro-2-butenyl, 4-bromo-4,4-difluoro-2-butenyl, 3-bromo-3-butenyl, 3,4,4-trifluoro-3-butenyl, 3,4,4-tribromo-3-butenyl, 3-bromo-2-methyl-2-propenyl, 3,3-difluoro-2-methyl-2-propenyl, 3,3,3-trifluoro-2-methylpropenyl, 3-chloro-4,4,4-trifluoro-2-butenyl, 3,3,3-trifluoro-1-methyl-1-propenyl, 3,4,4-trifluoro-1,3-butadienyl, 3,4-dibromo-1-pentenyl, 4,4-difluoro-3-methyl-3-butenyl, 3,3,4,4,5,5,5-heptafluoro-1-pentenyl, 5,5-difluoro-4-pentenyl, 4,5,5-trifluoro-4-pentenyl, 3,4,4,4-tetrafluoro-3-trifluoromethyl-1-butenyl, 4,4,4-trifluoromethyl-3-methyl-2-butenyl, 3,5,5-trifluoro-2,4-pentadienyl, 4,4,5,5,6,6,6-heptafluoro-2-hexenyl, 3,4,4,5,5,5-hexafluoro-3-trifluoromethyl-1-pentenyl, 4,5,5,5-tetrafluoro-4-trifluoromethyl-2-pentenyl, or 5-bromo-4,5,5-trifluoro-4-trifluoromethyl-2-pentenyl.

The $C_2$-$C_6$ haloalkynyl group represents, unless particularly limited, a linear or branched alkynyl group having 2 to 6 carbon atoms substituted with 1 to 4 identical or different halogen atoms. Examples thereof include groups such as 3-chloro-2-propynyl, 3-bromo-2-propynyl, 3-iodo-2-propynyl, 3-chloro-1-propynyl, and 5-chloro-4-pentynyl.

The amino-$C_1$-$C_6$ alkyl group represents, unless particularly limited, an alkyl group having 1 to 6 carbon atoms substituted with an amino group, in which the alkyl moiety has the same meaning as defined above. Examples thereof include groups such as 2-aminoethyl and 3-aminopropyl.

The mono($C_1$-$C_6$ alkyl)amino-$C_1$-$C_6$ alkyl group represents, unless particularly limited, a linear or branched alkyl group having 1 to 6 carbon atoms substituted with an amino group which is mono-substituted with an alkyl group, in which the alkyl moiety has the same meaning as defined above. Examples thereof include groups such as 2-(methylamino)ethyl and 3-(methylamino)propyl.

The di($C_1$-$C_6$ alkyl)amino-$C_1$-$C_6$ alkyl group represents, unless particularly limited, a linear or branched alkyl group having 1 to 6 carbon atoms substituted with an amino group which is di-substituted with alkyl groups, in which the alkyl moiety has the same meaning as defined above. Examples thereof include groups such as N,N-dimethylaminomethyl and 2-(N,N-dimethylamino)ethyl.

The $C_1$-$C_6$ alkylthio-$C_1$-$C_6$ alkyl group represents, unless particularly limited, an alkyl group having 1 to 6 carbon atoms substituted with an alkylthio group having 1 to 6 carbon atoms, in which the alkyl moiety, and the alkyl moiety of the alkylthio respectively have the same meanings as defined above. Examples thereof include groups such as methylthiomethyl or ethylthiomethyl.

The $C_1$-$C_6$ alkylsulfinyl-$C_1$-$C_6$ alkyl group represents, unless particularly limited, an alkyl group having 1 to 6 carbon atoms substituted with an alkylsulfinyl group having 1 to 6 carbon atoms, in which the alkyl moiety and the alkyl moiety of the alkylsulfinyl respectively have the same meanings as defined above. Examples thereof include groups such as methylsulfinylmethyl or ethylsulfinylmethyl.

The $C_1$-$C_6$ alkylsulfonyl-$C_1$-$C_6$ alkyl group represents, unless particularly limited, an alkyl group having 1 to 6 carbon atoms substituted with an alkylsulfonyl group having 1 to 6 carbon atoms, in which the alkyl moiety and the alkyl moiety of the alkylsulfonyl respectively have the same meanings as defined above. Examples thereof include groups such as methylsulfonylmethyl or ethylsulfonylmethyl.

The $C_1$-$C_6$ haloalkylthio-$C_1$-$C_6$ alkyl group represents, unless particularly limited, an alkyl group having 1 to 6 carbon atoms substituted with a (haloalkyl)-S— group having 1 to 6 carbon atoms, in which the alkyl moiety and the haloalkyl moiety respectively have the same meanings as defined above. Examples thereof include groups such as difluoromethylthiomethyl and trifluoromethylthiomethyl.

The $C_1$-$C_6$ haloalkylsulfinyl-$C_1$-$C_6$ alkyl group represents, unless particularly limited, an alkyl group having 1 to 6 carbon atoms substituted with a (haloalkyl)-SO— group having 1 to 6 carbon atoms, in which the alkyl moiety and the haloalkyl moiety respectively have the same meanings as defined above. Examples thereof include groups such as difluoromethylsulfinylmethyl and trifluoromethylsulfinylmethyl.

The $C_1$-$C_6$ haloalkylsulfonyl-$C_1$-$C_6$ alkyl group represents, unless particularly limited, an alkyl group having 1 to 6 carbon atoms substituted with a (haloalkyl)-$SO_2$— group having 1 to 6 carbon atoms, in which the alkyl moiety and the haloalkyl moiety respectively have the same meanings as defined above. Examples thereof include groups such as difluoromethylsulfonylmethyl and trifluoromethylsulfonylmethyl.

The phenyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is further substituted with a phenyl, in which the alkyl moiety and the alkoxy moiety respectively have the same meanings as defined above. Examples thereof include groups such as benzyloxymethyl or 2-(benzyloxy)ethyl.

The phenyl $C_1$-$C_6$ alkyloxycarbonyl group represents, unless particularly limited, an (alkyl)-O—CO— group having 1 to 6 carbon atoms substituted with a phenyl, in which the alkyl moiety has the same meaning as defined above. Examples thereof include groups such as benzyloxycarbonyl or phenethyloxycarbonyl.

The $C_1$-$C_6$ alkoxy-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is further substituted with an alkoxy group having 1 to 6 carbon atoms, in which the alkyl moiety and the alkoxy moiety respectively have the same meanings as defined above. Examples thereof include groups such as 2-(2-methoxyethoxy)ethyl or 2-(2-ethoxyethoxy)ethyl.

The $C_3$-$C_8$ cycloalkyloxy-$C_1$-$C_6$ alkyl group represents, unless particularly limited, an alkyl group having 1 to 6 carbon atoms substituted with a (cycloalkyl)-O— group having 3 to 8 carbon atoms, in which the alkyl moiety and the cycloalkyl moiety respectively have the same meanings as defined above. Examples thereof include groups such as cyclopropyloxymethyl, cyclobutyloxymethyl, cyclopentyloxymethyl, or cyclohexyloxymethyl.

The phenyloxy-$C_1$-$C_6$ alkyl group represents, unless particularly limited, an alkyl group having 1 to 6 carbon atoms substituted with a (phenyl)-O— group, in which the alkyl moiety has the same meanings as defined above. Examples thereof include groups such as phenoxymethyl, 2-phenoxyethyl, and 3-phenoxypropyl.

The phenylthio-$C_1$-$C_6$ alkyl group represents, unless particularly limited, an alkyl group having 1 to 6 carbon atoms substituted with a (phenyl)-S— group, in which the alkyl moiety has the same meaning as defined above. Examples thereof include groups such as phenylthiomethyl, 2-phenylthioethyl, and 3-phenylthiopropyl.

The $C_1$-$C_6$ haloalkoxy group represents, unless particularly limited, a linear or branched alkyl-O— group having 1 to 6 carbon atoms substituted with 1 to 13, and preferably 1 to 5, identical or different halogen atoms, in which the haloalkyl moiety has the same meaning as defined above. Examples thereof include groups such as chloromethoxy, difluoromethoxy, chlorodifluoromethoxy, trifluoromethoxy, or 2,2,2-trifluoroethoxy.

The $C_1$-$C_6$ haloalkoxy-$C_1$-$C_6$ alkyl group represents, unless particularly limited, an alkyl group having 1 to 6 carbon atoms substituted with a haloalkoxy group having 1 to 6 carbon atoms, in which the haloalkoxy moiety and the alkyl moiety respectively have the same meanings as defined above. Examples thereof include groups such as chloromethoxymethyl, difluoromethoxymethyl, chlorodifluoromethoxymethyl, trifluoromethoxymethyl, or 2,2,2-trifluoroethoxymethyl.

The $C_1$-$C_6$ haloalkoxy-$C_1$-$C_6$ alkoxy group represents, unless particularly limited, an alkoxy group having 1 to 6 carbon atoms substituted with a haloalkoxy group having 1 to 6 carbon atoms, in which the haloalkoxy moiety and the alkoxy moiety respectively have the same meanings as defined above. Examples thereof include groups such as chloromethoxymethoxy, difluoromethoxymethoxy, chlorodifluoromethoxymethoxy, trifluoromethoxymethoxy, or 2,2,2-trifluoroethoxymethoxy.

The $C_1$-$C_6$ alkylthio-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is further substituted with an alkylthio group having 1 to 6 carbon atoms, in which the alkylthio moiety, the alkoxy moiety, and the alkyl moiety respectively have the same meanings as defined above. Examples thereof include groups such as 2-methylthioethoxymethyl and 2-ethylthioethoxymethyl.

The $C_1$-$C_6$ alkylsulfinyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is further substituted with an alkylsulfinyl group having 1 to 6 carbon atoms, in which the alkylsulfinyl moiety, the alkoxy moiety, and the alkyl moiety respectively have the same meanings as defined above. Examples thereof include groups such as 2-methylsulfinylethoxymethyl and 2-ethylsulfinylethoxymethyl.

The $C_1$-$C_6$ alkylsulfonyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is further substituted with an alkylsulfonyl group having 1 to 6 carbon atoms, in which the alkylsulfonyl moiety, the alkoxy moiety, and the alkyl moiety respectively have the same meanings as defined above. Examples thereof include groups such as 2-methylsulfonylethoxymethyl and 2-ethylsulfonylethoxymethyl.

The cyano-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is further substituted with a cyano group, in which the alkoxy moiety and the alkyl moiety respectively have the same meanings as defined above. Examples thereof include groups such as 2-cyanoethoxymethyl and 3-cyanopropoxymethyl.

The cyano-$C_1$-$C_6$ alkyl group represents, unless particularly limited, an alkyl group having 1 to 6 carbon atoms substituted with a cyano group, in which the alkyl moiety has the same meaning as defined above. Examples thereof include groups such as cyanomethyl and 2-cyanoethyl.

The $C_1$-$C_6$ alkylcarbonyloxy-$C_1$-$C_6$ alkyl group represents, unless particularly limited, an alkyl group having 1 to 6 carbon atoms substituted with an (alkyl)-C(=O)O— group having 1 to 6 carbon atoms, in which the alkyl moiety has the same meaning as defined above. Examples thereof include groups such as acetoxymethyl, propionyloxymethyl, isopropionyloxymethyl, and pivaloyloxymethyl.

The $C_1$-$C_6$ acyl-$C_1$-$C_6$ alkyl group represents, unless particularly limited, an alkyl group having 1 to 6 carbon atoms substituted with an acyl group having 1 to 6 carbon atoms, in which the acyl moiety and the alkyl moiety respectively have the same meanings as defined above. Examples thereof include groups such as 2-oxopropyl, 3-oxopropyl, and 2-oxobutyl.

The di($C_1$-$C_6$ alkoxy)-$C_1$-$C_6$ alkyl group represents, unless particularly limited, an alkyl group having 1 to 6 carbon atoms which is di-substituted with alkoxy group having 1 to 6 carbon atoms, in which the alkoxy moiety and the alkyl moiety respectively have the same meanings as defined above. Examples thereof include groups such as (2,2-dimethoxy)ethyl, (3,3-dimethoxy)propyl, (2,2-diethoxy)ethyl, and (3,3-diethoxy)propyl.

The $C_1$-$C_6$ alkoxycarbonyl-$C_1$-$C_6$ alkyl group represents, unless particularly limited, an alkyl group having 1 to 6 carbon atoms substituted with an alkoxycarbonyl group having 1 to 6 carbon atoms, in which the alkoxy moiety and the alkyl moiety respectively have the same meanings as defined above. Examples thereof include groups such as 2-methoxy-2-oxoethyl, 2-ethoxy-2-oxoethyl, and 2-tert-butoxy-2-oxoethyl.

The $C_1$-$C_6$ alkoxyimino-$C_1$-$C_6$ alkyl group represents, unless particularly limited, an alkyl group having 1 to 6 carbon atoms substituted with an (alkoxy)-N= having 1 to 6 carbon atoms, in which the alkoxy moiety and the alkyl moiety respectively have the same meanings as defined above. Examples thereof include groups such as 2-methoxyiminoethyl and 3-methoxyiminopropyl.

Examples of the $C_6$-$C_{10}$ aryl group include groups such as phenyl or naphthyl.

The $C_6$-$C_{10}$ aryl-$C_1$-$C_6$ alkyl group represents, unless particularly limited, an alkyl group having 1 to 6 carbon atoms substituted with an aryl group having 6 to 10 carbon atoms, in which the aryl moiety and the alkyl moiety respectively have the same meanings as defined above. Examples thereof include groups such as benzyl, phenethyl, 3-phenylpropyl, naphthalen-1-ylmethyl, and naphthalen-2-ylmethyl.

The $C_3$-$C_8$ halocycloalkyl group represents, unless particularly limited, a cycloalkyl group having 3 to 8 carbon atoms substituted with 1 to 5, and preferably 1 to 3, halogen atoms, in which the cycloalkyl moiety and the halogen atom respectively have the same meanings as defined above. Examples thereof include groups such as 2,2-difluorocyclopropyl and 2,2-dichlorocyclopropyl.

The nitro-$C_1$-$C_6$ alkyl group represents, unless particularly limited, an alkyl group having 1 to 6 carbon atoms substituted with a nitro group, in which the alkyl moiety has the same meaning as defined above. Examples thereof include groups such as nitromethyl and 2-nitroethyl.

The hydroxy-$C_1$-$C_6$ alkyl group represents, unless particularly limited, an alkyl group having 1 to 6 carbon atoms substituted with a hydroxyl group, in which the alkyl moiety has the same meaning as defined above. Examples thereof include groups such as 2-hydroxyethyl and 3-hydroxypropyl.

The $C_1$-$C_6$ acylamino group represents, unless particularly limited, an amino group substituted with an acyl group having 1 to 6 carbon atoms, in which the acyl moiety has the same meaning as defined above. Examples thereof include groups such as formamide, acetamide, and propionamide.

The $(R^6R^7N\!\!-\!\!C\!=\!\!O)\!-\!C_1\!-\!C_6$ alkyl group represents, unless particularly limited, an alkyl group having 1 to 6 carbon atoms substituted with $(R^6R^7N\!\!-\!\!C\!=\!\!O)$, in which the alkyl moiety has the same meaning as defined above, and $R^6$ and $R^7$ represent the groups described above. Examples thereof include groups such as N,N-dimethylaminocarbonylmethyl, 2-(N,N-dimethylaminocarbonyl)ethyl, and N-methyl-N-ethylaminocarbonylmethyl.

The $C_2$-$C_5$ alkylene chain represents, unless particularly limited, a divalent alkyl group formed from a linear or branched alkyl group having 2 to 5 carbon atoms in which the valence comes from two different carbon atoms. Examples thereof include groups such as ethylene, trimethylene, propylene, tetramethylene, and pentamethylene.

The heterocyclic-oxy-$C_1$-$C_6$ alkyl group in which the heterocyclic moiety has 2 to 10 carbon atoms and 1 to 5 heteroatoms selected from an oxygen atom, a sulfur atom, and a nitrogen atom represents, unless particularly limited, an alkyl group having 1 to 6 carbon atoms substituted with a (heterocyclic)-O— group, in which the alkyl moiety and the heterocyclic moiety having 2 to 10 carbon atoms and 1 to 5 heteroatoms selected from an oxygen atom, a sulfur atom, and a nitrogen atom respectively have the same meanings as defined above. Examples thereof include groups such as 2-(2-pyridyloxy)ethyl, 2-(2-pyrazinyloxy)ethyl, and 2-(2-thiazolyl)ethyl.

The $C_3$-$C_8$ cycloalkyl-$C_1$-$C_6$ alkoxy-$C_1$-$C_6$ alkyl group represents, unless particularly limited, an alkyl group having 1 to 6 carbon atoms substituted with an alkoxy group having 1 to 6 carbon atoms which is further substituted with a cycloalkyl group having 3 to 8 carbon atoms, in which the alkyl moiety, the alkoxy moiety, and the cycloalkyl moiety respectively have the same meanings as defined above. Examples thereof include groups such as cyclopropylmethyloxymethyl, cyclobutylmethyloxymethyl, cyclopentylmethyloxymethyl, or cyclohexylmethyloxymethyl.

The phenylsulfinyl-$C_1$-$C_6$ alkyl group represents, unless particularly limited, an alkyl group having 1 to 6 carbon atoms substituted with a (phenyl)-SO— group, in which the alkyl moiety has the same meaning as defined above. Examples thereof include groups such as phenylsulfinylmethyl, 2-phenylsulfinylethyl, and 3-phenylsulfinylpropyl.

The phenylsulfonyl-$C_1$-$C_6$ alkyl group represents, unless particularly limited, an alkyl group having 1 to 6 carbon atoms substituted with a (phenyl)-$SO_2$— group, in which the alkyl moiety has the same meaning as defined above. Examples thereof include groups such as 2-phenylsulfonylethyl, 3-phenylsulfonylpropyl, and 4-phenylsulfonylbutyl.

The $C_1$-$C_6$ alkylidene group represents, unless particularly limited, a divalent alkyl group formed from a linear or branched alkyl group having 1 to 6 carbon atoms in which the two valences come from a same carbon atom. Examples thereof include groups such as methylene, ethylidene, propylidene, and isopropylidene.

The $C_1$-$C_6$ alkylideneaminooxy-$C_1$-$C_6$ alkyl group represents, unless particularly limited, an alkyl group having 1 to 6 carbon atoms substituted with an (alkylidene)=N—O— having 1 to 6 carbon atoms, in which the alkylidene moiety and the alkyl moiety respectively have the same meanings as defined above. Examples thereof include groups such as methyleneaminooxymethyl, 2-(ethylideneaminooxy)ethyl, and 2-(isopropylideneaminooxy)ethyl.

The $C_3$-$C_8$ halocycloalkyl-$C_1$-$C_6$ alkyl group represents, unless particularly limited, an alkyl group having 1 to 6 carbon atoms substituted with a cycloalkyl group having 3 to 8 carbon atoms which is further substituted with 1 to 5, preferably 1 to 3, halogen atoms, in which the cycloalkyl moiety, the alkyl moiety, and the halogen atom respectively have the same meanings as defined above. Examples thereof include groups such as 2,2-difluorocyclopropylmethyl, and 2,2-dichlorocyclopropylmethyl.

The alkali metal is preferably sodium, potassium, or the like.

The phrases "two adjacent $R^2$ may be joined to form, together with the carbon atom to which they are directly bound, a 4- to 8-membered carbocyclic ring, or a 4- to 8-membered heterocyclic ring having 1 to 4 heteroatoms selected from an oxygen atom, a sulfur atom, and a nitrogen atom," "two adjacent $R^2$ may be joined to form, together with the carbon atom to which they are directly bound, a 4- to 8-membered carbocyclic ring, or a 4- to 8-membered heterocyclic ring having 1 to 4 heteroatoms selected from an oxygen atom, a sulfur atom, and a nitrogen atom," "two adjacent $R^4$ may be joined to form, together with the carbon atoms to which they are directly bound, a 4- to 8-membered carbocyclic ring, or a 4- to 8-membered heterocyclic ring having 1 to 4 heteroatoms selected from an oxygen atom, a sulfur atom, and a nitrogen atom," and "two adjacent $R^5$ may be joined to form, together with the carbon atoms to which they are directly bound, a 4- to 8-membered carbocyclic ring, or a 4- to 8-membered heterocyclic ring having 1 to 4 heteroatoms selected from an oxygen atom, a sulfur atom, and a nitrogen atom" may indicate, unless particularly limited, the following structures.

[Chemical Formula 2]

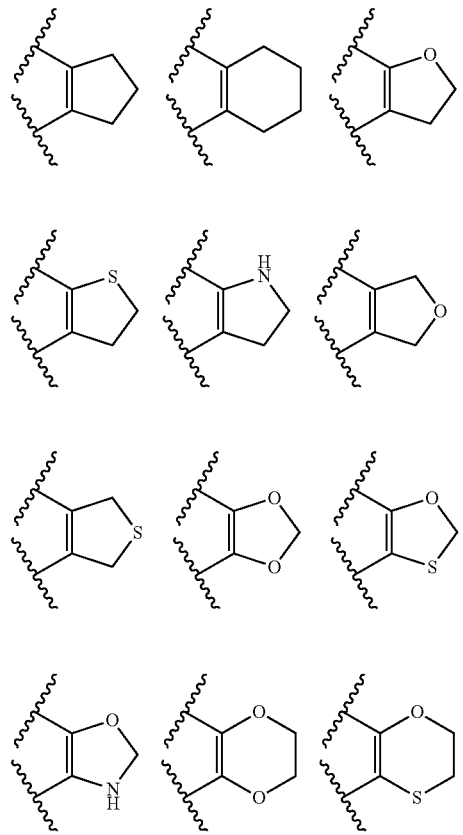

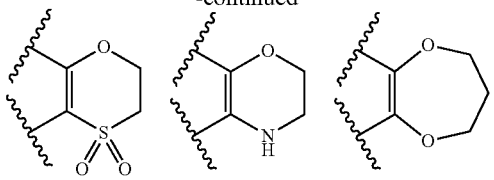

The rings formed in this case may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group, or an oxo group.

Examples of $X^1$ in the formula [I] of the present invention include an oxygen atom or a sulfur atom. A preferred example of $X^1$ may be an oxygen atom. With regard to the formula [I], $X^1$ is described in the form of a (thio)carbonyl group; however, when the substituent $R^1$ on the adjacent nitrogen atom is such as a hydrogen atom, $X^1$ may exist, not in a carbonyl form, but in an enol form which is a tautomer of the carbonyl form.

$X^2$, $X^3$, and $X^4$ in the formula [I] of the present invention each independently represent =CH— or =N(O)$_m$— (provided that m represents an integer of 0 or 1). Preferred combinations of $X^2$, $X^3$, and $X^4$ include, for example, the following. When $X^2$, $X^3$ and $X^4$ all represent =CH—, the 6-membered ring containing $X^2$ turns to be a benzene ring which is fused with the pyridine ring, and thus forms a quinoline ring. When $X^2$ represents =N(O)$_m$—, and $X^3$ and $X^4$ each represent =CH—, the 6-membered ring containing $X^2$ turns to be a pyridine ring that is fused with the pyridine ring, and thus forms a 1,8-naphthyridine ring. When $X^2$ and $X^3$ each represent =N(O)$_m$—, and $X^4$ represents =CH—, the 6-membered ring containing $X^2$ turns to be a pyrimidine ring that is fused with the pyridine ring, and thus forms a pyridopyrimidine ring. When $X^2$ and $X^3$ each represent =CH—, and $X^4$ represents =N(O)$_m$—, the 6-membered ring containing $X^2$ turns to be a pyridine ring that is fused with the pyridine ring, and thus forms a 1,5-naphthyridine ring. The carbon atoms of the 6-membered ring containing $X^2$ thus formed may be substituted with substituents group $R^2$. In the present specification, this is expressed as "the relevant carbon atoms may be substituted with $R^2$." Furthermore, in the case where $X^2$, $X^3$, or $X^4$ represents =N(O)$_m$—, when m is 1, the nitrogen atom of the 6-membered ring containing $X^2$ forms N-oxide, and forms an N-oxide ring. Preferred examples of $X^2$, $X^3$, and $X^4$ in the formula [I] of the present invention include =CH—, =C($R^2$)—, or =N—.

Preferred examples of $R^1$ for the formula [I] of the present invention include a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a phenyloxy-$C_1$-$C_6$ alkyl group; a $C_1$-$C_6$ haloalkoxy-$C_1$-$C_6$ alkyl group; a tetrahydrofuranyl-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl-group; a $C_1$-$C_6$ alkylcarbonyloxy-$C_1$-$C_6$ alkyl group; a $C_1$-$C_6$ acyl-$C_1$-$C_6$ alkyl group; a $C_1$-$C_6$ alkoxycarbonyl-$C_1$-$C_6$ alkyl group; a ($R^6R^7$N—C=O)—$C_1$-$C_6$ alkyl group; a $C_6$-$C_{10}$ aryl-$C_1$-$C_6$ alkyl group (the aryl moiety of this group may be substituted with one or two or more of identical or different $R^4$); a heterocyclic-$C_1$-$C_6$ alkyl group (this group may be substituted with one or two or more of identical or different $R^5$); a $NR^8R^9$ group; a $C_6$-$C_{10}$ aryl group (this group may be substituted with one or two or more of identical or different $R^4$); and a heterocyclic group (this group may be substituted with one or two or more of identical or different $R^5$).

More preferred examples of $R^1$ include a $C_1$-$C_{12}$ alkyl group; a $C_2$-$C_6$ alkenyl group; a $C_2$-$C_6$ alkynyl group; a $C_3$-$C_8$ cycloalkyl group; a $C_1$-$C_6$ haloalkyl group; a $C_2$-$C_6$ haloalkenyl group; a $C_1$-$C_6$ alkylthio-$C_1$-$C_6$ alkyl group; a $C_1$-$C_6$ alkylsulfonyl-$C_1$-$C_6$ alkyl group; a $C_1$-$C_6$ alkoxy-$C_1$-$C_6$ alkyl group; a $C_1$-$C_6$ alkoxy-$C_1$-$C_6$ alkoxy-$C_1$-$C_6$ alkyl group; a $C_1$-$C_6$ haloalkoxy-$C_1$-$C_6$ alkyl group; a tetrahydrofuranyl-$C_1$-$C_6$ alkoxy-$C_1$-$C_6$ alkyl group; a cyano-$C_1$-$C_6$ alkyl group; a $C_1$-$C_6$ alkoxycarbonyl-$C_1$-$C_6$ alkyl group; a $C_6$-$C_{10}$ aryl-$C_1$-$C_6$ alkyl group (the aryl moiety of this group may be substituted with one or two or more of identical or different $R^4$); a heterocyclic-$C_1$-$C_6$ alkyl group (this group may be substituted with one or two or more of identical or different $R^5$); a $C_6$-$C_{10}$ aryl group (this group may be substituted with one or two or more of identical or different $R^4$); or a heterocyclic group (this group may be substituted with one or two or more of identical or different $R^5$).

Preferred examples of $R^2$ for the formula [I] of the present invention include a halogen atom; a nitro group; a $C_1$-$C_6$ alkyl group; a $C_1$-$C_6$ haloalkyl group; a $C_1$-$C_6$ alkoxy group; a $C_1$-$C_6$ alkylthio group; a $C_1$-$C_6$ alkoxy-$C_1$-$C_6$ alkyl group; or a $C_1$-$C_6$ alkylsulfonyl group.

More preferred examples of $R^2$ include a halogen atom; a $C_1$-$C_6$ alkyl group; a $C_1$-$C_6$ haloalkyl group; a $C_1$-$C_6$ alkoxy group; a $C_1$-$C_6$ alkylthio group; or a $C_1$-$C_6$ alkylsulfonyl group. Even more preferred examples thereof include a halogen atom; a $C_1$-$C_6$ alkyl group; a $C_1$-$C_6$ haloalkyl group; and a $C_1$-$C_6$ alkoxy group.

n for the formula [I] of the present invention is preferably 0 to 2, and more preferably 0 to 1.

Preferred examples of $R^3$ for the formula [I] of the present invention include a hydroxyl group; O-M+ (M+ represents an alkali metal cation or an ammonium cation); an amino group; a halogen atom; a $C_1$-$C_6$ alkylsulfonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a $C_2$-$C_6$ alkenylcarbonyloxy group; a $C_2$-$C_6$ alkynylcarbonyloxy group; a phenoxy group (this group may be substituted with one $R^{10}$, or two to five identical or different $R^{10}$); a phenylthio group (this group may be substituted with one $R^{10}$, or two to five identical or different $R^{10}$); a phenylsulfinyl group (this group may be substituted with one $R^{10}$, or two to five identical or different $R^{10}$); a phenylsulfonyl group (this group may be substituted with one $R^{10}$, or two to five identical or different $R^{10}$); a phenylsulfonyloxy group (this group may be substituted with one $R^{10}$, or two to five identical or different $R^{10}$); a phenylcarbonyloxy group (this group may be substituted with one $R^{10}$, or two to five identical or different $R^{10}$); a 1,2,4-triazol-1-yl group; an imidazol-1-yl group; a pyrazol-1-yl group; or a tetrazol-1-yl group.

A more preferred example of $R^3$ may be a hydroxyl group. This hydroxyl group may be salts or derivatives such as ethers and esters of these groups. Furthermore, a free hydroxy group may exist in a keto form, which is a tautomer thereof, due to the adjacent double bond.

Preferred examples of $R^4$ for the formula [I] of the present invention include a halogen atom; a hydroxyl group; a nitro group; a cyano group; a $C_1$-$C_6$ alkyl group; a $C_3$-$C_8$ cycloalkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; a $C_1$-$C_6$ alkylthio group; a $C_1$-$C_6$ alkylsulfonyl group; a $C_1$-$C_6$ haloalkylthio group; a $C_1$-$C_6$ alkoxy-$C_1$-$C_6$ alkyl group; a $C_3$-$C_8$ cycloalkyl-$C_1$-$C_6$ alkyloxy group; a $C_1$-$C_6$ haloalkoxy-$C_1$-$C_6$ alkoxy group; a cyano-$C_1$-$C_6$ alkoxy group; a $C_1$-$C_6$ acyl group; a $C_1$-$C_6$ alkoxycarbonyl group; a di($C_1$-$C_6$ alkyl)amino group; or a heterocyclic-$C_1$-$C_6$ alkoxy group (the heterocyclic moiety having 2 to 10 carbon atoms and 1 to 5 heteroatoms selected from an oxygen atom, a sulfur atom, and a nitrogen atom in this group, may be substituted with one $R^{10}$, or two to five identical or different $R^{10}$).

More preferred examples of $R^4$ include a halogen atom; a $C_1$-$C_6$ alkyl group; a $C_1$-$C_6$ haloalkyl group; a $C_1$-$C_6$ alkoxy group; a $C_2$-$C_6$ alkenyloxy group; a $C_2$-$C_6$ alkynyloxy group; a $C_1$-$C_6$ haloalkoxy group; or a $C_1$-$C_6$ acyl group.

Even more preferred examples of $R^4$ include a halogen atom; a $C_1$-$C_6$ alkyl group; a $C_1$-$C_6$ haloalkyl group; a $C_1$-$C_6$ alkoxy group; or a $C_1$-$C_6$ haloalkoxy group.

It is also preferable for $R^4$ that two adjacent $R^4$ are joined and form, together with the carbon atoms to which the respective $R^4$ are directly bonded, a 4- to 8-membered carbocyclic ring, or a 4- to 8-membered heterocyclic ring having 1 to 4 heteroatoms selected from an oxygen atom, a sulfur atom, and a nitrogen atom.

Preferred examples of such a carbocyclic ring and such a heterocyclic ring include those moieties represented by the following structural formulas.

[Chemical Formula 3]

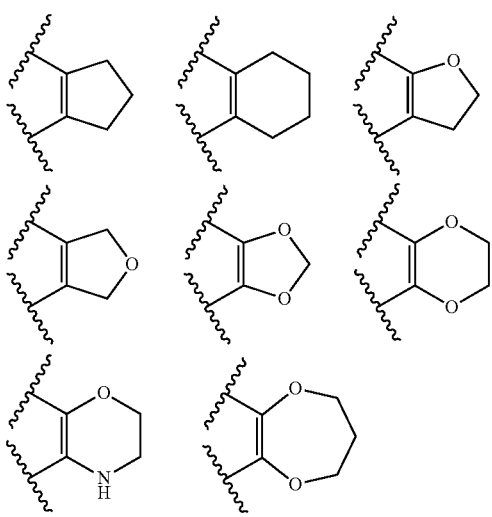

More preferred examples of the heterocyclic ring include moieties represented by the following structural formulas.

[Chemical Formula 4]

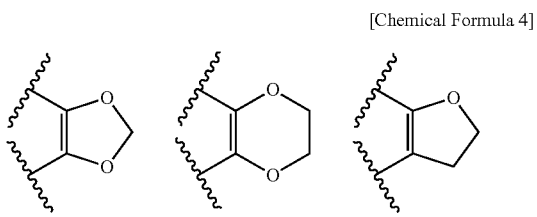

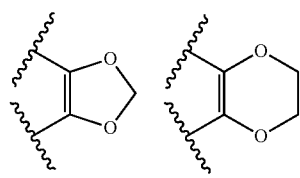

Even more preferred examples of the heterocyclic ring include moieties represented by the following structural formulas.

[Chemical Formula 5]

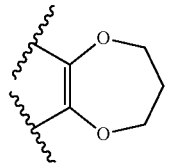

Preferred examples of $R^s$ for the formula [I] of the present invention include a halogen atom; a cyano group; a nitro group; a $C_1$-$C_6$ alkyl group; a $C_1$-$C_6$ haloalkyl group; a $C_1$-$C_6$ alkoxy group; a $C_1$-$C_6$ haloalkoxy group; a $C_1$-$C_6$ alkylthio group; a $C_1$-$C_6$ alkylsulfonyl group; or an oxo group.

More preferred examples of $R^5$ include a halogen atom; a $C_1$-$C_6$ alkyl group; or a $C_1$-$C_6$ haloalkyl group.

$A^1$ in the formula [I] of the present invention represents —$C(R^{11}R^{12})$—.

$A^2$ in the formula [I] of the present invention represents —$C(R^{13}R^{14})$— or $C$=$O$.

$A^3$ in the formula [I] of the present invention represents —$C(R^{15}R^{16})$—.

That is, -$A^1$-$A^2$-$A^3$- in the formula [I] of the present invention represents:

—$C(R^{11}R^{12})$—$C(R^{13}R^{14})$—$C(R^{15}R^{16})$— or

—$C(R^{11}R^{12})$—$C(=O)$—$C(R^{15}R^{16})$—, and these form a 6-membered carbocyclic ring together with adjacent carbon atoms.

$R^{11}$, $R^{12}$, $R^{13}$, $R^{14}$, $R^{15}$, and $R^{16}$ as use herein each independently represent a hydrogen atom; or a $C_1$-$C_6$ alkyl group. Furthermore, $R^{11}$ and $R^{16}$ may be joined to form a 5- to 10-membered, and preferably 5- to 8-membered, carbocyclic ring together with adjacent carbon atoms. That is, $R^{11}$ and $R^{16}$ may be joined to form a divalent linear or branched $C_2$-$C_5$ alkylene chain. A preferred alkylene group may be an ethylene group.

Specific examples of the heterocyclic group as indicated in the "heterocyclic group having 2 to 10 carbon atoms and 1 to 5 heteroatoms arbitrarily selected from an oxygen atom, a sulfur atom, and a nitrogen atom," "heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom, and a nitrogen atom," "heterocyclic-$C_1$-$C_6$ alkyl group in which the heterocyclic moiety has 2 to 10 carbon atoms and 1 to 5 heteroatoms selected from an oxygen atom, a sulfur atom, and a nitrogen atom," or "heterocyclic-$C_1$-$C_6$ alkoxy group in which the heterocyclic moiety has 2 to 10 carbon atoms and 1 to 5 heteroatoms arbitrarily selected from an oxygen atom, a sulfur atom, and a nitrogen atom," include tetrahydrofuran, tetrahydrothiophene, tetrahydrothiophene dioxide, tetrahydrothiopyrane, tetrahydrothiopyrane dioxide, 4,5-dihydroisoxazole, thiophene, pyrazole, oxazole, isoxazole, thiazole, isothiazole, 1,2,4-triazole, 1,2,4-oxadiazole, 1,3,4-thiadiazole, pyridine, pyridazine, pyrimidine, pyrazine, 2,3-dihydrobenzofuran, 1,3-benzodioxole, benzo-1,4-dioxane, benzofuran, and indole.

A group of preferred examples of the heterocyclic ring includes 4,5-dihydroisoxazole, thiophene, pyrazole, oxazole, isoxazole, triazole, isothiazole, pyridine, pyrazine, 1,3-benzodioxole, and benzo-1,4-dioxane. More preferred examples of the heterocyclic ring include thiophene, isoxazole, pyridine, 1,3-benzodioxole, and benzo-1,4-dioxane.

The heterocyclic group formed from the heterocyclic ring shown in the formula [I] of the present invention can be made into a group attached at any position of a selected heterocyclic ring. Even in the case where the selected heterocyclic ring is a ring fused with a benzene ring, the position at which the group is formed is not limited to the heterocyclic moiety, and a position on the benzene ring can also be selected for the purpose.

Next, specific preferred examples of the compound represented by the formula [I] of the present invention will be listed in the following Table 1 to Table 66. However, the compound of the present invention is not intended to be limited to these compounds. In addition, reference will be made to the compound numbers in the following descriptions.

The following notations in the tables in the present specification respectively represent relevant groups as shown below.

For example,
Me represents a methyl group;
Et represents an ethyl group;
n-Pr represents an n-propyl group;
i-Pr represents an isopropyl group;
c-Pr represents a cyclopropyl group;
n-Bu represents an n-butyl group;
s-Bu represents a sec-butyl group;
i-Bu represents an isobutyl group;
t-Bu represents a tert-butyl group;
c-Bu represents a cyclobutyl group;
n-Pen represents an n-pentyl group;
c-Pen represents a cyclopentyl group;
n-Hex represents an n-hexyl group;
Ph represents a phenyl group;
Bn represents a benzyl group;
symbol "-" for $R^2$ and $R^{22}$ represents that those substituents are not present;
(4-Cl)Bn represents a 4-chlorobenzyl group;
3,4-($CH_2CH_2CH_2CH_2$)— represents the following chemical structure in which the 3-position and the 4-position are linked by the butylene group and form a ring:

[Chemical Formula 6]

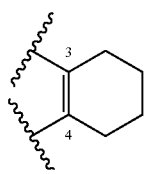

3,4-($OCH_2CH_2O$)— represents the following chemical structure in which the 3-position and the 4-position are similarly linked by the ethylenedioxy group and form a ring:

[Chemical Formula 7]

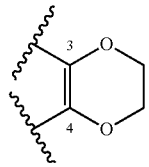

TABLE 1

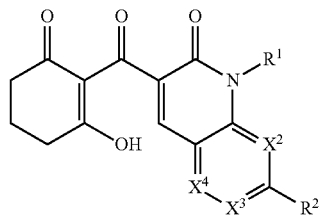

| Compound No. | $R^1$ | $R^2$ | $X^2$ | $X^3$ | $X^4$ |
|---|---|---|---|---|---|
| I-1 | H | H | CH | CH | CH |
| I-2 | Me | H | CH | CH | CH |
| I-3 | Et | H | CH | CH | CH |
| I-4 | n-Pr | H | CH | CH | CH |
| I-5 | i-Pr | H | CH | CH | CH |
| I-6 | c-Pr | H | CH | CH | CH |
| I-7 | n-Bu | H | CH | CH | CH |
| I-8 | i-Bu | H | CH | CH | CH |
| I-9 | t-Bu | H | CH | CH | CH |
| I-10 | c-Pen | H | CH | CH | CH |
| I-11 | $CH_2CH=CH_2$ | H | CH | CH | CH |
| I-12 | $CH_2C\equiv CH$ | H | CH | CH | CH |
| I-13 | $CH_2CF_3$ | H | CH | CH | CH |
| I-14 | $C_2H_4OCH_3$ | H | CH | CH | CH |
| I-15 | $C_2H_4OC_2H_5$ | H | CH | CH | CH |
| I-16 | CH(Me)OEt | H | CH | CH | CH |
| I-17 | $CH_2OCH_2CF_3$ | H | CH | CH | CH |
| I-18 | $CH_2SMe$ | H | CH | CH | CH |
| I-19 | $CH_2SEt$ | H | CH | CH | CH |
| I-20 | $CH_2SOMe$ | H | CH | CH | CH |
| I-21 | $CH_2SOEt$ | H | CH | CH | CH |
| I-22 | $CH_2SO_2Me$ | H | CH | CH | CH |
| I-23 | $CH_2SO_2Et$ | H | CH | CH | CH |
| I-24 | Bn | H | CH | CH | CH |
| I-25 | (2-F)Bn | H | CH | CH | CH |
| I-26 | (3-F)Bn | H | CH | CH | CH |
| I-27 | (4-F)Bn | H | CH | CH | CH |
| I-28 | (2-Cl)Bn | H | CH | CH | CH |
| I-29 | (3-Cl)Bn | H | CH | CH | CH |
| I-30 | (4-Cl)Bn | H | CH | CH | CH |

TABLE 2

| Compound No. | $R^1$ | $R^2$ | $X^2$ | $X^3$ | $X^4$ |
|---|---|---|---|---|---|
| I-31 | (2-Me)Bn | H | CH | CH | CH |
| I-32 | (3-Me)Bn | H | CH | CH | CH |
| I-33 | (4-Me)Bn | H | CH | CH | CH |
| I-34 | (2-$CF_3$)Bn | H | CH | CH | CH |
| I-35 | (3-$CF_3$)Bn | H | CH | CH | CH |
| I-36 | (4-$CF_3$)Bn | H | CH | CH | CH |
| I-37 | (2-OMe)Bn | H | CH | CH | CH |
| I-38 | (3-OMe)Bn | H | CH | CH | CH |
| I-39 | (4-OMe)Bn | H | CH | CH | CH |
| I-40 | CH(Me)Ph | H | CH | CH | CH |
| I-41 | Ph | H | CH | CH | CH |
| I-42 | (2-F)Ph | H | CH | CH | CH |
| I-43 | (3-F)Ph | H | CH | CH | CH |
| I-44 | (4-F)Ph | H | CH | CH | CH |
| I-45 | (2-Cl)Ph | H | CH | CH | CH |
| I-46 | (3-Cl)Ph | H | CH | CH | CH |

TABLE 2-continued

| Compound No. | R¹ | R² | X² | X³ | X⁴ |
|---|---|---|---|---|---|
| I-47 | (4-Cl)Ph | H | CH | CH | CH |
| I-48 | (2-Me)Ph | H | CH | CH | CH |
| I-49 | (3-Me)Ph | H | CH | CH | CH |
| I-50 | (4-Me)Ph | H | CH | CH | CH |
| I-51 | (2-CF₃)Ph | H | CH | CH | CH |
| I-52 | (3-CF₃)Ph | H | CH | CH | CH |
| I-53 | (4-CF₃)Ph | H | CH | CH | CH |
| I-54 | (2-OMe)Ph | H | CH | CH | CH |
| I-55 | (3-OMe)Ph | H | CH | CH | CH |
| I-56 | (4-OMe)Ph | H | CH | CH | CH |
| I-57 | (3-F-4-OMe)Ph | H | CH | CH | CH |
| I-58 | (3-F-4-Me)Ph | H | CH | CH | CH |
| I-59 | (4-F-3-Me)Ph | H | CH | CH | CH |
| I-60 | 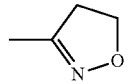 | H | CH | CH | CH |
| I-61 | 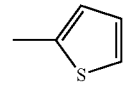 | H | CH | CH | CH |
| I-62 | 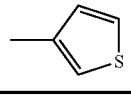 | H | CH | CH | CH |

TABLE 3

| Compound No. | R¹ | R² | X² | X³ | X⁴ |
|---|---|---|---|---|---|
| I-63 | 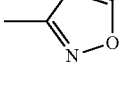 | H | CH | CH | CH |
| I-64 | 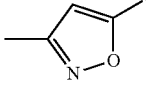 | H | CH | CH | CH |
| I-65 | 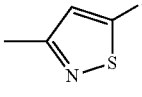 | H | CH | CH | CH |
| I-66 | 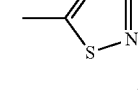 | H | CH | CH | CH |
| I-67 | 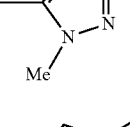 | H | CH | CH | CH |
| I-68 | 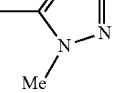 | H | CH | CH | CH |
| I-69 | 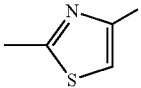 | H | CH | CH | CH |
| I-70 | 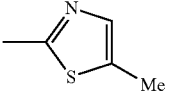 | H | CH | CH | CH |
| I-71 | 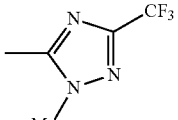 | H | CH | CH | CH |
| I-72 | 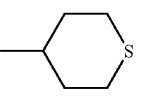 | H | CH | CH | CH |
| I-73 | 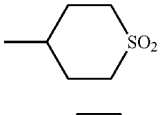 | H | CH | CH | CH |
| I-74 | 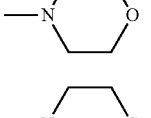 | H | CH | CH | CH |
| I-75 | 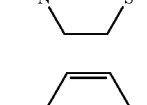 | H | CH | CH | CH |
| I-76 | 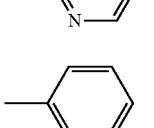 | H | CH | CH | CH |
| I-77 | 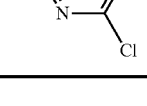 | H | CH | CH | CH |

TABLE 4

| Compound No. | R¹ | R² | X² | X³ | X⁴ |
|---|---|---|---|---|---|
| I-78 | 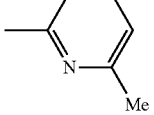 | H | CH | CH | CH |
| I-79 | 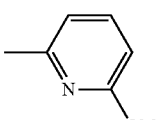 | H | CH | CH | CH |
| I-80 | 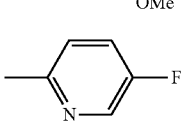 | H | CH | CH | CH |
| I-81 | 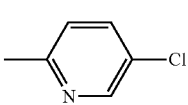 | H | CH | CH | CH |

TABLE 4-continued

| Compound No. | R¹ | R² | X² | X³ | X⁴ |
|---|---|---|---|---|---|
| I-82 | 2-methyl-5-methylpyridin-yl | H | CH | CH | CH |
| I-83 | 2-methyl-5-CF₃-pyridinyl | H | CH | CH | CH |
| I-84 | 2-methyl-5-OMe-pyridinyl | H | CH | CH | CH |
| I-85 | 2,4-dimethylpyridinyl | H | CH | CH | CH |
| I-86 | 2-methyl-4-CF₃-pyridinyl | H | CH | CH | CH |
| I-87 | 2-methyl-4-OMe-pyridinyl | H | CH | CH | CH |
| I-88 | 3-methylpyridinyl | H | CH | CH | CH |
| I-89 | 5-methyl-2-Cl-pyridinyl | H | CH | CH | CH |
| I-90 | 5-methyl-2-Me-pyridinyl | H | CH | CH | CH |
| I-91 | 5-methyl-2-CF₃-pyridinyl | H | CH | CH | CH |
| I-92 | 5-methyl-2-OMe-pyridinyl | H | CH | CH | CH |
| I-93 | 4-methylpyridinyl | H | CH | CH | CH |
| I-94 | 2-methylpyrimidinyl | H | CH | CH | CH |

TABLE 5

| Compound No. | R¹ | R² | X² | X³ | X⁴ |
|---|---|---|---|---|---|
| I-95 | 2-methyl-4-CF₃-pyrimidinyl | H | CH | CH | CH |
| I-96 | 2-methyl-4,6-diOMe-pyrimidinyl | H | CH | CH | CH |
| I-97 | methyl-dihydrobenzofuranyl | H | CH | CH | CH |
| I-98 | methyl-benzo[1,3]dioxolyl | H | CH | CH | CH |
| I-99 | methyl-difluoro-benzo[1,3]dioxolyl | H | CH | CH | CH |
| I-100 | CH₂-tetrahydrofuranyl | H | CH | CH | CH |
| I-101 | CH₂-3-methyl-4,5-dihydroisoxazolyl | H | CH | CH | CH |
| I-102 | CH₂-3-methylisoxazolyl | H | CH | CH | CH |
| I-103 | NH₂ | H | CH | CH | CH |
| I-104 | NHMe | H | CH | CH | CH |
| I-105 | OMe | H | CH | CH | CH |
| I-106 | OEt | H | CH | CH | CH |
| I-107 | CH₂CH₂OMe | H | CH | CH | CH |
| I-108 | 1-methylnaphthalenyl | H | CH | CH | CH |
| I-109 | 2-methylnaphthalenyl | H | CH | CH | CH |
| I-110 | 1,5-dimethyl-3-methylpyrazolyl | H | CH | CH | CH |

TABLE 5-continued

| Compound No. | R¹ | R² | X² | X³ | X⁴ |
|---|---|---|---|---|---|
| I-111 | 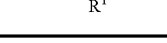 | H | CH | CH | CH |

TABLE 6

| Compound No. | R¹ | R² | X² | X³ | X⁴ |
|---|---|---|---|---|---|
| I-112 | (5-Me-1,3,4-thiadiazol-2-yl) | H | CH | CH | CH |
| I-113 | (5-Br-pyridin-2-yl) | H | CH | CH | CH |
| I-114 | (5-benzofuranyl) | H | CH | CH | CH |
| I-115 | CH₂CH₂O-(pyridin-2-yl) | H | CH | CH | CH |
| I-116 | (5-NO₂-pyridin-2-yl) | H | CH | CH | CH |
| I-117 | (6-benzo[1,4]dioxinyl) | H | CH | CH | CH |
| I-118 | (5-CN-pyridin-2-yl) | H | CH | CH | CH |
| I-119 | CH₂OCH₂-(tetrahydrofuran-2-yl) | H | CH | CH | CH |
| I-120 | CH₂CN | H | CH | CH | CH |
| I-121 | Me | Me | CH | CH | CH |
| I-122 | Et | Me | CH | CH | CH |
| I-123 | Ph | Me | CH | CH | CH |
| I-124 | Bn | Me | CH | CH | CH |
| I-125 | (4-OMe)Ph | Me | CH | CH | CH |
| I-126 | Me | Et | CH | CH | CH |
| I-127 | Et | Et | CH | CH | CH |
| I-128 | Ph | Et | CH | CH | CH |
| I-129 | Bn | Et | CH | CH | CH |
| I-130 | (4-OMe)Ph | Et | CH | CH | CH |
| I-131 | Me | i-Pr | CH | CH | CH |
| I-132 | Et | i-Pr | CH | CH | CH |
| I-133 | Ph | i-Pr | CH | CH | CH |
| I-134 | Bn | i-Pr | CH | CH | CH |
| I-135 | (4-OMe)Ph | i-Pr | CH | CH | CH |
| I-136 | Me | CF₃ | CH | CH | CH |

TABLE 7

| Compound No. | R¹ | R² | X² | X³ | X⁴ |
|---|---|---|---|---|---|
| I-137 | Et | CF₃ | CH | CH | CH |
| I-138 | Ph | CF₃ | CH | CH | CH |
| I-139 | Bn | CF₃ | CH | CH | CH |
| I-140 | (4-OMe)Ph | CF₃ | CH | CH | CH |
| I-141 | Me | CF₂Cl | CH | CH | CH |
| I-142 | Et | CF₂Cl | CH | CH | CH |
| I-143 | Ph | CF₂Cl | CH | CH | CH |
| I-144 | Bn | CF₂Cl | CH | CH | CH |
| I-145 | (4-OMe)Ph | CF₂Cl | CH | CH | CH |
| I-146 | Me | OCH₃ | CH | CH | CH |
| I-147 | Et | OCH₃ | CH | CH | CH |
| I-148 | Ph | OCH₃ | CH | CH | CH |
| I-149 | Bn | OCH₃ | CH | CH | CH |
| I-150 | (4-OMe)Ph | OCH₃ | CH | CH | CH |
| I-151 | Me | H | CH | CH | CCH₃ |
| I-152 | Et | H | CH | CH | CCH₃ |
| I-153 | Ph | H | CH | CH | CCH₃ |
| I-154 | Bn | H | CH | CH | CCH₃ |
| I-155 | (4-OMe)Ph | H | CH | CH | CCH₃ |
| I-156 | Me | H | CH | CH | CCl |
| I-157 | Et | H | CH | CH | CCl |
| I-158 | Ph | H | CH | CH | CCl |
| I-159 | Bn | H | CH | CH | CCl |
| I-160 | (4-OMe)Ph | H | CH | CH | CCl |
| I-161 | Me | H | CH | CH | CF |
| I-162 | Et | H | CH | CH | CF |
| I-163 | Ph | H | CH | CH | CF |
| I-164 | Bn | H | CH | CH | CF |
| I-165 | (4-OMe)Ph | H | CH | CH | CF |
| I-166 | Me | H | CH | CH | CBr |
| I-167 | Et | H | CH | CH | CBr |
| I-168 | Ph | H | CH | CH | CBr |
| I-169 | Bn | H | CH | CH | CBr |
| I-170 | (4-OMe)Ph | H | CH | CH | CBr |
| I-171 | Me | Cl | CH | CH | CCl |

TABLE 8

| Compound No. | R¹ | R² | X² | X³ | X⁴ |
|---|---|---|---|---|---|
| I-172 | Et | Cl | CH | CH | CCl |
| I-173 | Ph | Cl | CH | CH | CCl |
| I-174 | Bn | Cl | CH | CH | CCl |
| I-175 | (4-OMe)Ph | Cl | CH | CH | CCl |
| I-176 | Me | F | CH | CH | CF |
| I-177 | Et | F | CH | CH | CF |
| I-178 | Ph | F | CH | CH | CF |
| I-179 | Bn | F | CH | CH | CF |
| I-180 | (4-OMe)Ph | F | CH | CH | CF |
| I-181 | Me | F | CF | CF | CF |
| I-182 | Et | F | CF | CF | CF |
| I-183 | Ph | F | CF | CF | CF |
| I-184 | Bn | F | CF | CF | CF |
| I-185 | (4-OMe)Ph | F | CF | CF | CF |
| I-186 | 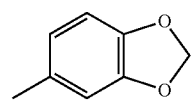 | Me | CH | CH | CH |
| I-187 | 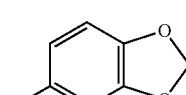 | OCH₃ | CH | CH | CH |
| I-188 | 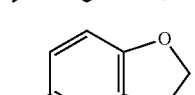 | H | CH | CH | CCH₃ |
| I-189 | 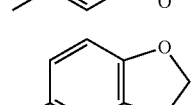 | H | CH | CH | CCl |

TABLE 8-continued

| Compound No. | R¹ | R² | X² | X³ | X⁴ |
|---|---|---|---|---|---|
| I-190 | (6-methyl-1,3-benzodioxole) | H | CH | CH | CF |
| I-191 | (6-methyl-1,3-benzodioxole) | H | CH | CH | CBr |
| I-192 | (methyl-2,3-dihydro-1,4-benzodioxine) | Me | CH | CH | CH |
| I-193 | (methyl-2,3-dihydro-1,4-benzodioxine) | OCH₃ | CH | CH | CH |
| I-194 | (methyl-2,3-dihydro-1,4-benzodioxine) | H | CH | CH | CCH₃ |
| I-195 | (methyl-2,3-dihydro-1,4-benzodioxine) | H | CH | CH | CCl |
| I-196 | (methyl-2,3-dihydro-1,4-benzodioxine) | H | CH | CH | CF |

TABLE 9

| Compound No. | R¹ | R² | X² | X³ | X⁴ |
|---|---|---|---|---|---|
| I-197 | (methyl-2,3-dihydro-1,4-benzodioxine) | H | CH | CH | CBr |
| I-198 | (2,5-dimethylpyridine) | Me | CH | CH | CH |
| I-199 | (2,5-dimethylpyridine) | OCH₃ | CH | CH | CH |
| I-200 | (2,5-dimethylpyridine) | H | CH | CH | CCH₃ |
| I-201 | (2,5-dimethylpyridine) | H | CH | CH | CCl |
| I-202 | (2,5-dimethylpyridine) | H | CH | CH | CF |

TABLE 9-continued

| Compound No. | R¹ | R² | X² | X³ | X⁴ |
|---|---|---|---|---|---|
| I-203 | (2,5-dimethylpyridine) | H | CH | CH | CBr |

TABLE 10

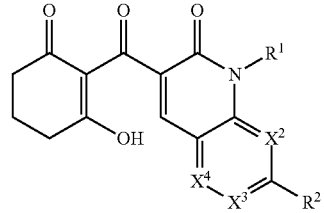

| Compound No. | R¹ | R² | X² | X³ | X⁴ |
|---|---|---|---|---|---|
| II-1 | H | H | N | CH | CH |
| II-2 | Me | H | N | CH | CH |
| II-3 | Et | H | N | CH | CH |
| II-4 | n-Pr | H | N | CH | CH |
| II-5 | i-Pr | H | N | CH | CH |
| II-6 | c-Pr | H | N | CH | CH |
| II-7 | n-Bu | H | N | CH | CH |
| II-8 | i-Bu | H | N | CH | CH |
| II-9 | t-Bu | H | N | CH | CH |
| II-10 | c-Pen | H | N | CH | CH |
| II-11 | CH₂CH=CH₂ | H | N | CH | CH |
| II-12 | CH₂C≡CH | H | N | CH | CH |
| II-13 | CH₂CF₃ | H | N | CH | CH |
| II-14 | C₂H₄OCH₃ | H | N | CH | CH |
| II-15 | C₂H₄OC₂H₅ | H | N | CH | CH |
| II-16 | CH(Me)OEt | H | N | CH | CH |
| II-17 | CH₂OCH₂CF₃ | H | N | CH | CH |
| II-18 | CH₂SMe | H | N | CH | CH |
| II-19 | CH₂SEt | H | N | CH | CH |
| II-20 | CH₂SOMe | H | N | CH | CH |
| II-21 | CH₂SOEt | H | N | CH | CH |
| II-22 | CH₂SO₂Me | H | N | CH | CH |
| II-23 | CH₂SO₃Et | H | N | CH | CH |
| II-24 | Bn | H | N | CH | CH |
| II-25 | (2-F)Bn | H | N | CH | CH |
| II-26 | (3-F)Bn | H | N | CH | CH |
| II-27 | (4-F)Bn | H | N | CH | CH |
| II-28 | (2-Cl)Bn | H | N | CH | CH |
| II-29 | (3-Cl)Bn | H | N | CH | CH |
| II-30 | (4-Cl)Bn | H | N | CH | CH |
| II-31 | (2-Me)Bn | H | N | CH | CH |
| II-32 | (3-Me)Bn | H | N | CH | CH |
| II-33 | (4-Me)Bn | H | N | CH | CH |
| II-34 | (2-CF₃)Bn | H | N | CH | CH |
| II-35 | (3-CF₃)Bn | H | N | CH | CH |

TABLE 11

| Compound No. | R¹ | R² | X² | X³ | X⁴ |
|---|---|---|---|---|---|
| II-36 | (4-CF₃)Bn | H | N | CH | CH |
| II-37 | (2-OMe)Bn | H | N | CH | CH |
| II-38 | (3-OMe)Bn | H | N | CH | CH |
| II-39 | (4-OMe)Bn | H | N | CH | CH |
| II-40 | CH(Me)Ph | H | N | CH | CH |
| II-41 | Ph | H | N | CH | CH |
| II-42 | (2-F)Ph | H | N | CH | CH |
| II-43 | (3-F)Ph | H | N | CH | CH |
| II-44 | (4-F)Ph | H | N | CH | CH |
| II-45 | (2-Cl)Ph | H | N | CH | CH |
| II-46 | (3-Cl)Ph | H | N | CH | CH |
| II-47 | (4-Cl)Ph | H | N | CH | CH |

TABLE 11-continued

| Compound No. | R¹ | R² | X² | X³ | X⁴ |
|---|---|---|---|---|---|
| II-48 | (2-Me)Ph | H | N | CH | CH |
| II-49 | (3-Me)Ph | H | N | CH | CH |
| II-50 | (4-Me)Ph | H | N | CH | CH |
| II-51 | (2-CF₃)Ph | H | N | CH | CH |
| II-52 | (3-CF₃)Ph | H | N | CH | CH |
| II-53 | (4-CF₃)Ph | H | N | CH | CH |
| II-54 | (2-OMe)Ph | H | N | CH | CH |
| II-55 | (3-OMe)Ph | H | N | CH | CH |
| II-56 | (4-OMe)Ph | H | N | CH | CH |
| II-57 | (3-F-4-OMe)Ph | H | N | CH | CH |
| II-58 | (2,5-Me₂)Ph | H | N | CH | CH |
| II-59 | (4-F-3-Me)Ph | H | N | CH | CH |
| II-60 | 3-methyl-4,5-dihydroisoxazol-5-yl | H | N | CH | CH |
| II-61 | thiophen-2-yl | H | N | CH | CH |
| II-62 | thiophen-3-yl | H | N | CH | CH |
| II-63 | 5-methylisoxazol-3-yl | H | N | CH | CH |
| II-64 | 5-(trifluoromethyl)isoxazol-3-yl | H | N | CH | CH |
| II-65 | 5-methylisothiazol-3-yl | H | N | CH | CH |
| II-66 | 5-methylisothiazol-3-yl (isomer) | H | N | CH | CH |

TABLE 12

| Compound No. | R¹ | R² | X² | X³ | X⁴ |
|---|---|---|---|---|---|
| II-67 | 1,3-dimethyl-1H-pyrazol-5-yl | H | N | CH | CH |
| II-68 | 1-methyl-3-(trifluoromethyl)-1H-pyrazol-5-yl | H | N | CH | CH |
| II-69 | 2,4-dimethylthiazol-5-yl | H | N | CH | CH |
| II-70 | 2,5-dimethylthiazol-4-yl | H | N | CH | CH |
| II-71 | 1-methyl-3-(trifluoromethyl)-1H-1,2,4-triazol-5-yl | H | N | CH | CH |
| II-72 | tetrahydro-2H-thiopyran-4-yl | H | N | CH | CH |
| II-73 | 1,1-dioxo-tetrahydro-2H-thiopyran-4-yl | H | N | CH | CH |
| II-74 | morpholin-4-yl | H | N | CH | CH |
| II-75 | thiomorpholin-4-yl | H | N | CH | CH |
| II-76 | pyridin-2-yl | H | N | CH | CH |
| II-77 | 6-chloropyridin-2-yl | H | N | CH | CH |
| II-78 | 6-methylpyridin-2-yl | H | N | CH | CH |
| II-79 | 6-methoxypyridin-2-yl | H | N | CH | CH |
| II-80 | 5-fluoropyridin-2-yl | H | N | CH | CH |

TABLE 13

| Compound No. | R¹ | R² | X² | X³ | X⁴ |
|---|---|---|---|---|---|
| II-81 | 5-chloropyridin-2-yl | H | N | CH | CH |

TABLE 13-continued

| Compound No. | R¹ | R² | X² | X³ | X⁴ |
|---|---|---|---|---|---|
| II-82 | 6-Me, 3-Me pyridin-2-yl | H | N | CH | CH |
| II-83 | 6-Me, 3-CF₃ pyridin-2-yl | H | N | CH | CH |
| II-84 | 6-Me, 3-OMe pyridin-2-yl | H | N | CH | CH |
| II-85 | 2-Me, 4-Me pyridin-... | H | N | CH | CH |
| II-86 | 2-Me, 4-CF₃ pyridin-... | H | N | CH | CH |
| II-87 | 2-Me, 4-OMe pyridin-... | H | N | CH | CH |
| II-88 | 5-Me pyridin-3-yl | H | N | CH | CH |
| II-89 | 5-Me, 2-Cl pyridin-... | H | N | CH | CH |
| II-90 | 5-Me, 2-Me pyridin-... | H | N | CH | CH |
| II-91 | 5-Me, 2-CF₃ pyridin-... | H | N | CH | CH |
| II-92 | 5-Me, 2-OMe pyridin-... | H | N | CH | CH |
| II-93 | 5-Me pyridin-2-yl | H | N | CH | CH |

TABLE 14

| Compound No. | R¹ | R² | X² | X³ | X⁴ |
|---|---|---|---|---|---|
| II-94 | 2-Me pyrimidin-... | H | N | CH | CH |
| II-95 | 2-Me, 4-CF₃ pyrimidin-... | H | N | CH | CH |
| II-96 | 2-Me, 4-OMe, 6-OMe pyrimidin-... | H | N | CH | CH |
| II-97 | 2,3-dihydrobenzofuranyl-Me | H | N | CH | CH |
| II-98 | benzo[d][1,3]dioxol-Me | H | N | CH | CH |
| II-99 | 2,2-difluorobenzo[d][1,3]dioxol-Me | H | N | CH | CH |
| II-100 | CH₂-tetrahydrofuran-2-yl | H | N | CH | CH |
| II-101 | CH₂-(3-Me-isoxazol-5-yl) | H | N | CH | CH |
| II-102 | CH₂-(3-Me-isoxazol-5-yl) | H | N | CH | CH |
| II-103 | NH₂ | H | N | CH | CH |
| II-104 | NHMe | H | N | CH | CH |
| II-105 | OMe | H | N | CH | CH |
| II-106 | OEt | H | N | CH | CH |
| II-107 | CH₂CH₂OMe | H | N | CH | CH |
| II-108 | Me-naphthalen-1-yl | H | N | CH | CH |

TABLE 14-continued

| Compound No. | R¹ | R² | X² | X³ | X⁴ |
|---|---|---|---|---|---|
| II-109 |  | H | N | CH | CH |

TABLE 15

| Compound No. | R¹ | R² | X² | X³ | X⁴ |
|---|---|---|---|---|---|
| II-110 | 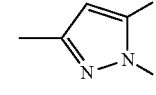 | H | N | CH | CH |
| II-111 | 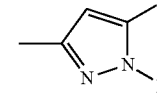 | H | N | CH | CH |
| II-112 | 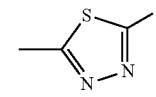 | H | N | CH | CH |
| II-113 | 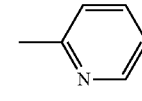 | H | N | CH | CH |
| II-114 | 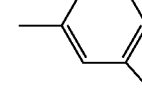 | H | N | CH | CH |
| II-115 | 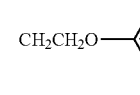 | H | N | CH | CH |
| II-116 | 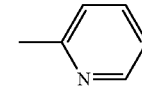 | H | N | CH | CH |
| II-117 | 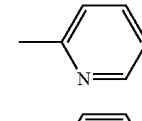 | H | N | CH | CH |
| II-118 | 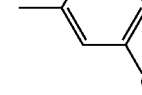 | H | N | CH | CH |
| II-119 | 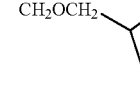 | H | N | CH | CH |
| II-120 | $CH_2CN$ | H | N | CH | CH |
| II-121 | Me | Me | N | CH | CH |
| II-122 | Et | Me | N | CH | CH |
| II-123 | Ph | Me | N | CH | CH |
| II-124 | Bn | Me | N | CH | CH |
| II-125 | (4-OMe)Ph | Me | N | CH | CH |
| II-126 | Me | i-Pr | N | CH | CH |
| II-127 | Et | i-Pr | N | CH | CH |

TABLE 15-continued

| Compound No. | R¹ | R² | X² | X³ | X⁴ |
|---|---|---|---|---|---|
| II-128 | Ph | i-Pr | N | CH | CH |
| II-129 | Bn | i-Pr | N | CH | CH |
| II-130 | (4-OMe)Ph | i-Pr | N | CH | CH |
| II-131 | Me | $CHF_2$ | N | CH | CH |
| II-132 | Et | $CHF_2$ | N | CH | CH |
| II-133 | Ph | $CHF_2$ | N | CH | CH |
| II-134 | Bn | $CHF_2$ | N | CH | CH |
| II-135 | (4-OMe)Ph | $CHF_2$ | N | CH | CH |
| II-136 | Me | $CF_3$ | N | CH | CH |
| II-137 | Et | $CF_3$ | N | CH | CH |

TABLE 16

| Compound No. | R¹ | R² | X² | X³ | X⁴ |
|---|---|---|---|---|---|
| II-138 | Ph | $CF_3$ | N | CH | CH |
| II-139 | Bn | $CF_3$ | N | CH | CH |
| II-140 | (4-OMe)Ph | $CF_3$ | N | CH | CH |
| II-141 | Me | $CF_2Cl$ | N | CH | CH |
| II-142 | Et | $CF_2Cl$ | N | CH | CH |
| II-143 | Ph | $CF_2Cl$ | N | CH | CH |
| II-144 | Bn | $CF_2Cl$ | N | CH | CH |
| II-145 | (4-OMe)Ph | $CF_2Cl$ | N | CH | CH |
| II-146 | Me | $OCH_3$ | N | CH | CH |
| II-147 | Et | $OCH_3$ | N | CH | CH |
| II-148 | Ph | $OCH_3$ | N | CH | CH |
| II-149 | Bn | $OCH_3$ | N | CH | CH |
| II-150 | (4-OMe)Ph | $OCH_3$ | N | CH | CH |
| II-151 | Me | H | N | CH | $CCH_3$ |
| II-152 | Et | H | N | CH | $CCH_3$ |
| II-153 | Ph | H | N | CH | $CCH_3$ |
| II-154 | Bn | H | N | CH | $CCH_3$ |
| II-155 | (4-OMe)Ph | H | N | CH | $CCH_3$ |
| II-156 | Me | H | N | CH | CCl |
| II-157 | Et | H | N | CH | CCl |
| II-158 | Ph | H | N | CH | CCl |
| II-159 | Bn | H | N | CH | CCl |
| II-160 | (4-OMe)Ph | H | N | CH | CCl |
| II-161 | Me | H | N | CH | CF |
| II-162 | Et | H | N | CH | CF |
| II-163 | Ph | H | N | CH | CF |
| II-164 | Bn | H | N | CH | CF |
| II-165 | (4-OMe)Ph | H | N | CH | CF |
| II-166 | Me | H | N | CH | CBr |
| II-167 | Et | H | N | CH | CBr |
| II-168 | Ph | H | N | CH | CBr |
| II-169 | Bn | H | N | CH | CBr |
| II-170 | (4-OMe)Ph | H | N | CH | CBr |
| II-171 | 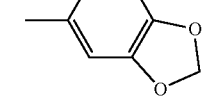 | Me | N | CH | CH |
| II-172 | 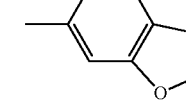 | $OCH_3$ | N | CH | CH |
| II-173 | 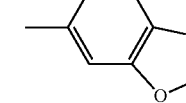 | H | N | CH | $CCH_3$ |

TABLE 17

| Compound No. | R¹ | R² | X² | X³ | X⁴ |
|---|---|---|---|---|---|
| II-174 | 6-methyl-1,3-benzodioxole | H | N | CH | CCl |
| II-175 | 6-methyl-1,3-benzodioxole | H | N | CH | CF |
| II-176 | 6-methyl-1,3-benzodioxole | H | N | CH | CBr |
| II-177 | 7-methyl-2,3-dihydro-1,4-benzodioxine | Me | N | CH | CH |
| II-178 | 7-methyl-2,3-dihydro-1,4-benzodioxine | OCH₃ | N | CH | CH |
| II-179 | 7-methyl-2,3-dihydro-1,4-benzodioxine | H | N | CH | CCH₃ |
| II-180 | 7-methyl-2,3-dihydro-1,4-benzodioxine | H | N | CH | CCl |
| II-181 | 7-methyl-2,3-dihydro-1,4-benzodioxine | H | N | CH | CF |
| II-182 | 7-methyl-2,3-dihydro-1,4-benzodioxine | H | N | CH | CBr |
| II-183 | 2,5-dimethylpyridin-2-yl | Me | N | CH | CH |
| II-184 | 2,5-dimethylpyridin-2-yl | OCH₃ | N | CH | CH |
| II-185 | 2,5-dimethylpyridin-2-yl | H | N | CH | CCH₃ |
| II-186 | 2,5-dimethylpyridin-2-yl | H | N | CH | CCl |
| II-187 | 2,5-dimethylpyridin-2-yl | H | CH | CH | CF |
| II-188 | 2,5-dimethylpyridin-2-yl | H | CH | CH | CBr |
| II-189 | 2,5-dimethylthiazol-2-yl | Me | N | CH | CH |
| II-190 | 2,5-dimethylthiazol-2-yl | OCH₃ | N | CH | CH |

TABLE 18

| Compound No. | R¹ | R² | X² | X³ | X⁴ |
|---|---|---|---|---|---|
| II-191 | 2,5-dimethylthiazol-2-yl | H | N | CH | CCH₃ |
| II-192 | 2,5-dimethylthiazol-2-yl | H | N | CH | CCl |
| II-193 | 2,5-dimethylthiazol-2-yl | H | CH | CH | CF |
| II-194 | 2,5-dimethylthiazol-2-yl | H | CH | CH | CBr |
| II-195 | (4-Me)Ph | Me | N | CH | CH |
| II-196 | (4-Me)Ph | OCH₃ | N | CH | CH |
| II-197 | (4-Me)Ph | H | N | CH | CCH₃ |
| II-198 | (4-Me)Ph | H | N | CH | CCl |
| II-199 | (4-Me)Ph | H | CH | CH | CF |
| II-200 | (4-Me)Ph | H | CH | CH | CBr |
| II-201 | CH₂c-Pr | H | N | CH | CH |
| II-202 | CH₂CH=CF₂ | H | N | CH | CH |
| II-203 | CH₂C≡CF | H | N | CH | CH |
| II-204 | 2,2-dichlorocyclopropyl | H | N | CH | CH |
| II-205 | 2,2-dichlorocyclopropylmethyl | H | N | CH | CH |
| II-206 | CH₂NH₂ | H | N | CH | CH |
| II-207 | CH₂NO₂ | H | N | CH | CH |
| II-208 | CH₂NHCH₃ | H | N | CH | CH |

TABLE 18-continued

| Compound No. | R¹ | R² | X² | X³ | X⁴ |
|---|---|---|---|---|---|
| II-209 | CH₂N(CH₃)₂ | H | N | CH | CH |
| II-210 | CH₂SCH₂CF₃ | H | N | CH | CH |
| II-211 | CH₂SOCH₂CF₃ | H | N | CH | CH |
| II-212 | CH₂SO₂CH₂CF₃ | H | N | CH | CH |
| II-213 | CH₂OH | H | N | CH | CH |
| II-214 | CH₂OBn | H | N | CH | CH |
| II-215 | C₂H₄OC₂H₄OCH₃ | H | N | CH | CH |
| II-216 | CH₂Oc-Pr | H | N | CH | CH |
| II-217 | CH₂OCH₂c-Pr | H | N | CH | CH |
| II-218 | CH₂OPh | H | N | CH | CH |
| II-219 | CH₂SPh | H | N | CH | CH |
| II-220 | CH₂SOPh | H | N | CH | CH |
| II-221 | CH₂SO₂Ph | H | N | CH | CH |
| II-222 | C₂H₄OC₂H₄SCH₃ | H | N | CH | CH |

TABLE 19

| Compound No. | R¹ | R² | X² | X³ | X⁴ |
|---|---|---|---|---|---|
| II-223 | C₂H₄OC₂H₄SOCH₃ | H | N | CH | CH |
| II-224 | C₂H₄OC₂H₄SO₂CH₃ | H | N | CH | CH |
| II-225 | CH₂OCH₂CN | H | N | CH | CH |
| II-226 | CH₂CN | H | N | CH | CH |
| II-227 | CH₂OCOCH₃ | H | N | CH | CH |
| II-228 | CH₂COCH₃ | H | N | CH | CH |
| II-229 | CH(OCH₃)₂ | H | N | CH | CH |
| II-230 | CH₂CO₂CH₃ | H | N | CH | CH |
| II-231 | CH₂CH=NOCH₃ | H | N | CH | CH |
| II-232 | CH₂ON=CHCH₃ | H | N | CH | CH |
| II-233 | CH₂CON(CH₃)₂ | H | N | CH | CH |
| II-234 | N(CH₃)₂ | H | N | CH | CH |
| II-235 | OCH₃ | H | N | CH | CH |
| II-236 | 2-Me-pyridin-5-yl | OH | N | CH | CH |
| II-237 | 2-Me-pyridin-5-yl | NO₂ | N | CH | CH |
| II-238 | 2-Me-pyridin-5-yl | CN | N | CH | CH |
| II-239 | 2-Me-pyridin-5-yl | c-Pr | N | CH | CH |
| II-240 | 2-Me-pyridin-5-yl | CH₂c-Pr | N | CH | CH |
| II-241 | 2-Me-pyridin-5-yl | CH₂CH=CH₂ | N | CH | CH |
| II-242 | 5-Me-thiazol-2-yl | CH₂C≡CH | N | CH | CH |
| II-243 | 5-Me-thiazol-2-yl | CH₂CH=CF₂ | N | CH | CH |
| II-244 | 5-Me-thiazol-2-yl | CH₂C≡CF | N | CH | CH |
| II-245 | 5-Me-thiazol-2-yl | (2,2-dichlorocyclopropyl)methyl | N | CH | CH |
| II-246 | 5-Me-thiazol-2-yl | 2-(2,2-dichlorocyclopropyl)ethyl | N | CH | CH |

TABLE 20

| Compound No. | R¹ | R² | X² | X³ | X⁴ |
|---|---|---|---|---|---|
| II-247 | 5-Me-thiazol-2-yl | Oc-Pr | N | CH | CH |
| II-248 | 5-Me-thiazol-2-yl | OCH₂c-Pr | N | CH | CH |
| II-249 | 5-Me-thiazol-2-yl | OCH₂CH=CH₂ | N | CH | CH |
| II-250 | 5-Me-thiazol-2-yl | OCH₂C≡CH | N | CH | CH |
| II-251 | 5-Me-thiazol-2-yl | OCHF₂ | N | CH | CH |
| II-252 | 5-Me-thiazol-2-yl | OCH₂OMe | N | CH | CH |
| II-253 | 5-Me-thiazol-2-yl | OCOCH₃ | N | CH | CH |
| II-254 | 2,3-dihydro-1,4-benzodioxin-6-yl | SCH₃ | N | CH | CH |
| II-255 | 2,3-dihydro-1,4-benzodioxin-6-yl | SOCH₃ | N | CH | CH |
| II-256 | 2,3-dihydro-1,4-benzodioxin-6-yl | SO₂CH₃ | N | CH | CH |

TABLE 20-continued

| Compound No. | R¹ | R² | X² | X³ | X⁴ |
|---|---|---|---|---|---|
| II-257 | 7-methyl-2,3-dihydro-1,4-benzodioxine | SCF₃ | N | CH | CH |
| II-258 | 7-methyl-2,3-dihydro-1,4-benzodioxine | SOCF₃ | N | CH | CH |
| II-259 | 7-methyl-2,3-dihydro-1,4-benzodioxine | SO₂CF₃ | N | CH | CH |
| II-260 | 7-methyl-2,3-dihydro-1,4-benzodioxine | NH₂ | N | CH | CH |
| II-261 | 7-methyl-2,3-dihydro-1,4-benzodioxine | NHCH₃ | N | CH | CH |
| II-262 | 7-methyl-2,3-dihydro-1,4-benzodioxine | N(CH₃)₂ | N | CH | CH |

TABLE 21

| Compound No. | R¹ | R² | X² | X³ | X⁴ |
|---|---|---|---|---|---|
| II-263 | 7-methyl-2,3-dihydro-1,4-benzodioxine | NHCOCH₃ | N | CH | CH |
| II-264 | 7-methyl-2,3-dihydro-1,4-benzodioxine | CH₂OH | N | CH | CH |
| II-265 | 7-methyl-2,3-dihydro-1,4-benzodioxine | CH₂OMe | N | CH | CH |
| II-266 | 7-methyl-2,3-dihydro-1,4-benzodioxine | CH₂SMe | N | CH | CH |
| II-267 | 7-methyl-2,3-dihydro-1,4-benzodioxine | CH₂SOMe | N | CH | CH |

TABLE 21-continued

| Compound No. | R¹ | R² | X² | X³ | X⁴ |
|---|---|---|---|---|---|
| II-268 | 7-methyl-2,3-dihydro-1,4-benzodioxine | CH₂SO₂Me | N | CH | CH |
| II-269 | 7-methyl-2,3-dihydro-1,4-benzodioxine | CH₂SCF₃ | N | CH | CH |
| II-270 | 7-methyl-2,3-dihydro-1,4-benzodioxine | CH₂SOCF₃ | N | CH | CH |
| II-271 | 7-methyl-2,3-dihydro-1,4-benzodioxine | CH₂SO₂CF₃ | N | CH | CH |
| II-272 | 7-methyl-2,3-dihydro-1,4-benzodioxine | CH₂CN | N | CH | CH |
| II-273 | 7-methyl-2,3-dihydro-1,4-benzodioxine | CH₂CH=NOCH₃ | N | CH | CH |
| II-274 | 7-methyl-2,3-dihydro-1,4-benzodioxine | CO₂H | N | CH | CH |
| II-275 | 7-methyl-2,3-dihydro-1,4-benzodioxine | CO₂Me | N | CH | CH |
| II-276 | 7-methyl-2,3-dihydro-1,4-benzodioxine | CONH₂ | N | CH | CH |
| II-277 | 7-methyl-2,3-dihydro-1,4-benzodioxine | CONHMe | N | CH | CH |
| II-278 | 7-methyl-2,3-dihydro-1,4-benzodioxine | CONMe₂ | N | CH | CH |

TABLE 21-continued

| Compound No. | R¹ | R² | X² | X³ | X⁴ |
|---|---|---|---|---|---|
| II-279 | [6-methyl-2,3-dihydro-1,4-benzodioxine] | [pyridin-2-yl] | N | CH | CH |
| II-280 | (4-NO₂)Ph | H | N | CH | CH |
| II-281 | (4-CN)Ph | H | N | CH | CH |
| II-282 | (4-CH₂=CHCH₂)Ph | H | N | CH | CH |
| II-283 | (4-CH≡CCH₂)Ph | H | N | CH | CH |

TABLE 22

| Compound No. | R¹ | R² | X² | X³ | X⁴ |
|---|---|---|---|---|---|
| II-284 | (4-c-Pr)Ph | H | N | CH | CH |
| II-285 | (4-OCHF₂)Ph | H | N | CH | CH |
| II-286 | (4-SMe)Ph | H | N | CH | CH |
| II-287 | (4-SOMe)Ph | H | N | CH | CH |
| II-288 | (4-SO₂Me)Ph | H | N | CH | CH |
| II-289 | (4-SCF₃)Ph | H | N | CH | CH |
| II-290 | (4-SOCF₃)Ph | H | N | CH | CH |
| II-291 | (4-SO₂CF₃)Ph | H | N | CH | CH |
| II-292 | (4-CO₂Me)Ph | H | N | CH | CH |
| II-293 | (4-COMe)Ph | H | N | CH | CH |
| II-294 | (4-CH₂OMe)Ph | H | N | CH | CH |
| II-295 | (4-CH₂c-Pr)Ph | H | N | CH | CH |
| II-296 | (4-CH₂CH=CF₂)Ph | H | N | CH | CH |
| II-297 | (4-CH₂CH≡CF)Ph | H | N | CH | CH |
| II-298 | 4-(2,2-dichlorocyclopropyl)Ph | H | N | CH | CH |
| II-299 | 4-((2,2-dichlorocyclopropyl)methyl)Ph | H | N | CH | CH |
| II-300 | 4-(cyclopropyloxy)Ph | H | N | CH | CH |
| II-301 | 4-(allyloxy)Ph | H | N | CH | CH |
| II-302 | 4-(prop-2-ynyloxy)Ph | H | N | CH | CH |
| II-303 | 4-(acetyloxy)Ph | H | N | CH | CH |
| II-304 | (4-NH₂)Ph | H | N | CH | CH |
| II-305 | 4-(N-acetylamino)Ph | H | N | CH | CH |
| II-306 | (4-NHMe)Ph | H | N | CH | CH |
| II-307 | (4-NMe₂)Ph | H | N | CH | CH |
| II-308 | (4-CH₂OH)Ph | H | N | CH | CH |

TABLE 23

| Compound No. | R¹ | R² | X² | X³ | X⁴ |
|---|---|---|---|---|---|
| II-309 | (4-CH₂SMe)Ph | H | N | CH | CH |
| II-310 | (4-CH₂SOMe)Ph | H | N | CH | CH |
| II-311 | (4-CH₂SO₂Me)Ph | H | N | CH | CH |
| II-312 | (4-CH₂SCF₃)Ph | H | N | CH | CH |
| II-313 | (4-CH₂SOMe)Ph | H | N | CH | CH |
| II-314 | (4-CH₂SO₂Me)Ph | H | N | CH | CH |
| II-315 | (4-CH₂CN)Ph | H | N | CH | CH |
| II-316 | (4-OCH₂OMe)Ph | H | N | CH | CH |
| II-317 | (4-OCH₂OCF₃)Ph | H | N | CH | CH |
| II-318 | (4-OCH₂CN)Ph | H | N | CH | CH |

TABLE 23-continued

| Compound No. | R¹ | R² | X² | X³ | X⁴ |
|---|---|---|---|---|---|
| II-319 | 4-(MeO-N=CH)-phenyl | H | N | CH | CH |
| II-320 | 4-COOH-phenyl | H | N | CH | CH |
| II-321 | 4-CONH₂-phenyl | H | N | CH | CH |
| II-322 | 4-CONHMe-phenyl | H | N | CH | CH |
| II-323 | 4-CONMe₂-phenyl | H | N | CH | CH |
| II-324 | 4-(oxiranyl)-phenyl | H | N | CH | CH |
| II-325 | 4-(oxiranylmethoxy)-phenyl | H | N | CH | CH |

TABLE 24

| Compound No. | R¹ | R² | X² | X³ | X⁴ |
|---|---|---|---|---|---|
| II-326 | 1-Me-2-oxo-6-CF₃-pyridin-3-yl | H | N | CH | CH |
| II-327 | 1-Me-2-thioxo-6-CF₃-pyridin-3-yl | H | N | CH | CH |
| II-328 | 5-ethynyl-pyridin-2-yl | H | N | CH | CH |
| II-329 | 5-vinyl-pyridin-2-yl | H | N | CH | CH |
| II-330 | 5-NO₂-pyridin-2-yl | H | N | CH | CH |
| II-331 | 5-CN-pyridin-2-yl | H | N | CH | CH |
| II-332 | 5-cyclopropyl-pyridin-2-yl | H | N | CH | CH |
| II-333 | 5-(cyclopropylmethyl)-pyridin-2-yl | H | N | CH | CH |
| II-334 | 5-(2,2-difluorovinyl)-pyridin-2-yl | H | N | CH | CH |
| II-335 | 5-(2,2-dichlorocyclopropyl)-pyridin-2-yl | H | N | CH | CH |
| II-336 | 5-((2,2-dichlorocyclopropyl)methyl)-pyridin-2-yl | H | N | CH | CH |
| II-337 | 5-(allyloxy)-pyridin-2-yl | H | N | CH | CH |
| II-338 | 5-(propargyloxy)-pyridin-2-yl | H | N | CH | CH |
| II-339 | 5-(cyclopropyloxy)-pyridin-2-yl | H | N | CH | CH |
| II-340 | 5-(cyclopropylmethoxy)-pyridin-2-yl | H | N | CH | CH |
| II-341 | 5-OCHF₂-pyridin-2-yl | H | N | CH | CH |
| II-342 | 5-(methoxymethoxy)-pyridin-2-yl | H | N | CH | CH |

TABLE 25

| Compound No. | R¹ | R² | X² | X³ | X⁴ |
|---|---|---|---|---|---|
| II-343 | 5-OCH₂OCF₃-pyridin-2-yl | H | N | CH | CH |

TABLE 25-continued

| Compound No. | R¹ | R² | X² | X³ | X⁴ |
|---|---|---|---|---|---|
| II-344 | 6-methylpyridin-3-yl-OCH₂CN | H | N | CH | CH |
| II-345 | 6-methylpyridin-3-yl-OC(O)Me | H | N | CH | CH |
| II-346 | 6-methylpyridin-3-yl-SMe | H | N | CH | CH |
| II-347 | 6-methylpyridin-3-yl-SOMe | H | N | CH | CH |
| II-348 | 6-methylpyridin-3-yl-SO₂Me | H | N | CH | CH |
| II-349 | 6-methylpyridin-3-yl-SCF₃ | H | N | CH | CH |
| II-350 | 6-methylpyridin-3-yl-SOCF₃ | H | N | CH | CH |
| II-351 | 6-methylpyridin-3-yl-SO₂CF₃ | H | N | CH | CH |
| II-352 | 6-methylpyridin-3-yl-NH₂ | H | N | CH | CH |
| II-353 | 6-methylpyridin-3-yl-NHMe | H | N | CH | CH |
| II-354 | 6-methylpyridin-3-yl-NMe₂ | H | N | CH | CH |
| II-355 | 6-methylpyridin-3-yl-NHC(O)Me | H | N | CH | CH |
| II-356 | 6-methylpyridin-3-yl-C(O)OH | H | N | CH | CH |
| II-357 | 6-methylpyridin-3-yl-C(O)OMe | H | N | CH | CH |
| II-358 | 6-methylpyridin-3-yl-C(O)NH₂ | H | N | CH | CH |
| II-359 | 6-methylpyridin-3-yl-C(O)NH-Me | H | N | CH | CH |

TABLE 26

| Compound No. | R¹ | R² | X² | X³ | X⁴ |
|---|---|---|---|---|---|
| II-360 | 6-methylpyridin-3-yl-C(O)NMe₂ | H | N | CH | CH |
| II-361 | 6-methylpyridin-3-yl-C(O)Me | H | N | CH | CH |
| II-362 | 6-methylpyridin-3-yl-CH=N-OMe | H | N | CH | CH |
| II-363 | 6-methylpyridin-3-yl-CH₂-O-Me | H | N | CH | CH |
| II-364 | 6-methylpyridin-3-yl-CH₂SMe | H | N | CH | CH |

TABLE 26-continued

| Compound No. | R¹ | R² | X² | X³ | X⁴ |
|---|---|---|---|---|---|
| II-365 | 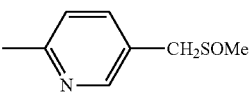 | H | N | CH | CH |
| II-366 | 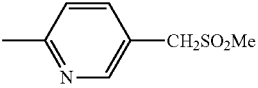 | H | N | CH | CH |
| II-367 | 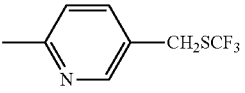 | H | N | CH | CH |
| II-368 | 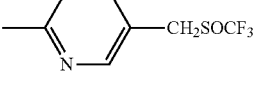 | H | N | CH | CH |
| II-369 | 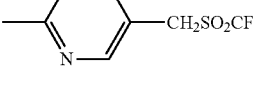 | H | N | CH | CH |
| II-370 | 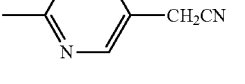 | H | N | CH | CH |
| II-371 | 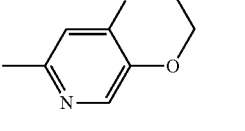 | H | N | CH | CH |
| II-372 | 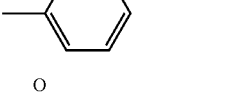 | H | N | C—O—C$_2$H$_4$—O—C | |
| II-373 | 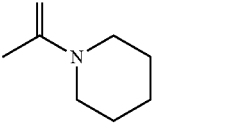 | H | N | CH | CH |
| II-374 | 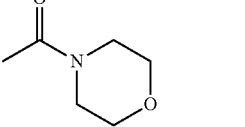 | H | N | CH | CH |
| II-375 | NHCO$_2$CH$_3$ | H | N | CH | CH |
| II-376 | NHCO$_2$Bn | H | N | CH | CH |
| II-377 | N(Me)CO$_2$Bn | H | N | CH | CH |
| II-378 | N(Et)CO$_2$Bn | H | N | CH | CH |
| II-379 | N(Pr)CO$_2$Bn | H | N | CH | CH |
| II-380 | N(Me)CO$_2$Me | H | N | CH | CH |

TABLE 27

| Compound No. | R¹ | R² | X² | X³ | X⁴ |
|---|---|---|---|---|---|
| II-381 | N(Et)CO$_2$Me | H | N | CH | CH |
| II-382 | N(Pr)CO$_2$Me | H | N | CH | CH |
| II-383 | NHCO$_2$Et | H | N | CH | CH |
| II-384 | N(Me)CO$_2$Et | H | N | CH | CH |
| II-385 | N(Et)CO$_2$Et | H | N | CH | CH |
| II-386 | N(Pr)CO$_2$Et | H | N | CH | CH |
| II-387 | NEt$_2$ | H | N | CH | CH |
| II-388 | NPr$_2$ | H | N | CH | CH |
| II-389 | (2,3-F$_2$)Ph | H | N | CH | CH |
| II-390 | (2,4-F$_2$)Ph | H | N | CH | CH |
| II-391 | (2,5-F$_2$)Ph | H | N | CH | CH |
| II-392 | (2,6-F$_2$)Ph | H | N | CH | CH |

TABLE 27-continued

| Compound No. | R¹ | R² | X² | X³ | X⁴ |
|---|---|---|---|---|---|
| II-393 | (3,4-F₂)Ph | H | N | CH | CH |
| II-394 | (3,5-F₂)Ph | H | N | CH | CH |
| II-395 | (2,3-Cl₂)Ph | H | N | CH | CH |
| II-396 | (2,4-Cl₂)Ph | H | N | CH | CH |
| II-397 | (2,5-Cl₂)Ph | H | N | CH | CH |
| II-398 | (2,6-Cl₂)Ph | H | N | CH | CH |
| II-399 | (3,4-Cl₂)Ph | H | N | CH | CH |
| II-400 | (3,5-Cl₂)Ph | H | N | CH | CH |
| II-401 | (2-F, 3-OMe)Ph | H | N | CH | CH |
| II-402 | (2-Cl, 3-OMe)Ph | H | N | CH | CH |
| II-403 | (2-Me, 3-OMe)Ph | H | N | CH | CH |
| II-404 | (2-Cl, 4-Me)Ph | H | N | CH | CH |
| II-405 | (2-Cl, 4-OMe)Ph | H | N | CH | CH |
| II-406 | (2,3-(OMe)₂)Ph | H | N | CH | CH |
| II-407 | (3-OMe, 4-F)Ph | H | N | CH | CH |
| II-408 | (3-OMe, 4-Cl)Ph | H | N | CH | CH |
| II-409 | (3-OMe, 4-Me)Ph | H | N | CH | CH |
| II-410 | (3,4-(OMe)₂)Ph | H | N | CH | CH |
| II-411 | (3-OMe, 5-F)Ph | H | N | CH | CH |
| II-412 | (3-OMe, 5-Cl)Ph | H | N | CH | CH |
| II-413 | (3-OMe, 5-Me)Ph | H | N | CH | CH |
| II-414 | (3,5-(OMe)₂)Ph | H | N | CH | CH |
| II-415 | (2-F, 4-Me)Ph | H | N | CH | CH |
| II-416 | (2-F, 4-OMe)Ph | H | N | CH | CH |
| II-417 | (2-Cl, 4-OMe)Ph | H | N | CH | CH |
| II-418 | (2-Me, 4-OMe)Ph | H | N | CH | CH |
| II-419 | (2,4-(OMe)₂)Ph | H | N | CH | CH |
| II-420 | (3-F, 4-Me)Ph | H | N | CH | CH |
| II-421 | (3-F, 4-OMe)Ph | H | N | CH | CH |
| II-422 | (3-Cl, 4-Me)Ph | H | N | CH | CH |

TABLE 28

| Compound No. | R¹ | R² | X² | X³ | X⁴ |
|---|---|---|---|---|---|
| II-423 | (3-Cl, 4-OMe)Ph | H | N | CH | CH |
| II-424 | (3-Me, 4-OMe)Ph | H | N | CH | CH |
| II-425 | (2-F, 5-OMe)Ph | H | N | CH | CH |
| II-426 | (2-Cl, 5-OMe)Ph | H | N | CH | CH |
| II-427 | (2-Me, 5-OMe)Ph | H | N | CH | CH |
| II-428 | (2,5-(OMe)₂)Ph | H | N | CH | CH |
| II-429 | (3,4,5-(OMe)₃)Ph | H | N | CH | CH |
| II-430 | —N(CH₂CH₂)₂SO₂ (thiomorpholine-S,S-dioxide) | H | N | CH | CH |
| II-431 | 3-Me-thiomorpholine-1,1-dioxide | H | N | CH | CH |
| II-432 | 2-Me-thiomorpholine-1,1-dioxide | H | N | CH | CH |
| II-433 | 2,3-diMe-thiomorpholine-1,1-dioxide | H | N | CH | CH |
| II-434 | Me | Et | N | CH | CH |
| II-435 | Et | Et | N | CH | CH |
| II-436 | Ph | Et | N | CH | CH |
| II-437 | Bn | Et | N | CH | CH |
| II-438 | (4-OMe)Ph | Et | N | CH | CH |
| II-439 | benzo[1,3]dioxol-5-yl | Et | N | CH | CH |
| II-440 | 2,3-dihydrobenzo[1,4]dioxin-6-yl | Et | N | CH | CH |
| II-441 | benzo[1,3]dioxol-5-yl | CHF₂ | N | CH | CH |
| II-442 | 2,3-dihydrobenzo[1,4]dioxin-6-yl | CHF₂ | N | CH | CH |
| II-443 | Me | CF₂CF₃ | N | CH | CH |
| II-444 | Et | CF₂CF₃ | N | CH | CH |
| II-445 | Ph | CF₂CF₃ | N | CH | CH |
| II-446 | Bn | CF₂CF₃ | N | CH | CH |
| II-447 | (4-OMe)Ph | CF₂CF₃ | N | CH | CH |

TABLE 29

| Compound No. | R¹ | R² | X² | X³ | X⁴ |
|---|---|---|---|---|---|
| II-448 | benzo[1,3]dioxol-5-yl | CF₂CF₃ | N | CH | CH |
| II-449 | 2,3-dihydrobenzo[1,4]dioxin-6-yl | CF₂CF₃ | N | CH | CH |
| II-450 | Me | H | N | CCH₃ | CH |
| II-451 | Et | H | N | CCH₃ | CH |
| II-452 | Ph | H | N | CCH₃ | CH |
| II-453 | Bn | H | N | CCH₃ | CH |
| II-454 | (4-OMe)Ph | H | N | CCH₃ | CH |
| II-455 | benzo[1,3]dioxol-5-yl | H | N | CCH₃ | CH |
| II-456 | 2,3-dihydrobenzo[1,4]dioxin-6-yl | H | N | CCH₃ | CH |
| II-457 | (3-F-4-Me)Ph | H | N | CH | CH |

TABLE 30

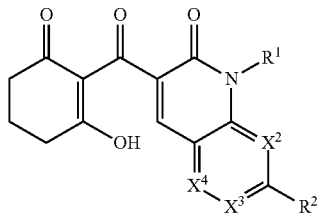

| Compound No. | R¹ | R² | X² | X³ | X⁴ |
| --- | --- | --- | --- | --- | --- |
| III-1 | H | H | CH | CH | N |
| III-2 | Me | H | CH | CH | N |
| III-3 | Et | H | CH | CH | N |
| III-4 | n-Pr | H | CH | CH | N |
| III-5 | i-Pr | H | CH | CH | N |
| III-6 | c-Pr | H | CH | CH | N |
| III-7 | n-Bu | H | CH | CH | N |
| III-8 | i-Bu | H | CH | CH | N |
| III-9 | t-Bu | H | CH | CH | N |
| III-10 | c-Pen | H | CH | CH | N |
| III-11 | CH$_2$CH=CH$_2$ | H | CH | CH | N |
| III-12 | CH$_2$C≡CH | H | CH | CH | N |
| III-13 | CH$_2$CF$_3$ | H | CH | CH | N |
| III-14 | C$_2$H$_4$OCH$_3$ | H | CH | CH | N |
| III-15 | C$_2$H$_4$OC$_2$H$_5$ | H | CH | CH | N |
| III-16 | CH(Me)OEt | H | CH | CH | N |
| III-17 | CH$_2$OCH$_2$CF$_3$ | H | CH | CH | N |
| III-18 | CH$_2$SMe | H | CH | CH | N |
| III-19 | CH$_2$SEt | H | CH | CH | N |
| III-20 | CH$_2$SOMe | H | CH | CH | N |
| III-21 | CH$_2$SOEt | H | CH | CH | N |
| III-22 | CH$_2$SO$_2$Me | H | CH | CH | N |
| III-23 | CH$_2$SO$_2$Et | H | CH | CH | N |
| III-24 | Bn | H | CH | CH | N |
| III-25 | (2-F)Bn | H | CH | CH | N |
| III-26 | (3-F)Bn | H | CH | CH | N |
| III-27 | (4-F)Bn | H | CH | CH | N |
| III-28 | (2-Cl)Bn | H | CH | CH | N |
| III-29 | (3-Cl)Bn | H | CH | CH | N |
| III-30 | (4-Cl)Bn | H | CH | CH | N |
| III-31 | (2-Me)Bn | H | CH | CH | N |
| III-32 | (3-Me)Bn | H | CH | CH | N |
| III-33 | (4-Me)Bn | H | CH | CH | N |
| III-34 | (2-CF$_3$)Bn | H | CH | CH | N |

TABLE 31

| Compound No. | R¹ | R² | X² | X³ | X⁴ |
| --- | --- | --- | --- | --- | --- |
| III-35 | (3-CF$_3$)Bn | H | CH | CH | N |
| III-36 | (4-CF$_3$)Bn | H | CH | CH | N |
| III-37 | (2-OMe)Bn | H | CH | CH | N |
| III-38 | (3-OMe)Bn | H | CH | CH | N |
| III-39 | (4-OMe)Bn | H | CH | CH | N |
| III-40 | CH(Me)Ph | H | CH | CH | N |
| III-41 | Ph | H | CH | CH | N |
| III-42 | (2-F)Ph | H | CH | CH | N |
| III-43 | (3-F)Ph | H | CH | CH | N |
| III-44 | (4-F)Ph | H | CH | CH | N |
| III-45 | (2-Cl)Ph | H | CH | CH | N |
| III-46 | (3-Cl)Ph | H | CH | CH | N |
| III-47 | (4-Cl)Ph | H | CH | CH | N |
| III-48 | (2-Me)Ph | H | CH | CH | N |
| III-49 | (3-Me)Ph | H | CH | CH | N |
| III-50 | (4-Me)Ph | H | CH | CH | N |
| III-51 | (2-CF$_3$)Ph | H | CH | CH | N |
| III-52 | (3-CF$_3$)Ph | H | CH | CH | N |
| III-53 | (4-CF$_3$)Ph | H | CH | CH | N |
| III-54 | (2-OMe)Ph | H | CH | CH | N |
| III-55 | (3-OMe)Ph | H | CH | CH | N |
| III-56 | (4-OMe)Ph | H | CH | CH | N |
| III-57 | (3-F-4-OMe)Ph | H | CH | CH | N |
| III-58 | (3-F-4-Me)Ph | H | CH | CH | N |
| III-59 | (4-F-3-Me)Ph | H | CH | CH | N |

TABLE 31-continued

| Compound No. | R¹ | R² | X² | X³ | X⁴ |
| --- | --- | --- | --- | --- | --- |
| III-60 | 3-methylisoxazol-5-yl | H | CH | CH | N |
| III-61 | 2-methylthiophen-5-yl | H | CH | CH | N |
| III-62 | 4-methylthiophen-3-yl | H | CH | CH | N |
| III-63 | 3,5-dimethylisoxazol-4-yl | H | CH | CH | N |
| III-64 | 3-methyl-5-CF$_3$-isoxazol-4-yl | H | CH | CH | N |
| III-65 | 3,5-dimethylisothiazol-4-yl | H | CH | CH | N |
| III-66 | 5-methylisothiazol-3-yl | H | CH | CH | N |

TABLE 32

| Compound No. | R¹ | R² | X² | X³ | X⁴ |
| --- | --- | --- | --- | --- | --- |
| III-67 | 1,3,5-trimethylpyrazol-4-yl | H | CH | CH | N |
| III-68 | 1,3-dimethyl-5-CF$_3$-pyrazol-4-yl | H | CH | CH | N |
| III-69 | 2,4-dimethylthiazol-5-yl | H | CH | CH | N |
| III-70 | 2,5-dimethylthiazol-4-yl | H | CH | CH | N |
| III-71 | 1,3-dimethyl-5-CF$_3$-1,2,4-triazol-4-yl | H | CH | CH | N |

TABLE 32-continued

| Compound No. | R¹ | R² | X² | X³ | X⁴ |
|---|---|---|---|---|---|
| III-72 | 4-tetrahydrothiopyranyl | H | CH | CH | N |
| III-73 | 4-(1,1-dioxo-tetrahydrothiopyranyl) | H | CH | CH | N |
| III-74 | morpholin-4-yl-methyl (N-linked morpholine) | H | CH | CH | N |
| III-75 | thiomorpholin-4-yl | H | CH | CH | N |
| III-76 | 2-pyridyl | H | CH | CH | N |
| III-77 | 6-chloro-2-pyridyl | H | CH | CH | N |
| III-78 | 6-methyl-2-pyridyl | H | CH | CH | N |
| III-79 | 6-methoxy-2-pyridyl | H | CH | CH | N |
| III-80 | 5-fluoro-2-pyridyl | H | CH | CH | N |
| III-81 | 5-chloro-2-pyridyl | H | CH | CH | N |
| III-82 | 5-methyl-2-pyridyl | H | CH | CH | N |
| III-83 | 5-trifluoromethyl-2-pyridyl | H | CH | CH | N |
| III-84 | 5-methoxy-2-pyridyl | H | CH | CH | N |

TABLE 33

| Compound No. | R¹ | R² | X² | X³ | X⁴ |
|---|---|---|---|---|---|
| III-85 | 4-methyl-2-pyridyl | H | CH | CH | N |
| III-86 | 4-trifluoromethyl-2-pyridyl | H | CH | CH | N |
| III-87 | 4-methoxy-2-pyridyl | H | CH | CH | N |
| III-88 | 3-pyridyl | H | CH | CH | N |
| III-89 | 6-chloro-3-pyridyl | H | CH | CH | N |
| III-90 | 6-methyl-3-pyridyl | H | CH | CH | N |
| III-91 | 6-trifluoromethyl-3-pyridyl | H | CH | CH | N |
| III-92 | 6-methoxy-3-pyridyl | H | CH | CH | N |
| III-93 | 4-pyridyl | H | CH | CH | N |
| III-94 | 2-pyrimidinyl | H | CH | CH | N |
| III-95 | 4-trifluoromethyl-2-pyrimidinyl | H | CH | CH | N |
| III-96 | 4,6-dimethoxy-2-pyrimidinyl | H | CH | CH | N |

TABLE 33-continued

| Compound No. | R¹ | R² | X² | X³ | X⁴ |
|---|---|---|---|---|---|
| III-97 | 5-methyl-2,3-dihydrobenzofuran | H | CH | CH | N |
| III-98 | 5-methyl-1,3-benzodioxole | H | CH | CH | N |

TABLE 34

| Compound No. | R¹ | R² | X² | X³ | X⁴ |
|---|---|---|---|---|---|
| III-99 | 5-methyl-2,2-difluoro-1,3-benzodioxole | H | CH | CH | N |
| III-100 | CH₂-(tetrahydrofuran-2-yl) | H | CH | CH | N |
| III-101 | CH₂-(3-methyl-4,5-dihydroisoxazol-5-yl) | H | CH | CH | N |
| III-102 | CH₂-(3-methylisoxazol-5-yl) | H | CH | CH | N |
| III-103 | NH₂ | H | CH | CH | N |
| III-104 | NHMe | H | CH | CH | N |
| III-105 | OMe | H | CH | CH | N |
| III-106 | OEt | H | CH | CH | N |
| III-107 | CH₂CH₂OMe | H | CH | CH | N |
| III-108 | 1-methylnaphthalene | H | CH | CH | N |
| III-109 | 2-methylnaphthalene | H | CH | CH | N |
| III-110 | 1,3-dimethyl-5-methylpyrazole | H | CH | CH | N |
| III-111 | 1-methyl-5-CF₃-3-methylpyrazole | H | CH | CH | N |
| III-112 | 2,5-dimethyl-1,3,4-thiadiazole | H | CH | CH | N |
| III-113 | 5-bromo-2-methylpyridine | H | CH | CH | N |
| III-114 | 5-methylbenzofuran | H | CH | CH | N |
| III-115 | CH₂CH₂O-(pyridin-2-yl) | H | CH | CH | N |
| III-116 | 5-nitro-2-methylpyridine | H | CH | CH | N |

TABLE 35

| Compound No. | R¹ | R² | X² | X³ | X⁴ |
|---|---|---|---|---|---|
| III-117 | 5-cyano-2-methylpyridine | H | CH | CH | N |
| III-118 | 7-methyl-2,3-dihydro-1,4-benzodioxine | H | CH | CH | N |
| III-119 | CH₂OCH₂-(tetrahydrofuran-2-yl) | H | CH | CH | N |
| III-120 | CH₂CN | H | CH | CH | N |
| III-121 | Me | Me | CH | CH | N |
| III-122 | Et | Me | CH | CH | N |
| III-123 | Ph | Me | CH | CH | N |
| III-124 | Bn | Me | CH | CH | N |
| III-125 | (4-OMe)Ph | Me | CH | CH | N |
| III-126 | Me | Et | CH | CH | N |
| III-127 | Et | Et | CH | CH | N |
| III-128 | Ph | Et | CH | CH | N |
| III-129 | Bn | Et | CH | CH | N |
| III-130 | (4-OMe)Ph | Et | CH | CH | N |
| III-131 | Me | i-Pr | CH | CH | N |
| III-132 | Et | i-Pr | CH | CH | N |
| III-133 | Ph | i-Pr | CH | CH | N |
| III-134 | Bn | i-Pr | CH | CH | N |
| III-135 | (4-OMe)Ph | i-Pr | CH | CH | N |
| III-136 | Me | CF₃ | CH | CH | N |
| III-137 | Et | CF₃ | CH | CH | N |
| III-138 | Ph | CF₃ | CH | CH | N |
| III-139 | Bn | CF₃ | CH | CH | N |
| III-140 | (4-OMe)Ph | CF₃ | CH | CH | N |
| III-141 | Me | CF₂Cl | CH | CH | N |
| III-142 | Et | CF₂Cl | CH | CH | N |
| III-143 | Ph | CF₂Cl | CH | CH | N |
| III-144 | Bn | CF₂Cl | CH | CH | N |
| III-145 | (4-OMe)Ph | CF₂Cl | CH | CH | N |
| III-146 | Me | OCH₃ | CH | CH | N |

TABLE 35-continued

| Compound No. | R¹ | R² | X² | X³ | X⁴ |
|---|---|---|---|---|---|
| III-147 | Et | OCH₃ | CH | CH | N |
| III-148 | Ph | OCH₃ | CH | CH | N |
| III-149 | Bn | OCH₃ | CH | CH | N |
| III-150 | (4-OMe)Ph | OCH₃ | CH | CH | N |

TABLE 36

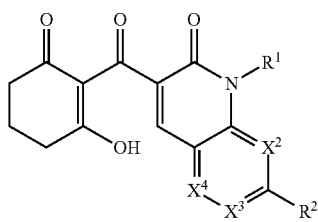

| Compound No. | R¹ | R² | X² | X³ | X⁴ |
|---|---|---|---|---|---|
| IV-1 | H | H | N | N | CH |
| IV-2 | Me | H | N | N | CH |
| IV-3 | Et | H | N | N | CH |
| IV-4 | n-Pr | H | N | N | CH |
| IV-5 | i-Pr | H | N | N | CH |
| IV-6 | c-Pr | H | N | N | CH |
| IV-7 | n-Bu | H | N | N | CH |
| IV-8 | i-Bu | H | N | N | CH |
| IV-9 | t-Bu | H | N | N | CH |
| IV-10 | c-Pen | H | N | N | CH |
| IV-11 | CH₂CH=CH₂ | H | N | N | CH |
| IV-12 | CH₂C≡CH | H | N | N | CH |
| IV-13 | CH₂CF₃ | H | N | N | CH |
| IV-14 | C₂H₄OCH₃ | H | N | N | CH |
| IV-15 | C₂H₄OC₂H₅ | H | N | N | CH |
| IV-16 | CH(Me)OEt | H | N | N | CH |
| IV-17 | CH₂OCH₂CF₃ | H | N | N | CH |
| IV-18 | CH₂SMe | H | N | N | CH |
| IV-19 | CH₂SEt | H | N | N | CH |
| IV-20 | CH₂SOMe | H | N | N | CH |
| IV-21 | CH₂SOEt | H | N | N | CH |
| IV-22 | CH₂SO₂Me | H | N | N | CH |
| IV-23 | CH₂SO₂Et | H | N | N | CH |
| IV-24 | Bn | H | N | N | CH |
| IV-25 | (2-F)Bn | H | N | N | CH |
| IV-26 | (3-F)Bn | H | N | N | CH |
| IV-27 | (4-F)Bn | H | N | N | CH |
| IV-28 | (2-Cl)Bn | H | N | N | CH |
| IV-29 | (3-Cl)Bn | H | N | N | CH |
| IV-30 | (4-Cl)Bn | H | N | N | CH |
| IV-31 | (2-Me)Bn | H | N | N | CH |
| IV-32 | (3-Me)Bn | H | N | N | CH |
| IV-33 | (4-Me)Bn | H | N | N | CH |
| IV-34 | (2-CF₃)Bn | H | N | N | CH |
| IV-35 | (3-CF₃)Bn | H | N | N | CH |
| IV-36 | (4-CF₃)Bn | H | N | N | CH |
| IV-37 | (2-OMe)Bn | H | N | N | CH |

TABLE 37

| Compound No. | R¹ | R² | X² | X³ | X⁴ |
|---|---|---|---|---|---|
| IV-38 | (3-OMe)Bn | H | N | N | CH |
| IV-39 | (4-OMe)Bn | H | N | N | CH |
| IV-40 | CH(Me)Ph | H | N | N | CH |
| IV-41 | Ph | H | N | N | CH |
| IV-42 | (2-F)Ph | H | N | N | CH |
| IV-43 | (3-F)Ph | H | N | N | CH |
| IV-44 | (4-F)Ph | H | N | N | CH |
| IV-45 | (2-Cl)Ph | H | N | N | CH |
| IV-46 | (3-Cl)Ph | H | N | N | CH |
| IV-47 | (4-Cl)Ph | H | N | N | CH |
| IV-48 | (2-Me)Ph | H | N | N | CH |

TABLE 37-continued

| Compound No. | R¹ | R² | X² | X³ | X⁴ |
|---|---|---|---|---|---|
| IV-49 | (3-Me)Ph | H | N | N | CH |
| IV-50 | (4-Me)Ph | H | N | N | CH |
| IV-51 | (2-CF₃)Ph | H | N | N | CH |
| IV-52 | (3-CF₃)Ph | H | N | N | CH |
| IV-53 | (4-CF₃)Ph | H | N | N | CH |
| IV-54 | (2-OMe)Ph | H | N | N | CH |
| IV-55 | (3-OMe)Ph | H | N | N | CH |
| IV-56 | (4-OMe)Ph | H | N | N | CH |
| IV-57 | (3-F-4-OMe)Ph | H | N | N | CH |
| IV-58 | (3-F-4-Me)Ph | H | N | N | CH |
| IV-59 | (4-F-3-Me)Ph | H | N | N | CH |
| IV-60 | 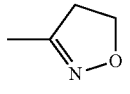 | H | N | N | CH |
| IV-61 | 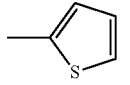 | H | N | N | CH |
| IV-62 | 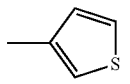 | H | N | N | CH |
| IV-63 | 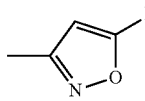 | H | N | N | CH |
| IV-64 | 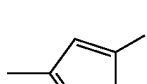 | H | N | N | CH |
| IV-65 | 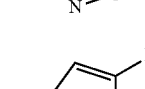 | H | N | N | CH |
| IV-66 | 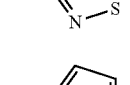 | H | N | N | CH |
| IV 67 | 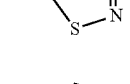 | H | N | N | CH |

TABLE 38

| Compound No. | R¹ | R² | X² | X³ | X⁴ |
|---|---|---|---|---|---|
| IV-68 | 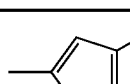 | H | N | N | CH |
| IV-69 | 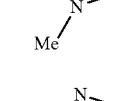 | H | N | N | CH |

TABLE 38-continued

| Compound No. | R¹ | R² | X² | X³ | X⁴ |
|---|---|---|---|---|---|
| IV-70 | 2-methyl-5-methyl-thiazole | H | N | N | CH |
| IV-71 | 1,5-dimethyl-3-CF₃-1,2,4-triazole | H | N | N | CH |
| IV-72 | 4-methyl-tetrahydrothiopyran | H | N | N | CH |
| IV-73 | 4-methyl-tetrahydrothiopyran-1,1-dioxide | H | N | N | CH |
| IV-74 | 4-methyl-morpholine | H | N | N | CH |
| IV-75 | 4-methyl-thiomorpholine | H | N | N | CH |
| IV-76 | 2-methyl-pyridine | H | N | N | CH |
| IV-77 | 6-chloro-2-methyl-pyridine | H | N | N | CH |
| IV-78 | 2,6-dimethyl-pyridine | H | N | N | CH |
| IV-79 | 6-methoxy-2-methyl-pyridazine | H | N | N | CH |
| IV-80 | 5-fluoro-2-methyl-pyridine | H | N | N | CH |
| IV-81 | 5-chloro-2-methyl-pyridine | H | N | N | CH |

TABLE 39

| Compound No. | R¹ | R² | X² | X³ | X⁴ |
|---|---|---|---|---|---|
| IV-82 | 2,5-dimethyl-pyridine | H | N | N | CH |
| IV-83 | 5-CF₃-2-methyl-pyridine | H | N | N | CH |
| IV-84 | 5-methoxy-2-methyl-pyridine | H | N | N | CH |
| IV-85 | 2,4-dimethyl-pyridine | H | N | N | CH |
| IV-86 | 4-CF₃-2-methyl-pyridine | H | N | N | CH |
| IV-87 | 4-methoxy-2-methyl-pyridine | H | N | N | CH |
| IV-88 | 3-methyl-pyridine | H | N | N | CH |
| IV-89 | 6-chloro-3-methyl-pyridine | H | N | N | CH |
| IV-90 | 2-methyl-5-methyl-pyridine | H | N | N | CH |
| IV-91 | 2-CF₃-5-methyl-pyridine | H | N | N | CH |
| IV-92 | 2-methoxy-5-methyl-pyridine | H | N | N | CH |
| IV-93 | 4-methyl-pyridine | H | N | N | CH |
| IV-94 | 2-methyl-pyrimidine | H | N | N | CH |

TABLE 39-continued

| Compound No. | R¹ | R² | X² | X³ | X⁴ |
|---|---|---|---|---|---|
| IV-95 | 2-methyl-4-(trifluoromethyl)pyrimidin-yl | H | N | N | CH |
| IV-96 | 4,6-dimethoxy-2-methylpyrimidin-yl | H | N | N | CH |

TABLE 40

| Compound No. | R¹ | R² | X² | X³ | X⁴ |
|---|---|---|---|---|---|
| IV-97 | 5-methyl-2,3-dihydrobenzofuran-yl | H | N | N | CH |
| IV-98 | 5-methylbenzo[d][1,3]dioxol-yl | H | N | N | CH |
| IV-99 | 5-methyl-2,2-difluorobenzo[d][1,3]dioxol-yl | H | N | N | CH |
| IV-100 | CH₂-(tetrahydrofuran-2-yl) | H | N | N | CH |
| IV-101 | CH₂-(3-methyl-4,5-dihydroisoxazol-5-yl) | H | N | N | CH |
| IV-102 | CH₂-(3-methylisoxazol-5-yl) | H | N | N | CH |
| IV-103 | NH₂ | H | N | N | CH |
| IV-104 | NHMe | H | N | N | CH |
| IV-105 | OMe | H | N | N | CH |
| IV-106 | OEt | H | N | N | CH |
| IV-107 | CH₂CH₂OMe | H | N | N | CH |
| IV-108 | 4-methylnaphthalen-1-yl | H | N | N | CH |
| IV-109 | 6-methylnaphthalen-2-yl | H | N | N | CH |
| IV-110 | 1,3,5-trimethylpyrazol-yl | H | N | N | CH |
| IV-111 | 1-methyl-3-methyl-5-(trifluoromethyl)pyrazol-yl | H | N | N | CH |
| IV-112 | 2,5-dimethyl-1,3,4-thiadiazol-yl | H | N | N | CH |
| IV-113 | 5-bromo-2-methylpyridin-yl | H | N | N | CH |
| IV-114 | 5-methylbenzofuran-yl | H | N | N | CH |

TABLE 41

| Compound No. | R¹ | R² | X² | X³ | X⁴ |
|---|---|---|---|---|---|
| IV-115 | CH₂CH₂O-(pyridin-2-yl) | H | N | N | CH |
| IV-116 | 2-methyl-5-nitropyridin-yl | H | N | N | CH |
| IV-117 | 6-methyl-3-cyanopyridin-yl | H | N | N | CH |
| IV-118 | 7-methyl-2,3-dihydro-1,4-benzodioxin-yl | H | N | N | CH |
| IV-119 | CH₂OCH₂-(tetrahydrofuran-2-yl) | H | N | N | CH |
| IV-120 | CH₂CN | H | N | N | CH |
| IV-121 | Me | Me | N | N | CH |
| IV-122 | Et | Me | N | N | CH |
| IV-123 | Ph | Me | N | N | CH |
| IV-124 | Bn | Me | N | N | CH |
| IV-125 | (4-OMe)Ph | Me | N | N | CH |
| IV-126 | Me | Et | N | N | CH |
| IV-127 | Et | Et | N | N | CH |
| IV-128 | Ph | Et | N | N | CH |

TABLE 41-continued

| Compound No. | R¹ | R² | X² | X³ | X⁴ |
|---|---|---|---|---|---|
| IV-129 | Bn | Et | N | N | CH |
| IV-130 | (4-OMe)Ph | Et | N | N | CH |
| IV-131 | Me | i-Pr | N | N | CH |
| IV-132 | Et | i-Pr | N | N | CH |
| IV-133 | Ph | i-Pr | N | N | CH |
| IV-134 | Bn | i-Pr | N | N | CH |
| IV-135 | (4-OMe)Ph | i-Pr | N | N | CH |
| IV-136 | Me | CF₃ | N | N | CH |
| IV-137 | Et | CF₃ | N | N | CH |
| IV-138 | Ph | CF₃ | N | N | CH |
| IV-139 | Bn | CF₃ | N | N | CH |
| IV-140 | (4-OMe)Ph | CF₃ | N | N | CH |
| IV-141 | Me | CF₂Cl | N | N | CH |
| IV-142 | Et | CF₂Cl | N | N | CH |
| IV-143 | Ph | CF₂Cl | N | N | CH |
| IV-144 | Bn | CF₂Cl | N | N | CH |
| IV-145 | (4-OMe)Ph | CF₂Cl | N | N | CH |
| IV-146 | Me | OCH₃ | N | N | CH |
| IV-147 | Et | OCH₃ | N | N | CH |
| IV-148 | Ph | OCH₃ | N | N | CH |
| IV-149 | Bn | OCH₃ | N | N | CH |

TABLE 42

| Compound No. | R¹ | R² | X² | X³ | X⁴ |
|---|---|---|---|---|---|
| IV-150 | (4-OMe)Ph | OCH₃ | N | N | CH |
| IV-151 | Me | H | N | N | CCH₃ |
| IV-152 | Et | H | N | N | CCH₃ |
| IV-153 | Ph | H | N | N | CCH₃ |
| IV-154 | Bn | H | N | N | CCH₃ |
| IV-155 | (4-OMe)Ph | H | N | N | CCH₃ |
| IV-156 | Me | H | N | N | CCl |
| IV-157 | Et | H | N | N | CCl |
| IV-158 | Ph | H | N | N | CCl |
| IV-159 | Bn | H | N | N | CCl |
| IV-160 | (4-OMe)Ph | H | N | N | CCl |
| IV-161 | Me | H | N | N | CF |
| IV-162 | Et | H | N | N | CF |
| IV-163 | Ph | H | N | N | CF |
| IV-164 | Bn | H | N | N | CF |
| IV-165 | (4-OMe)Ph | H | N | N | CF |
| IV-166 | Me | H | N | N | CBr |
| IV-167 | Et | H | N | N | CBr |
| IV-168 | Ph | H | N | N | CBr |
| IV-169 | Bn | H | N | N | CBr |
| IV-170 | (4-OMe)Ph | H | N | N | CBr |

TABLE 43

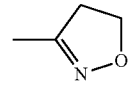

| Compound No. | R¹ | R² | X² | X³ | X⁴ |
|---|---|---|---|---|---|
| V-1 | H | H | N | CH | CH |
| V-2 | Me | H | N | CH | CH |
| V-3 | Et | H | N | CH | CH |
| V-4 | n-Pr | H | N | CH | CH |
| V-5 | i-Pr | H | N | CH | CH |
| V-6 | c-Pr | H | N | CH | CH |
| V-7 | n-Bu | H | N | CH | CH |
| V-8 | i-Bu | H | N | CH | CH |
| V-9 | t-Bu | H | N | CH | CH |
| V-10 | c-Pen | H | N | CH | CH |

TABLE 43-continued

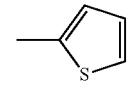

| Compound No. | R¹ | R² | X² | X³ | X⁴ |
|---|---|---|---|---|---|
| V-11 | CH₂CH=CH₂ | H | N | CH | CH |
| V-12 | CH₂C≡CH | H | N | CH | CH |
| V-13 | CH₂CF₃ | H | N | CH | CH |
| V-14 | C₂H₄OCH₃ | H | N | CH | CH |
| V-15 | C₂H₄OC₂H₅ | H | N | CH | CH |
| V-16 | CH(Me)OEt | H | N | CH | CH |
| V-17 | CH₂OCH₂CF₃ | H | N | CH | CH |
| V-18 | CH₂SMe | H | N | CH | CH |
| V-19 | CH₂SEt | H | N | CH | CH |
| V-20 | CH₂SOMe | H | N | CH | CH |
| V-21 | CH₂SOEt | H | N | CH | CH |
| V-22 | CH₂SO₂Me | H | N | CH | CH |
| V-23 | CH₂SO₂Et | H | N | CH | CH |
| V-24 | Bn | H | N | CH | CH |
| V-25 | (2-F)Bn | H | N | CH | CH |
| V-26 | (3-F)Bn | H | N | CH | CH |
| V-27 | (4-F)Bn | H | N | CH | CH |
| V-28 | (2-Cl)Bn | H | N | CH | CH |
| V-29 | (3-Cl)Bn | H | N | CH | CH |
| V-30 | (4-Cl)Bn | H | N | CH | CH |
| V-31 | (2-Me)Bn | H | N | CH | CH |
| V-32 | (3-Me)Bn | H | N | CH | CH |
| V-33 | (4-Me)Bn | H | N | CH | CH |
| V-34 | (2-CF₃)Bn | H | N | CH | CH |
| V-35 | (3-CF₃)Bn | H | N | CH | CH |
| V-36 | (4-CF₃)Bn | H | N | CH | CH |

TABLE 44

| Compound No. | R¹ | R² | X² | X³ | X⁴ |
|---|---|---|---|---|---|
| V-37 | (2-OMe)Bn | H | N | CH | CH |
| V-38 | (3-OMe)Bn | H | N | CH | CH |
| V-39 | (4-OMe)Bn | H | N | CH | CH |
| V-40 | CH(Me)Ph | H | N | CH | CH |
| V-41 | Ph | H | N | CH | CH |
| V-42 | (2-F)Ph | H | N | CH | CH |
| V-43 | (3-F)Ph | H | N | CH | CH |
| V-44 | (4-F)Ph | H | N | CH | CH |
| V-45 | (2-Cl)Ph | H | N | CH | CH |
| V-46 | (3-Cl)Ph | H | N | CH | CH |
| V-47 | (4-Cl)Ph | H | N | CH | CH |
| V-48 | (2-Me)Ph | H | N | CH | CH |
| V-49 | (3-Me)Ph | H | N | CH | CH |
| V-50 | (4-Me)Ph | H | N | CH | CH |
| V-51 | (2-CF₃)Ph | H | N | CH | CH |
| V-52 | (3-CF₃)Ph | H | N | CH | CH |
| V-53 | (4-CF₃)Ph | H | N | CH | CH |
| V-54 | (2-OMe)Ph | H | N | CH | CH |
| V-55 | (3-OMe)Ph | H | N | CH | CH |
| V-56 | (4-OMe)Ph | H | N | CH | CH |
| V-57 | (3-F-4-OMe)Ph | H | N | CH | CH |
| V-58 | (2,5-Me₂)Ph | H | N | CH | CH |
| V-59 | (4-F-3-Me)Ph | H | N | CH | CH |
| V-60 | 3-methylisoxazolin-5-yl | H | N | CH | CH |
| V-61 | 2-thienyl | H | N | CH | CH |

TABLE 44-continued

| Compound No. | R¹ | R² | X² | X³ | X⁴ |
|---|---|---|---|---|---|
| V-62 | 4-methylthiophene | H | N | CH | CH |
| V-63 | 3,5-dimethylisoxazole | H | N | CH | CH |
| V-64 | 3-methyl-5-(trifluoromethyl)isoxazole | H | N | CH | CH |
| V-65 | 3,5-dimethylisothiazole | H | N | CH | CH |
| V-66 | 5-methylisothiazole | H | N | CH | CH |

TABLE 45

| Compound No. | R¹ | R² | X² | X³ | X⁴ |
|---|---|---|---|---|---|
| V-67 | 1,3,5-trimethylpyrazole | H | N | CH | CH |
| V-68 | 1,5-dimethyl-3-(trifluoromethyl)pyrazole | H | N | CH | CH |
| V-69 | 2,4-dimethylthiazole | H | N | CH | CH |
| V-70 | 2,5-dimethylthiazole | H | N | CH | CH |
| V-71 | 1,5-dimethyl-3-(trifluoromethyl)-1,2,4-triazole | H | N | CH | CH |
| V-72 | 4-methyltetrahydrothiopyran | H | N | CH | CH |
| V-73 | 4-methyltetrahydrothiopyran-1,1-dioxide | H | N | CH | CH |

TABLE 45-continued

| Compound No. | R¹ | R² | X² | X³ | X⁴ |
|---|---|---|---|---|---|
| V-74 | N-methylmorpholine | H | N | CH | CH |
| V-75 | N-methylthiomorpholine | H | N | CH | CH |
| V-76 | 2-methylpyridine | H | N | CH | CH |
| V-77 | 2-methyl-6-chloropyridine | H | N | CH | CH |
| V-78 | 2,6-dimethylpyridine | H | N | CH | CH |
| V-79 | 2-methyl-6-methoxypyridine | H | N | CH | CH |
| V-80 | 2-methyl-5-fluoropyridine | H | N | CH | CH |

TABLE 46

| Compound No. | R¹ | R² | X² | X³ | X⁴ |
|---|---|---|---|---|---|
| V-81 | 2-methyl-5-chloropyridine | H | N | CH | CH |
| V-82 | 2,5-dimethylpyridine | H | N | CH | CH |
| V-83 | 2-methyl-5-(trifluoromethyl)pyridine | H | N | CH | CH |
| V-84 | 2-methyl-5-methoxypyridine | H | N | CH | CH |
| V-85 | 2,4-dimethylpyridine | H | N | CH | CH |

TABLE 46-continued

| Compound No. | R¹ | R² | X² | X³ | X⁴ |
|---|---|---|---|---|---|
| V-86 | 2-methyl-4-(trifluoromethyl)pyridin-5-yl | H | N | CH | CH |
| V-87 | 4-methoxy-2-methylpyridin-5-yl | H | N | CH | CH |
| V-88 | 5-methylpyridin-3-yl | H | N | CH | CH |
| V-89 | 6-chloro-5-methylpyridin-3-yl | H | N | CH | CH |
| V-90 | 6-methyl-5-methylpyridin-3-yl | H | N | CH | CH |
| V-91 | 6-(trifluoromethyl)-5-methylpyridin-3-yl | H | N | CH | CH |
| V-92 | 6-methoxy-5-methylpyridin-3-yl | H | N | CH | CH |
| V-93 | 4-methylpyridin-3-yl | H | N | CH | CH |
| V-94 | 2-methylpyrimidin-5-yl | H | N | CH | CH |

TABLE 47

| Compound No. | R¹ | R² | X² | X³ | X⁴ |
|---|---|---|---|---|---|
| V-95 | 2-methyl-4-(trifluoromethyl)pyrimidin-5-yl | H | N | CH | CH |
| V-96 | 4,6-dimethoxy-2-methylpyrimidin-5-yl | H | N | CH | CH |
| V-97 | 2,3-dihydrobenzofuran-5-yl (methyl) | H | N | CH | CH |
| V-98 | 6-methyl-1,3-benzodioxol-5-yl | H | N | CH | CH |
| V-99 | 2,2-difluoro-6-methyl-1,3-benzodioxol-5-yl | H | N | CH | CH |
| V-100 | CH₂-(tetrahydrofuran-2-yl) | H | N | CH | CH |
| V-101 | CH₂-(3-methyl-4,5-dihydroisoxazol-5-yl) | H | N | CH | CH |
| V-102 | CH₂-(3-methylisoxazol-5-yl) | H | N | CH | CH |
| V-103 | NH₂ | H | N | CH | CH |
| V-104 | NHMe | H | N | CH | CH |
| V-105 | OMe | H | N | CH | CH |
| V-106 | OEt | H | N | CH | CH |
| V-107 | CH₂CH₂OMe | H | N | CH | CH |
| V-108 | 1-methylnaphthalen-5-yl | H | N | CH | CH |
| V-109 | 6-methylnaphthalen-2-yl | H | N | CH | CH |
| V-110 | 1,3,5-trimethylpyrazol-4-yl | H | N | CH | CH |
| V-111 | 1,3-dimethyl-5-(trifluoromethyl)pyrazol-4-yl | H | N | CH | CH |

TABLE 48

| Compound No. | R¹ | R² | X² | X³ | X⁴ |
|---|---|---|---|---|---|
| V-112 | 2,5-dimethyl-1,3,4-thiadiazol-yl | H | N | CH | CH |

TABLE 48-continued

| Compound No. | R¹ | R² | X² | X³ | X⁴ |
|---|---|---|---|---|---|
| V-113 | 5-bromo-2-pyridyl (CH₂-linked) | H | N | CH | CH |
| V-114 | 5-methylbenzofuran-yl (CH₂-linked) | H | N | CH | CH |
| V-115 | 2-(pyridin-2-yloxy)ethyl (CH₂CH₂O-pyridyl) | H | N | CH | CH |
| V-116 | 5-nitro-2-pyridyl (CH₂-linked) | H | N | CH | CH |
| V-117 | 5-cyano-2-pyridyl (CH₂-linked) | H | N | CH | CH |
| V-118 | 2,3-dihydro-1,4-benzodioxin-6-yl (CH₂-linked) | H | N | CH | CH |
| V-119 | (tetrahydrofuran-2-yl)methoxymethyl (CH₂OCH₂-THF) | H | N | CH | CH |
| V-120 | CH₂CN | H | N | CH | CH |
| V-121 | Me | Me | N | CH | CH |
| V-122 | Et | Me | N | CH | CH |
| V-123 | Ph | Me | N | CH | CH |
| V-124 | Bn | Me | N | CH | CH |
| V-125 | (4-OMe)Ph | Me | N | CH | CH |
| V-126 | Me | Et | N | CH | CH |
| V-127 | Et | Et | N | CH | CH |
| V-128 | Ph | Et | N | CH | CH |
| V-129 | Bn | Et | N | CH | CH |
| V-130 | (4-OMe)Ph | Et | N | CH | CH |
| V-131 | Me | i-Pr | N | CH | CH |
| V-132 | Et | i-Pr | N | CH | CH |
| V-133 | Ph | i-Pr | N | CH | CH |
| V-134 | Bn | i-Pr | N | CH | CH |
| V-135 | (4-OMe)Ph | i-Pr | N | CH | CH |
| V-136 | Me | CF₃ | N | CH | CH |
| V-137 | Et | CF₃ | N | CH | CH |
| V-138 | Ph | CF₃ | N | CH | CH |
| V-139 | Bn | CF₃ | N | CH | CH |
| V-140 | (4-OMe)Ph | CF₃ | N | CH | CH |
| V-141 | Me | CF₂Cl | N | CH | CH |
| V-142 | Et | CF₂Cl | N | CH | CH |
| V-143 | Ph | CF₂Cl | N | CH | CH |

TABLE 49

| Compound No. | R¹ | R² | X² | X³ | X⁴ |
|---|---|---|---|---|---|
| V-144 | Bn | CF₂Cl | N | CH | CH |
| V-145 | (4-OMe)Ph | CF₂Cl | N | CH | CH |
| V-146 | Me | OCH₃ | N | CH | CH |
| V-147 | Et | OCH₃ | N | CH | CH |
| V-148 | Ph | OCH₃ | N | CH | CH |
| V-149 | Bn | OCH₃ | N | CH | CH |
| V-150 | (4-OMe)Ph | OCH₃ | N | CH | CH |
| V-151 | Me | H | N | CH | CCH₃ |
| V-152 | Et | H | N | CH | CCH₃ |
| V-153 | Ph | H | N | CH | CCH₃ |
| V-154 | Bn | H | N | CH | CCH₃ |
| V-155 | (4-OMe)Ph | H | N | CH | CCH₃ |
| V-156 | Me | H | N | CH | CCl |
| V-157 | Et | H | N | CH | CCl |
| V-158 | Ph | H | N | CH | CCl |
| V-159 | Bn | H | N | CH | CCl |
| V-160 | (4-OMe)Ph | H | N | CH | CCl |
| V-161 | Me | H | N | CH | CF |
| V-162 | Et | H | N | CH | CF |
| V-163 | Ph | H | N | CH | CF |
| V-164 | Bn | H | N | CH | CF |
| V-165 | (4-OMe)Ph | H | N | CH | CF |
| V-166 | Me | H | N | CH | CBr |
| V-167 | Et | H | N | CH | CBr |
| V-168 | Ph | H | N | CH | CBr |
| V-169 | Bn | H | N | CH | CBr |
| V-170 | (4-OMe)Ph | H | N | CH | CBr |
| V-171 | Me | H | N | N | CH |
| V-172 | Et | H | N | N | CH |
| V-173 | Ph | H | N | N | CH |
| V-174 | Bn | H | N | N | CH |
| V-175 | (4-OMe)Ph | H | N | N | CH |
| V-176 | Me | H | CH | CH | CH |
| V-177 | Et | H | CH | CH | CH |
| V-178 | Ph | H | CH | CH | CH |
| V-179 | Bn | H | CH | CH | CH |
| V-180 | (4-OMe)Ph | H | CH | CH | CH |
| V-181 | Me | H | N | N | CH |
| V-182 | Et | H | N | N | CH |
| V-183 | Ph | H | N | N | CH |
| V-184 | Bn | H | N | N | CH |

TABLE 50

| Compound No. | R¹ | R² | X² | X³ | X⁴ |
|---|---|---|---|---|---|
| V-185 | (4-OMe)Ph | H | N | CH | CH |
| V-186 | Me | H | CH | CH | N |
| V-187 | Et | H | CH | CH | N |
| V-188 | Ph | H | CH | CH | N |
| V-189 | Bn | H | CH | CH | N |
| V-190 | (4-OMe)Ph | H | CH | CH | N |
| V-191 | (1,3-benzodioxol-5-yl)methyl | H | N | CH | CCH₃ |
| V-192 | (1,3-benzodioxol-5-yl)methyl | H | N | CH | CCl |
| V-193 | (1,3-benzodioxol-5-yl)methyl | H | N | CH | CF |
| V-194 | (1,3-benzodioxol-5-yl)methyl | H | N | CH | CBr |

TABLE 50-continued

| Compound No. | R¹ | R² | X² | X³ | X⁴ |
|---|---|---|---|---|---|
| V-195 | 6-methyl-2,3-dihydro-1,4-benzodioxin-yl | H | N | CH | CCH$_3$ |
| V-196 | 6-methyl-2,3-dihydro-1,4-benzodioxin-yl | H | N | CH | CCl |
| V-197 | 6-methyl-2,3-dihydro-1,4-benzodioxin-yl | H | N | CH | CF |
| V-198 | 6-methyl-2,3-dihydro-1,4-benzodioxin-yl | H | N | CH | CBr |
| V-199 | 6-methylpyridin-3-yl | H | N | CH | CCH$_3$ |
| V-200 | 6-methylpyridin-3-yl | H | N | CH | CCl |
| V-201 | 6-methylpyridin-3-yl | H | CH | CH | CF |
| V-202 | 6-methylpyridin-3-yl | H | CH | CH | CBr |

TABLE 51

| Compound No. | R¹ | A¹ | A² | A³ | X² | X⁴ |
|---|---|---|---|---|---|---|
| VI-1 | 6-methyl-1,3-benzodioxol-yl | C(CH$_3$)$_2$ | CO | C(CH$_3$)$_2$ | CH | CH |
| VI-2 | 6-methyl-1,3-benzodioxol-yl | C(CH$_3$)$_2$ | CO | C(CH$_3$)$_2$ | N | CH |
| VI-3 | 6-methyl-1,3-benzodioxol-yl | C(CH$_3$)$_2$ | CO | C(CH$_3$)$_2$ | CH | CCl |
| VI-4 | 6-methyl-1,3-benzodioxol-yl | C(CH$_3$)$_2$ | CO | C(CH$_3$)$_2$ | CH | CF |
| VI-5 | 6-methyl-1,3-benzodioxol-yl | C(CH$_3$)$_2$ | CO | C(CH$_3$)$_2$ | CH | CCH3 |
| VI-6 | 6-methyl-1,3-benzodioxol-yl | CHCH$_3$ | CH$_2$ | CH$_2$ | CH | CH |
| VI-7 | 6-methyl-1,3-benzodioxol-yl | CH$_2$ | CHCH$_3$ | CH$_2$ | CH | CH |
| VI-8 | 6-methyl-1,3-benzodioxol-yl | CHCH$_3$ | CHCH$_3$ | CHCH$_3$ | CH | CH |
| VI-9 | 6-methyl-1,3-benzodioxol-yl | CHCH$_3$ | CH$_2$ | CH$_2$ | N | CH |
| VI-10 | 6-methyl-1,3-benzodioxol-yl | CH$_2$ | CHCH$_3$ | CH$_2$ | N | CH |

TABLE 52

| Compound No. | R¹ | A¹ | A² | A³ | X² | X⁴ |
|---|---|---|---|---|---|---|
| VI-11 | benzo[1,3]dioxole | CHCH₃ | CHCH₃ | CHCH₃ | N | CH |
| VI-12 | benzo[1,3]dioxole | C(CH₃)₂ | CH₂ | CH₂ | CH | CH |
| VI-13 | benzo[1,3]dioxole | CH₂ | C(CH₃)₂ | CH₂ | CH | CH |
| VI-14 | benzo[1,3]dioxole | CHCH₃ | CH₂ | C(CH₃)₂ | CH | CH |
| VI-15 | benzo[1,3]dioxole | C(CH₃)₂ | CH₂ | CH₂ | N | CH |
| VI-16 | benzo[1,3]dioxole | CH₂ | C(CH₃)₂ | CH₂ | N | CH |
| VI-17 | benzo[1,3]dioxole | CHCH₃ | CH₂ | C(CH₃)₂ | N | CH |
| VI-18 | benzo[1,3]dioxole | CHCH₃ | CH₂ | CHCH₃ | CH | CH |
| VI-19 | benzo[1,3]dioxole | CHCH₃ | CHCH₃ | CH₂ | CH | CH |
| VI-20 | benzo[1,3]dioxole | CHCH₃ | CH₂ | CHCH₃ | N | CH |
| VI-21 | 2,3-dihydro-1,4-benzodioxine | C(CH₃)₂ | CO | C(CH₃)₂ | CH | CH |
| VI-22 | 2,3-dihydro-1,4-benzodioxine | C(CH₃)₂ | CO | C(CH₃)₂ | N | CH |
| VI-23 | 2,3-dihydro-1,4-benzodioxine | C(CH₃)₂ | CO | C(CH₃)₂ | CH | CCl |

TABLE 53

| Compound No. | R¹ | A¹ | A² | A³ | X² | X⁴ |
|---|---|---|---|---|---|---|
| VI-24 | 2,3-dihydro-1,4-benzodioxine | C(CH₃)₂ | CO | C(CH₃)₂ | CH | CF |
| VI-25 | 2,3-dihydro-1,4-benzodioxine | C(CH₃)₂ | CO | C(CH₃)₂ | CH | CCH3 |
| VI-26 | 2,3-dihydro-1,4-benzodioxine | CHCH₃ | CH₂ | CH₂ | CH | CH |
| VI-27 | 2,3-dihydro-1,4-benzodioxine | CH₂ | CHCH3 | CH₂ | CH | CH |
| VI-28 | 2,3-dihydro-1,4-benzodioxine | CHCH₃ | CHCH₃ | CHCH₃ | CH | CH |
| VI-29 | 2,3-dihydro-1,4-benzodioxine | CHCH₃ | CH₂ | CH₂ | N | CH |
| VI-30 | 2,3-dihydro-1,4-benzodioxine | CH₂ | CHCH₃ | CH₂ | N | CH |
| VI-31 | 2,3-dihydro-1,4-benzodioxine | CHCH₃ | CHCH₃ | CHCH₃ | N | CH |
| VI-32 | 2,3-dihydro-1,4-benzodioxine | C(CH₃)₂ | CH₂ | CH₂ | CH | CH |

TABLE 53-continued

| Compound No. | R¹ | A¹ | A² | A³ | X² | X⁴ |
|---|---|---|---|---|---|---|
| VI-33 | 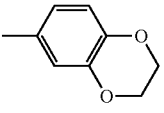 | $CH_2$ | $C(CH_3)_2$ | $CH_2$ | CH | CH |
| VI-34 | 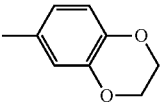 | $CHCH_3$ | $CH_2$ | $C(CH_3)_2$ | CH | CH |
| VI-35 | 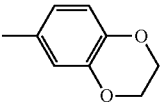 | $C(CH_3)_2$ | $CH_2$ | $CH_2$ | N | CH |
| VI-36 | 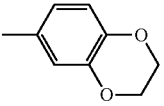 | $CH_2$ | $C(CH_3)_2$ | $CH_2$ | N | CH |
| VI-37 | 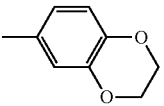 | $CHCH_3$ | $CH_2$ | $C(CH_3)_2$ | N | CH |
| VI-38 | 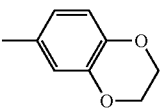 | $CHCH_3$ | $CH_2$ | $CHCH_3$ | CH | CH |
| VI-39 | 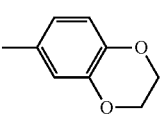 | $CHCH_3$ | $CHCH_3$ | $CH_2$ | CH | CH |

TABLE 54

| Compound No. | R¹ | A¹ | A² | A³ | X² | X⁴ |
|---|---|---|---|---|---|---|
| VI-40 | 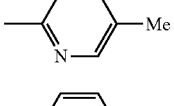 | $CHCH_3$ | $CH_2$ | $CHCH_3$ | N | CH |
| VI-41 | 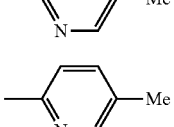 | $C(CH_3)_2$ | CO | $C(CH_3)_2$ | CH | CH |
| VI-42 | 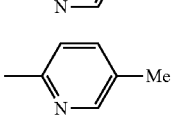 | $C(CH_3)_2$ | CO | $C(CH_3)_2$ | N | CH |
| VI-43 | 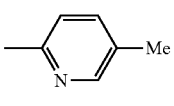 | $C(CH_3)_2$ | CO | $C(CH_3)_2$ | CH | CCl |
| VI-44 | 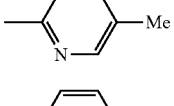 | $C(CH_3)_2$ | CO | $C(CH_3)_2$ | CH | CF |

TABLE 54-continued

| Compound No. | R¹ | A¹ | A² | A³ | X² | X⁴ |
|---|---|---|---|---|---|---|
| VI-45 | 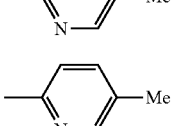 | $C(CH_3)_2$ | CO | $C(CH_3)_2$ | CH | CCH3 |
| VI-46 | 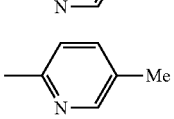 | $CHCH_3$ | $CH_2$ | $CH_2$ | CH | CH |
| VI-47 |  | $CH_2$ | $CHCH_3$ | $CH_2$ | CH | CH |
| VI-48 |  | $CHCH_3$ | $CHCH_3$ | $CHCH_3$ | CH | CH |
| VI-49 | 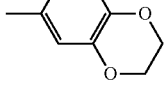 | $CHCH_3$ | $CH_2$ | $CH_2$ | N | CH |
| VI-50 | 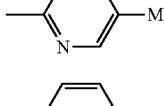 | $CH_2$ | $CHCH_3$ | $CH_2$ | N | CH |
| VI-51 | 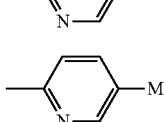 | $CHCH_3$ | $CHCH_3$ | $CHCH_3$ | N | CH |
| VI-52 | 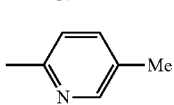 | $C(CH_3)_2$ | $CH_2$ | $CH_2$ | CH | CH |
| VI-53 |  | $CH_2$ | $C(CH_3)_2$ | $CH_2$ | CH | CH |

TABLE 55

| Compound No. | R¹ | A¹ | A² | A³ | X² | X⁴ |
|---|---|---|---|---|---|---|
| VI-54 | 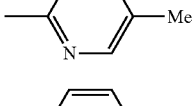 | $CHCH_3$ | $CH_2$ | $C(CH_3)_2$ | CH | CH |
| VI-55 | 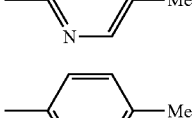 | $C(CH_3)_2$ | $CH_2$ | $CH_2$ | N | CH |
| VI-56 | 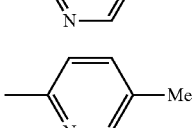 | $CH_2$ | $C(CH_3)_2$ | $CH_2$ | N | CH |
| VI-57 | 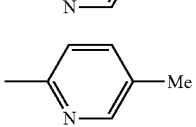 | $CHCH_3$ | $CH_2$ | $C(CH_3)_2$ | N | CH |
| VI-58 |  | $CHCH_3$ | $CH_2$ | $CHCH_3$ | CH | CH |

TABLE 55-continued

| Compound No. | R¹ | A¹ | A² | A³ | X² | X⁴ |
|---|---|---|---|---|---|---|
| VI-59 | 2,5-dimethylpyridin-yl | CHCH₃ | CHCH₃ | CH₂ | CH | CH |
| VI-60 | 2,5-dimethylpyridin-yl | CHCH₃ | CH₂ | CHCH₃ | N | CH |
| VI-61 | 2,5-dimethylthiazol-yl | C(CH₃)₂ | CO | C(CH₃)₂ | CH | CH |
| VI-62 | 2,5-dimethylthiazol-yl | C(CH₃)₂ | CO | C(CH₃)₂ | N | CH |
| VI-63 | 2,5-dimethylthiazol-yl | C(CH₃)₂ | CO | C(CH₃)₂ | CH | CCl |
| VI-64 | 2,5-dimethylthiazol-yl | C(CH₃)₂ | CO | C(CH₃)₂ | CH | CF |
| VI-65 | 2,5-dimethylthiazol-yl | C(CH₃)₂ | CO | C(CH₃)₂ | CH | CCH3 |
| VI-66 | 2,5-dimethylthiazol-yl | CHCH₃ | CH₂ | CH₂ | CH | CH |

TABLE 56

| Compound No. | R¹ | A¹ | A² | A³ | X² | X⁴ |
|---|---|---|---|---|---|---|
| VI-67 | 2,5-dimethylthiazol-yl | CH₂ | CHCH₃ | CH₂ | CH | CH |
| VI-68 | 2,5-dimethylthiazol-yl | CHCH₃ | CHCH₃ | CHCH₃ | CH | CH |
| VI-69 | 2,5-dimethylthiazol-yl | CHCH₃ | CH₂ | CH₂ | N | CH |
| VI-70 | 2,5-dimethylthiazol-yl | CH₂ | CHCH₃ | CH₂ | N | CH |
| VI-71 | 2,5-dimethylthiazol-yl | CHCH₃ | CHCH₃ | CHCH₃ | N | CH |
| VI-72 | 2,5-dimethylthiazol-yl | C(CH₃)₂ | CH₂ | CH₂ | CH | CH |
| VI-73 | 2,5-dimethylthiazol-yl | CH₂ | C(CH₃)₂ | CH₂ | CH | CH |
| VI-74 | 2,5-dimethylthiazol-yl | CHCH₃ | CH₂ | C(CH₃)₂ | CH | CH |
| VI-75 | 2,5-dimethylthiazol-yl | C(CH₃)₂ | CH₂ | CH₂ | N | CH |
| VI-76 | 2,5-dimethylthiazol-yl | CH₂ | C(CH₃)₂ | CH₂ | N | CH |
| VI-77 | 2,5-dimethylthiazol-yl | CHCH₃ | CH₂ | C(CH₃)₂ | N | CH |

TABLE 57

| Compound No. | R¹ | A¹ | A² | A³ | X² | X⁴ |
|---|---|---|---|---|---|---|
| VI-78 | 2,5-dimethylthiazol-yl | CHCH₃ | CH₂ | CHCH₃ | CH | CH |
| VI-79 | 2,5-dimethylthiazol-yl | CHCH₃ | CHCH₃ | CH₂ | CH | CH |
| VI-80 | 2,5-dimethylthiazol-yl | CHCH₃ | CH₂ | CHCH₃ | N | CH |
| VI-81 | (4-OMe)Ph | C(CH₃)₂ | CO | C(CH₃)₂ | CH | CH |
| VI-82 | (4-OMe)Ph | C(CH₃)₂ | CO | C(CH₃)₂ | N | CH |
| VI-83 | (4-OMe)Ph | C(CH₃)₂ | CO | C(CH₃)₂ | CH | CCl |
| VI-84 | (4-OMe)Ph | C(CH₃)₂ | CO | C(CH₃)₂ | CH | CF |
| VI-85 | (4-OMe)Ph | C(CH₃)₂ | CO | C(CH₃)₂ | CH | CCH3 |
| VI-86 | (4-OMe)Ph | CHCH₃ | CH₂ | CH₂ | CH | CH |
| VI-87 | (4-OMe)Ph | CH₂ | CHCH₃ | CH₂ | CH | CH |
| VI-88 | (4-OMe)Ph | CHCH₃ | CHCH₃ | CHCH₃ | CH | CH |
| VI-89 | (4-OMe)Ph | CHCH₃ | CH₂ | CH₂ | N | CH |
| VI-90 | (4-OMe)Ph | CH₂ | CHCH₃ | CH₂ | N | CH |
| VI-91 | (4-Me)Ph | CHCH₃ | CHCH₃ | CHCH₃ | N | CH |

TABLE 57-continued

| Compound No. | R¹ | A¹ | A² | A³ | X² | X⁴ |
|---|---|---|---|---|---|---|
| VI-92 | (4-Me)Ph | C(CH₃)₂ | CH₂ | CH₂ | CH | CH |
| VI-93 | (4-Me)Ph | CH₂ | C(CH₃)₂ | CH₂ | CH | CH |
| VI-94 | (4-Me)Ph | CHCH₃ | CH₂ | C(CH₃)₂ | CH | CH |
| VI-95 | (4-Me)Ph | C(CH₃)₂ | CH₂ | CH₂ | N | CH |
| VI-96 | (4-Me)Ph | CH₂ | C(CH₃)₂ | CH₂ | N | CH |
| VI-97 | (4-Me)Ph | CHCH₃ | CH₂ | C(CH₃)₂ | N | CH |
| VI-98 | (4-Me)Ph | CHCH₃ | CH₂ | CHCH₃ | CH | CH |
| VI-99 | (4-Me)Ph | CHCH₃ | CHCH₃ | CH₂ | CH | CH |
| VI-100 | (4-Me)Ph | CHCH₃ | CH₂ | CHCH₃ | N | CH |
| VI-101 | (3-F-4-Me)Ph | C(CH₃)₂ | CO | C(CH₃)₂ | CH | CH |
| VI-102 | (3-F-4-Me)Ph | C(CH₃)₂ | CO | C(CH₃)₂ | N | CH |
| VI-103 | (3-F-4-Me)Ph | C(CH₃)₂ | CO | C(CH₃)₂ | CH | CCl |
| VI-104 | (3-F-4-Me)Ph | C(CH₃)₂ | CO | C(CH₃)₂ | CH | CF |
| VI-105 | (3-F-4-Me)Ph | C(CH₃)₂ | CO | C(CH₃)₂ | CH | CCH₃ |
| VI-106 | (3-F-4-Me)Ph | CHCH₃ | CH₂ | CH₂ | CH | CH |
| VI-107 | (3-F-4-Me)Ph | CH₂ | CHCH₃ | CH₂ | CH | CH |
| VI-108 | (3-F-4-Me)Ph | CHCH₃ | CHCH₃ | CHCH₃ | CH | CH |
| VI-109 | (3-F-4-Me)Ph | CHCH₃ | CH₂ | CH₂ | N | CH |
| VI-110 | (3-F-4-Me)Ph | CH₂ | CHCH₃ | CH₂ | N | CH |
| VI-111 | (3-F-4-OMe)Ph | CHCH₃ | CHCH₃ | CHCH₃ | N | CH |

TABLE 58

| Compound No. | R¹ | A¹ | A² | A³ | X² | X⁴ |
|---|---|---|---|---|---|---|
| VI-112 | (3-F-4-OMe)Ph | C(CH₃)₂ | CH₂ | CH₂ | CH | CH |
| VI-113 | (3-F-4-OMe)Ph | CH₂ | C(CH₃)₂ | CH₂ | CH | CH |
| VI-114 | (3-F-4-OMe)Ph | CHCH₃ | CH₂ | C(CH₃)₂ | CH | CH |
| VI-115 | (3-F-4-OMe)Ph | C(CH₃)₂ | CH₂ | CH₂ | N | CH |
| VI-116 | (3-F-4-OMe)Ph | CH₂ | C(CH₃)₂ | CH₂ | N | CH |
| VI-117 | (3-F-4-OMe)Ph | CHCH₃ | CH₂ | C(CH₃)₂ | N | CH |
| VI-118 | (3-F-4-OMe)Ph | CHCH₃ | CH₂ | CHCH₃ | CH | CH |
| VI-119 | (3-F-4-OMe)Ph | CHCH₃ | CHCH₃ | CH₂ | CH | CH |
| VI-120 | (3-F-4-OMe)Ph | CHCH₃ | CH₂ | CHCH₃ | N | CH |

TABLE 59

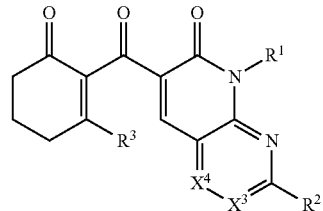

| Compound No. | R¹ | R² | R³ | X³ | X⁴ |
|---|---|---|---|---|---|
| VII-1 | benzo[1,3]dioxol-5-yl | H | NH₂ | CH | CH |
| VII-2 | benzo[1,3]dioxol-5-yl | H | Cl | CH | CH |

TABLE 59-continued

| Compound No. | R¹ | R² | R³ | X³ | X⁴ |
|---|---|---|---|---|---|
| VII-3 | benzo[1,3]dioxol-5-yl | H | OSO₂Me | CH | CH |
| VII-4 | benzo[1,3]dioxol-5-yl | H | SCH₃ | CH | CH |
| VII-5 | benzo[1,3]dioxol-5-yl | H | SOCH₃ | CH | CH |
| VII-6 | benzo[1,3]dioxol-5-yl | H | SO₂CH₃ | CH | CH |
| VII-7 | benzo[1,3]dioxol-5-yl | H | SCH₂CF₃ | CH | CH |
| VII-8 | benzo[1,3]dioxol-5-yl | H | SOCH₂CF₃ | CH | CH |
| VII-9 | benzo[1,3]dioxol-5-yl | H | SO₂CH₂CF₃ | CH | CH |
| VII-10 | benzo[1,3]dioxol-5-yl | H | OCOCH₃ | CH | CH |
| VII-11 | benzo[1,3]dioxol-5-yl | H | OPh | CH | CH |

TABLE 60

| Compound No. | R¹ | R² | R³ | X³ | X⁴ |
|---|---|---|---|---|---|
| VII-12 | 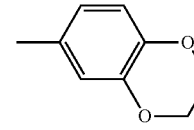 | H | SPh | CH | CH |
| VII-13 | 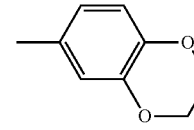 | H | SOPh | CH | CH |
| VII-14 | 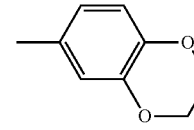 | H | SO₂Ph | CH | CH |
| VII-15 | 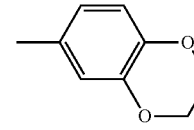 | H | OSO₂Ph | CH | CH |
| VII-16 | 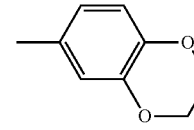 | H | OCOPh | CH | CH |
| VII-17 | 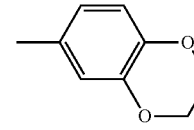 | H | 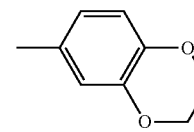 (1,2,4-triazol-1-yl) | CH | CH |
| VII-18 | 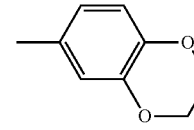 | H | 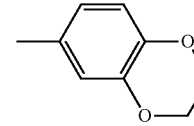 (imidazol-1-yl) | CH | CH |
| VII-19 | 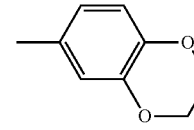 | H | 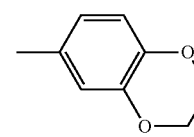 (tetrazol-1-yl) | CH | CH |
| VII-20 | 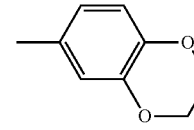 | H | 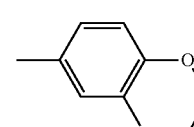 (pyrazol-1-yl) | CH | CH |
| VII-21 | 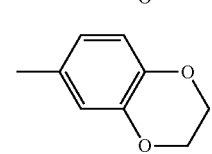 | H | NH₂ | CH | CH |
| VII-22 | 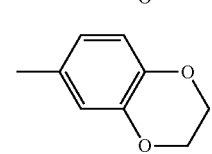 | H | Cl | CH | CH |

TABLE 60-continued

| Compound No. | R¹ | R² | R³ | X³ | X⁴ |
|---|---|---|---|---|---|
| VII-23 | 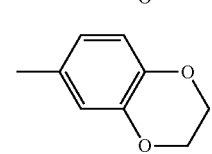 | H | OSO₂Me | CH | CH |
| VII-24 | 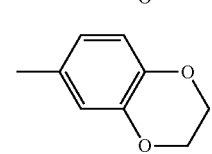 | H | SCH₃ | CH | CH |

TABLE 61

| Compound No. | R¹ | R² | R³ | X³ | X⁴ |
|---|---|---|---|---|---|
| VII-25 | 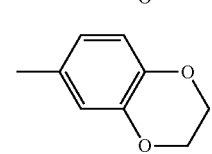 | H | SOCH₃ | CH | CH |
| VII-26 | 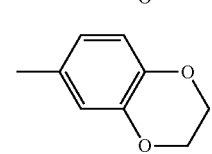 | H | SO₂CH₃ | CH | CH |
| VII-27 | 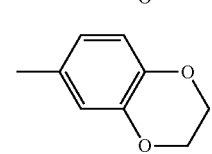 | H | SCH₂CF₃ | CH | CH |
| VII-28 | 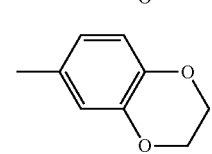 | H | SOCH₂CF₃ | CH | CH |
| VII-29 | 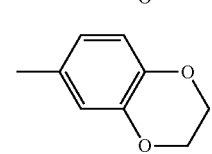 | H | SO₂CH₂CF₃ | CH | CH |
| VII-30 | 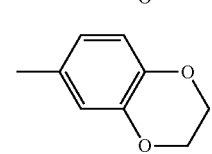 | H | OCOCH₃ | CH | CH |
| VII-31 | 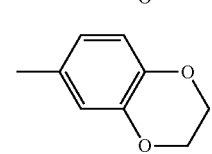 | H | OPh | CH | CH |
| VII-32 | 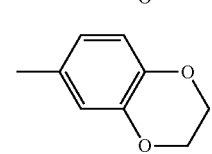 | H | SPh | CH | CH |

TABLE 61-continued

| Compound No. | R¹ | R² | R³ | X³ | X⁴ |
|---|---|---|---|---|---|
| VII-33 | 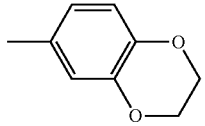 | H | SOPh | CH | CH |
| VII-34 | 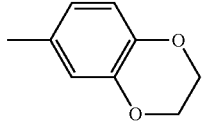 | H | SO₂Ph | CH | CH |
| VII-35 | 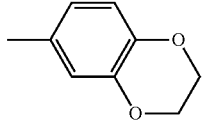 | H | OSO₂Ph | CH | CH |
| VII-36 | 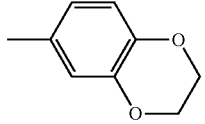 | H | OCOPh | CH | CH |
| VII-37 | 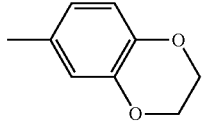 | H |  | CH | CH |
| VII-38 | 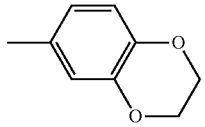 | H | 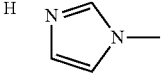 | CH | CH |

TABLE 62

| Compound No. | R¹ | R² | R³ | X³ | X⁴ |
|---|---|---|---|---|---|
| VII-39 | 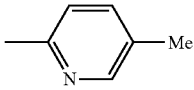 | H | 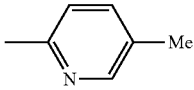 | CH | CH |
| VII-40 | 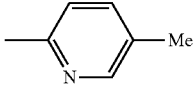 | H | 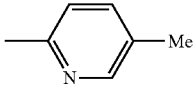 | CH | CH |
| VII-41 | 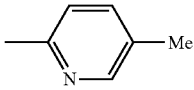 | H | NH₂ | CH | CH |
| VII-42 | 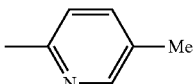 | H | Cl | CH | CH |

TABLE 62-continued

| Compound No. | R¹ | R² | R³ | X³ | X⁴ |
|---|---|---|---|---|---|
| VII-43 | 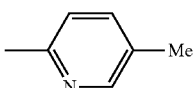 | H | OSO₂Me | CH | CH |
| VII-44 | 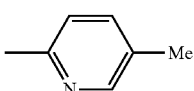 | H | SCH₃ | CH | CH |
| VII-45 | 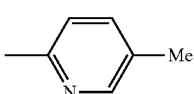 | H | SOCH₃ | CH | CH |
| VII-46 | 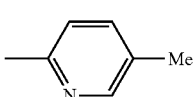 | H | SO₂CH₃ | CH | CH |
| VII-47 | 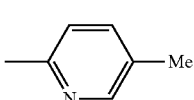 | H | SCH₂CF₃ | CH | CH |
| VII-48 | 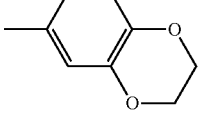 | H | SOCH₂CF₃ | CH | CH |
| VII-49 |  | H | SO₂CH₂CF₃ | CH | CH |
| VII-50 | 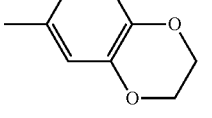 | H | OCOCH₃ | CH | CH |
| VII-51 | 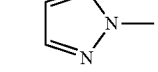 | H | OPh | CH | CH |
| VII-52 | 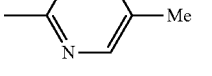 | H | SPh | CH | CH |
| VII-53 | 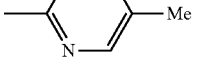 | H | SOPh | CH | CH |

TABLE 63

| Compound No. | R¹ | R² | R³ | X³ | X⁴ |
|---|---|---|---|---|---|
| VII-54 | 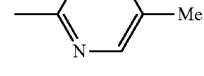 | H | SO₂Ph | CH | CH |
| VII-55 | 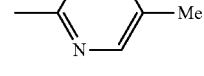 | H | OSO₂Ph | CH | CH |

TABLE 63-continued

| Compound No. | R$^1$ | R$^2$ | R$^3$ | X$^3$ | X$^4$ |
|---|---|---|---|---|---|
| VII-56 | 5-Me-pyridin-2-yl | H | OCOPh | CH | CH |
| VII-57 | 5-Me-pyridin-2-yl | H | 1,2,4-triazol-1-yl | CH | CH |
| VII-58 | 5-Me-pyridin-2-yl | H | imidazol-1-yl | CH | CH |
| VII-59 | 5-Me-pyridin-2-yl | H | tetrazol-1-yl | CH | CH |
| VII-60 | 5-Me-pyridin-2-yl | H | pyrazol-1-yl | CH | CH |
| VII-61 | 5-Me-thiazol-2-yl | H | NH$_2$ | CH | CH |
| VII-62 | 5-Me-thiazol-2-yl | H | Cl | CH | CH |
| VII-63 | 5-Me-thiazol-2-yl | H | OSO$_2$Me | CH | CH |
| VII-64 | 5-Me-thiazol-2-yl | H | SCH$_3$ | CH | CH |
| VII-65 | 5-Me-thiazol-2-yl | H | SOCH$_3$ | CH | CH |

TABLE 64

| Compound No. | R$^1$ | R$^2$ | R$^3$ | X$^3$ | X$^4$ |
|---|---|---|---|---|---|
| VII-66 | 5-Me-thiazol-2-yl | H | SO$_2$CH$_3$ | CH | CH |
| VII-67 | 5-Me-thiazol-2-yl | H | SCH$_2$CF$_3$ | CH | CH |
| VII-68 | 5-Me-thiazol-2-yl | H | SOCH$_2$CF$_3$ | CH | CH |
| VII-69 | 5-Me-thiazol-2-yl | H | SO$_2$CH$_2$CF$_3$ | CH | CH |
| VII-70 | 5-Me-thiazol-2-yl | H | OCOCH$_3$ | CH | CH |
| VII-71 | 5-Me-thiazol-2-yl | H | OPh | CH | CH |
| VII-72 | 5-Me-thiazol-2-yl | H | SPh | CH | CH |
| VII-73 | 5-Me-thiazol-2-yl | H | SOPh | CH | CH |
| VII-74 | 5-Me-thiazol-2-yl | H | SO$_2$Ph | CH | CH |
| VII-75 | 5-Me-thiazol-2-yl | H | OSO$_2$Ph | CH | CH |

TABLE 65

| Compound No. | R$^1$ | R$^2$ | R$^3$ | X$^3$ | X$^4$ |
|---|---|---|---|---|---|
| VII-76 | 5-Me-thiazol-2-yl | H | OCOPh | CH | CH |
| VII-77 | 5-Me-thiazol-2-yl | H | 1,2,4-triazol-1-yl | CH | CH |
| VII-78 | 5-Me-thiazol-2-yl | H | imidazol-1-yl | CH | CH |

TABLE 65-continued

| Compound No. | R¹ | R² | R³ | X³ | X⁴ |
|---|---|---|---|---|---|
| VII-79 | 2-methyl-5-Me-thiazol-4-yl | H | 1H-tetrazol-1-yl | CH | CH |
| VII-80 | 2-methyl-5-Me-thiazol-4-yl | H | 1H-pyrazol-1-yl | CH | CH |
| VII-81 | (4-OMe)Ph | H | NH₂ | CH | CH |
| VII-82 | (4-OMe)Ph | H | Cl | CH | CH |
| VII-83 | (4-OMe)Ph | H | OSO₂Me | CH | CH |
| VII-84 | (4-OMe)Ph | H | SCH₃ | CH | CH |
| VII-85 | (4-OMe)Ph | H | SOCH₃ | CH | CH |
| VII-86 | (4-OMe)Ph | H | SO₂CH₃ | CH | CH |
| VII-87 | (4-OMe)Ph | H | SCH₂CF₃ | CH | CH |
| VII-88 | (4-OMe)Ph | H | SOCH₂CF₃ | CH | CH |
| VII-89 | (4-OMe)Ph | H | SO₂CH₂CF₃ | CH | CH |
| VII-90 | (4-OMe)Ph | H | OCOCH₃ | CH | CH |
| VII-91 | (4-Me)Ph | H | OPh | CH | CH |
| VII-92 | (4-Me)Ph | H | SPh | CH | CH |
| VII-93 | (4-Me)Ph | H | SOPh | CH | CH |
| VII-94 | (4-Me)Ph | H | SO₂Ph | CH | CH |
| VII-95 | (4-Me)Ph | H | OSO₂Ph | CH | CH |
| VII-96 | (4-Me)Ph | H | OCOPh | CH | CH |
| VII-97 | (4-Me)Ph | H | 1H-1,2,4-triazol-1-yl | CH | CH |

TABLE 66

| Compound No. | R¹ | R² | R³ | X³ | X⁴ |
|---|---|---|---|---|---|
| VII-98 | (4-Me)Ph | H | 1H-imidazol-1-yl | CH | CH |
| VII-99 | (4-Me)Ph | H | 1H-tetrazol-1-yl | CH | CH |
| VII-100 | (4-Me)Ph | H | 1H-pyrazol-1-yl | CH | CH |
| VII-101 | (3-F-4-Me)Ph | H | SCH₂CH=CH₂ | CH | CH |
| VII-102 | (3-F-4-Me)Ph | H | SOCH₂CH=CH₂ | CH | CH |
| VII-103 | (3-F-4-Me)Ph | H | SO₂CH₂CH=CH₂ | CH | CH |
| VII-104 | (3-F-4-Me)Ph | H | SCH₂CH≡CH | CH | CH |
| VII-105 | (3-F-4-Me)Ph | H | SOCH₂CH≡CH | CH | CH |
| VII-106 | (3-F-4-Me)Ph | H | SO₂CH₂CH≡CH | CH | CH |
| VII-107 | (3-F-4-Me)Ph | H | OCOCH=CH₂ | CH | CH |
| VII-108 | (3-F-4-Me)Ph | H | S-(4-Cl-phenyl) | CH | CH |
| VII-109 | (3-F-4-Me)Ph | H | S-(4-NO₂-phenyl) | CH | CH |
| VII-110 | (3-F-4-Me)Ph | H | S-(4-CN-phenyl) | CH | CH |
| VII-111 | (3-F-4-OMe)Ph | H | S-(4-OCHF₂-phenyl) | CH | CH |
| VII-112 | (3-F-4-OMe)Ph | H | S-(4-OMe-phenyl) | CH | CH |
| VII-113 | (3-F-4-OMe)Ph | H | S-(4-CF₃-phenyl) | CH | CH |

Representative methods for producing the compound of the present invention represented by formula [I] will be described below, but the production method is not intended to be limited to these methods.

<Production Method 1>

The compound of the present invention represented by the following formula [1a] can be produced by a method based on the reaction scheme illustrated below.

[Chemical Formula 8]

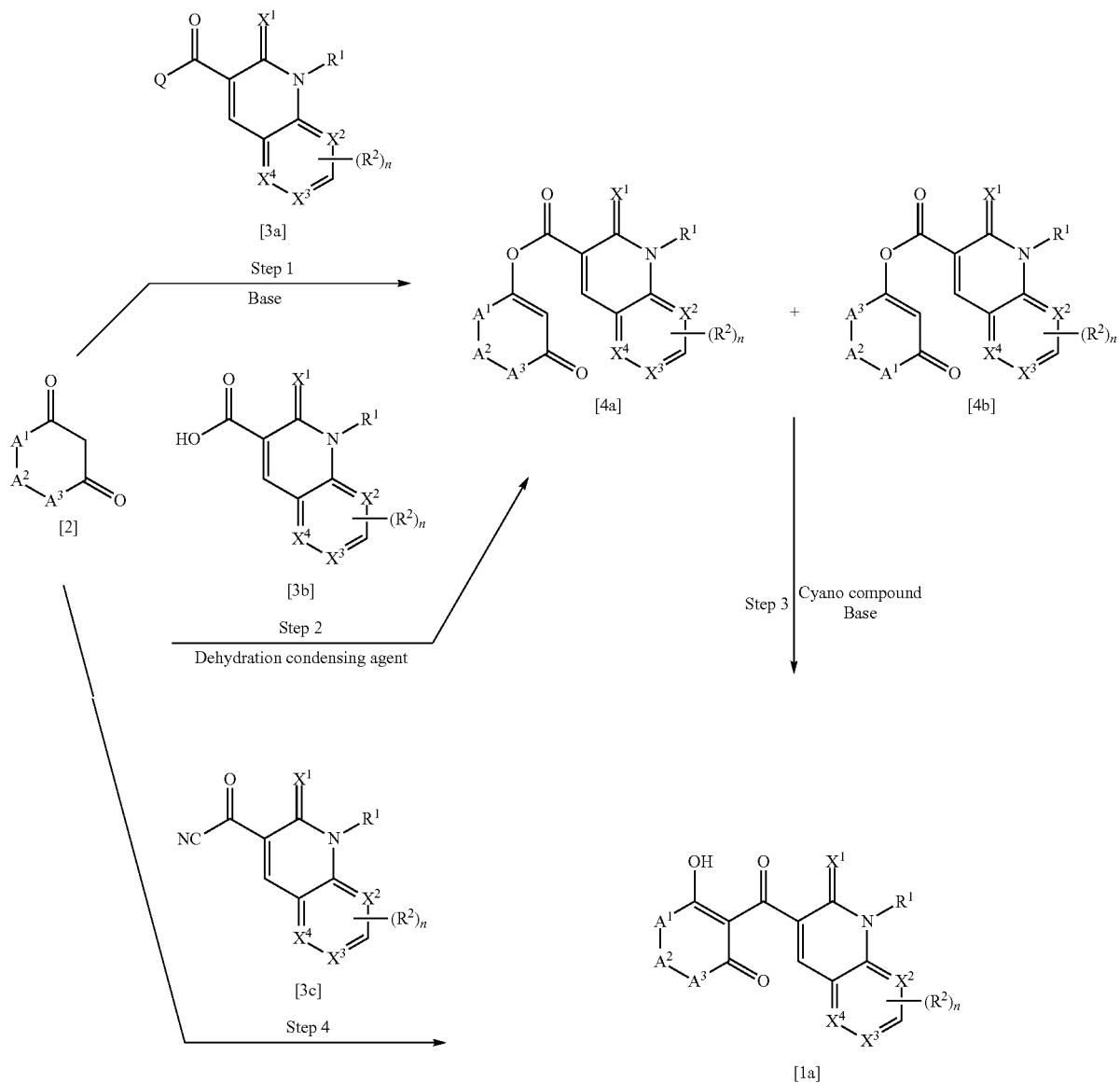

wherein $R^1$, $R^2$, $A^1$, $A^2$, $A^3$, n, $X^1$, $X^2$, $X^3$, and $X^4$ respectively have the same meanings as defined above; Q represents a leaving group such as halogen, an alkylcarbonyloxy group, an alkoxycarbonyloxy group, a haloalkylcarbonyloxy group, a haloalkoxycarbonyloxy group, a benzoyloxy group, a pyridyl group, or an imidazolyl group.

(Step 1)

Enol ester compounds represented by formulas [4a] and [4b] can be produced by allowing a compound represented by formula [2] to react with a compound represented by formula [3a] in a solvent, in the presence of a base.

(Hereinafter, for example, the "compound represented by formula [2]" may also be simply described as "formula [2]".)

The amount of use of the formula [3a] as used herein may be appropriately selected in the range of 0.5 to 10 moles, and preferably 1.0 to 1.2 moles, relative to one mole of the formula [2].

Examples of the base that can be used in the current step include organic amines such as triethylamine, pyridine, 4-dimethylaminopyridine, N,N-dimethylaniline, and 1,8-diazabicyclo[5.4.0]-7-undecene; carboxylic acid metal salts, represented by metal carbonates such as sodium carbonate, potassium carbonate, magnesium carbonate, and calcium carbonate; metal hydrogen carbonates such as sodium hydrogen carbonate and potassium hydrogen carbonate; and metal acetates such as sodium acetate, potassium acetate, calcium acetate, and magnesium acetate; metal alkoxides such as sodium methoxide, sodium ethoxide, sodium tertiary butoxide, potassium methoxide, and potassium tertiary butoxide; metal hydroxides such as sodium hydroxide, potassium hydroxide, calcium hydroxide, and magnesium hydroxide; and metal hydrides such as lithium hydride, sodium hydride, potassium hydride and calcium hydride.

The amount of use of the base may be appropriately selected in the range of 0.5 to 10 moles, and preferably 1.0 to 1.2 moles, relative to one mole of the formula [2].

Any solvent can be used in the current step as long as it does not inhibit the progress of the present reaction, and examples of the solvent that can be used include nitriles such as acetonitrile; ethers such as diethyl ether, diisopropyl ether, tetrahydrofuran, dioxane, monoglyme, and diglyme; halogenated hydrocarbons such as dichloroethane, chloroform, carbon tetrachloride, and tetrachloroethane; aromatic hydrocarbons such as benzene, chlorobenzene, nitrobenzene, and toluene; amides such as N,N-dimethylformamide and N,N-dimethylacetamide; imidazolinones such as 1,3-dimethyl-2-imidazolinone; and sulfur compounds such as dimethyl sulfoxide. Furthermore, solvent mixtures of these can also be used.

The amount of use of the solvent is 0.01 to 100 L, and preferably 0.1 to 10 L, relative to one mole of the formula [2].

The reaction temperature may be selected in the range of −20° C. to the boiling point region of the inert solvent used, and it is preferable to carry out the reaction in the temperature range of 0° C. to 100° C.

Furthermore, the reaction can be carried out using a phase transfer catalyst such as a quaternary ammonium salt. In the case of using a phase transfer catalyst, the amount of use thereof is 0.0001 to 1.0 mole, and preferably 0.001 to 0.1 moles, relative to one mole of the formula [2].

The reaction time may vary depending on the reaction temperature, reaction substrate, the extent of reaction, and the like; however, the reaction time is usually 10 minutes to 48 hours.

The compounds of formula [4a] and formula [4b], which are the target products of the reaction, can be collected from the reaction system by a routine method after completion of the reaction, and then can be purified, if necessary, by operations such as column chromatography and recrystallization.

(Step 2)

The formulas [4a] and [4b] can also be produced by allowing the formula [2] and the formula [3b] to react in a solvent in the presence of a dehydration condensing agent, in the presence or absence of a base.

The amount of use of the formula [3b] used in the current step may be appropriately selected in the range of 0.5 to 10 moles, and preferably 1.0 to 1.2 moles, relative to one mole of the formula [2].

Examples of the dehydration condensing agent that can be used include dicyclohexylcarbodiimide (DCC), N-(3-dimethylaminopropyl)-N'-ethylcarbodiimide (EDC or WSC), N,N-carbonyldiimidazole, 2-chloro-1,3-dimethylimidazolium chloride, and 2-chloro-1-pyridinium iodide.

Examples of the base and the solvent that can be used in the current step include the same bases and solvents as described with regard to Step 1.

The amount of the base used in the current step is 0 to 100 moles, and preferably 0 to 10 moles, relative to one mole of the formula [2].

The amount of use of the solvent is 0.01 to 100 L, and preferably 0.1 to 10 L, relative to one mole of the formula [2].

The reaction temperature may be selected in the range of −20° C. to the boiling point region of the inert solvent used, and it is preferable to carry out the reaction in the temperature range of 0° C. to 100° C.

The reaction time may vary depending on the reaction temperature, reaction substrate, the extent of reaction, and the like; however, the reaction time is usually 10 minutes to 48 hours.

(Step 3)

The formula [1a] can be produced by allowing the formula [4a] and the formula [4b] produced in Step 1 or 2, to react with a cyano compound in the presence of a base.

Examples of the base that can be used in the current step may be the same bases as those described with regard to Step 1.

The amount of use of the base may be appropriately selected in the range of 0.5 to 10 moles, and preferably 1.0 to 1.2 moles, relative to one mole of the formula [4a] and formula [4b].

Examples of the cyano compound that can be used in the current step include potassium cyanide, sodium cyanide, acetone cyanohydrin, hydrogen cyanide, and a polymer carrying hydrogen cyanide.

The amount of use of the cyano compound may be appropriately selected in the range of 0.01 to 1.0 moles, and preferably 0.05 to 0.2 moles, relative to one mole of the formulas [4a] and [4b].

Furthermore, it is also acceptable in the current step to use a phase transfer catalyst such as a crown ether.

The amount of use of the phase transfer catalyst is 0.001 to 10 moles, and preferably 0.01 to 1.0 mole, relative to one mole of the formulas [4a] and [4b].

Examples of the solvent that can be used in the current step may be the same solvents as those described with regard to Step 1, and the amount of use of the solvent is 0.01 to 100 L, and preferably 0.1 to 10 L, relative to one mole of the formulas [4a] and [4b].

The reaction temperature may be selected in the range of −20° C. to the boiling point region of the inert solvent used, and it is preferable to carry out the reaction in the temperature range of 0° C. to 100° C.

The reaction time may vary depending on the reaction temperature, reaction substrate, the extent of reaction, and the like; however, the reaction time is usually 10 minutes to 48 hours.

Additionally, in the current step, the formula [1a] can still be produced even if the formulas [4a] and [4b] produced in Step 1 or Step 2 are directly used without being isolated.

(Step 4)

The compound of the formula [1a] can also be produced by allowing the formula [2] to react with the formula [3c] in a solvent in the presence of a base or a Lewis acid.

The amount of use of the formula [3c] used in the current step may be appropriately selected in the range of 0.5 to 10 moles, and preferably 1.0 to 1.2 moles, relative to one mole of the formula [2].

Examples of the Lewis acid that can be used include zinc chloride and aluminum chloride.

In the case of using a Lewis acid, the amount of use of the Lewis acid may be appropriately selected in the range of 0.01 to 100 moles, and preferably 0.1 to 10 moles, relative to one mole of the formula [2].

Examples of the base that can be used in the current step may be the same bases as those described with regard to Step 1.

In the case of using a base, the amount of use of the base may be appropriately selected in the range of 0.5 to 10 moles, and preferably 1.0 to 1.2 moles, relative to one mole of the formula [2].

Examples of the solvent that can be used in the current step may be the same solvents as those described with regard to Step 1, and the amount of use of the solvent is 0.01 to 100 L, and preferably 0.1 to 10 L, relative to one mole of the formula [2].

The reaction temperature may be selected in the range of −20° C. to the boiling point region of the inert solvent used, and it is preferable to carry out the reaction in the temperature range of 0° C. to 100° C.

The reaction time may vary depending on the reaction temperature, reaction substrate, the extent of reaction, and the like; however, the reaction time is usually 10 minutes to 48 hours.

Here, the production intermediate of the formula [3c] can be produced by allowing a compound represented by formula [3a-1] to react with a cyanating agent.

[Chemical Formula 9]

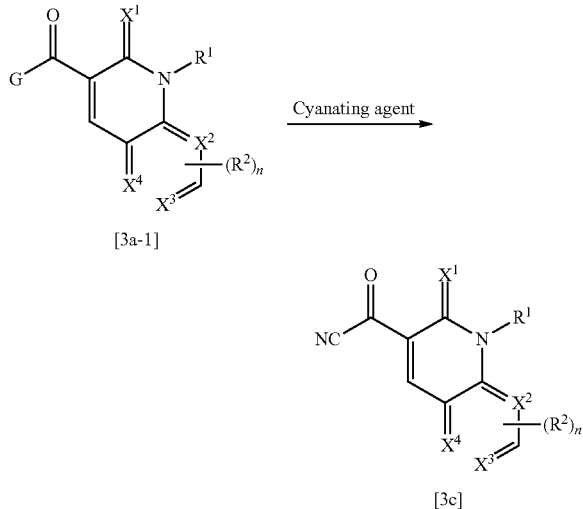

wherein $R^1$, $R^2$, n, $X^1$, $X^2$, $X^3$, and $X^4$ respectively have the same meanings as defined above; and G represents a halogen atom such as chlorine or bromine.

Examples of the cyanating agent that may be used include alkali metal cyanides and alkaline earth metal cyanides.

The amount of use of the cyanating agent may be appropriately selected in the range of 0.5 to 10 moles, and preferably 0.9 to 1.1 moles, relative to one mole of the compound [3a-1].

The reaction temperature may be selected in the range of −20° C. to the boiling point region of the inert solvent used, and it is preferable to carry out the reaction in the temperature range of 0° C. to 100° C.

The reaction time may vary depending on the reaction temperature, reaction substrate, the extent of reaction, and the like; however, the reaction time is usually 10 minutes to 48 hours.

<Production Method 2>

Furthermore, compounds represented by formulas [1b] and [1c] of the present invention can be produced from the compound represented by the formula [1a] of the present invention, according to the following production method.

[Chemical Formula 10]

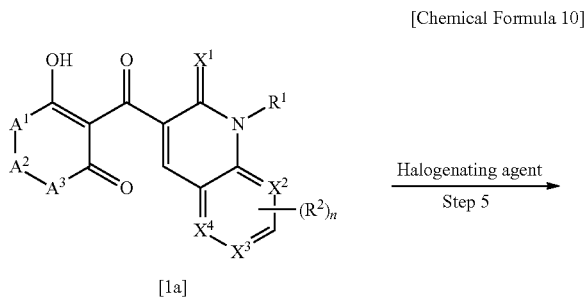

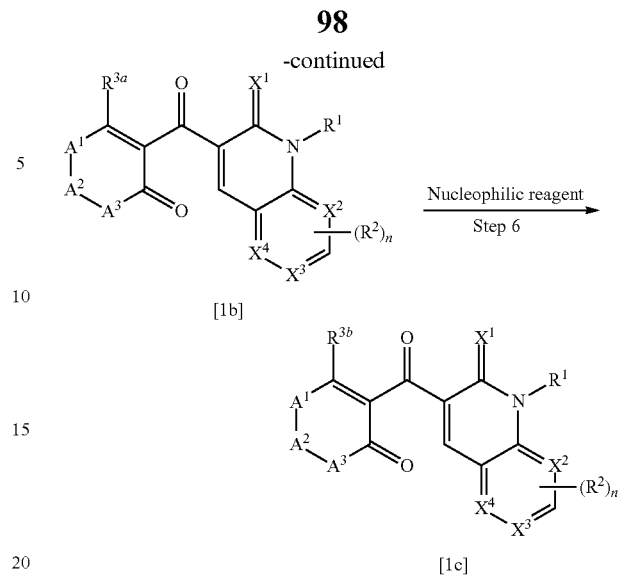

wherein $R^{3a}$ represents a halogen atom such as chlorine or bromine; $R^{3b}$ represents a $C_1$-$C_6$ alkoxy group, a $C_1$-$C_6$ alkylthio group, a $C_2$-$C_6$ alkenylthio group, a $C_2$-$C_6$ alkynylthio group, a phenoxy group (this group may be substituted with one $R^{10}$, or two to five identical or different $R^{10}$), a phenylthio group (this group may be substituted with one $R^{10}$, or two to five identical or different $R^{10}$), an amino group, a $C_1$-$C_6$ haloalkylthio group, a $C_1$-$C_6$ alkylcarbonyloxy group, a $C_2$-$C_6$ alkenylcarbonyloxy group, a $C_2$-$C_6$ alkynylcarbonyloxy group, a phenylcarbonyloxy group (this group may be substituted with one $R^{10}$, or two to five identical or different $R^{10}$), a 1,2,4-triazol-1-yl group, a 1,2,3-triazol-1-yl group, a 1,2,3-triazol-2-yl group, an imidazol-1-yl group, a pyrazol-1-yl group, a tetrazol-1-yl group, or a tetrazol-2-yl group; and $X^1$, $X^2$, $X^3$, $X^4$, $R^1$, $R^2$, $A^1$, $A^2$, $A^3$, n, and $R^{10}$ respectively have the same meanings as defined above.

That is, the compound of formula [1b] can be produced by allowing the compound of formula [1a] to react with a halogenating agent in a solvent, and the compound of formula [1c] can be produced by further allowing the compound of formula [1b] to react with a nucleophilic reagent in a solvent, in the presence of a base.

Examples of the halogenating agent that can be used in Step 5 include thionyl chloride, thionyl bromide, phosphorus oxychloride, phosphorus oxybromide, phenyltrimethylammonium tribromide, and Meldrum's acid tribromide.

The amount of use of the halogenating agent may be appropriately selected in the range of 0.5 to 10 moles, preferably 1.0 to 1.2 moles, relative to one mole of the compound of formula [1a].

Examples of the solvent that can be used herein may be the same solvents as those described in Step 1 of the production method 1, and the amount of use of the solvent is 0.01 to 100 L, and preferably 0.1 to 10 L, relative to one mole of the formula [1a].

The reaction temperature may be selected in the range of −20° C. to the boiling point region of the inert solvent used, and it is preferable to carry out the reaction in the temperature range of 0° C. to 100° C.

The reaction time may vary depending on the reaction temperature, reaction substrate, the extent of reaction, and the like; however, the reaction time is usually 10 minutes to 48 hours.

Examples of the nucleophilic reagent that can be used in Step 6 include $C_1$-$C_6$ alkyl alcohols such as methanol or ethanol; $C_1$-$C_6$ alkyl mercaptans such as methyl mercaptan or ethyl mercaptan; $C_2$-$C_6$ alkenyl mercaptans such as allyl mercaptan; $C_2$-$C_6$ alkynyl mercaptans such as 2-pentyne-1-mercaptan; phenols such as p-cresol or phenol; thiophenols such as p-chlorothiophenol; $C_1$-$C_6$ haloalkyl mercaptans such as 2,2,2-trifluoroethyl mercaptan; $C_1$-$C_6$ alkyl acids such as acetic acid; $C_1$-$C_6$ alkenyl acids such as acrylic acid; $C_1$-$C_6$ alkynyl acids such as propiolic acid; benzoic acids; 1H-1,2,3-triazoles; 1H-1,2,4-triazoles; 1H-imidazoles; 1H-pyrazoles; 1H-tetrazoles; and ammonia.

$R^{3b}$ represents a $C_1$-$C_6$ alkoxy group, a $C_1$-$C_6$ alkylthio group, a $C_2$-$C_6$ alkenylthio group, a $C_2$-$C_6$ alkynylthio group, a phenoxy group (this group may be substituted with one $R^{10}$, or two to five identical or different $R^{10}$), a phenylthio group (this group may be substituted with one $R^{10}$, or two to five identical or different $R^{10}$), an amino group, a $C_1$-$C_6$ haloalkylthio group, a $C_1$-$C_6$ alkylcarbonyloxy group, a $C_2$-$C_6$ alkenylcarbonyloxy group, a $C_2$-$C_6$ alkynylcarbonyloxy group, a phenylcarbonyloxy group (this group may be substituted with one $R^{10}$, or two to five identical or different $R^{10}$), a 1,2,4-triazol-1-yl group, a 1,2,3-triazol-1-yl group, a 1,2,3-triazol-2-yl group, an imidazol-1-yl group, a pyrazol-1-yl group, a tetrazol-1-yl group, or a tetrazol-2-yl group.

The amount of use of the nucleophilic reagent may be appropriately selected in the range of 0.5 to 10 moles, and preferably 1.0 to 1.2 moles, relative to one mole of the compound of formula [1b].

Examples of the base that can be used may be the same bases as those described with regard to Step 1 of the production method 1, and the amount of use of the base may be appropriately selected in the range of 0.5 to 10 moles, and preferably 1.0 to 1.2 moles, relative to one mole of the formula [1a].

Examples of the solvent that can be used may be the same solvents as those described with regard to Step 1 of the production method 1, and the amount of use of the solvent is 0.01 to 100 L, and preferably 0.1 to 10 L, based on the formula [1a].

The reaction temperature may be selected in the range of −20° C. to the boiling point region of the inert solvent used, and it is preferable to carry out the reaction in the temperature range of 0° C. to 100° C. The reaction time may vary depending on the reaction temperature, reaction substrate, the extent of reaction, and the like; however, the reaction time is usually 10 minutes to 48 hours.

<Production Method 3>

Furthermore, the compound of the present invention represented by the following formula [1d] can be produced by a method based on the reaction scheme illustrated below.

[Chemical Formula 11]

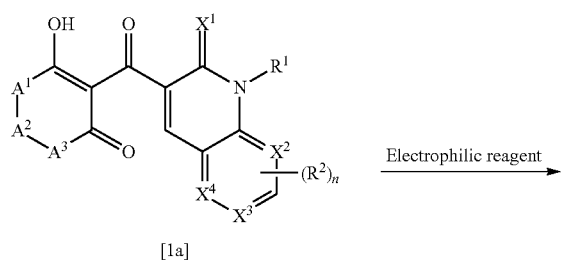

[1a]

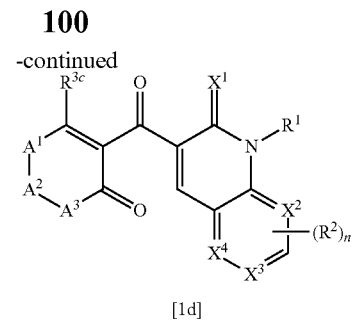

[1d]

wherein $R^{3c}$ represents a $C_1$-$C_6$ alkoxy group, a benzyloxy group, a $C_1$-$C_6$ alkylsulfonyloxy group, a $C_1$-$C_6$ alkylcarbonyloxy group, a $C_2$-$C_6$ alkenylcarbonyloxy group, a $C_2$-$C_6$ alkynylcarbonyloxy group, a phenylsulfonyloxy group (this group may be substituted with one $R^{10}$, or two to five identical or different $R^{10}$), or a phenylcarbonyloxy group (this group may be substituted with one $R^{10}$, or two to five identical or different $R^{10}$; and $X^1$, $X^2$, $X^3$, $R^1$, $R^2$, $A^1$, $A^2$, $A^3$, n, and $R^{10}$ respectively have the same meanings as defined above.

That is, the compound of formula [1d] can be produced by allowing the compound of formula [1a] to react with an electrophilic reagent in a solvent, in the presence or absence of a base.

Examples of the electrophilic reagent that can be used include $C_1$-$C_6$ alkyl halides such as methyl iodide and propyl chloride; benzyl halides such as benzyl bromide; $C_1$-$C_6$ alkylcarbonyl halides such as acetyl chloride and propionyl chloride; benzoyl halides such as benzoyl chloride; $C_2$-$C_6$ alkenylcarbonyl halides such as methacryl chloride or crotonyl chloride; $C_2$-$C_6$ alkynylcarbonyl halides such as 4-pentynoyl chloride; $C_1$-$C_6$ alkylsulfonic acid halides such as methanesulfonyl chloride or ethanesulfonyl chloride; benzenesulfonic acid halides such as benzenesulfonyl chloride or p-toluenesulfonyl chloride; and di-$C_1$-$C_6$ alkylsulfuric acid esters such as dimethyl sulfate and diethyl sulfate.

The amount of use of the electrophilic reagent may be appropriately selected in the range of 0.1 to 10 moles, and preferably 1.0 to 1.2 moles, relative to one mole of the compound of formula [1a].

Examples of the base that can be used may be the same bases as those described with regard to Step 1 of the production method 1. The amount of use of the base may be appropriately selected in the range of 0 to 10 moles, and preferably 1.0 to 1.2 moles, relative to one mole of the compound of formula [1a].

Examples of the solvent that can be used may be the same solvents as those described with regard to Step 1 of the production method 1, and the amount of use of the solvent is 0.01 to 100 L, and preferably 0.1 to 10 L, relative to one mole of the formula [1a].

The reaction temperature may be selected in the range of −20° C. to the boiling point region of the inert solvent used, and it is preferable to carry out the reaction in the temperature range of 0° C. to 100° C.

The reaction time may vary depending on the reaction temperature, reaction substrate, the extent of reaction, and the like; however, the reaction time is usually 10 minutes to 48 hours.

Next, methods for producing the production intermediates of the compound of the present invention will be described.

101
<Intermediate Production Method 1>

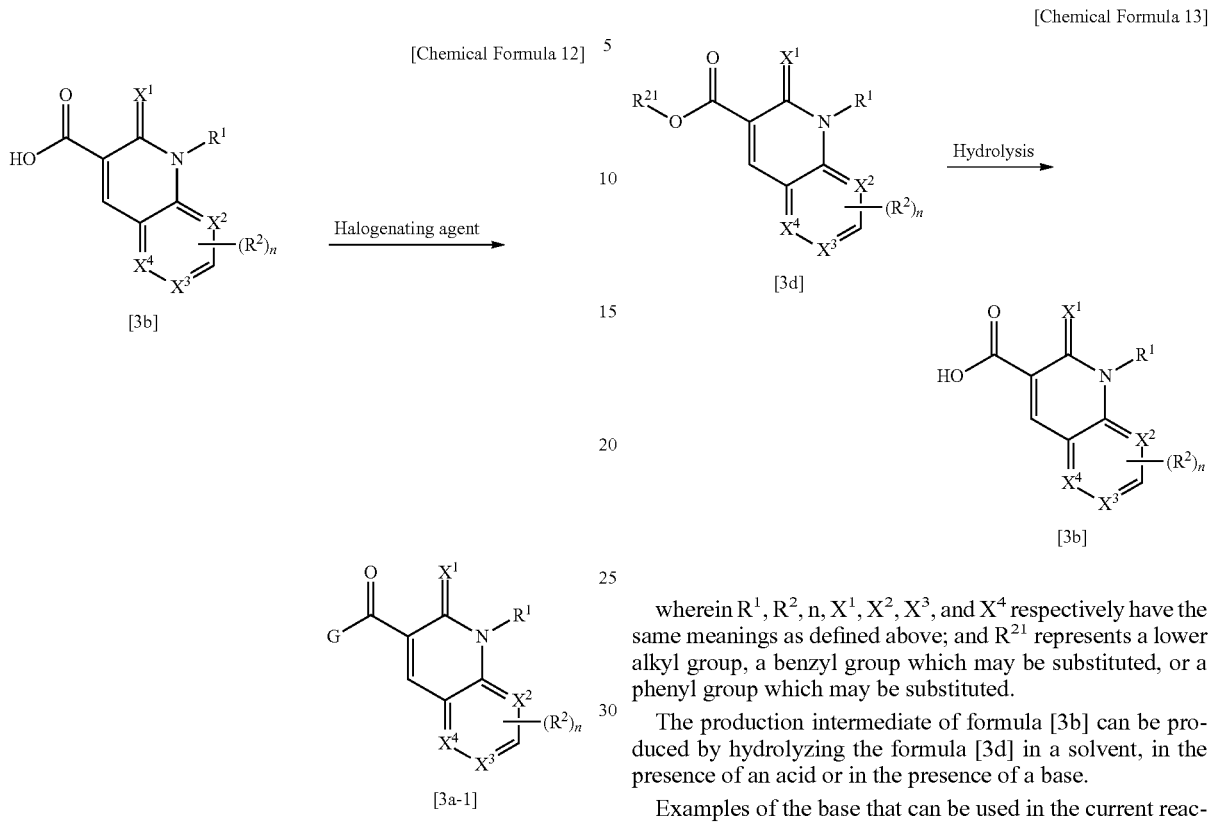

[Chemical Formula 12]

[3b]

[3a-1]

wherein $R^1$, $R^2$, n, $X^1$, $X^2$, $X^3$, $X^4$, and G respectively have the same meanings as defined above.

The formula [3a-1], which is a production intermediate for the compound of the present invention, can be produced by allowing the formula [3b] to react with a halogenating agent in a solvent or without solvent.

Examples of the halogenating agent that can be used in the current reaction include oxalyl chloride and thionyl chloride.

The amount of use of the halogenating agent may be appropriately selected in the range of 0.01 to 100 moles, and preferably 0.1 to 10 moles, relative to one mole of the formula [3b].

Examples of the solvent include halogenated hydrocarbons such as dichloromethane or chloroform; ethers such as diethyl ether or tetrahydrofuran; and aromatic hydrocarbons such as benzene or toluene.

The amount of use of the solvent is 0 to 100 L, and preferably 0.01 to 10 L, relative to one mole of the formula [3b].

The reaction temperature may be selected in the range of −100° C. to 200° C., and it is preferable to carry out the reaction at 0° C. to 100° C.

The reaction time may vary depending on the reaction temperature, reaction substrate, the extent of reaction, and the like; however, the reaction time is usually 10 minutes to 24 hours.

Furthermore, in the current reaction, a catalytic amount of an amide such as DMF (N,N-dimethylformamide) may also be added.

102
<Intermediate Production Method 2>

[Chemical Formula 13]

[3d]

[3b]

wherein $R^1$, $R^2$, n, $X^1$, $X^2$, $X^3$, and $X^4$ respectively have the same meanings as defined above; and $R^{21}$ represents a lower alkyl group, a benzyl group which may be substituted, or a phenyl group which may be substituted.

The production intermediate of formula [3b] can be produced by hydrolyzing the formula [3d] in a solvent, in the presence of an acid or in the presence of a base.

Examples of the base that can be used in the current reaction include inorganic bases such as lithium hydroxide, potassium carbonate, sodium hydride or sodium hydroxide; and organic bases such as 1,8-diazabicyclo[5,4,0]-7-undecene.

The amount of use of the base may be appropriately selected in the range of 0.01 to 100 moles, preferably 0.1 to 10 moles, relative to one mole of the compound [3d].

Examples of the acid that can be used in the current reaction include inorganic acids such as hydrochloric acid, hydrobromic acid, and sulfuric acid; and organic acids such as acetic acid and trifluoroacetic acid.

The amount of use of the acid can be from 1 mole to a large excess, and preferably 1 to 100 moles, relative to one mole of the compound of formula [3d].

The solvent that can be used in the current reaction is water, or a solvent mixture of water and an organic solvent.

Examples of the organic solvent include alcohols such as methanol or ethanol; ethers such as tetrahydrofuran; ketones such as acetone or methyl isobutyl ketone; amides such as N,N-dimethylformamide and N,N-dimethylacetamide; sulfur compounds such as dimethyl sulfoxide or sulfolane; acetonitrile; or mixtures thereof.

The amount of use of the solvent is 0.01 to 100 L, and preferably 0.1 to 10 L, relative to one mole of the formula [3d].

The reaction temperature may be selected in the range of −100° C. to 200° C., and it is preferable to carry out the reaction at 0° C. to 100° C.

The reaction time may vary depending on the reaction temperature, reaction substrate, the extent of reaction, and the like; however, the reaction time is usually 10 minutes to 24 hours.

Intermediate Production Method 3

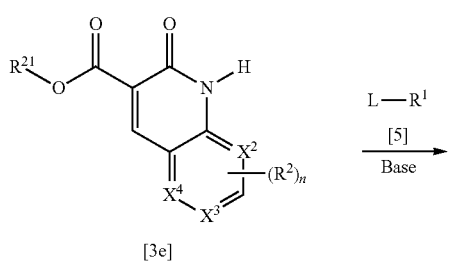

[3e]

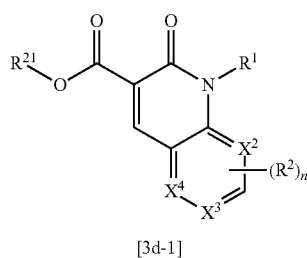

[3d-1]

wherein L represents a leaving group such as a halogen atom, a $C_1$-$C_4$ alkylsulfonyloxy group, a $C_1$-$C_4$ alkylsulfonyl group, a benzylsulfonyl group which may be substituted, a phenylsulfonyl group which may be substituted, a phenylsulfonyloxy group which may be substituted, or a benzylsulfonyloxy group which may be substituted; and $R^1$, $R^2$, $R^{21}$, n, $X^2$, $X^3$, and $X^4$ respectively have the same meanings as defined above; provided that when $R^1$ is a haloalkyl group, L represents a leaving group having higher reactivity than the halogen atom remaining behind after haloalkylation. For example, when $R^1$ is a $CHF_2$ group, L represents a chlorine atom or a bromine atom, and when $R^1$ is a $CH_2CF_3$ group, L represents a leaving group such as a chlorine atom, a bromine atom, a p-toluenesulfonyloxy group, a methylsulfonyloxy group, or a trifluoromethanesulfonyloxy group.

The production intermediate for the formula [3d-1] can be produced by allowing formula [3e] to react with formula [5] in the presence or absence of a base, in a solvent or without solvent.

The amount of use of the formula [5] used in the current reaction may be appropriately selected in the range of 0.01 to 100 moles, and preferably 0.1 to 10 moles, relative to one mole of the formula [3e].

Examples of the base that can be used in the current reaction include alkali metal carbonates such as sodium carbonate or potassium carbonate; alkali metal hydroxides such as sodium hydroxide or potassium hydroxide; alkali metal hydrides such as potassium hydride or sodium hydride; alkali metal alcoholates such as sodium ethoxide or sodium methoxide; or organic bases such as 1,8-diazabicyclo[5,4,0]-7-undecene.

The amount of use of the base that can be used in the current reaction may be appropriately selected in the range of 0 to 100 moles, and preferably 0.1 to 10 moles, relative to one mole of the formula [3e].

Examples of the solvent that can be used in the current reaction include halogenated hydrocarbons such as dichloromethane or chloroform; ethers such as diethyl ether or tetrahydrofuran; aromatic hydrocarbons such as benzene or toluene; aliphatic hydrocarbons such as hexane or heptane; ketones such as acetone or methyl isobutyl ketone; ester such as ethyl acetate or methyl acetate; amides such as N-methylpyrrolidone or N,N-dimethylformamide; sulfur compounds such as dimethyl sulfoxide or sulfolane; nitriles such as acetonitrile; or mixtures thereof.

The amount of use of the solvent that can be used in the current reaction may be appropriately selected in the range of 0 to 100 L, and preferably 0 to 10 L, relative to one mole of the formula [3e].

The reaction temperature of the current reaction may be selected in the range of −100° C. to the boiling point region of the inert solvent used, and it is preferable to carry out the reaction in the temperature range of −20° C. to 100° C.

The reaction time of the current reaction may vary depending on the reaction temperature, reaction substrate, the extent of reaction, and the like; however, the reaction time is usually from 1 hour to 168 hours.

Intermediate Production Method 4

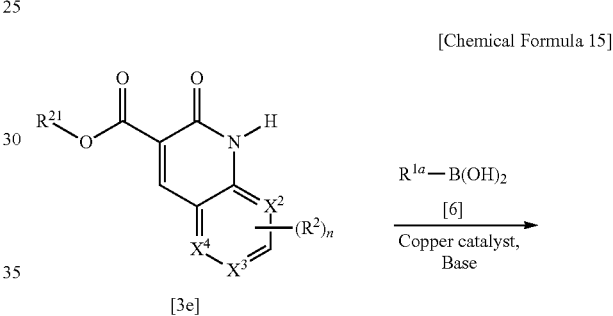

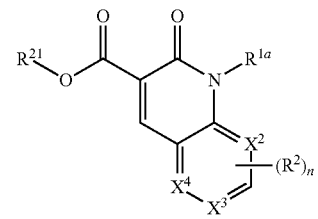

[3d-2]

wherein $R^{1a}$ represents a $C_6$-$C_{10}$ aryl group (this group may be substituted with one $R^4$, or two to five identical or different $R^4$), or a heterocyclic group having 2 to 10 carbon atoms and 1 to 5 heteroatoms selected from an oxygen atom, a sulfur atom, and a nitrogen atom (this group may be substituted with one $R^5$, or two to five identical or different $R^5$); and $R^2$, $R^{21}$, n, $X^2$, $X^3$, and $X^4$ respectively have the same meanings as defined above.

The production intermediate of formula [3d-2] can be produced by allowing the formula [3e] to react with the formula [6] in the presence of a copper catalyst and a base, according to the method described in Tetrahedron, Vol. 55, pp. 12757-12770 (1999).

<Intermediate Production Method 5>

[Chemical Formula 16]

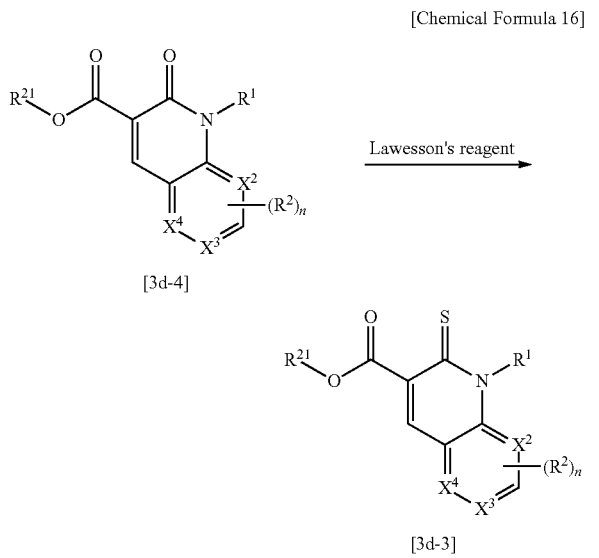

wherein $R^1$, $R^2$, $R^{21}$, n, $X^2$, $X^3$, and $X^4$ respectively have the same meanings as defined above.

The production intermediate of formula [3d-3] can be produced by allowing the compound represented by formula [3d-4] to react with the Lawesson's Reagent, according to the method described in US 2005/256000.

<Intermediate Production Method 6>

[Chemical Formula 17]

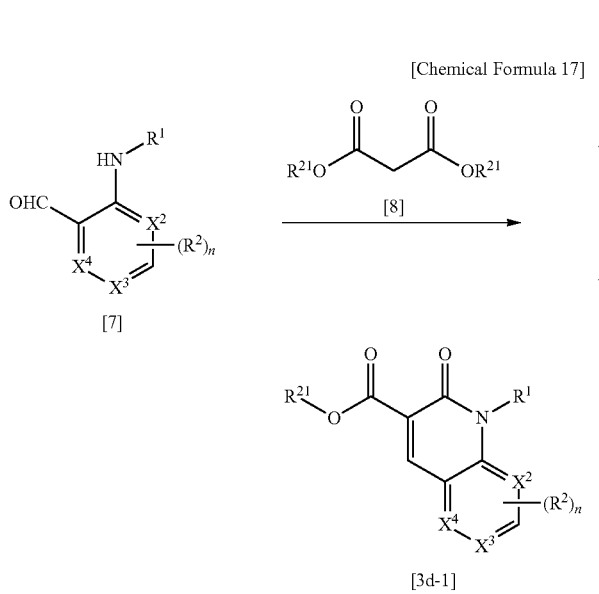

wherein $R^1$, $R^2$, $R^{21}$, n, $X^2$, $X^3$, and $X^4$ respectively have the same meanings as defined above.

The production intermediate of formula [3d-1] can be produced by allowing the formula [7] to react with a malonic acid diester represented by formula [8], according to the methods described in U.S. Pat. No. 6,562,811, WO 2007/53131, and Journal of the Organic Chemistry, Vol. 58, pp. 6625-6628 (1993).

<Intermediate Production Method 7>

[Chemical Formula 18]

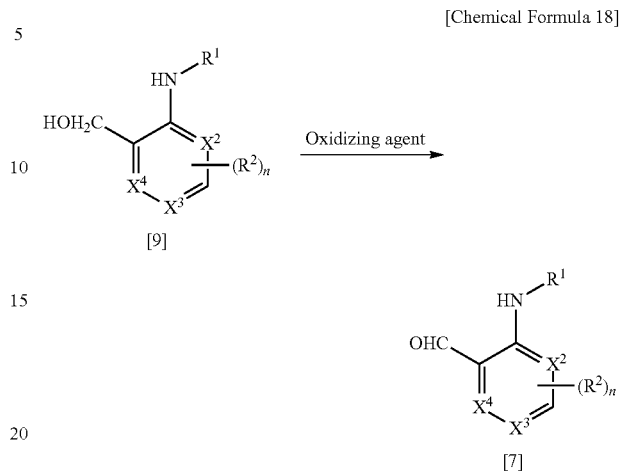

wherein $R^1$, $R^2$, n, $X^2$, $X^3$, and $X^4$ respectively have the same meanings as defined above.

The formula [7] can be produced by oxidizing an alcohol compound represented by formula [9], according to the descriptions in the Lectures on Experimental Chemistry, 4$^{th}$ Edition, Vol. 23, p. 21, "Section on Oxidation by Activated Manganese Dioxide", published by Maruzen Co., Ltd.

<Intermediate Production Method 8>

[Chemical Formula 19]

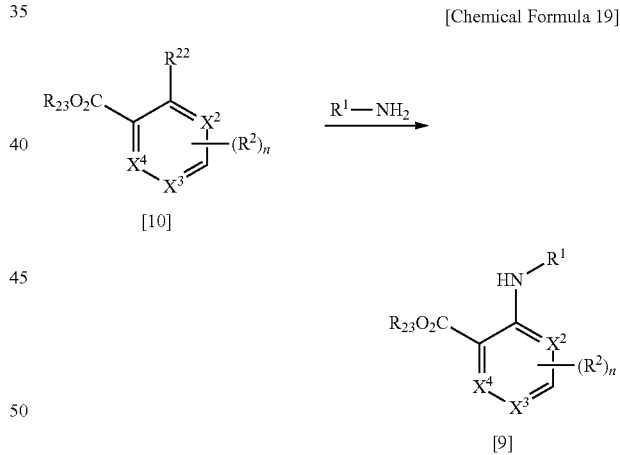

wherein $R^1$, $R^2$, n, $X^2$, $X^3$, and $X^4$ respectively have the same meanings as defined above; $R^{22}$ represents a halogen atom such as a fluorine atom, a chlorine atom or a bromine atom, or a leaving group such as a trifluoromethanesulfonyloxy group, a methanesulfonyloxy group, or a para-toluenesulfonyloxy group; and $R^{23}$ represents a hydrogen atom or a $C_1$-$C_6$ alkyl group.

The production intermediate of formula [9] can be produced by allowing the formula [10] to react with $R^1$—$NH_2$ according to the methods described in WO 2004/20414; US 2008/176827; Journal of Medicinal Chemistry, Vol. 31, pp. 2108-2121 (1988); Journal of Medicinal Chemistry, Vol. 48, No. 12, pp. 4100-4110 (2005); and the like.

107

<Intermediate Production Method 9>

[Chemical Formula 20]

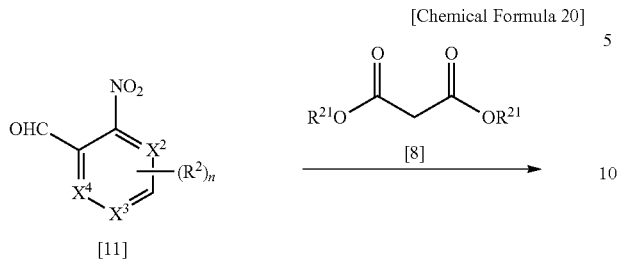

[11]

[12]

[3e]

wherein $R^2$, $R^{21}$, n, $X^2$, $X^3$, and $X^4$ respectively have the same meanings as defined above.

The production intermediate of formula [3e] can be produced by the steps shown above.

That is, the formula [3e] can be produced by subjecting the formula [12] which is obtained by allowing the formula [11] to react with the formula [8], to a reduction reaction according to the methods described in U.S. Pat. No. 5,571,820; U.S. Pat. No. 5,733,917; Chemical and Pharmaceutical Bulletin, Vol. 48, No. 12, pp. 2003-2008 (2000); and the like.

<Intermediate Production Method 10>

[Chemical Formula 21]

[3d-5]

108

-continued

[3d-6]

[3d-7]

wherein $R^2$, $R^{21}$, $X^2$, $X^3$, and $X^4$ respectively have the same meanings as defined above; $R^{24}$ represents a $C_1$-$C_6$ alkoxy group, a $C_3$-$C_8$ cycloalkyloxy group, a $C_1$-$C_6$ haloalkoxy group, a phenoxy group, a $C_1$-$C_6$ alkylcarbonyloxy group, a $C_1$-$C_6$ alkoxy-$C_1$-$C_6$ alkoxy group, a $C_1$-$C_6$ alkylsulfonyl-$C_1$-$C_6$ alkoxy group, a cyano-$C_1$-$C_6$ alkoxy group, a heterocyclic-$C_1$-$C_6$ alkoxy group in which the heterocyclic moiety has 2 to 10 carbon atoms and 1 to 5 heteroatoms which may be identical or different and are selected from an oxygen atom, a sulfur atom, and a nitrogen atom, or a $C_1$-$C_6$ alkylthio group; $M^{I+}$ represents an alkali metal cation; and $X^5$ represents an oxygen atom or a sulfur atom.

The production intermediate of formula [3d-7] can be produced by the steps shown above.

That is, the formula [3d-6] can be produced by allowing the formula [3d-5] to react with N-bromosuccinimide according to the methods described in EP 1982978 or the like.

The formula [3d-7] can be produced by allowing the formula [3d-6] to react with a compound represented by formula [13] or formula [14] according to the methods described in U.S. Pat. No. 5,155,272; EP 1228067; U.S. Pat. No. 4,058,392; Journal of the Chemical Society Perkin Transactions 1, pp. 781-790 (1987); and the like.

<Intermediate Production Method 11>

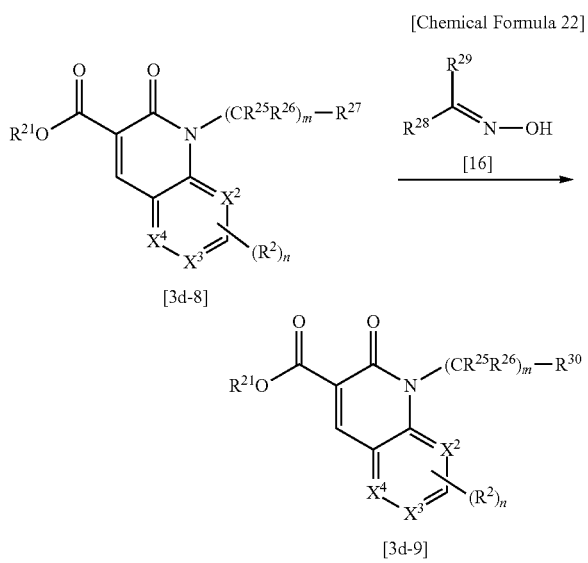

wherein $R^2$, $R^{21}$, $X^2$, $X^3$, $X^4$, and n respectively have the same meanings as defined above; $R^{27}$ represents a group represented by the following formula [17a] or formula [17b]:

$R^{30}$ represents a group represented by the following formula [18a] or [18b]:

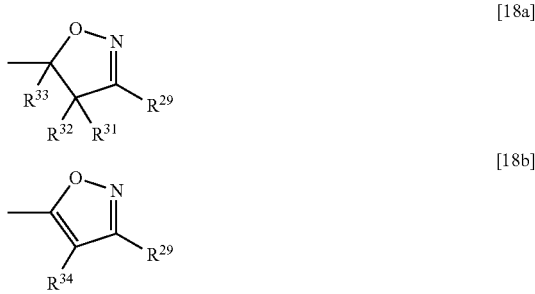

$R^{25}$, $R^{26}$, $R^{31}$, $R^{32}$, $R^{33}$, and $R^{34}$ each independently represent a hydrogen atom, a $C_1$-$C_4$ alkyl group, a $C_1$-$C_4$ alkenyl group, a $C_1$-$C_4$ alkynyl group, a $C_1$-$C_4$ cycloalkyl group, or a $C_1$-$C_4$ haloalkyl group; $R^{29}$ represents a $C_1$-$C_4$ alkyl group, a $C_1$-$C_4$ alkenyl group, a $C_1$-$C_4$ alkynyl group, a $C_1$-$C_4$ alkoxy group, a $C_1$-$C_4$ cycloalkyl group, a $C_1$-$C_4$ haloalkyl group, or a $C_1$-$C_4$ haloalkenyl group; $R^{28}$ represents a halogen atom; m represents an integer from 0 to 6; provided that when $R^{27}$ represents formula [17a], $R^{30}$ represents formula [18a], and when $R^{27}$ represents formula [17b], $R^{30}$ represents formula [18b].

The production intermediate of formula [3d-9] can be produced by allowing the formula [3d-8] to react with the formula [16] according to the methods described in WO 2005/26123; Tetrahedron, Vol. 40, p. 2985 (1984); Synthetic Communications, Vol. 18, p. 1171 (1988); and the like.

The herbicide and the agrochemical composition of the present invention are characterized by containing the 2-pyridone derivative represented by formula [I] of the present invention or an agrochemically acceptable salt thereof as an active ingredient. Furthermore, the present invention relates to an agrochemical composition containing one kind or two or more kinds of the 2-pyridone derivative represented by formula [I] of the present invention or agrochemically acceptable salts thereof, and a carrier acceptable for agrochemical preparations, and more particularly, to a herbicidal composition.

The herbicide of the present invention can contain additive components (carriers) that are conventionally used in agrochemical preparations as necessary.

Examples of these additive components include a carrier such as a solid carrier or a liquid carrier, a surfactant, a binder or a tackifier, a thickening agent, a colorant, an extending agent, a spreading agent, an antifreezing agent, an anticaking agent, a disintegrant, and a degradation preventing agent. In addition to these, an antiseptic, plant pieces, and the like may also be used as the additive components according to necessity.

These additive components may be used singly, or two or more kinds may be used in combination.

The above-described additive components will be discussed.

Examples of the solid carrier include naturally occurring minerals such as quartz, clay, kaolinite, pyrophyllite, sericite, talc, bentonite, acid clay, attapulgite, zeolite, and diatomaceous earth; inorganic salts such as calcium carbonate, ammonium sulfate, sodium sulfate, and potassium chloride; organic solid carriers such as synthetic silicic acid, synthetic silicates, starch, celluloses, and plant powders; and plastic carriers such as polyethylene, polypropylene, and polyvinylidene chloride. These may be used singly, or two or more kinds may be used in combination.

Examples of the liquid carrier include alcohols which are roughly classified into monohydric alcohols such as methanol, ethanol, propanol, isopropanol, and butanol; and polyhydric alcohols such as ethylene glycol, diethylene glycol, propylene glycol, hexylene glycol, polyethylene glycol, polypropylene glycol, and glycerin; polyhydric alcohol derivatives such as propylene-based glycol ethers; ketones such as acetone, methyl ethyl ketone, methyl isobutyl ketone, diisobutyl ketone, cyclohexanone, and isophorone; ethers such as ethyl ether, dioxane, cellosolve, dipropyl ether, and tetrahydrofuran; aliphatic hydrocarbons such as normal paraffin, naphthene, isoparaffin, kerosene, and mineral oil; aromatic hydrocarbons such as benzene, toluene, xylene, solvent naphtha, and alkylnaphthalene; halogenated hydrocarbons such as dichloroethane, chloroform, and tetrachlorocarbon; esters such as ethyl acetate, diisopropyl phthalate, dibutyl phthalate, dioctyl phthalate, and dimethyl adipate; lactones such as γ-butyrolactone; amides such as dimethylformamide, diethylformamide, dimethylacetamide, and N-alkylpyrrolidinone; nitriles such as acetonitrile; sulfur compounds such as dimethyl sulfoxide; plant oils such as soybean oil, rapeseed oil, cotton seed oil, and castor oil; and water. These may be used singly, or two or more kinds may be used in combination.

There are no particular limitations on the surfactant, but a preferred surfactant is a surfactant which gelates or exhibits swellability in water. Examples thereof include nonionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene alkyl ethers, polyoxyethylene alkyl phenyl ethers, polyoxyethylene dialkylphenyl ethers, polyoxyethylene alkyl phenyl ether-formalin condensates, polyoxyethylene-polyoxypropylene block polymers, alkyl polyoxyethylene-polypropylene block polymer ethers, polyoxyethylene alkylamines, polyoxyethylene fatty acid amides, polyoxyethylene fatty acid bisphenyl ethers, polyalkylene benzyl phenyl ethers, polyoxyalkylene styryl phenyl ethers, acetylenediol, polyoxyalkylene-added acetylenediol, polyoxyethylene ether type silicones, ester type silicones, fluorine-based surfactants, polyoxyethylene castor oil, and polyoxyethylene hydrogenated castor oil; anionic surfactants such as alkyl sulfates, polyoxyethylene alkyl ether sulfates, polyoxyethylene alkyl phenyl ether sulfates, polyoxyethylene styryl phenyl ether sulfates, alkyl benzenesulfonates, lignin sulfonates, alkyl sulfosuccinates, naphthalenesulfonates, alkyl naphthalenesulfonates, salts of naphthalenesulfonic acid-formalin condensate, salts of alkyl naphthalenesulfonic acid-formalin condensate, fatty acid salts, polycarboxylic acid salts, N-methyl-fatty acid sarcosinate, resin acid salts, polyoxyethylene alkyl ether phosphates, and polyoxyethylene alkyl phenyl ether phosphates; cationic surfactants such as alkylamine salts such as laurylamine hydrochlorides, stearylamine hydrochlorides, oleylamine hydrochlorides, stearylamine acetates, stearylaminopropylamine acetates, alkyltrimethylammonium chlorides, and alkyldimethylbenzalkonium chlorides; and amphoteric surfactants such as amino acid type or betaine type surfactants.

These surfactants may be used singly, or two or more kinds may be used in combination.

Furthermore, examples of the binder or tackifier include carboxymethylcellulose or salts thereof, dextrin, water-soluble starch, xanthan gum, guar gum, sucrose, polyvinylpyrrolidone, gum arabic, polyvinyl alcohol, polyvinyl acetate, sodium polyacrylate, polyethylene glycol having an average molecular weight of 6,000 to 20,000, polyethylene oxide having an average molecular weight of 100,000 to 5,000,000, and naturally occurring phospholipids (for example, cephalic acid and lecithin).

Examples of the thickening agent include water-soluble polymers such as xanthan gum, guar gum, carboxymethylcellulose, polyvinylpyrrolidone, carboxyvinyl polymers, acrylic polymers, starch derivatives, and polysaccharides; and inorganic fine powders such as high purity bentonite and white carbon.

Examples of the colorant include inorganic pigments such as iron oxide, titanium oxide, and Prussian Blue; and organic dyes such as alizarin dyes, azo dyes, and metal phthalocyanine dyes.

Examples of the extending agent include silicone-based surfactants, cellulose powders, dextrin, processed starch, polyaminocarboxylic acid chelate compounds, crosslinked polyvinylpyrrolidone, maleic acid and styrenes, methacrylic acid copolymers, half esters composed of a polyhydric alcohol polymer and a dicarboxylic acid anhydride, and water-soluble salts of polystyrenesulfonic acid.

Examples of the spreading agent include various surfactants such as sodium dialkylsulfosuccinate, polyoxyethylene alkyl ethers, polyoxyethylene alkyl phenyl ethers, and polyoxyethylene fatty acid esters; paraffins, terpenes, polyamide resins, polyacrylates, polyoxyethylene, waxes, polyvinyl alkyl ethers, alkylphenol-formalin condensates, and synthetic resin emulsions.

Examples of the antifreezing agent include polyhydric alcohols such as ethylene glycol, diethylene glycol, propylene glycol, and glycerin.

Examples of the anticaking agent include polysaccharides such as starch, alginic acid, mannose, and galactose; polyvinylpyrrolidone, white carbon, ester gums, and petroleum resins.

Examples of the disintegrant include sodium tripolyphosphate, sodium hexametaphosphate, stearic acid metal salts, cellulose powders, dextrin, copolymers of methacrylic acid esters, polyvinylpyrrolidone, polyaminocarboxylic acid chelate compounds, sulfonated styrene-isobutylene-maleic anhydride copolymers, and starch-polyacrylonitrile graft copolymers.

Examples of the degradation preventing agent include drying agents such as zeolites, quicklime, and magnesium oxide; antioxidants of phenol type, amine type, sulfur type, and phosphoric acid type; and ultraviolet absorbers of salicylic acid type, and benzophenone type.

Examples of the antiseptic include potassium sorbate, and 1,2-benzothiazolin-3-one.

Examples of the plant pieces include sawdust, coconut shell, corncob, tobacco stalk, and kenaf stalks.

In the case of incorporating the additive components into the herbicide of the present invention, the content ratio is selected usually in the range of 5% to 95%, and preferably 20% to 90%, for the carrier; usually in the range of 0.1% to 30%, and preferably 0.5% to 10%, for the surfactant; and usually in the range of 0.1% to 30%, and preferably 0.5% to 10%, for the other additives, all on a mass basis.

The herbicide of the present invention is used after being formulated into any formulation, such as a liquid formulation, an emulsifiable concentrate, a wettable powder formulation, a dust formulation, an oil formulation, a water-dispersible granule formulation, a flowable formulation, a granule formulation, a jumbo formulation, a suspoemulsion or a Mametsubu (registered trademark) formulation.

At the time of this formulation, the herbicide can be prepared into a mixed composition with at least one selected from agrochemicals such as other herbicides, insecticides, bactericides and plant growth regulators, as well as a safener, a fertilizer, and the like.

These formulations may be diluted to an appropriate concentration and sprayed, or may be directly applied.

At the time of use, the 2-pyridone derivative represented by formula [I] of the present invention or an agrochemically acceptable salt thereof can be used alone as an active ingredient.

Furthermore, at the time of use, the 2-pyridone derivative or an agrochemically acceptable salt thereof may also be used in mixture or in combination with at least one selected from agrochemicals such as other herbicides, insecticides, bactericides and plant growth regulators, as well as a safener, a fertilizer, and the like.

Examples of known herbicidal compounds and plant growth regulators which may be used in mixture or in combination will be listed below:

quinoclamine, 2,3,6-TBA, 2,4-D (including salts with amine, diethylamine, triethanolamine, isopropylamine, sodium, lithium, and the like), 2,4-DB, DNOC (including salts with amine, sodium, and the like), EPTC, HOK-201, MCPA, MCPA-thioethyl, MCPB, S-metolachlor, TCA (including salts with sodium, calcium, ammonia, and the like), TH-547 (Code No.), ioxynil (Ioxynil-octanoate), aclonifen, acrolein, azafenidin, acifluorfen-sodium, azimsulfuron, asulam, acetochlor, atrazine, anilofos, amicarbazone, amidosulfuron, amitrole, aminopyralid, aminocyclopyrachlor, ametryn, alachlor, alloxydim, isouron, isoxaflutole, isoxaben, isoproturon, ipfencarbazone, imazaquin, imazapic (including salts with amine and the like), imazapyr (including salts with isopropylamine and the like), imazamethabenz-methyl, imazamox (including salts with amine salts and the like), imazethapyr (including salts with amine salts and the like), imazosulfuron, indanofan, esprocarb, ethametsulfuron-methyl, ethaifluralin, ethoxysulfuron, ethoxyfen-ethyl, ethofumesate, etobenzanid, oxadiazon, oxadiargyl, oxaziclomefone, oxasulfuron, oxyfluorfen, oryzalin, orthosulfamuron, orbencarb, cafenstrole, carfentrazone-ethyl, karbutilate, carbetamide, quizalofop-ethyl, quizalofop-P-ethyl, quizalofop-P-tefuryl, quinclorac, quinmerac, cumyluron, glyphosate (including salts with sodium, potassium, amine, propylamine, isopropylamine, dimethylamine, trimesium, and the like), glufosinate (including salts with amine, sodium, and the like), clethodim, clodinafop-propargyl, clopyralid, clomazone, clomeprop, cloransulam-methyl, chloridazon, chlorimuron-ethyl, chlorsulfuron, chlorthal-dimethyl, chlorthiamid, chlorphthalim, chlorflurenol (including lower alkyl esters), chlorpropham, chlorotoluron, cyanazine, cyanamide, diuron, dicamba (including salts with amine, diethylamine, isopropylamine, diglycolamine, sodium, lithium, and the like), cycloate, cycloxydim, diclosulam, cyclosulfamuron, dichlobenil, diclofop-P-methyl, diclofop-methyl, dichlorprop, dichlorprop-P, diquat (-dibromide), dithiopyr, siduron, dinitramine, cinidon-ethyl, cinosulfuron, dinoterb, cyhalofop-butyl, diphenamid, difenzoquat, diflufenican, diflufenzopyr, simazine, dimethachlor, dimethametryn, dimethenamid, simetryn, dimepiperate, dimefuron, cinmethylin, sulcotrione, sulfentrazone, sulfosulfuron, sulfometuron-methyl, sethoxydim, terbacil, daimuron, dalapon, thiazopyr, thiencarbazone, thiobencarb, thidiazimin, thifensulfuron-methyl, desmedipham, thenylchlor, tebuthiuron, tepraloxydim, tefuryltrione, terbuthylazine, terbutryn, terbumeton, tembotrione, topramezone, tralkoxydim, triaziflam, triasulfuron, tri-allate, trietazine, triclopyr (-butotyl), tritosulfuron, triflusulfuron-methyl, trifluralin, trifloxysulfuron sodium, tribenuron-methyl, naptalam (including salts with sodium and the like), napropamide, nicosulfuron, neburon, norflurazon, paraquat dichloride, haloxyfop-methyl, haloxyfop-P-methyl, halosulfuron-methyl, picloram, picolinafen, bispyribac sodium, pinoxaden, bifenox, piperophos, pyraclonil, pyrasulfotole, pyrazoxyfen, pyrazosulfuron-ethyl, pyrazolynate, bilanafos-sodium, pyraflufen-ethyl, pyridafol, pyrithiobac sodium, pyridate, pyriftalid, pyributicarb, pyribenzoxim, pyrimisulfan, pyriminobac-methyl, pyroxasulfone, pyroxsulam, fenoxaprop-P-ethyl, fentrazamide, phenmedipham, foramsulfuron, butachlor, butafenacil, butamifos, butylate, butralin, butroxydim, flazasulfuron, flamprop-methyl, flamprop-M-methyl, flamprop-ethyl, flamprop-isopropyl, flamprop-M-isopropyl, primisulfuron-methyl, fluazifop-butyl, fluazifop-P-butyl, fluometuron, fluoroglycofen-ethyl, flucarbazone sodium, flucetosulfuron, fluthiacet-methyl, flupyrsulfuron-methyl-sodium, flufenacet, flufenpyr-ethyl, flupropanate sodium, flupoxam, flumioxazin, flumiclorac-pentyl, flumetsulam, fluridone, flurtamone, fluoroxypyr, fluorochloridone, pretilachlor, prodiamine, prosulfuron, prosulfocarb, propaquizafop, propachlor, propazine, propanil, propyzamide, propisochlor, propham, propoxycarbazone sodium, profoxydim, bromacil, prometryn, prometon, bromoxynil (including esters with butyric acid, octanoic acid, heptanoic acid, and the like), bromobutide, florasulam, hexazinone, pethoxamid, benazolin, penoxsulam, beflubutamid, pebulate, bencarbazone, pendimethalin, benzfendizone, bensulide, bensulfuron-methyl, benzobicyclon, benzofenap, bentazone (including salts with sodium and the like), pentanochlor, pentoxazone, benfluralin, benfuresate, fosamine-ammonium, fomesafen, mecoprop-potassium, mecoprop-P potassium, mesosulfuron-methyl, mesotrione, metazachlor, methabenzthiazuron, metamitron, metamifop, methyldymron, metoxuron, metosulam, metsulfuron-methyl, metolachlor, metribuzin, mefenacet, monolinuron, molinate, iodosulfulon-methyl sodium, lactofen, linuron, rimsulfuron, lenacil, saflufenacil, amiprofos-methyl, ancymidol, isoxachlortole, ethidimuron, chlomethoxyfen, chloramben, chlorbromuron, chloroxuron, tiocarbazil, desmetryne, tebutam, naproanilide, vernolate, fenuron, fluazolate, profluazol, metobromuron, metobenzuron, AE-F-150944 (Code No.), SYP-298 (Code No.), SYP-300 (Code No.), NC-620 (Code No.), α-naphthalene acetamide, 1-methylcyclopropene, 2,6-d iisopropylnaphthalene, 4-CPA, aviglycine, ancymidol, inabenfide, indole acetic acid, indole butyric acid, uniconazole, uniconazole-P, ethychlozate, ethephon, carvone, cloxyfonac-sodium, cloxyfonac potassium, cloprop, chlormequat, cytokinins, cyclanilide, dikegulac, gibberellic acid, dimethipin, sintofen, daminozide, thidiazuron, n-decanol, 1-triacontanol, trinexapac-ethyl, paclobutrazol, flumetralin, flurprimidol, flurenol, prohydrojasmon, prohexadione calcium, (6-) benzylaminopurine, forchlorfenuron, maleic hydrazide, mepiquat chloride, mefluidide, meptyldinocap, indaziflam, propyrisulfuron, methiozolin, xazasulfuron (dioxasulfuron), bicyclopyrone, metazosulfuron, heptamaloxyloglucan, EL101GV (Code No.), dimethyl disulfide, and an isoxazoline derivative represented by the following formula [C]:

[Chemical Formula 25]

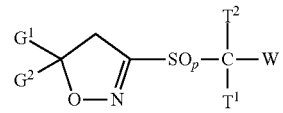

[C]

wherein p represents an integer from 0 to 2; $T^1$ and $T^2$ each independently represent a hydrogen atom, a halogen atom, a cyano group, a $C_1$-$C_6$ alkoxycarbonyl group, or a $C_1$-$C_6$ alkyl group; $G^1$ and $G^2$ each independently represent a hydrogen atom, a $C_1$-$C_6$ alkyl group, or a $C_1$-$C_6$ haloalkyl group; W represents a phenyl group (which is substituted with one to five identical or different V); and V represents a hydrogen atom, a $C_1$-$C_6$ alkyl group {which may be substituted with one to three identical or different halogen atoms, a $C_1$-$C_6$ alkoxy group, a hydroxyl group, a $C_1$-$C_6$ alkylthio group, a $C_1$-$C_6$ alkylsulfinyl group, a $C_1$-$C_6$ alkylsulfonyl group, a $C_1$-$C_6$ alkylamino group, a $C_1$-$C_6$ dialkylamino group, a cyano group, or a phenoxy group (which may be substituted) }, a $C_1$-$C_6$ alkoxy group (which may be substituted with one to three identical or different halogen atoms, a $C_1$-$C_6$ alkoxy group, a $C_2$-$C_6$ alkenyl group, a $C_2$-$C_6$ alkynyl group, a $C_1$-$C_6$ alkoxycarbonyl group, a $C_1$-$C_6$ alkylcarbonyl group, or a $C_3$-$C_8$ cycloalkyl group), a $C_3$-$C_8$ cycloalkyloxy group, or a halogen atom.

Examples of known bactericidal compounds which may be used in mixture or in combination will be listed below:

AF-0201 (Code No.), BAG-010 (Code No.), BAF-045 (Code No.), BYF-14182 (Code No.), copper dioctanoate, DBEDC, IKF-309 (Code No.), OK-5203 (Code No.), S-2188 (Code No.), SYP-Z-048 (Code No.), TPTA, TPTC, TPTH, acibenzolar-S-methyl, azoxystrobin, amisulbrom, aldimorph, sulfur, isotianil, isopyrazam, isoprothiolane, ipconazole, iprodione, iprovalicarb, iprobenfos, imazalil, iminoctadine albesilate, iminoctadine triacetate, imibenconazole, edifenphos, ethaboxam, ethoxyquin, etridiazole, enestroburin, epoxiconazole, copper oxychloride, oxadixyl, oxazinylazole, oxycarboxin, oxine-copper, oxytetracycline, oxpoconazole fumarate, oxolinic acid, octhilinone, ofurace, orysastrobin, ortho-phenylphenol, kasugamycin, captafol, carpropamid, carbendazim, carboxin, quinoxyfen, chinomethionat, captan, silver, quintozene, guazatine, kresoxim-methyl, chlorothalonil, chloroneb, cuprous oxide, cyazofamid, diethofencarb, diclocymet, dichlofluanid, diclomezine, dicloran, dithianon, diniconazole, zineb, dinocap, diphenyl, diphenylamine, difenoconazole, difenzoquat metilsulfate, cyflufenamid, diflumetorim, cyproconazole, cyprodinil, simeconazole, dimethomorph, cymoxanil, dimoxystrobin, ziram, silthiofam, copper hydroxide, streptomycin, spiroxamine, zoxamide, dazomet, potassium bicarbonate, tiadinil, thiabendazole, thiophanate methyl, thifluzamide, thiram, tecnazene, tecloftalam, tetraconazole, debacarb, tebuconazole, dodine, dodemorph, triadimenol, triadimefon, triazoxide, tricyclazole, triticonazole, tridemorph, triflumizole, trifloxystrobin, triforine, tolylfluanid, tolclofos-methyl, tolnifanide, nabam, nitrothal-isopropyl, nuarimol, validamycin, bixafen, picoxystrobin, bitertanol, piperalin, hymexazol, pyraclostrobin, pyrazophos, pyrifenox, pyributicarb, pyribencarb, pyrimethanil, pyroquilon, vinclozolin, ferbam, famoxadone, fenamidone, fenarimol, fenoxanil, ferimzone, fenbuconazole, fenfuram, fenpropidin, fenpropimorph, fenhexamid, folpet, phthalide, bupirimate, fuberidazole, furametpyr, furalaxyl, fluazinam, fluoxastrobin, fluopicolide, fluopyram, fluoroimide, fluquinconazole, fludioxonil, flusilazole, flusulfamide, flutolanil, flutriafol, flumorph, proquinazid, prochloraz, procymidone, prothioconazole, bronopol, propamocarb hydrochloride, propiconazole, propineb, probenazole, bromuconazole, hexaconazole, benalaxyl, benalaxyl-M, benomyl, pefurazoate, penconazole, pencycuron, benthiavalicarb-isopropyl, penthiopyrad, boscalid, fosetyl-aluminium, polyoxin, polycarbamate, Bordeaux mixture, mancopper, mancozeb, mandipropamid, maneb, myclobutanil, mildiomycin, methasulfocarb, metam, metalaxyl, metalaxyl-M, metconazole, metominostrobin, metrafenone, mepanipyrim, mepronil, oxyquinoline sulfate, copper sulfate, sedaxane, penflufen, trimetopyr (erysicos), fenpyrazamine (ipfenpyrazolone), valifenalate, tebufloquin, pyrametostrobin, ametoctradin, fluxapyroxad, pyroxazole, pyrisoxazole, pyraromaxazole, chlorodincarbamate, copper (nonylphenyl) sulfonate, dimethyl disufide, and silver nitrate.

Examples of known insecticidal and nematocidal compounds which may be used in mixture or in combination will be listed below:

1,3-dichloropropene, CL900167 (Code No.), cryolite, DCIP, DNOC, EPN, RU15525 (Code No.), XMC, ZXI8901 (Code No.), acrinathrin, azamethiphos, azinphos-ethyl, azinphos-methyl, acequinocyl acetamiprid, acetoprol, acephate, azocyclotin, abamectin, amitraz, alanycarb, aldicarb, alpha-cypermethrin, allethrin, isoxathion, isofenphos-methyl, isocarbophos, isoprocarb, imicyafos, imidacloprid, imiprothrin, indoxacarb, esfenvalerate, ethiofencarb, ethion, ethiprole, etoxazole, etofenprox, ethoprophos, emamectin, endosulfan, empenthrin, oxamyl, oxydemeton-methyl, omethoate, cadusafos, karanjin, cartap, carbaryl, carbosulfan, carbofuran, gamma-cyhalothrin, xylylcarb, quinalphos, kinoprene, chinomethionat, coumaphos, clothianidin, clofentezine, chromafenozide, chlorantraniliprole, chlorethoxyfos, chlordane, chloropicrin, chlorpyrifos, chlorpyrifos-methyl, chlorfenapyr, chlorfenvinphos, chlorfluazuron, chlormephos, cyazypyr, cyanophos, diafenthiuron, dienochlor, cyenopyrafen, dicrotophos, dichlofenthion, cycloprothrin, dichlorvos, dicofol, dicyclanil, disulfoton, dinotefuran, dinobuton, cyhalothrin, cyphenothrin, cyfluthrin, diflubenzuron, cyflumetofen, diflovidazin, cyhexatin, cypermethrin, dimethylvinphos, dimethoate, silafluofen, cyromazine, spinetoram, spinosad, spirodiclofen, spirotetramat, spiromesifen, sulcofuron-sodium, sulflramid, sulfotep, sulfoxaflor (IUPAC name: [methyl(oxo){1-[6-(trifluoromethyl)-3-pyridyl]ethyl}-λ6-sulfanylidene]cyanamide), zeta-cypermethrin, diazinon, tau-fluvalinate, thiacloprid, thiamethoxam, thiodicarb, thiocyclam, thiosultap, thiofanox, thiometon, tetrachlorvinphos, tetradifon, tetramethrin, tebupirimfos, tebufenozide, tebufenpyrad, tefluthrin, teflubenzuron, demeton-S-methyl, temephos, deltamethrin, terbufos, tralomethrin, transfluthrin, triazamate, triazophos, trichlorfon, triflumuron, trimethacarb, tolfenpyrad, naled, nicotine, nitenpyram, novaluron, noviflumuron, hydroprene, vamidothion, parathion, parathion-methyl, halfenprox, halofenozide, bioallethrin, bioresmethrin, bistrifluoron, hydramethylnon, bifenazate, bifenthrin, pymetrozine, pyraclofos, pyridaphenthion, pyridaben, pyridalyl, pyrifluquinazon, pyriproxyfen, pirimicarb, pyrimidifen, pirimiphos-methyl, famphur, fipronil, fenazaquin, fenamiphos, fenitrothion, fenoxycarb, fenothiocarb, phenothrin, fenobucarb, fenthion, phenthoate, fenvalerate, fenpyroximate, fenbutatin oxide, fenpropathrin, butocarboxim, butoxycarboxim, buprofezin, furathiocarb, prallethrin, fluacrypyrim, flucycloxuron, flucythrinate, flusulfamide, fluvalinate, flupyrazofos, flufenerim, flufenoxuron, flubendiamide, flumethrin, flurimfen, prothiofos, flonicamid, propaphos, propargite, profenofos, propetamphos, propoxur, bromopropylate, beta-cyfluthrin, hexythiazox, hexaflumuron, heptenophos, permethrin, bensultap, benzoximate, bendiocarb, benfuracarb, phoxim, phosalone, fosthiazate, phosphamidon, phosmet, formetanate, phorate, malathion, milbemectin, mecarbam, mesulfenfos, methomyl, metaflumizon, methamidophos, metham, methiocarb, methidathion, methyl isothiocyanate, methoxychlor, methoxyfenozide, methothrin, metofluthrin, methoprene, mevinphos, monocrotophos, lambda-cyhalothrin, lufenuron, resmethrin, lepmectin, rotenone, cyantraniliprole, pyrifluquinazone, thiazosulfen, tetramethylfluthlin, meperfluthrin, fluphprole, dicloxystrobin, enaminostrobin, cypropene, and NI-30 (Code No.).

Examples of known safeners which may be used in mixture or in combination will be listed below:

benoxacor, furilazole, dichlormid, dicyclonone, DKA-24 (N1,N2-diallyl-N2-dichloroacetylglycinamide), AD-67 (4-dichloroacetyl-1-oxa-4-azaspiro[4.5]decane), PPG-1292 (2,2-dichloro-N-(1,3-dioxan-2-ylmethyl)-N-(2-propenyl)acetamide), R-29148 (3-dichloroacetyl-2,2,5-trimethyl-1,3-oxazolidine), cloquintcet-mexyl, 1,8-Naphthalic Anhydride), mefenpyr-diethyl, mefenpyr, mefenpyr-ethyl, fenchlorazole O ethyl, fenclorim, MG-191 (2-dichloromethyl-2-methyl-1, 3-dioxane), cyometrinil, flurazole, fluxofenim, isoxadifen, isoxadifen-ethyl, mecoprop, MCPA, daimuron, 2,4-D, MON4660 (Code No.), oxabetrinil, cyprosulfamide, and TI35 (Code No.).

The mixing ratio of the active ingredient in the herbicide of the present invention is appropriately selected according to necessity; however, in the case of a dust formulation, a granule formulation or the like, the mixing ratio may be appropriately selected in the range of 0.01% to 10% by weight, and preferably 0.05% to 5% by weight. In the case of an emulsifiableconcentrate, a wettable powder formulation and the like, the mixing ratio may be appropriately selected in the range of 1% to 50% by weight, and preferably 5% to 30% by weight. In the case of a flowable formulation and the like, the mixing ratio may be appropriately selected in the range of 1% to 40% by weight, and preferably 5% to 30% by weight.

The amount of application of the herbicide of the present invention may vary depending on the type of the compound used, weed to be treated, tendency of occurrence, environmental conditions, formulation used, and the like. However, in the case of using the herbicide as received such as in the form of a dust formulation or a granule formulation, the amount of application may be appropriately selected in the range of 1 g to 50 kg, and preferably 10 g to 10 kg, in terms of the active ingredient per hectare. In the case of using the herbicide in the liquid state such as in the form of an emulsifiable concentrate, a wettable powder formulation, or a flowable formulation, the amount of application may be appropriately selected in the range of 0.1 to 50,000 ppm, and preferably 10 to 10,000 ppm.

The herbicide of the present invention can be put to use by means of foliar application, soil application, or submerged application, to farmlands, paddy fields, orchards, and the like. The herbicide of the present invention can also be used for the purpose of controlling general weeds in fallow fields, ridges between rice fields, farm roads, drainage ditches, reclaimed pastures, burial grounds, parklands, streets, playgrounds, vacant lots around buildings, reclaimed lands, track ends, forests, and the like. Furthermore, the herbicide of the present invention can also be used on seeds or tubers of useful crops, after being treated by coating, powder coating, film-forming, or immersion.

The herbicide of the present invention exhibits excellent herbicidal effects on a variety of weeds that cause problems in farmlands, for example, *Persicaria* spp. such as *Polygonum lapathifolium, Polygonum longisetum* DeBruyn, and *Rumex japonicus* Houtt.; *Amaranthus* spp. such as *Amaranthus viridis* L., *Amaranthus palmeri* S. Wats., and *Amaranthus retroflexus*; broad leaf weeds such as *Solanum carolinense* L., *Solanum nigrum* L., *Chenopodium album* L., *Abutilon theophrasti medicus, Sida spinosa* L., *Sesbania exaltata* Cory, *Ambrosia* elatior L., *Papaver rhoeas* L., *Ipomoea* spp., *Xanthium strumarium* L., *Stellaria media* Villars, *Matricaria chamomilla* L, *Matricaria inodora* L., *Kochia scoparia, Anthemis cotula, Ambrosia trifida* L, *Commelina communis* L., *Galium spurium* L. var. *echinospermon Hayek, Viola mandshurica, Veronica persica* Poiret, *Veronica hederifolia* L., *Lamium amplexicaule* L., *Vicia angustifolia* L., *Senecio vulgaris* L., *Capsella Bursa-pastoris* (L.) medic, *Salsola tragus* L., *Maireana sedifolia, Lamium purpureum* L., and *-Breea setosum*; perennial or annual cyperaceous weeds such as *Cyperus rotundus* L., *Cyperus esculentus* L., *Cyperus brevifolius* Hassk. var. *leiolepis* T. Koyama, *Cyperus microiria* Steud., and *Cyperus iria*; and graminaceous weeds such as *Echinochloa esculenta* (A. Braun) H. Scholz, *Digitaria ciliaris* (Retz.) Koel., *Setaria viridis* (L.) P. Beauv., *Poa annua* L., *Alopecurus aequalis* Sobol. var. *amurensis* Ohwi, *Sorghum halepense* Pers., *Alopecurus myosuroides* Huds., *Lolium multiflorum* Lamarck., *Avena sativa* L., and *Urochloa platyphylla* Munro ex C. Wright, over a wide range of from pre-emergence to the growing period. The herbicide of the present invention can also control weeds growing in paddy fields, for example, annual weeds such as *Echinochloa oryzicola* Vasing, *Echinochloa crus-galli* (L.) P. Beauv. var. *crus-galli, Urochloa platyphylla* Munro ex C. Wright, *Cyperus difformis* L., *Leptochloa chinensis* (L.) Nees, *Monochoria vaginalis* (Burm. f.) Presl var. *plantaginea* (Roxb.) Solms-Laub., *Lindernia* dubia (L.) Pennell, *Lindernia procumbens* (Krock.) Philcox., *Rotala indica* (Willd.) Koehne var. *uliginosa* (Miq.) Koehne, *Vandellia angustifolia* Benth., *Limnophila sessiliflora, Ammannia multiflora* Roxb., *Elatine triandra* Schk. var. *pedicellata* Krylov., *Monochoria korsakowii* Regel et Maack, *Ludwigia prostrata* Roxb., *Eclipta prostrata* L., *Bidens frondosa* L., *Aeschynomene indica* L., and *Murdannia keisak* Hand-Mazz.; cyperaceous weeds such as *Sagittaria pygmaea* Miq., *Sagittaria triflolia* L., *Cyperus serotinus* Rottb., *Eleocharis kuroguwai* Ohwi, *Scirpus juncoides* Roxb., *Scirpus juncoides* var. *ohwianus*, and *Scirpus wallichii* Nees; and perennial weeds such as *Alisma canaliculatum* A. Br. et Bouche, *Schoenoplectus nipponicus* (Makino) Sojak, *Scirpus maritimus* L., *Potamogeton distinctus* A. Bennett, *Leersia japonica* Makino, *Paspalum distichum* L., *Leersia oryzoides* (L.) Swartz, *Eleocharis acicularis* Roem. et Schult. var. *longiseta* Svenson, and *Isachne g*lobosa* (Thunb.) Kuntze.

Furthermore, the herbicide of the present invention is highly safe for useful plants and useful crops, and exhibits high safety for, for example, crops such as rice, wheat, barley, common oat, rye, foxtail millet, common millet, corn, and grain sorghum; soybean, cotton, sugar beet, sugarcane, onion, sunflower, rapeseed, peanut, flax, tobacco, coffee, sweet potato, potato, tomato, and other vegetables, as well as turf and the like.

The useful crops and useful plants as used herein also include so-called genetically modified crops and breedings of corn, soybean, cotton, rapeseed, sugarcane, and the like, which have been transformed by genetic engineering technologies to exhibit resistance to herbicides, pests, diseases, or the like; and plants exhibiting resistance to herbicides, pests, diseases, and the like through screening.

Hereinafter, the method for producing the compound of formula [I] of the present invention, production examples, and uses of the compound will be described in detail by way of the following Examples; however, the present invention is not intended to be limited to these Examples.

Furthermore, in the following descriptions, "percent (%)" indicates percentage by mass, and the unit "parts" indicates parts by mass.

Example 1

Production of 3-(2-hydroxy-6-oxo-1-cyclohexenecarbonyl)-1-methylquinolin-2(1H)-one (Compound of present invention No.: I-2)

(1) Production of 3-oxo-1-cyclohexenyl 1-methyl-2-oxo-1,2-dihydroquinoline-3-carboxylate 0.76 g (3.7 mmol) of 1-methyl-2-oxo-1,2-dihydroquinoline-3-carboxylic acid was dissolved in dichloromethane (50 mL), and 1.0 mL (12 mmol) of oxalyl chloride was added to the above solution. Two droplets of N,N-dimethylformamide were added to this mixture, and the resulting mixture was stirred for 1 hour at 40° C. The reaction solution was concentrated under reduced pressure, and thus 1-methyl-2-oxo-1,2-dihydroquinoline-3-carboxylic acid chloride was obtained. The acid chloride thus obtained was dissolved in acetonitrile (30 mL), and this solution was added to an acetonitrile (50 mL) solution of 0.46 g (4.1 mmol) of 1,3-cyclohexanedione and 0.63 mL (4.5 mmol) of triethylamine under ice cooling. The mixture was stirred overnight at room temperature. This reaction mixture was poured into water and was extracted with ethyl acetate. The organic phase was washed with water, an aqueous solution of sodium hydrogen carbonate, and water in this order, and then was dried and concentrated. The residue was purified by column chromatography (ethyl acetate: n-hexane=1:4 to 1:0), and thus 0.48 g (yield: 43%) of the title compound was obtained as a pale yellow powder.

$^1$H-NMR data (CDCl$_3$/TMS δ (ppm)):
2.10-2.16 (2H, m), 2.47 (2H, t), 2.73 (2H, t), 3.77 (3H, s), 6.04 (1H, s), 7.32 (1H, t), 7.40 (1H, d), 7.70-7.75 (1H, m), 8.53 (1H, s)

(2) Production of 3-(2-hydroxy-6-oxo-1-cyclohexenecarbonyl)-1-methylquinolin-2(1H)-one 0.48 g (1.6 mmol) of 3-oxo-1-cyclohexenyl 1-methyl-2-oxo-1,2-dihydroquinolin-3-carboxylate was dissolved in acetonitrile (40 mL), and 0.25 mL (1.8 mmol) of triethylamine and 0.15 g (1.8 mmol) of acetone cyanohydrin were added to the solution. The resulting mixture was stirred for one whole day and night at room temperature. The reaction mixture was poured into a saturated aqueous solution of sodium hydrogen carbonate, and the mixture was washed with ethyl acetate. Citric acid was added to the aqueous phase to adjust the aqueous phase to pH 3 to 4, and the reaction mixture was extracted with ethyl acetate. The organic phase was washed with water, dried, and concentrated. Diisopropyl ether was added to the residue to perform crystallization, and the crystals were further washed with diisopropyl ether. Thus, 0.24 g (yield: 50%) of the title compound was obtained as a yellow powder.

$^1$H-NMR data (CDCl$_3$/TMS δ (ppm)):
2.03-2.11 (2H, m), 2.49 (2H, t), 2.74 (2H, t), 3.70 (3H, s), 7.24 (1H, t), 7.36 (1H, d), 7.58-7.62 (1H, m), 7.77 (1H, s), 16.6 (1H, s)

Example 2

Production of 3-(2-hydroxy-6-oxo-1-cyclohexenecarbonyl)-1-methyl-1,8-naphthyridin-2(1H)-one (Compound of present invention No.: II-2)

(1) Production of 3-oxo-1-cyclohexenyl 1-methyl-2-oxo-1,2-dihydro-1,8-naphthyridin-3-carboxylate 1.0 g (4.9 mmol) of 1-methyl-2-oxo-1,2-dihydro-1,8-naphthyridin-3-carboxylic acid was dissolved in dichloromethane (50 mL), and 1.0 mL (12 mmol) of oxalyl chloride was added thereto. Three droplets of N,N-dimethylformamide were added to the above mixture, and the resulting mixture was stirred for one hour at 40° C. The reaction solution was concentrated under reduced pressure, and thus 1-methyl-2-oxo-1,2-dihydro-1,8-naphthyridin-3-carboxylic acid chloride was obtained. The acid chloride thus obtained was dissolved in acetonitrile (30 mL), and this solution was added to an acetonitrile (50 mL) solution of 0.60 g (5.4 mmol) of 1,3-cyclohexanedione and 0.82 mL (5.9 mmol) of triethylamine under ice cooling. The resulting mixture was stirred for one hour at room temperature. The reaction mixture was poured into water, and the mixture was extracted with ethyl acetate. The organic phase was washed with water, an aqueous solution of sodium hydrogen carbonate, and water in this order, and then was dried and concentrated. The residue was washed with diisopropyl ether, and thus 0.83 g of the title compound was obtained as a light yellow solid (yield: 57%).

$^1$H-NMR data (CDCl$_3$/TMS δ (ppm)):
2.09-2.18 (2H, m), 2.47 (2H, t), 2.73 (2H, t), 3.89 (3H, s), 6.05 (1H, s), 7.25-7.29 (1H, m), 8.03 (1H, dd), 8.49 (1H, s), 8.75 (1H, dd)

(2) Production of 3-(2-hydroxy-6-oxo-1-cyclohexenecarbonyl)-1-methyl-1,8-naphthyridin-2(1H)-one 0.83 g (2.8 mmol) of 3-oxo-1-cyclohexenyl 1-methyl-2-oxo-1,2-dihydro-1,8-naphthyridine-3-carboxylate was dissolved in acetonitrile (50 mL). 0.43 mL (3.1 mmol) of triethylamine and 0.26 g (3.1 mmol) of acetone cyanohydrin were added to the above solution, and the resulting mixture was stirred for one whole day and night at room temperature. The reaction mixture was poured into a saturated aqueous solution of sodium hydrogen carbonate, and the mixture was washed with ethyl acetate. Citric acid was added to the aqueous phase to adjust the aqueous phase to pH 3 to 4, and the reaction mixture was extracted with ethyl acetate. The organic phase was washed with water, dried, and concentrated. The residue was purified by column chromatography (ethyl acetate:n-hexane=1:1 to 1:0), and thus, 0.30 g of the title compound was obtained as a pale yellow powder (yield: 36%).

$^1$H-NMR data (CDCl$_3$/TMS δ (ppm)):
2.03-2.12 (2H, m), 2.49 (2H, t), 2.75 (2H, t), 3.92 (3H, s), 7.17-7.21 (1H, m), 7.69 (1H, s), 7.91 (1H, dd), 8.63 (1H, dd), 16.5 (1H, s)

Example 3

Production of 1-(ethylthiomethyl)-3-(2-hydroxy-6-oxo-1-cyclohexenecarbonyl)-1,8-naphthyridin-2(1H)-one (Compound of present invention No.: II-19)

(1) Production of 3-oxo-1-cyclohexenyl 1-(ethylthiomethyl)-2-oxo-1,2-dihydro-1,8-naphthyridine-3-carboxylate 2.20 g (8.3 mmol) of 1-(ethylthiomethyl)-2-oxo-1,2-dihydro-1,8-naphthyridine-3-carboxylic acid was dissolved in dichloromethane (80 mL), and 5.0 mL (60 mmol) of oxalyl chloride was added thereto. One droplet of N,N-dimethylformamide was added to the above mixture, and the resulting mixture was stirred for one hour at room temperature. The reaction solution was concentrated under reduced pressure, and thus 1-(ethylthiomethyl)-2-oxo-1,2-dihydro-1,8-naphthyridine-3-carboxylic acid chloride was obtained. The acid chloride thus obtained was dissolved in dichloromethane (80 mL), and 1.02 g (9.1 mmol) of 1,3-cyclohexanedione and 1.40 mL (10.0 mmol) of triethylamine were added to the above solution under ice cooling. The resulting mixture was stirred for 2 hours at room temperature. The reaction mixture was poured into an aqueous solution of sodium hydrogen carbonate, and the mixture was extracted with dichloromethane. The organic phase was dried and concentrated. The residue was washed with diisopropyl ether, and 2.99 g of the title compound was obtained as a light yellow solid (yield: quantitative).

$^1$H-NMR data (CDCl$_3$/TMS δ (ppm)):
1.32 (3H, t), 2.10-2.16 (2H, m), 2.47 (2H, t), 2.72 (2H, t), 2.84 (2H, q), 5.68 (2H, s), 6.04 (1H, s), 7.28-7.31 (1H, m), 8.03 (1H, d), 8.50 (1H, s), 8.75 (1H, d)

(2) Production of 1-(ethylthiomethyl)-3-(2-hydroxy-6-oxo-1-cyclohexenecarbonyl)-1,8-naphthyridin-2(1H)-one 2.97 g (8.3 mmol) of 3-oxo-1-cyclohexenyl 1-(ethylthiomethyl)-2-oxo-1,2-dihydro-1,8-naphthyridine-3-carboxylate was dissolved in dichloromethane (80 mL). 1.40 mL (10.0 mmol) of triethylamine and 0.77 g (9.1 mmol) of acetone cyanohydrin were added to the above solution, and the resulting mixture was stirred overnight at room temperature. The reaction mixture was poured into an aqueous solution of citric acid, and the mixture was extracted with dichloromethane. The organic phase was washed with water, dried, and concentrated. The residue was purified by column chromatography (ethyl acetate:n-hexane=1:4), and thus 0.77 g of the title compound was obtained as pale orange-colored crystals (yield: 26%).

$^1$H-NMR data (CDCl$_3$/TMS δ (ppm)):

1.29 (3H, t), 2.05-2.12 (2H, m), 2.47 (2H, t), 2.73-2.82 (4H, m), 5.63 (2H, s), 7.19-7.24 (1H, m), 7.69 (1H, s), 7.91 (1H, d), 8.65 (1H, d), 16.43 (1H, s)

Example 4

Production of 1-benzyl-3-(2-hydroxy-6-oxo-1-cyclohexenecarbonyl)-1,8-naphthyridin-2(1H)-one (Compound of present invention No.: II-24)

(1) Production of 3-oxo-1-cyclohexenyl 1-benzyl-2-oxo-1,2-dihydro-1,8-naphthyridine-3-carboxylate 1.61 g (5.7 mmol) of 1-benzyl-2-oxo-1,2-dihydro-1,8-naphthyridine-3-carboxylic acid was dissolved in dichloromethane (60 mL), and 3.5 mL (42 mmol) of oxalyl chloride was added thereto. One droplet of N,N-dimethylformamide was added to the above mixture, and the resulting mixture was stirred for one hour at 40° C. The reaction solution was concentrated under reduced pressure, and thus 1-benzyl-2-oxo-1,2-dihydro-1,8-naphthyridine-3-carboxylic acid chloride was obtained. The acid chloride thus obtained was dissolved in dichloromethane (60 mL), and 0.71 g (6.3 mmol) of 1,3-cyclohexanedione and 0.97 mL (6.9 mmol) of triethylamine were added to the above solution. The resulting mixture was stirred for 2 hours at room temperature. The reaction mixture was poured into an aqueous solution of sodium hydrogen carbonate, and the mixture was extracted with dichloromethane. The organic phase was dried and concentrated. The residue was washed with diisopropyl ether, and thus 2.13 g of the title compound was obtained as a light yellow solid (yield: quantitative).

$^1$H-NMR data (CDCl$_3$/TMS δ (ppm)):

2.10-2.17 (2H, m), 2.46 (2H, t), 2.72 (2H, t), 5.79 (2H, s), 6.03 (1H, s), 7.22-7.30 (4H, m), 7.51-7.54 (2H, m), 8.02 (1H, d), 8.49 (1H, s), 8.75 (1H, d)

(2) Production of 1-benzyl-3-(2-hydroxy-6-oxo-1-cyclohexenecarbonyl)-1,8-naphthyridin-2(1H)-one 2.13 g (5.7 mmol) of 3-oxo-1-cyclohexenyl 1-benzyl-2-oxo-1,2-dihydro-1,8-naphthyridine-3-carboxylate was dissolved in dichloromethane (60 mL), and 0.97 mL (6.9 mmol) of triethylamine and 0.54 g (6.3 mmol) of acetone cyanohydrin were added to the above solution. The resulting mixture was stirred for one whole day and night at room temperature. The reaction mixture was poured into an aqueous solution of citric acid, and the mixture was extracted with dichloromethane. The organic phase was washed with water, dried, and concentrated. The residue was washed with methanol, and 1.31 g of the title compound was obtained as dark yellow crystals (yield: 62%).

$^1$H-NMR data (CDCl$_3$/TMS δ (ppm)):

2.06-2.09 (2H, m), 2.49 (2H, t), 2.74 (2H, t), 5.73 (2H, s), 7.16-7.27 (4H, m), 7.46 (1H, d), 7.71 (1H, s), 7.90 (1H, d), 8.61 (1H, d), 16.41 (1H, s)

Example 5

Production of 3-(2-hydroxy-6-oxo-1-cyclohexenecarbonyl)-1-(2-methoxybenzyl)-1,8-naphthyridin-2(1H)-one (Compound of present invention No.: II-37)

(1) Production of 3-oxo-1-cyclohexenyl 1-(2-methoxybenzyl)-2-oxo-1,2-dihydro-1,8-naphthyridine-3-carboxylate 3.83 g (12.3 mmol) of 1-(2-methoxybenzyl)-2-oxo-1,2-dihydro-1,8-naphthyridine-3-carboxylic acid was dissolved in dichloromethane (100 mL), and 7.5 mL (89 mmol) of oxalyl chloride was added thereto. One droplet of N,N-dimethylformamide was added to the above mixture, and the resulting mixture was stirred for one hour at 40° C. The reaction solution was concentrated under reduced pressure, and thus 1-(2-methoxybenzyl)-2-oxo-1,2-dihydro-1,8-naphthyridine-3-carboxylic acid chloride was obtained. The acid chloride thus obtained was dissolved in dichloromethane (100 mL), and this solution was added to a dichloromethane (100 mL) solution of 1.52 g (13.6 mmol) of 1,3-cyclohexanedione and 2.11 mL (14.8 mmol) of triethylamine under ice cooling. The mixture was stirred for 2 hours at room temperature. The reaction mixture was poured into an aqueous solution of sodium hydrogen carbonate, and the mixture was extracted with dichloromethane. The organic phase was dried and concentrated. The residue was washed with diisopropyl ether, and thus 4.82 g of the title compound was obtained as a light yellow solid (yield: 97%).

$^1$H-NMR data (CDCl$_3$/TMS δ (ppm)):

2.06-2.14 (2H, m), 2.44 (2H, t), 2.71 (2H, t), 3.89 (3H, s), 5.80 (2H, s), 6.03 (1H, s), 6.60 (1H, d), 6.74 (1H, t), 6.88 (1H, d), 7.15-7.27 (2H, m), 8.05 (1H, d), 8.56 (1H, s), 8.66 (1H, s)

(2) Production of 3-(2-hydroxy-6-oxo-1-cyclohexenecarbonyl)-1-(2-methoxybenzyl)-1,8-naphthyridine-2(1H)-one 4.82 g (11.9 mmol) of 3-oxo-1-cyclohexenyl 1-(2-methoxybenzyl)-2-oxo-1,2-dihydro-1,8-naphthyridine-3-carboxylate was dissolved in dichloromethane (100 mL), and 2.01 mL (14.3 mmol) of triethylamine and 1.11 g (13.1 mmol) of acetone cyanohydrin were added to the above solution. The mixture was stirred for one whole day and night at room temperature. The reaction mixture was poured into an aqueous solution of citric acid, and the mixture was extracted with dichloromethane. The organic phase was washed with water, dried, and concentrated. The residue was purified by column chromatography (ethyl acetate:n-hexane=1:3 to 1:1), and thus 1.59 g (yield: 33%) of the title compound was obtained as yellow crystals.

$^1$H-NMR data (CDCl$_3$/TMS δ (ppm)):

2.00-2.08 (2H, m), 2.45 (2H, t), 2.71 (2H, t), 3.90 (3H, s), 5.73 (2H, s), 6.72-6.80 (1H, m), 6.87 (1H, d), 7.13-7.18 (2H, m), 7.80 (1H, s), 7.94 (1H, d), 8.54 (1H, d), 16.31 (1H, s)

Example 6

Production of 3-(2-hydroxy-6-oxo-1-cyclohexenecarbonyl)-1-phenyl-1,8-naphthyridin-2(1H)-one (Compound of present invention No.: II-41)

(1) Production of 3-oxo-1-cyclohexenyl 2-oxo-1-phenyl-1,2-dihydro-1,8-naphthyridine-3-carboxylate 1.62 g (6.1 mmol) of 2-oxo-1-phenyl-1,2-dihydro-1,8-naphthyridine-3-carboxylic acid was dissolved in dichloromethane (60 mL), and 3.7 mL (44 mmol) of oxalyl chloride was added thereto. One droplet of N,N-dimethylformamide was added to the above mixture, and the resulting mixture was stirred for one hour at 40° C. The reaction mixture was concentrated under reduced pressure, and thus 2-oxo-1-phenyl-1,2-dihydro-1,8-naphthyridine-3-carboxylic acid chloride was obtained. The acid chloride thus obtained was dissolved in dichloromethane (60 mL), and 0.75 g (6.7 mmol) of 1,3-cyclohexanedione and 1.03 mL (7.3 mmol) of triethylamine were added to the above solution. The resulting mixture was stirred for 2 hours at room temperature. The reaction mixture was poured into an aqueous solution of sodium hydrogen carbonate, and the mixture was extracted with dichloromethane. The organic phase was dried and concentrated. The residue was washed with diisopropyl ether, and thus 2.16 g (yield: 99%) of the title compound was obtained as a light yellow solid.

$^1$H-NMR data (CDCl$_3$/TMS δ (ppm)):
2.06-2.14 (2H, m), 2.45 (2H, t), 2.70 (2H, t), 6.04 (3H, s), 7.24-7.29 (3H, m), 7.49-7.62 (3H, m), 8.08 (1H, d), 8.57-8.60 (3H, m)

(2) Production of 3-(2-hydroxy-6-oxo-1-cyclohexenecarbonyl)-1-phenyl-1,8-naphthyridin-2(1H)-one 2.16 g (6.0 mmol) of 3-oxo-1-cyclohexenyl 1-phenyl-2-oxo-1,2-dihydro-1,8-naphthyridine-3-carboxylate was dissolved in dichloromethane (50 mL), and 1.01 mL (7.2 mmol) of triethylamine and 0.56 g (6.6 mmol) of acetone cyanohydrin were added to the above solution. The resulting mixture was stirred for one whole day and night at room temperature. The reaction mixture was poured into an aqueous solution of citric acid, and the mixture was extracted with dichloromethane. The organic phase was washed with water, dried, and concentrated. The residue was washed with methanol, and thus 1.01 g (yield: 47%) of the title compound was obtained as pale brown crystals.

$^1$H-NMR data (CDCl$_3$/TMS δ (ppm)):
1.99-2.05 (2H, m), 2.44 (2H, t), 2.70 (2H, t), 7.16-7.19 (1H, m), 7.31 (2H, d), 7.45-7.49 (1H, m), 7.56 (2H, t), 7.82 (1H, s), 7.95 (1H, d), 8.48 (1H, d), 16.38 (1H, s)

Example 7

Production of 3-(2-hydroxy-6-oxo-1-cyclohexenecarbonyl)-1-(5-methyl-3-isoxazolyl)-1,8-naphthyridin-2(1H)-one (Compound of present invention No.: II-63)

(1) Production of 3-(2-hydroxy-6-oxo-1-cyclohexenecarbonyl)-1-(5-methyl-3-isoxazolyl)-1,8-naphthyridin-2(1H)-one 1.7 g (6.3 mmol) of 1-(5-methyl-3-isoxazolyl)-2-oxo-1,2-dihydro-1,8-naphthyridine-3-carboxylic acid was dissolved in dichloromethane (50 mL), and 3.0 mL (36 mmol) of oxalyl chloride was added thereto. One droplet of N,N-dimethylformamide was added to the above mixture, and the resulting mixture was stirred for one hour at room temperature. The reaction solution was concentrated under reduced pressure, and thus 1-(5-methyl-3-isoxazolyl)-2-oxo-1,2-dihydro-1,8-naphthyridine-3-carboxylic acid chloride was obtained. The acid chloride thus obtained was dissolved in dichloromethane (50 mL), and 0.77 g (6.9 mmol) of 1,3-cyclohexanedione and 1.1 mL (7.5 mmol) of triethylamine were added to the above solution under ice cooling. The mixture was stirred for 30 minutes under ice cooling. 0.97 mL (6.9 mmol) of triethylamine and 0.59 g (6.9 mmol) of acetone cyanohydrin were added to the above mixture, and the resulting mixture was stirred for one hour at 40° C. The reaction mixture was poured into an aqueous solution of citric acid, and the mixture was extracted with dichloromethane. The organic phase was washed with water, dried, and concentrated. The residue was purified by column chromatography (ethyl acetate:n-hexane=1:1 to 9:1), and thus 0.27 g (yield: 12%) of the title compound was obtained as yellow crystals.

$^1$H-NMR data (CDCl$_3$/TMS δ (ppm)):
2.01-2.07 (2H, m), 2.46 (2H, t), 2.55 (1H, s), 2.72 (2H, t), 6.21 (1H, d), 7.22-7.26 (1H, m), 7.81 (1H, s), 7.96 (1H, d), 8.53 (1H, d), 16.31 (1H, s)

Example 8

Production of 3-(2-hydroxy-6-oxo-1-cyclohexenecarbonyl)-1-(6-methoxy-3-pyridinyl)-1,8-naphthyridin-2(1H)-one (Compound of present invention No.: II-92)

(1) Production of 3-oxo-1-cyclohexenyl 1-(6-methoxy-3-pyridinyl)-2-oxo-1,2-dihydro-1,8-naphthyridine-3-carboxylate 1.35 g (4.5 mmol) of 1-(6-methoxy-3-pyridinyl)-2-oxo-1,2-dihydro-1,8-naphthyridine-3-carboxylic acid was dissolved in dichloromethane (50 mL), and 2.5 mL (30 mmol) of oxalyl chloride was added thereto. One droplet of N,N-dimethylformamide was added to the above mixture, and the resulting mixture was stirred for 2 hours at room temperature. The reaction solution was concentrated under reduced pressure, and thus 1-(6-methoxy-3-pyridyl)-2-oxo-1,2-dihydro-1,8-naphthyridine-3-carboxylic acid chloride was obtained. The acid chloride thus obtained was dissolved in dichloromethane (50 mL), and 0.56 g (5.0 mmol) of 1,3-cyclohexanedione and 1.54 mL (10.8 mmol) of triethylamine were added to the above solution under ice cooling. The resulting mixture was stirred for 2 hours at room temperature. The reaction mixture was poured into water, and the mixture was extracted with dichloromethane. The organic phase was dried and concentrated. The residue was washed with diisopropyl ether, and thus 1.78 g (yield: quantitative) of the title compound was obtained as a light yellow solid.

$^1$H-NMR data (CDCl$_3$/TMS δ (ppm)):
2.07-2.16 (2H, m), 2.46 (2H, t), 2.70 (2H, t), 4.01 (3H, s), 6.05 (1H, s), 6.93 (1H, d), 7.29 (1H, dd), 7.51 (1H, dd), 8.07-8.11 (2H, m), 8.58-8.61 (2H, m)

(2) Production of 3-(2-hydroxy-6-oxo-1-cyclohexenecarbonyl)-1-(6-methoxy-3-pyridinyl)-1,8-naphthyridin-2(1H)-one 1.78 g (4.5 mmol) of 3-oxo-1-cyclohexenyl 1-(6-methoxy-3-pyridyl)-2-oxo-1,2-dihydro-1,8-naphthyridine-3-carboxylate was dissolved in dichloromethane (50 mL), and 0.77 mL (5.5 mmol) of triethylamine and 0.43 g (5.0 mmol) of acetone cyanohydrin were added to the above solution. The resulting mixture was stirred overnight at room temperature. The reaction mixture was poured into an aqueous solution of citric acid, and the mixture was extracted with dichloromethane. The organic phase was washed with water, dried, and concentrated. The residue was purified by column chromatography (ethyl acetate:n-hexane=1:1 to 7:3), and thus 0.37 g (yield: 21%) of the title compound was obtained as orange-colored crystals.

$^1$H-NMR data (CDCl$_3$/TMS δ (ppm)):
2.01-2.04 (2H, m), 2.44 (2H, t), 2.72 (2H, t), 3.99 (3H, s), 6.91 (1H, d), 7.20 (1H, dd), 7.54 (1H, dd), 7.81 (1H, s), 7.97 (1H, d), 8.14 (1H, d), 8.48 (1H, d), 16.36 (1H, s)

Example 9

Production of 1-(2,3-dihydrobenzo[b][1,4]dioxin-6-yl)-3-(2-hydroxy-6-oxo-1-cyclohexenecarbonyl)-1,8-naphthyridin-2(1H)-one (Compound of present invention No.: II-118)

(1) Production of 3-oxo-1-cyclohexenyl 1-(2,3-dihydrobenzo[b][1,4]dioxin-6-yl)-2-oxo-1,2-dihydro-1,8-naphthyridine-3-carboxylate 3.0 g (9.3 mmol) of 1-(2,3-dihydrobenzo[b][1,4]dioxin-6-yl)-2-oxo-1,2-dihydro-1,8-naphthyridine-3-carboxylic acid was dissolved in dichloromethane (70 mL), and 3 mL (35 mmol) of oxalyl chloride was added thereto. Five droplets of N,N-dimethylformamide were added to the above mixture, and the resulting mixture was stirred for one hour at 40° C. The reaction solution was concentrated under reduced pressure, and thus 1-(2,3-dihydrobenzo[b][1,4]dioxin-6-yl)-2-oxo-1,2-dihydroxy-1,8-naphthyridine-3-carboxylic acid chloride was obtained. The acid chloride thus obtained was dissolved in dichloromethane (70 mL), and this solution was added to a dichloromethane (70 mL) solution of 1.14 g (10.1 mmol) of 1,3-cyclohexanedione and 1.55 mL (11.1 mmol) of triethylamine under ice cooling. The resulting mixture was stirred for one hour at room temperature. The reaction mixture was poured into water, and the mixture was extracted with dichloromethane. The organic phase was washed with an aqueous solution of sodium hydrogen carbonate and water in this order, and was dried and concentrated. The residue was washed with diisopropyl ether, and 3.32 g (yield: 86%) of the title compound was obtained as a light yellow solid.

$^1$H-NMR data (CDCl$_3$/TMS δ (ppm)):
2.05-2.14 (2H, m), 2.45 (2H, t), 2.70 (2H, t), 4.31 (4H, s), 6.04 (1H, s), 6.73 (1H, dd), 6.80 (1H, d), 7.23-7.28 (1H, m), 8.06 (1H, dd), 8.57 (1H, s), 8.63 (1H, dd)

(2) Production of 1-(2,3-dihydrobenzo[b][1,4]dioxin-6-yl)-3-(2-hydroxy-6-oxo-1-cyclohexenecarbonyl)-1,8-naphthyridin-2 (1H)-one 3.32 g (7.9 mmol) of 3-oxo-1-cyclohexenyl 1-(2,3-dihydrobenzo[b][1,4] dioxin-6-yl)-2-oxo-1,2-dihydro-1,8-naphthyridine-3-carboxylate was dissolved in acetonitrile (150 mL), and 0.88 g (8.7 mmol) of triethylamine and 0.77 g (8.7 mmol) of acetone cyanohydrin were added to the above solution. The resulting mixture was stirred for one whole day and night at room temperature. The reaction mixture was poured into a saturated aqueous solution of sodium hydrogen carbonate, and was washed with chloroform. Citric acid was added to the aqueous phase to adjust the aqueous phase to pH 3 to 4, and the reaction mixture was extracted with chloroform. The organic phase was washed with water, dried, and concentrated, and the residue was purified by column chromatography (ethyl acetate:n-hexane=1:1 to 1:0). Thus, 0.90 g (yield: 27%) of the title compound was obtained as a pale orange powder.

$^1$H-NMR data (CDCl$_3$/TMS δ (ppm)):
1.98-2.06 (2H, m), 2.44 (2H, t), 2.70 (2H, t), 4.30 (4H, s), 6.77 (1H, dd), 7.01 (1H, d), 7.15-7.19 (1H, m), 7.80 (1H, s), 7.94 (1H, dd), 8.52 (1H, dd), 16.36 (1H, s)

Example 10

Production of 3-(2-hydroxy-6-oxo-1-cyclohexenecarbonyl)-1-methyl-7-(trifluoromethyl)-1,8-naphthyridin-2(1H)-one (Compound of present invention No.: II-136)

(1) Production of 3-oxo-1-cyclohexenyl 1-methyl-2-oxo-7-(trifluoromethyl)-1,2-dihydro-1,8-naphthyridine-3-carboxylate 0.83 g (3.0 mmol) of 1-methyl-2-oxo-7-(trifluoromethyl)-1,2-dihydro-1,8-naphthyridine-3-carboxylic acid was dissolved in dichloromethane (50 mL), and 1.0 mL (12 mmol) of oxalyl chloride was added thereto. Two droplets of N,N-dimethylformamide were added to the above mixture, and the resulting mixture was stirred for 2 hours at 40° C. The reaction solution was concentrated under reduced pressure, and thus 1-methyl-2-oxo-7-(trifluoromethyl)-1,2-dihydro-1,8-naphthyridine-3-carboxylic acid chloride was obtained. The acid chloride thus obtained was dissolved in acetonitrile (30 mL), and this solution was added to an acetonitrile (50 mL) solution of 0.38 g (3.4 mmol) of 1,3-cyclohexanedione and 0.51 mL (3.7 mmol) of triethylamine under ice cooling. The resulting mixture was stirred for 2 hours at room temperature. The reaction mixture was poured into water, and the mixture was extracted with ethyl acetate. The organic phase was washed with water, an aqueous solution of sodium hydrogen carbonate, and water in this order, and was dried and concentrated. The residue was washed with diisopropyl ether, and thus 0.51 g (yield: 46%) of the title compound was obtained as brown crystals.

$^1$H-NMR data (CDCl$_3$/TMS δ (ppm)):
2.05-2.17 (2H, m), 2.49 (2H, t), 2.73 (2H, t), 3.89 (3H, s), 6.05 (1H, s), 7.61 (1H, d, J=8.1 Hz), 8.22 (1H, d, J=8.0 Hz), 8.49 (1H, s)

(2) Production of 3-(2-hydroxy-6-oxo-1-cyclohexenecarbonyl)-1-methyl-7-(trifluoromethyl)-1,8-naphthyridin-2(1H)-one 0.51 g (1.4 mmol) of 3-oxo-1-cyclohexenyl 1-methyl-2-oxo-7-(trifluoromethyl)-1,2-dihydro-1,8-naphthyridine-3-carboxylate was dissolved in acetonitrile (50 mL), and 0.15 g (1.5 mmol) of triethylamine and 0.14 g (1.6 mmol) of acetone cyanohydrin were added to the above solution. The resulting mixture was stirred for one whole day and night at room temperature. The reaction mixture was poured into a saturated aqueous solution of sodium hydrogen carbonate, and the mixture was washed with ethyl acetate. Citric acid was added to the aqueous phase to adjust the aqueous phase to pH 3 to 4, and the reaction mixture was extracted with ethyl acetate. The organic phase was washed with water, dried, and concentrated, and the residue was washed with diisopropyl ether. Thus, 0.17 g (yield: 33%) of the title compound was obtained as light brown crystals.

$^1$H-NMR data (CDCl$_3$/TMS δ (ppm)):
2.03-2.12 (2H, m), 2.47 (2H, t), 2.77 (2H, t), 3.83 (3H, s), 7.53 (1H, d, J=8.0 Hz), 7.73 (1H, s), 8.06 (1H, d, J=7.7 Hz), 16.5 (1H, s).

The compounds obtained in Examples 1 to 10 described above, and the property values of the compounds of the present invention produced in the same manner as in these Examples are presented in Table 67.

TABLE 67

| Compound No. | Melting point (° C.) or Refractive index ($n_D^{20}$) |
| --- | --- |
| I-2 | Melting point 179-181 |
| I-56 | Melting point 161-164 |
| I-157 | Melting point 178-181 |
| II-2 | Melting point 151-153 |
| II-3 | Melting point 140-142 |
| II-4 | Melting point 39-41 |
| II-15 | Melting point 112-114 |
| II-19 | Melting point 108-110 |
| II-24 | Melting point 190-192 |
| II-28 | Melting point 157-159 |
| II-29 | Melting point 148-151 |
| II-30 | Melting point 149-151 |
| II-37 | Melting point 147-150 |
| II-38 | Melting point 192-194 |
| II-39 | Melting point 125-127 |
| II-41 | Melting point 212-214 |
| II-43 | Melting point 229-231 |
| II-48 | Melting point 220-222 |
| II-52 | Melting point 163-164 |
| II-54 | Melting point 127-129 |
| II-55 | Melting point 257-259 |
| II-56 | Melting point 247-250 |
| II-58 | Melting point 183-186 |
| II-63 | Melting point 113-116 |
| II-92 | Melting point 220-222 |
| II-118 | Melting point 226-228 |
| II-121 | Melting point 176-179 |
| II-123 | Melting point 239-240 |
| II-126 | Melting point 66-67 |
| II-128 | Melting point 150-152 |
| II-131 | Melting point 192-194 |
| II-133 | Melting point 184-187 |
| II-136 | Melting point 194-196 |
| II-138 | Melting point 147-149 |
| II-141 | Melting point 144-145 |
| II-143 | Melting point 172-174 |
| II-434 | Melting point 116-118 |
| II-442 | Melting point 238-241 |
| III-2 | Melting point 177-179 |
| III-41 | Melting point 205-207 |
| IV-41 | Melting point 210-212 |
| V-41 | Melting point 207-208 |

Reference Example 1

(Production intermediate) Production of 1-methyl-2-oxo-1,2-dihydroquinoline-3-carboxylic acid (Production intermediate compound No.: VIII-1)

(1) Production of diethyl 2-(2-nitrobenzylidene)malonate 32.3 g (0.21 mol) of 2-nitrobenzaldehyde and 35.0 g (0.21 mol) of diethyl malonate were added to 100 mL of acetic anhydride at room temperature. 27.0 g (0.32 mol) of sodium hydrogen carbonate was added to this mixture, and the resulting mixture was allowed to react overnight at 100° C. The reaction mixture was concentrated under reduced pressure to approximately a half of the original volume, and ice water was added to this reaction mixture. The reaction mixture was extracted with ethyl acetate. The organic phase was washed with an aqueous solution of sodium hydrogen carbonate and water in this order, and was dried and concentrated under reduced pressure. The residue was purified by column chromatography (ethyl acetate:n-hexane=1:9 to 1:4), and thus 37.0 g (yield: 59%) of the title compound was obtained as light yellow crystals.

$^1$H-NMR data (CDCl$_3$/TMS δ (ppm)):
1.02 (3H, t), 1.38 (3H, t), 4.08 (2H, q), 4.35 (2H, q), 7.43 (1H, d), 7.55-7.67 (2H, m), 8.20 (1H, s), 8.22 (1H, d)

(2) Production of ethyl 2-oxo-1,2-dihydroquinoline-3-carboxylate 29.0 g (0.21 mol) of diethyl 2-(2-nitrobenzylidene)malonate was added to 100 mL of acetic acid at room temperature, and the mixture was heated to 80° C. 37.0 g (0.66 mol) of an iron powder was slowly added to the above mixture, and thus the reaction temperature increased to 100° C. After the reaction temperature decreased, the reaction was carried out at 80° C. for 5 hours. The reaction mixture was cooled to room temperature, and then ethyl acetate and water were added thereto. Insoluble materials were filtered off, and the filtrate was neutralized by adding sodium hydrogen carbonate. A solid precipitated therefrom was separated by filtration, and this solid was dissolved in ethyl acetate. The filtrate was further extracted with ethyl acetate, and the extract was combined with the solution mentioned above. This solution was washed with citric acid and water in this order, and was dried and concentrated. The residue was washed with diisopropyl ether, and thus 13.6 g (yield: 63%) of the title compound was obtained as pale yellow crystals.

$^1$H-NMR data (CDCl$_3$/TMS δ (ppm)):
1.46 (3H, t), 4.46 (2H, q), 7.26 (1H, t), 7.51 (1H, d), 7.59-7.67 (2H, m), 8.57 (1H, s), 12.59 (1H, s)

(3) Production of ethyl 1-methyl-2-oxo-1,2-dihydroquinoline-3-carboxylate 3.5 g (16 mmol) of ethyl 2-oxo-1,2-dihydroquinoline-3-carboxylate was dissolved in a mixed solvent of N,N-dimethylformamide (80 mL) and 1,2-dimethoxyethane (25 mL), and under a nitrogen gas stream, 0.71 g (18 mmol) of 60% sodium hydride (oily) was added to the solution at room temperature. The mixture was stirred for 15 minutes at room temperature. 5.6 g (64 mmol) of lithium bromide was added to the above mixture at room temperature, and the resulting mixture was stirred for 15 minutes at room temperature. 4.6 g (32 mmol) of iodomethane was further added to the mixture at room temperature, and the resulting mixture was stirred for 3 hours at 60° C. The reaction mixture was poured into an aqueous solution of citric acid, and the mixture was extracted with ethyl acetate. The organic phase was washed with brine, an aqueous solution of sodium hydrogen carbonate, and brine in this order, and was dried and concentrated. The residue was purified by column chromatography (ethyl acetate:n-hexane=1:4 to 4:1), and thus 2.4 g (yield: 64%) of the title compound was obtained as light yellow crystals.

$^1$H-NMR data (CDCl$_3$/TMS δ (ppm)):
1.42 (3H, t), 3.75 (3H, s), 4.43 (2H, q), 7.27 (1H, t), 7.37 (1H, d), 7.64-7.69 (2H, m), 8.39 (1H, s)

(4) Production of 1-methyl-2-oxo-1,2-dihydroquinoline-3-carboxylic acid 2.4 g (10.4 mmol) of ethyl 1-methyl-2-oxo-1,2-dihydroquinoline-3-carboxylate was dissolved in 1,4-dioxane (50 mL), and 0.65 g (15 mmol) of lithium hydroxide monohydrate and 10 mL of water were added to the solution at room temperature. The resulting mixture was stirred for 24 hours at room temperature. The reaction mixture was poured into an aqueous solution of sodium hydrogen carbonate, and the mixture was washed with ethyl acetate. The aqueous phase was acidified with citric acid, and then the mixture was extracted with chloroform. The organic phase was washed with water, dried, and concentrated. The residue thus obtained was washed with ethyl acetate, and thus 2.02 g (yield: 96%) of the title compound was obtained as light yellow crystals.

$^1$H-NMR data (CDCl$_3$/TMS δ (ppm)):
3.88 (3H, s), 7.45 (1H, t), 7.53 (1H, d), 7.82 (1H, t), 8.93 (1H, s), 14.55 (1H, s)

Reference Example 2

(Production intermediate) Production of 1-methyl-2-oxo-1,2-dihydro-1,8-naphthyridine-3-carboxylic acid (Production intermediate compound No.: VIII-4)

(1) Production of 3-formyl-2-(pivaloylamino)pyridine 11.4 g (64 mmol) of 2-(pivaloylamino)pyridine was dissolved in 50 mL of tetrahydrofuran, and 100 mL (0.16 mol) of 1.6 M normal-butyllithium was added dropwise thereto at −60° C. The mixture was allowed to react for 3 hours at −10° C. To this reaction mixture, 14 g (0.19 mol) of N,N-dimethylformamide was added dropwise at −60° C., and the reaction liquid was stirred overnight at room temperature. The reaction mixture was poured into ice, and 6 N hydrochloric acid was added thereto to acidify the reaction mixture. Subsequently, potassium carbonate was added to make the reaction mixture alkaline, and the mixture was extracted with ethyl acetate. The organic phase was washed with water, and was dried and concentrated. The residue thus obtained was purified by column chromatography (ethyl acetate:n-hexane=1:4 to 1:0), and thus 6.57 g (yield 50%) of the title compound was obtained as a pale yellow liquid.

$^1$H-NMR data (CDCl$_3$/TMS δ (ppm)):
1.38 (9H, s), 7.19-7.22 (1H, m), 8.05 (1H, dd), 8.69 (1H, dd), 9.94 (1H, s), 10.90 (1H, br)

(2) Production of ethyl 2-oxo-1,2-dihydro-1,8-naphthyridine-3-carboxylate 6.57 g (32 mmol) of 3-formyl-2-(pivaloylamino)pyridine was dissolved in ethanol (50 mL), and 10.2 g (64 mmol) of diethyl malonate and 1.6 mL (16 mmol) of pyrrolidine were added to the above solution. The resulting mixture was stirred overnight at 100° C. The reaction mixture was cooled to room temperature, and a solid precipitated therefrom was washed with ethanol. Thus, 2.2 g (yield: 32%) of the title compound was obtained as a yellow solid.

$^1$H-NMR data (CDCl$_3$/TMS δ (ppm)):
1.44 (3H, t), 4.45 (2H, q), 7.26-7.30 (1H, m), 8.05 (1H, dd), 8.47 (1H, s), 9.93 (1H, dd)

(3) Production of ethyl 1-methyl-2-oxo-1,2-dihydro-1,8-naphthyridine-3-carboxylate 2.2 g (10 mmol) of ethyl 2-oxo-1,2-dihydro-1,8-naphthyridine-3-carboxylate was dissolved in a mixed solvent of N,N-dimethylformamide (50 mL) and 1,2-dimethoxyethane (15 mL), and under a nitrogen gas stream, 0.45 g (11 mmol) of 60% sodium hydride (oily) was added thereto at room temperature. The mixture was further stirred for 30 minutes at room temperature. 3.5 g (40 mmol) of lithium bromide was added to the above mixture under ice cooling, and the resulting mixture was stirred for 30 minutes at room temperature. 3.9 g (27.5 mmol) of iodomethane was further added to the mixture at room temperature, and the resulting mixture was stirred for 6 hours at 60° C. The reaction mixture was poured into an aqueous solution of citric acid, and the mixture was extracted with ethyl acetate. The organic phase was washed with brine, an aqueous solution of sodium hydrogen carbonate, and brine in this order, and was dried and concentrated. The residue was washed with diisopropyl ether, and thus 1.66 g (yield: 71%) of the title compound was obtained as a light purple solid.

$^1$H-NMR data (CDCl$_3$/TMS δ (ppm)):
1.42 (3H, t), 3.87 (3H, s), 4.43 (2H, q), 7.21-7.25 (1H, m), 7.97 (1H, dd), 8.34 (1H, s), 8.69 (1H, dd)

(4) Production of 1-methyl-2-oxo-1,2-dihydro-1,8-naphthyridine-3-carboxylic acid 1.66 g (7.1 mmol) of ethyl 1-methyl-2-oxo-1,2-dihydro-1,8-naphthyridine-3-carboxylate was dissolved in 1,4-dioxane (50 mL), and 0.45 g (11 mmol) of lithium hydroxide monohydrate and 10 mL of water were added to the solution at room temperature. The resulting mixture was stirred for 1.5 hours at room temperature. The reaction mixture was poured into an aqueous solution of sodium hydrogen carbonate, and the mixture was washed with ethyl acetate. The aqueous phase was acidified with citric acid, and then the mixture was extracted with ethyl acetate. The organic phase was washed with water, dried, and concentrated. The residue was washed with diisopropyl ether, and 1.30 g (yield: 89%) of the title compound was obtained as colorless crystals.

$^1$H-NMR data (CDCl$_3$/TMS δ (ppm)):
3.99 (3H, s), 7.39-7.43 (1H, m), 8.16 (1H, dd), 7.83 (1H, dd), 8.92 (1H, s), 14.34 (1H, s)

Reference Example 3

(Production intermediate) Production of 1-(ethylthiomethyl)-2-oxo-1,2-dihydro-1,8-naphthyridine-3-carboxylic acid (Production intermediate compound No.: VIII-8)

(1) Production of (2-(methylamino)-3-pyridinyl)methanol 30.0 g (0.19 mol) of 2-chloronicotinic acid was dissolved in N,N-dimethylformamide (400 mL), and 31.0 g (0.38 mol) of methylamine hydrochloride, 105 g (0.76 mol) of potassium carbonate, and 2.73 g (19.0 mmol) of copper(I) bromide were added to the solution. The mixture was stirred for 20 hours at 100° C. After the mixture was cooled to room temperature, insoluble materials were filtered off, and the filtrate was concentrated. A 10% aqueous solution of sodium hydroxide was added to the residue thus obtained, and the mixture was washed with diethyl ether. Concentrated hydrochloric acid was added to the aqueous phase to adjust the aqueous phase to pH 6 to 7, and a solid obtained by concentrating the aqueous phase was dried. Thus, crude 2-(methylamino)nicotinic acid was obtained.

Under a nitrogen gas stream, 14.4 g (0.38 mol) of lithium aluminum hydride was added to tetrahydrofuran (300 mL) under ice cooling, and a tetrahydrofuran (100 mL) solution of crude 2-(methylamino)nicotinic acid was added dropwise to the above mixture. The resulting mixture was stirred overnight at room temperature. Ethyl acetate was added to the reaction mixture, and 152 mL of a 10% aqueous solution of sodium hydroxide was further added thereto. Insoluble materials were filtered off. The filtrate was concentrated, and the residue was purified by column chromatography (ethyl acetate:n-hexane=1:1 to 4:1). Thus, 9.10 g (yield: 35%) of the title compound was obtained as a pale yellow viscous product.

$^1$H-NMR data (CDCl$_3$/TMS δ (ppm)):
2.10 (1H, s), 3.01 (3H, d), 4.59 (2H, s), 5.38 (1H, s), 6.48-6.52 (1H, m), 7.21 (1H, d), 8.01 (1H, d)

(2) Production of 2-(methylamino)nicotinaldehyde 9.10 g (66.0 mmol) of (2-(methylamino)-3-pyridinyl)methanol was dissolved in chloroform (70 mL), and 17.4 g (200 mmol) of manganese dioxide was added thereto. The mixture was stirred overnight at 60° C. The reaction mixture was filtered, and the filtrate was concentrated. Thus, 8.66 g (yield: 96%) of the title compound was obtained as an orange-colored solid.

$^1$H-NMR data (CDCl$_3$/TMS δ (ppm)):
3.10 (3H, d), 6.62-6.66 (1H, m), 7.74 (1H, d), 8.36 (1H, d), 9.80 (1H, s)

(3) Production of methyl 1-methyl-2-oxo-1,2-dihydro-1,8-naphthyridine-3-carboxylate 8.66 g (64.5 mmol) of 2-(methylamino)nicotinaldehyde was dissolved in methanol (100 mL), and 12.68 g (96.0 mmol) of dimethyl malonate and 2.18 g (25.6 mmol) of piperidine were added to the solution. The resulting mixture was stirred for 7 hours at 80° C. The mixture was cooled, and a solid precipitated therefrom was separated by filtration. The solid was washed with diisopropyl ether, and thus 11.71 g (yield: 84%) of the title compound was obtained as a pale yellow solid.

$^1$H-NMR data (CDCl$_3$/TMS δ (ppm)):
3.87 (3H, s), 3.97 (3H, s), 7.21-7.27 (1H, m), 7.98 (1H, d), 8.39 (1H, s), 8.70 (1H, d)

(4) Production of methyl 1-(bromomethyl)-2-oxo-1,2-dihydro-1,8-naphthyridine-3-carboxylate 10.71 g (49.0 mmol) of methyl 1-methyl-2-oxo-1,2-dihydro-1,8-naphthyridine-3-carboxylate was dissolved in carbon tetrachloride (200 mL), and 8.64 g (49.0 mmol) of N-bromosuccinimide and 0.1 g of 1,2-azobis(2-methylpropionitrile) were added thereto. While the mixture was irradiated with light, the mixture was stirred for 4 hours. 3.0 g (17.0 mmol) of N-bromosuccinimide was further added to the mixture, and the resulting mixture was stirred for 3 hours while the mixture was irradiated with light. The reaction mixture was poured into water, and the mixture was extracted with chloroform. The organic phase was washed with water, dried, and concentrated. The residue was purified by column chromatography (ethyl acetate:chloroform=1:19), and thus 10.56 g (yield: 73%) of the title compound was obtained as colorless crystals.

$^1$H-NMR data (CDCl$_3$/TMS δ (ppm)):
3.98 (3H, s), 6.36 (2H, d, J=85.3 Hz), 7.32-7.35 (1H, m), 8.02 (1H, d), 8.46 (1H, s), 8.78 (1H, d)

(5) Production of methyl 1-(ethylthiomethyl)-2-oxo-1,2-dihydro-1,8-naphthyridine-3-carboxylate 3.00 g (10.1 mmol) of methyl 1-(bromomethyl)-2-oxo-1,2-dihydro-1,8-naphthyridine-3-carboxylate was dissolved in N,N-dimethylformamide (40 mL), and 0.94 g (15.1 mmol) of ethanethiol and 2.09 g (15.1 mmol) of potassium carbonate were added to the solution. The resulting mixture was stirred overnight at room temperature. The reaction mixture was poured into water, and the mixture was extracted with ethyl acetate. The organic phase was washed with water, dried, and concentrated. Thus, 2.85 g (yield: quantitative) of the title compound was obtained as pale yellow crystals.

$^1$H-NMR data (CDCl$_3$/TMS δ (ppm)):
1.31 (3H, t), 2.84 (2H, q), 3.97 (3H, s), 5.68 (2H, s), 7.23-7.28 (1H, m), 7.99 (1H, d), 8.41 (1H, s), 8.71 (1H, d)

(6) Production of 1-(ethylthiomethyl)-2-oxo-1,2-dihydro-1,8-naphthyridine-3-carboxylic acid 2.81 g (10.1 mmol) of methyl 1-(ethylthiomethyl)-2-oxo-1,2-dihydro-1,8-naphthyridine-3-carboxylate was dissolved in 1,4-dioxane (70 mL), and 6 N hydrochloric acid (20 mL) was added thereto at room temperature. The resulting mixture was stirred for 3 hours at 50° C. The solvent of the reaction mixture was distilled off under reduced pressure, and the residue thus obtained was washed sequentially with water and diisopropyl ether. Thus, 2.20 g of the title compound was obtained as pale yellow crystals (yield: 82%).

$^1$H-NMR data (CDCl$_3$/TMS δ (ppm)):
1.33 (3H, t), 2.71 (2H, q), 5.77 (2H, s), 7.41-7.45 (1H, m), 8.18 (1H, d), 8.84 (1H, d), 8.92 (1H, s), 14.06 (1H, s)

Reference Example 4

(Production intermediate) Production of 1-benzyl-2-oxo-1,2-dihydro-1,8-naphthyridine-3-carboxylic acid (Production intermediate compound No.: VIII-9)

(1) Production of ethyl 1-benzyl-2-oxo-1,2-dihydro-1,8-naphthyridine-3-carboxylate 1.50 g (6.9 mmol) of ethyl 2-oxo-1,2-dihydro-1,8-naphthyridine-3-carboxylate was dissolved in N,N-dimethylformamide (30 mL), and 1.43 g (10.4 mmol) of potassium carbonate and 1.36 g (7.9 mmol) of benzyl bromide were added thereto. The resulting mixture was stirred for one whole day and night at room temperature. The reaction mixture was poured into water, and the mixture was extracted with diethyl ether. The organic phase was dried, filtered, and concentrated. The residue was purified by column chromatography (ethyl acetate:n-hexane=3:7 to 1:1), and thus 1.95 g (yield: 92%) of the title compound was obtained as colorless crystals.

$^1$H-NMR data (CDCl$_3$/TMS δ (ppm)):
1.41 (3H, t), 4.42 (2H, q), 5.78 (2H, s), 7.18-17.28 (4H, m), 7.52 (2H, d), 7.96 (1H, d), 86.35 (1H, s), 8.69 (1H, s)

(2) Production of 1-benzyl-2-oxo-1,2-dihydro-1,8-naphthyridine-3-carboxylic acid 1.95 g (6.3 mmol) of ethyl 1-benzyl-2-oxo-1,2-dihydro-1,8-naphthyridine-3-carboxylate was dissolved in 1,4-dioxane (30 mL), and 1.31 g (9.5 mmol) of potassium carbonate and 60 mL of water were added to this solution at room temperature. The resulting mixture was stirred for 3 hours at 50° C. The solvent of the reaction mixture was distilled off under reduced pressure, and the residue was dissolved in water. Concentrated hydrochloric acid was added to make the solution acidic, and the mixture was extracted with chloroform. The organic phase was dried, filtered, and concentrated, and thus 1.71 g (yield: 97%) of the title compound was obtained as colorless crystals.

¹H-NMR data (CDCl₃/TMS δ (ppm)):
5.88 (2H, s), 7.26-7.33 (3H, m), 7.39-7.43 (1H, m), 7.51 (2H, d), 8.16 (1H, d), 8.85 (1H, d), 8.91 (1H, s), 14.27 (1H, s)

Reference Example 5

(Production intermediate) Production of 1-(2-methoxybenzyl)-2-oxo-1,2-dihydro-1,8-naphthyridine-3-carboxylic acid (Production intermediate compound No.: VIII-20)

(1) Production of 2-(2-methoxybenzylamino)nicotinic acid 7.00 g (44.2 mmol) of 2-chloronicotinic acid and 12.13 g (88.4 mmol) of 2-methoxybenzylamine were heated at 140° C. for 4 hours. The mixture was left to cool to room temperature, and then a 10% aqueous solution of sodium hydroxide was added to the reaction mixture. The resulting mixture was washed with chloroform. Concentrated hydrochloric acid was added to the aqueous phase to adjust the aqueous phase to pH 6 to 7, and a solid precipitated therefrom was separated by filtration and dried. Thus, 8.50 g (yield: 74%) of the title compound was obtained as a pale yellow powder.
¹H-NMR data (CDCl₃/TMS δ (ppm)):
3.87 (3H, s), 4.78 (2H, s), 6.52-6.56 (1H, m), 6.87-6.92 (2H, m), 7.23-7.33 (2H, m), 8.18 (1H, d), 8.33 (1H, d), 8.34 (1H, s)

(2) Production of (2-(2-methoxybenzylamino)-3-pyridinyl)methanol

Under a nitrogen gas stream, 2.50 g (65.8 mmol) of lithium aluminum hydride was added to tetrahydrofuran (100 mL) under ice cooling, and a tetrahydrofuran (70 mL) solution of 8.50 g (32.9 mmol) of 2-(2-methoxybenzylamino)nicotinic acid was added dropwise to the above solution. The resulting mixture was stirred for one hour at room temperature. Ethyl acetate was added to the reaction mixture, and then 26.4 mL of a 10% aqueous solution of sodium hydroxide was added thereto. Insoluble materials were filtered off. The filtrate was concentrated, and the residue thus obtained was dissolved in ethyl acetate, dried, filtered, and concentrated. Thus, 8.18 g (yield: quantitative) of the title compound was obtained as a pale yellow viscous product.
¹H-NMR data (CDCl₃/TMS δ (ppm)):
3.85 (3H, s), 4.56 (2H, s), 4.68 (2H, d), 5.80 (1H, s), 6.47-6.51 (1H, m), 6.86-6.92 (2H, m), 7.20-7.26 (2H, m), 7.33 (1H, d), 8.08 (1H, d)

(3) Production of 2-(2-methoxybenzylamino)nicotinaldehyde 8.03 g (32.9 mmol) of (2-(2-methoxybenzylamino)-3-pyridinyl)methanol was dissolved in chloroform (100 mL), and 8.60 g (98.7 mmol) of manganese dioxide was added thereto. The resulting mixture was stirred overnight at 60° C. The reaction mixture was filtered, and the filtrate was concentrated. Thus, 7.40 g (yield: 93%) of the title compound was obtained as an orange-colored solid.
¹H-NMR data (CDCl₃/TMS δ (ppm)):
3.90 (3H, s), 4.80 (2H, d), 6.59-6.64 (1H, m), 6.88-6.92 (2H, m), 7.22-7.33 (2H, m), 7.72 (1H, d), 8.33 (1H, d), 8.83 (1H, s), 9.80 (1H, s)

(4) Production of ethyl 1-(2-methoxybenzyl)-2-oxo-1,2-dihydro-1,8-naphthyridine-3-carboxylate 7.40 g (30.5 mmol) of 2-(2-methoxybenzylamino)nicotinaldehyde was dissolved in ethanol (100 mL), and 7.34 g (45.8 mmol) of diethyl malonate and 0.95 g (10.0 mmol) of piperidine were added thereto. The resulting mixture was stirred for 48 hours at 100° C. The mixture was cooled, and a solid precipitated thereby was separated by filtration. The solid was washed with hexane, and thus 7.71 g (yield: 75%) of the title compound was obtained as a pale yellow solid.
¹H-NMR data (CDCl₃/TMS δ (ppm)):
1.41 (3H, t), 3.90 (3H, s), 4.42 (2H, q), 5.79 (2H, s), 6.59 (1H, d), 6.73 (1H, t), 6.88 (1H, d), 7.14-7.22 (2H, m), 8.00 (1H, d), 8.61 (1H, d)

(5) Production of 1-(2-methoxybenzyl)-2-oxo-1,2-dihydro-1,8-naphthyridine-3-carboxylic acid 3.00 g (8.90 mmol) of ethyl 1-(2-methoxybenzyl)-2-oxo-1,2-dihydro-1,8-naphthyridine-3-carboxylate was dissolved in 1,4-dioxane (90 mL), and 6 N hydrochloric acid (16 mL) was added thereto at room temperature. The resulting mixture was stirred for 5 hours at 50° C., and then the solvent was distilled off under reduced pressure from the reaction mixture. The residue was washed with water and dried, and thus 2.80 g (yield: quantitative) of the title compound was obtained as colorless crystals.
¹H-NMR data (CDCl₃/TMS δ (ppm)):
3.91 (3H, s), 5.90 (2H, s), 6.57 (1H, d), 6.78 (1H, t), 6.93 (1H, d), 7.21-7.30 (1H, m), 7.37-7.41 (1H, m), 8.19 (1H, d), 8.77 (1H, d), 8.98 (1H, s), 14.24 (1H, s)

Reference Example 6

(Production intermediate) Production of 2-oxo-1-phenyl-1,2-dihydro-1,8-naphthyridine-3-carboxylic acid (Production intermediate compound No.: VIII-16)

(1) Production of 2-(phenylamino)nicotinic acid 5.0 g (31.7 mmol) of 2-chloronicotinic acid, 5.9 g (63.5 mmol) of aniline, and 0.1 g of potassium iodide were heated up 140° C., and toluene (30 mL) was added to this reaction mixture. The resulting mixture was stirred for 2 hours at 100° C. The reaction mixture was cooled, and then the solvent was distilled off. Chloroform was added to the residue, and insoluble materials were filtered off. The filtrate was concentrated, and thus 7.5 g of the title compound was obtained as crude pale yellow crystals (yield: quantitative).
¹H-NMR data (CDCl₃/TMS δ (ppm)):
6.76-6.79 (1H, m), 7.09 (1H, t), 7.35 (2H, t), 7.59 (2H, d), 8.33-8.39 (2H, m), 10.27 (1H, s), 10.59 (1H, s)

(2) Production of (2-phenylamino-3-pyridinyl)methanol

Under a nitrogen gas stream, 2.41 g (63.4 mmol) of lithium aluminum hydride was added to tetrahydrofuran (80 mL) under ice cooling, and a tetrahydrofuran (30 mL) solution of 6.79 g (31.7 mmol) of 2-(phenylamino)nicotinic acid was added dropwise to the above solution. The resulting mixture was stirred for 2 hours at room temperature. Ethyl acetate was added to the reaction mixture, and 25 mL of a 10% aqueous solution of sodium hydroxide was further added thereto. Insoluble materials were filtered off. The filtrate was concentrated, and the residue thus obtained was dissolved in ethyl acetate, dried, filtered, and concentrated. Thus, 6.9 g of the title compound was obtained as a yellow viscous product (yield: quantitative).

¹H-NMR data (CDCl₃/TMS δ (ppm)):
1.89 (1H, s), 4.70 (2H, s), 6.69-6.73 (1H, m), 6.99 (1H, t), 7.29-7.37 (3H, m), 7.56 (2H, d), 7.68 (1H, s), 8.19 (1H, d)

(3) Production of 2-(phenylamino)nicotinaldehyde 6.35 g (31.7 mmol) of (2-phenylamino-3-pyridinyl)methanol was dissolved in chloroform (100 mL), and 8.27 g (95.1 mmol) of manganese dioxide was added thereto. The resulting mixture was stirred for 7 hours at 60° C. The reaction mixture was filtered, and the filtrate was concentrated. Thus, 6.58 g of the title compound was obtained as an orange-colored solid (yield: quantitative).
¹H-NMR data (CDCl₃/TMS δ (ppm)):
6.82-6.86 (1H, m), 7.10 (1H, t), 7.34-7.39 (2H, m), 7.74 (2H, d), 7.86 (1H, d), 8.42 (1H, d), 9.88 (1H, s), 10.45 (1H, s)

(4) Production of ethyl 2-oxo-1-phenyl-1,2-dihydro-1,8-naphthyridine-3-carboxylate 6.28 g (31.7 mmol) of 2-(phenylamino)nicotinaldehyde was dissolved in ethanol (150 mL), and 7.62 g (47.6 mmol) of diethyl malonate and 1.35 g (15.9 mmol) of piperidine were added thereto. The resulting mixture was stirred overnight at 100° C. The reaction mixture was cooled, and a solid precipitated thereby was separated by filtration. The solid was washed sequentially with ethanol and diisopropyl ether. Thus, 7.42 g of the title compound was obtained as a pale yellow solid (yield: 800).
¹H-NMR data (CDCl₃/TMS δ (ppm)):
1.40 (3H, t), 4.42 (2H, q), 7.19-7.22 (1H, m), 7.26-7.28 (2H, m), 7.47-7.51 (1H, m), 7.54-7.59 (2H, m), 8.02 (1H, d), 8.44 (1H, s), 8.53 (1H, d)

(5) Production of 2-oxo-1-phenyl-1,2-dihydro-1,8-naphthyridine-3-carboxylic acid 2.00 g (6.8 mmol) of ethyl 2-oxo-1-phenyl-1,2-dihydro-1,8-naphthyridine-3-carboxylate was dissolved in 1,4-dioxane (100 mL), and 1.41 g (10.2 mmol) of potassium carbonate and 200 mL of water were added thereto at room temperature. The resulting mixture was stirred for 3 hours at 50° C. The solvent was distilled off under reduced pressure from the reaction mixture, and the residue was dissolved in water. Concentrated hydrochloric acid was added thereto to make the solution acidic. A solid precipitated therefrom was separated by filtration, and was dried. Thus, 1.72 g of the title compound was obtained as pale yellow crystals (yield: 95%).
¹H-NMR data (CDCl₃/TMS δ (ppm)):
7.30-7.32 (2H, m), 7.38-7.41 (1H, m), 7.57-7.67 (3H, m), 8.23 (1H, d), 8.67 (1H, d), 9.05 (1H, s), 13.91 (1H, s)

Reference Example 7

(Production intermediate) Production of 1-(5-methyl-3-isoxazolyl)-2-oxo-1,2-dihydro-1,8-naphthyridine-3-carboxylic acid (Production intermediate compound No.: VIII-24)

(1) Production of methyl 2-(trifluoromethylsulfonyloxy)nicotinate 10.3 g (70 mmol) of methyl 2-hydroxynicotinate was dissolved in 300 mL of dichloromethane, and 7.8 g (77 mmol) of triethylamine was added thereto. 20.9 g (74 mmol) of trifluoromethanesulfonic acid anhydride was added dropwise to the above mixture at −60° C., and the resulting mixture was further allowed to react for 30 minutes at −60° C. The reaction mixture was poured into water, and the mixture was extracted with dichloromethane. The organic phase was washed with water, and then was dried and concentrated. The residue was purified by column chromatography (ethyl acetate:n-hexane=1:4), and thus 12.8 g of the title compound was obtained as a pale yellow liquid (yield: 67%).
¹H-NMR data (CDCl₃/TMS δ (ppm)):
4.00 (3H, s), 7.49-7.53 (1H, m), 8.49 (1H, dd), 8.54 (1H, dd)

(2) Production of methyl 2-(5-methyl-3-isoxazolyl)aminonicotinate 6.7 g (24 mmol) of methyl 2-(trifluoromethylsulfonyloxy) nicotinate and 3.0 g (31 mmol) of 3-amino-5-methylisoxazole were dissolved in toluene (100 mL), and 13.1 g (40 mmol) of cesium carbonate, 1.5 g (1.6 mmol) of tris(dibenzylideneacetone)dipalladium(0), and 1.9 g (3.4 mmol) of 4,5-bis(diphenylphosphino)-9,9-dimethylxanthene were added to the solution. The resulting mixture was heated and stirred for one hour at 80° C. The reaction mixture was cooled, and then the solvent was distilled off. The residue was purified by column chromatography (ethyl acetate:n-hexane=1:4), and thus 4.3 g of the title compound was obtained as an orange-colored viscous product (yield: 78%).
¹H-NMR data (CDCl₃/TMS δ (ppm)):
2.42 (3H, s), 3.94 (3H, s), 6.81-6.86 (2H, m), 8.26 (1H, d), 8.41 (1H, d), 10.46 (1H, dd)

(3) Production of (2-(5-methyl-3-isoxazolyl)amino-3-pyridinyl)methanol

Under a nitrogen gas stream, 0.75 g (20 mmol) of lithium aluminum hydride was added to tetrahydrofuran (70 mL) under ice cooling, and a tetrahydrofuran (30 mL) solution of 2.3 g (9.9 mmol) of methyl 2-(5-methyl-3-isoxazolyl)aminonicotinate was added dropwise to the above solution. The resulting mixture was stirred for one hour under ice cooling. Ethyl acetate was added to the reaction mixture, and 8.0 mL of a 10% aqueous solution of sodium hydroxide was further added thereto. Insoluble materials were filtered off. The filtrate was concentrated, and the residue was dissolved in ethyl acetate, dried, filtered, and concentrated. Thus, 2.2 g of the title compound was obtained as an orange-colored viscous product (yield: quantitative).
¹H-NMR data (CDCl₃/TMS δ (ppm)):
2.37 (1H, br), 2.41 (3H, s), 4.74 (2H, s), 6.77-6.82 (2H, m), 7.41 (1H, d), 8.21 (1H, d), 8.27 (1H, s)

(4) Production of (2-(5-methyl-3-isoxazolyl)amino)nicotinaldehyde 3.3 g (16 mmol) of (2-(5-methyl-3-isoxazolyl)amino-3-pyridinyl)methanol was dissolved in chloroform (60 mL), and 4.3 g (49 mmol) of manganese dioxide was added thereto. The resulting mixture was stirred for 48 hours at 60° C. The reaction mixture was filtered, and the filtrate was concentrated. Thus, 3.3 g of the title compound was obtained as an orange-colored viscous product (yield: quantitative).
¹H-NMR data (CDCl₃/TMS δ (ppm)):
2.43 (3H, s), 6.90 (1H, s), 6.95-7.00 (1H, m), 7.94 (1H, d), 8.46 (1H, d), 9.92 (1H, s), 10.68 (1H, s)

(5) Production of ethyl 1-(5-methyl-3-isoxazolyl)-2-oxo-1,2-dihydro-1,8-naphthyridine-3-carboxylate 3.3 g (16 mmol) of (2-(5-methyl-3-isoxazolyl)amino)nicotinaldehyde was dissolved in ethanol (60 mL), and 3.9 g (24 mmol) of diethyl malonate and 0.56 g (6.5 mmol) of piperidine were added thereto. The resulting mixture was stirred overnight at 90° C. The reaction mixture was cooled, and then the solvent was distilled off. The residue was purified by column chromatography (ethyl acetate:n-hexane=1:4 to 7:3), and thus 2.7 g of the title compound was obtained as pale yellow crystals (yield: 55%).

$^1$H-NMR data (CDCl$_3$/TMS δ (ppm)):
1.40 (3H, t), 2.57 (3H, s), 4.42 (2H, q), 6.19 (1H, s), 7.25-7.29 (1H, m), 8.03 (1H, d), 8.50 (1H, s), 8.58 (1H, d)

(6) Production of 1-(5-methyl-3-isoxazolyl)-2-oxo-1,2-dihydro-1,8-naphthyridine-3-carboxylic acid 1.8 g (6.0 mmol) of ethyl 1-(5-methyl-3-isoxazolyl)-2-oxo-1,2-dihydro-1,8-naphthyridine-3-carboxylate was dissolved in acetic acid (50 mL), and 6 N hydrochloric acid (10 mL) was added to this solution at room temperature. The resulting mixture was stirred for 5 hours at 60° C. The solvent was distilled off from the reaction mixture, and the residue was dissolved in toluene. The solvent was distilled off under reduced pressure, and thus 1.7 g of the title compound was obtained as colorless crystals (yield: quantitative).

$^1$H-NMR data (CDCl$_3$/TMS δ (ppm)):
2.62 (3H, s), 6.24 (1H, s), 7.43-7.47 (1H, d), 8.23 (1H, d), 8.71 (1H, d), 9.04 (1H, s), 13.32 (1H, br)

Reference Example 8

(Production intermediate) Production of 1-(6-methoxy-3-pyridinyl)-2-oxo-1,2-dihydro-1,8-naphthyridine-3-carboxylic acid (Production intermediate compound No.: VIII-25)

(1) Production of methyl 2-chloronicotinate 15.0 g (95.2 mmol) of 2-chloronicotinic acid was dissolved in dichloromethane (150 mL), and 8.37 mL (94.5 mmol) of oxalyl chloride was added thereto. Six droplets of N,N-dimethylformamide were added to the above mixture, and the resulting mixture was stirred for 3 hours at room temperature. 40.1 mL (286 mmol) of triethylamine and 37 mL (914 mmol) of methanol were sequentially added dropwise to the above reaction mixture under ice cooling, and the resulting mixture was stirred for 30 minutes under ice cooling. The solvent was distilled off under reduced pressure from the reaction mixture, and then an aqueous solution of sodium hydrogen carbonate was added to the residue. The resulting mixture was extracted with diethyl ether. The organic phase was washed with water, dried, and concentrated, and the residue was purified by column chromatography (ethyl acetate:n-hexane=1:4). 13.9 g of the title compound was obtained as a pale yellow liquid (yield: 86%).

$^1$H-NMR data (CDCl$_3$/TMS δ (ppm)):
3.97 (3H, s), 7.33 (1H, dd), 8.17 (1H, dd), 8.53 (1H, dd)

(2) Production of methyl 2-(6-methoxy-3-pyridinyl)aminonicotinate 5.0 g (29 mmol) of methyl 2-chloronicotinate and 4.3 g (35 mmol) of 6-methoxypyridine-3-amine were dissolved in toluene (80 mL), and 16.1 g (50 mmol) of cesium carbonate, 1.3 g (1.5 mmol) of tris(dibenzylideneacetone)dipalladium (0), and 1.8 g (3.1 mmol) of 4,5-bis(diphenylphosphino)-9,9-dimethylxanthene were added to the solution. The resulting mixture was heated and stirred for 72 hours at 90° C. The solvent was distilled off from the reaction mixture, water and ethyl acetate were added to the residue, and the mixture was filtered. The filtrate was extracted with ethyl acetate, and the organic phase was dried and concentrated. The residue was purified by column chromatography (ethyl acetate:n-hexane=1:4 to 1:1), and thus 6.8 g of the title compound was obtained as a pale yellow viscous product (yield: 96%).

$^1$H-NMR data (CDCl$_3$/TMS δ (ppm)):
3.94 (6H, s), 6.68-6.77 (2H, m), 7.94 (1H, dd), 8.22 (1H, dd), 8.31 (1H, dd), 8.36 (1H, d), 9.88 (1H, s)

(3) Production of (2-(6-methoxy-3-pyridinyl)amino-3-pyridinyl)methanol

Under a nitrogen gas stream, 2.1 g (56 mmol) of lithium aluminum hydride was added to tetrahydrofuran (100 mL) under ice cooling, and a tetrahydrofuran (60 mL) solution of 6.8 g (28 mmol) of methyl 2-(6-methoxy-3-pyridinyl)aminonicotinate was added dropwise to the above solution. The resulting mixture was stirred for 2 hours at room temperature. Ethyl acetate was added to the reaction mixture, and 23 mL of a 10% aqueous solution of sodium hydroxide was further added thereto. Insoluble materials were filtered off. The filtrate was concentrated, and the residue was dissolved in ethyl acetate, dried, filtered, and concentrated. 6.6 g of the title compound was obtained as a yellow viscous product (yield: quantitative).

$^1$H-NMR data (CDCl$_3$/TMS δ (ppm)):
1.67 (1H, br), 3.92 (3H, s), 4.72 (2H, s), 6.66-6.75 (2H, m), 7.33 (1H, dd), 7.51 (1H, s), 7.91 (1H, dd), 8.10 (1H, dd), 8.21 (1H, d)

(4) Production of 2-(6-methoxy-3-pyridinylamino)nicotinaldehyde 6.48 g (28 mmol) of (2-(6-methoxy-3-pyridinyl)amino-3-pyridinyl)methanol was dissolved in chloroform (200 mL), and 7.3 g (84 mmol) of manganese dioxide was added thereto. The resulting mixture was stirred for 48 hours at 50° C. The reaction mixture was filtered, and the filtrate was concentrated. Thus, 6.5 g of the title compound was obtained as an orange-colored solid (yield: quantitative).

$^1$H-NMR data (CDCl$_3$/TMS δ (ppm)):
3.94 (3H, s), 6.76 (1H, d), 6.84 (1H, dd), 7.88 (1H, dd), 7.96 (1H, dd), 8.37 (1H, dd), 8.42 (1H, d), 9.90 (1H, d), 10.20 (1H, s)

(5) Production of ethyl 1-(6-methoxy-3-pyridyl)-2-oxo-1,2-dihydro-1,8-naphthyridine-3-carboxylate 6.4 g (28 mmol) of 2-(6-methoxy-3-pyridinylamino)nicotinaldehyde was dissolved in ethanol (50 mL), and 6.7 g (42 mmol) of diethyl malonate and 0.95 g (11 mmol) of piperidine were added thereto. The resulting mixture was stirred for 4 hours at 100° C. The solvent was distilled off under reduced pressure from the reaction mixture, and the residue was washed with a mixed solution of ethyl acetate and diisopropyl ether. Thus, 4.1 g of the title compound was obtained as a pale yellow solid (yield: 45%).

$^1$H-NMR data (CDCl$_3$/TMS δ (ppm)):
1.41 (3H, t), 4.00 (3H, s), 4.43 (2H, q), 6.92 (1H, d), 7.24 (1H, dd), 7.51 (1H, dd), 8.03 (1H, d), 8.08 (1H, d), 8.49 (1H, s), 8.54 (1H, dd)

(5) Production of 1-(6-methoxy-3-pyridinyl)-2-oxo-1,2-dihydro-1,8-naphthyridine-3-carboxylic acid 4.1 g (13 mmol) of ethyl (6-methoxy-3-pyridinyl)-2-oxo-1,2-dihydro-1,8-naphthyridine-3-carboxylate was dissolved in 1,4-dioxane (60 mL), and 2.6 g (19 mmol) of potassium carbonate and 100 mL of water were added thereto at room temperature. The resulting mixture was stirred for 3 hours at 60° C. The solvent was distilled off under reduced pressure from the reaction mixture, and the residue was dissolved in water and washed with chloroform. Concentrated hydrochloric acid was added to the aqueous phase to make the aqueous phase acidic, and the mixture was extracted with chloroform. The organic phase was dried and concentrated. Thus, 1.45 g of the title compound was obtained as colorless crystals (yield: 39%).

$^1$H-NMR data (CDCl$_3$/TMS δ (ppm)):
4.04 (3H, s), 6.99 (1H, d), 7.42 (1H, dd), 7.52 (1H, dd), 8.12 (1H, d), 8.23 (1H, d), 8.68 (1H, dd), 9.04 (1H, s), 13.76 (1H, s)

Reference Example 9

(Production intermediate) Production of 1-(2,3-dihydrobenzo[b][1,4]dioxin-6-yl)-2-oxo-1,2-dihydro-1,8-naphthyridine-3-carboxylic acid (Production intermediate compound No.: VIII-26)

(1) Production of methyl 2-(trifluoromethylsulfonyloxy)nicotinate 12.4 g (81 mmol) of methyl 2-hydroxynicotinate was dissolved in 150 mL of dichloromethane, and 9.0 g (89 mmol) of triethylamine was added thereto. Subsequently, 25.1 g (89 mmol) of trifluoromethanesulfonic acid anhydride was added dropwise to the mixture at −30° C. The reaction mixture was allowed to react for 5 hours at room temperature, and the reaction mixture was poured into water. The resulting mixture was stirred for one hour at room temperature, and then was extracted with dichloromethane. The organic phase was washed with water, and then was dried and concentrated. 21.2 g of the title compound was obtained as an orange-colored liquid (yield: 92%).

$^1$H-NMR data (CDCl$_3$/TMS δ (ppm)):
4.00 (3H, s), 7.49-7.53 (1H, m), 8.49 (1H, dd), 8.54 (1H, dd)

(2) Production of methyl 2-(2,3-dihydrobenzo[b][1,4]dioxin-6-yl)aminonicotinate 10.6 g (37 mmol) of methyl 2-(trifluoromethylsulfonyloxy)nicotinate and 6.2 g (41 mmol) of 3,4-ethylenedioxybenzylamine were dissolved in toluene (100 mL), and 17.0 g (52 mmol) of cesium carbonate, 1.0 g (1.1 mmol) of tris(dibenzylideneacetone)dipalladium(0), and 1.3 g (5.2 mmol) of 4,5-bis(diphenylphosphino)-9,9-dimethylxanthene were added thereto. The resulting mixture was heated and stirred for 2 hours at 80° C. The solvent was distilled off from the reaction mixture, water and ethyl acetate were added to the residue, and the resulting mixture was filtered. The filtrate was extracted with ethyl acetate, and the organic phase was washed with an aqueous solution of citric acid and water in this order, and then was dried and concentrated. The residue was purified by column chromatography (ethyl acetate:n-hexane=1:9 to 1:2), and thus 9.86 g of the title compound was obtained as an orange-colored viscous product (yield: 93%).

$^1$H-NMR data (CDCl$_3$/TMS δ (ppm)):
3.91 (3H, s), 4.24 (4H, br), 6.64-6.66 (1H, m), 6.83 (1H, d), 6.97 (1H, dd), 7.37 (1H, d), 8.19 (1H, dd), 8.33 (1H, dd), 9.92 (1H, br)

(3) Production of 2-(2,3-dihydrobenzo[b][1,4]dioxin-6-yl)amino-3-pyridinylmethanol Under a nitrogen gas stream, 1.70 g (41 mmol) of lithium aluminum hydride was added to tetrahydrofuran (100 mL) under ice cooling, and a tetrahydrofuran (30 mL) solution of 9.86 g (34 mmol) of methyl 2-(2,3-dihydrobenzo[b][1,4]dioxin-6-yl)aminonicotinate was added dropwise to the mixture. Ethyl acetate was added to the reaction mixture, and subsequently, 17 mL of a 10% aqueous solution of sodium hydroxide was added thereto. Insoluble materials were filtered off. The filtrate was concentrated, and the residue was dissolved in ethyl acetate, dried, filtered, and concentrated. Thus, 8.9 g of the title compound was obtained as an orange-colored viscous product (yield: quantitative).

$^1$H-NMR data (CDCl$_3$/TMS δ (ppm)):
2.78 (1H, br), 4.20 (4H, br), 4.56 (1H, s), 6.59-6.63 (1H, m), 6.77-6.86 (2H, m), 7.18-7.26 (2H, m), 7.47 (1H, br), 8.07 (1H, dd)

(4) Production of (2-(2,3-dihydrobenzo[b][1,4]dioxin-6-yl)amino)nicotinaldehyde 8.9 g (34 mmol) of 2-(2,3-dihydrobenzo[b][1,4]dioxin-6-yl)amino-3-pyridinylmethanol was dissolved in chloroform (100 mL), and 10.1 g (0.10 mol) of manganese dioxide was added thereto. The resulting mixture was stirred overnight at 50° C. The reaction mixture was filtered and concentrated, and the residue thus obtained was dissolved in ethyl acetate, dried, filtered, and concentrated. The oily product thus obtained was purified by column chromatography (ethyl acetate:n-hexane=1:9 to 1:1), and thus 7.69 g of the title compound was obtained as an orange-colored viscous product (yield: 87%).

$^1$H-NMR data (CDCl$_3$/TMS δ (ppm)):
4.26 (4H, br), 6.77-6.81 (1H, m), 6.87 (1H, d), 7.43 (1H, d), 7.82 (1H, dd), 8.38 (1H, dd), 9.85 (1H, s), 10.25 (1H, br)

(5) Production of ethyl 1-(2,3-dihydrobenzo[b][1,4]dioxin-6-yl)-2-oxo-1,2-dihydro-1,8-naphthyridine-3-carboxylate 7.69 g (30 mmol) of (2-(2,3-dihydrobenzo[b][1,4]dioxin-6-yl)amino)nicotinaldehyde was dissolved in ethanol (150 mL), and 7.2 g (45 mmol) of diethyl malonate and 1.5 mL (15 mmol) of pyrrolidine were added thereto. The resulting mixture was stirred overnight at 100° C. The mixture was cooled, and a solid precipitated thereby was purified by column chromatography (ethyl acetate:n-hexane=1:1 to 1:0). Thus, 4.3 g of the title compound was obtained as a pale yellow solid (yield: 41%).

$^1$H-NMR data (CDCl$_3$/TMS δ (ppm)):
1.40 (3H, t), 4.31 (4H, br), 4.42 (2H, q), 6.73 (1H, dd), 6.79 (1H, d), 7.03 (1H, d), 7.18-7.23 (1H, m), 8.00 (1H, dd), 8.46 (1H, s), 8.58 (1H, dd)

(6) Production of 1-(2,3-dihydrobenzo[b][1,4]dioxin-6-yl)-2-oxo-1,2-dihydro-1,8-naphthyridine-3-carboxylic acid 4.3 g (12 mmol) of ethyl 1-(2,3-dihydrobenzo[b][1,4]dioxin-6-yl)-2-oxo-1,2-dihydro-1,8-naphthyridine-3-carboxylate was dissolved in 1,4-dioxane (100 mL), and 1.0 g (24 mmol) of lithium hydroxide monohydrate and 50 mL of water were added thereto at room temperature. The resulting mixture was stirred overnight at room temperature. Water was added to the reaction mixture, and a solid precipitated therefrom was dissolved in chloroform. This solution was washed with an aqueous solution of citric acid and water in this order, and was dried and concentrated. The solid thus obtained was washed with diisopropyl ether, and thus 3.96 g of the title compound was obtained as pale yellow crystals (yield: quantitative).

$^1$H-NMR data (CDCl$_3$/TMS δ (ppm)):
4.34 (4H, br), 6.75 (1H, dd), 6.82 (1H, d), 7.09 (1H, d), 7.37-7.42 (1H, m), 8.20 (1H, dd), 8.72 (1H, dd), 9.02 (1H, s), 13.94 (1H, s)

Reference Example 10

(Production intermediate) Production of 1-methyl-2-oxo-7-(trifluoromethyl)-1,2-dihydro-1,8-naphthyridine-3-carboxylic acid (Production intermediate compound No.: VIII-33)

(1) Production of ethyl 2-amino-6-(trifluoromethyl)nicotinate 19.5 g (0.12 mol) of ethyl 3-amino-3-iminopropanoate (described in Chemical and Pharmaceutical Bulletin, vol. 43, No. 5, p. 793 (1995)) was added to 100 mL of acetonitrile, and 18.6 g (0.12 mol) of 1,8-diazabicyclo[5.4.0]-7-undecene was added thereto at room temperature. The resulting mixture was stirred for 5 minutes. 20.6 g (0.12 mol) of 4-ethoxy-1,1,1-trifluoro-3-buten-2-one was added to the above mixture, and 18.6 g (0.12 mol) of 1,8-diazabicyclo[5.4.0]-7-undecene was added thereto. The resulting mixture was stirred for 3 hours at 80° C. The solvent was distilled off under reduced pressure from the reaction mixture, and the residue was concentrated to half the original volume. Ice water was added thereto. Crystals precipitated therefrom were separated by filtration, and were dissolved in ethyl acetate. The filtrate was extracted with ethyl acetate. The solution having the crystals dissolved therein and the organic phase extracted were combined, and the resultant was washed with brine, and then was dried and concentrated. The residue was purified by column chromatography (ethyl acetate:n-hexane=1:9 to 1:4), and thus 17.8 g of the title compound was obtained as colorless crystals (yield: 62%).

$^1$H-NMR data (CDCl$_3$/TMS δ (ppm)):
1.40 (3H, s), 4.38 (2H, q), 5.5-7.5 (2H, br), 6.95 (1H, d, J=7.95 Hz), 8.29 (1H, d, J=7.95 Hz)

(2) Production of ethyl 2-formamide-6-(trifluoromethyl)nicotinate 5.0 g (21 mmol) of ethyl 2-amino-6-(trifluoromethyl)nicotinate was mixed with 10 mL of formic acid, and the mixture was heated and stirred for one whole day and night at 100° C. The reaction mixture was cooled and then concentrated. The residue was purified by column chromatography (ethyl acetate:n-hexane=1:9 to 4:6), and 3.7 g of the title compound was obtained as colorless crystals (yield: 66%).

$^1$H-NMR data (CDCl$_3$/TMS δ (ppm)):
1.44 (3H, s), 4.45 (2H, q), 7.43 (1H, d, J=8.22 Hz), 8.50 (1H, d, J=7.38 Hz), 9.71 (1H, d, J=9.87 Hz), 10.59 (1H, br)

(3) Production of 2-(methylamino)-6-(trifluoromethyl)-3-pyridinemethanol

Under a nitrogen gas stream, 1.75 g (42 mmol) of lithium aluminum hydride was added to tetrahydrofuran (100 mL), and a tetrahydrofuran (30 mL) solution of 3.7 g (14 mmol) of ethyl 2-formamide-6-(trifluoromethyl)nicotinate was added dropwise thereto. The resulting mixture was stirred for 2 hours at 40° C. Ethyl acetate was added to the reaction mixture, and subsequently, 18 mL of a 10% aqueous solution of sodium hydroxide was added thereto. Insoluble materials were filtered off. The filtrate was concentrated, and the residue thus obtained was dissolved in ethyl acetate, dried, filtered, and concentrated. A solid thus obtained was washed with diisopropyl ether, and thus 2.30 g of the title compound was obtained as pale yellow crystals (yield: 79%).

$^1$H-NMR data (CDCl$_3$/TMS δ (ppm)):
3.04 (3H, d), 4.61 (2H, s), 4.56 (1H, s), 6.84 (1H, d), 7.27 (1H, d)

(4) Production of 2-(methylamino)-6-(trifluoromethyl)-3-nicotinaldehyde 2.3 g (11 mmol) of 2-(methylamino)-6-(trifluoromethyl)-3-pyridinemethanol was dissolved in chloroform (100 mL), and 3.3 g (33 mmol) of manganese dioxide was added thereto. The resulting mixture was stirred for 8 hours at 50° C. The reaction mixture was filtered, and the filtrate was concentrated. The residue was purified by column chromatography (ethyl acetate:n-hexane=1:4 to 3:7), and thus 1.26 g of the title compound was obtained as a yellow solid (yield: 55%).

$^1$H-NMR data (CDCl$_3$/TMS δ (ppm)):
3.10 (3H, d), 6.93 (1H, d), 7.86 (1H, d), 8.38 (1H, br), 9.88 (1H, br)

(5) Production of ethyl 1-methyl-2-oxo-7-(trifluoromethyl)-1,2-dihydro-1,8-naphthyridine-3-carboxylate 1.26 g (6.2 mmol) of 2-(methylamino)-6-(trifluoromethyl)-3-nicotinaldehyde was dissolved in ethanol (50 mL), and 1.5 g (9.4 mmol) of diethyl malonate and 0.3 mL (3 mmol) of pyrrolidine were added thereto. The resulting mixture was stirred overnight at 100° C. The reaction mixture was cooled and then concentrated, and a solid precipitated thereby was washed with diisopropyl ether. Thus, 1.24 g of the title compound was obtained as a pale yellow solid (yield: 67%).

$^1$H-NMR data (CDCl$_3$/TMS δ (ppm)):
1.43 (3H, t), 3.87 (3H, s), 4.44 (2H, q), 7.56 (1H, d), 8.14 (1H, d), 8.35 (1H, s)

(6) Production of 1-methyl-2-oxo-7-(trifluoromethyl)-1,2-dihydro-1,8-naphthyridine-3-carboxylic acid 1.24 g (4.1 mmol) of ethyl 1-methyl-2-oxo-7-(trifluoromethyl)-1,2-dihydro-1,8-naphthyridine-3-carboxylate was dissolved in 1,4-dioxane (50 mL), and 0.35 g (8.3 mmol) of lithium hydroxide monohydrate and 10 mL of water were added thereto at room temperature. The resulting mixture was stirred overnight at room temperature. The reaction mixture was poured into an aqueous solution of sodium hydrogen carbonate, and the mixture was washed with ethyl acetate. The aqueous phase was acidified with citric acid, and the mixture was extracted with ethyl acetate. The organic phase was washed with water, dried, and concentrated. The residue was washed with normal-hexane, and thus 1.02 g of the title compound was obtained as colorless crystals (yield: 91%).

$^1$H-NMR data (CDCl$_3$/TMS δ (ppm)):
4.01 (3H, s), 7.74 (1H, d), 8.37 (1H, d), 8.96 (1H, s), 14.04 (1H, s)

The structural formulas of the intermediates of the compound [I] of the present invention produced according to the Intermediate Production Examples described above, including Reference Examples 1 to 10, are presented below. The symbols in the tables have the same meanings as defined above.

TABLE 68

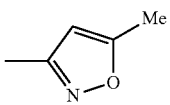

| Compound No. | $R^1$ | $R^2$ | $X^2$ | $X^3$ | $X^4$ |
|---|---|---|---|---|---|
| VIII-1 | Me | H | CH | CH | CH |
| VIII-2 | (4-OMe)Ph | H | CH | CH | CH |
| VIII-3 | Et | H | CH | CH | CCl |
| VIII-4 | Me | H | N | CH | CH |
| VIII-5 | Et | H | N | CH | CH |
| VIII-6 | n-Pr | H | N | CH | CH |
| VIII-7 | $C_2H_4OC_2H_5$ | H | N | CH | CH |
| VIII-8 | $CH_2SEt$ | H | N | CH | CH |
| VIII-9 | Bn | H | N | CH | CH |
| VIII-10 | (2-Cl)Bn | H | N | CH | CH |
| VIII-11 | (3-Cl)Bn | H | N | CH | CH |
| VIII-12 | (4-Cl)Bn | H | N | CH | CH |
| VIII-13 | (2-OMe)Bn | H | N | CH | CH |
| VIII-14 | (3-OMe)Bn | H | N | CH | CH |
| VIII-15 | (4-OMe)Bn | H | N | CH | CH |
| VIII-16 | Ph | H | N | CH | CH |
| VIII-17 | (3-F)Ph | H | N | CH | CH |
| VIII-18 | (3-Me)Ph | H | N | CH | CH |
| VIII-19 | $(3-CF_3)$Ph | H | N | CH | CH |
| VIII-20 | (2-OMe)Ph | H | N | CH | CH |
| VIII-21 | (3-OMe)Ph | H | N | CH | CH |
| VIII-22 | (4-OMe)Ph | H | N | CH | CH |
| VIII-23 | $(2,5-Me_2)$Ph | H | N | CH | CH |
| VIII-24 | 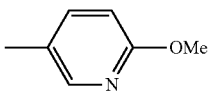 | H | N | CH | CH |
| VIII-25 | 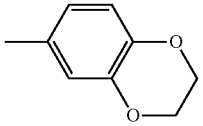 | H | N | CH | CH |
| VIII-26 | 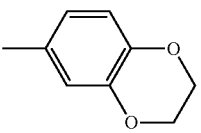 | H | N | CH | CH |

TABLE 69

| Compound No. | $R^1$ | $R^2$ | $X^2$ | $X^3$ | $X^4$ |
|---|---|---|---|---|---|
| VIII-27 | Me | Me | N | CH | CH |
| VIII-28 | Ph | Me | N | CH | CH |
| VIII-29 | Me | i-Pr | N | CH | CH |
| VIII-30 | Ph | i-Pr | N | CH | CH |
| VIII-31 | Me | $CHF_2$ | N | CH | CH |
| VIII-32 | Ph | $CHF_2$ | N | CH | CH |
| VIII-33 | Me | $CF_3$ | N | CH | CH |
| VIII-34 | Ph | $CF_3$ | N | CH | CH |
| VIII-35 | Me | $CF_2Cl$ | N | CH | CH |
| VIII-36 | Ph | $CF_2Cl$ | N | CH | CH |
| VIII-37 | Me | Et | N | CH | CH |

TABLE 69-continued

| Compound No. | $R^1$ | $R^2$ | $X^2$ | $X^3$ | $X^4$ |
|---|---|---|---|---|---|
| VIII-38 | 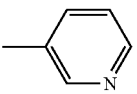 | $CHF_2$ | N | CH | CH |
| VIII-39 | Me | H | CH | CH | N |
| VIII-40 | Ph | H | CH | CH | N |
| VIII-41 | Ph | H | N | N | CH |
| VIII-42 | $CH_2SO_2Et$ | H | N | CH | CH |
| VIII-43 | 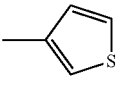 | $CF_3$ | N | CH | CH |
| VIII-44 | Et | H | CH | CH | CF |
| VIII-45 | (4-OMe)Ph | H | CH | CH | CF |
| VIII-46 | c-Pr | H | N | CH | CH |
| VIII-47 | (3-Cl)Ph | H | N | CH | CH |
| VIII-48 | (4-Cl)Ph | H | N | CH | CH |
| VIII-49 | 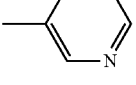 | H | N | CH | CH |
| VIII-50 | 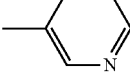 | H | N | CH | CH |
| VIII-51 | 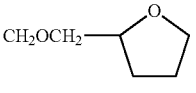 | H | N | CH | CH |
| VIII-52 | $CH_2OCH_2$—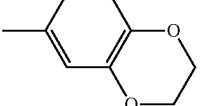 | H | N | CH | CH |
| VIII-53 | 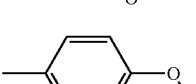 | Et | N | CH | CH |
| VIII-54 | 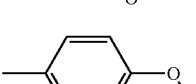 | $CF_3$ | N | CH | CH |
| VIII-55 | $(3-CF_3)$Ph | H | CH | CH | CF |

The property values of the Reference Examples described above will be shown below.

TABLE 70

| Compound No. | Melting point (° C.) or Refractive index ($n_D^{20}$) |
|---|---|
| VIII-1 | Melting point 220-223 |
| VIII-2 | Melting point 255-256 |
| VIII-3 | Melting point 192-195 |
| VIII-4 | Melting point 220-222 |
| VIII-5 | Melting point 180-182 |
| VIII-6 | Melting point 155-157 |
| VIII-7 | Melting point 141-142 |
| VIII-8 | Melting point 168-170 |

TABLE 70-continued

| Compound No. | Melting point (° C.) or Refractive index ($n_D^{20}$) |
|---|---|
| VIII-9 | Melting point 170-173 |
| VIII-10 | Melting point 212-214 |
| VIII-11 | Melting point 184-185 |
| VIII-12 | Melting point 220-222 |
| VIII-13 | Melting point 188-191 |
| VIII-14 | Melting point 152-154 |
| VIII-15 | Melting point 193-195 |
| VIII-16 | Melting point 239-241 |
| VIII-17 | Melting point 176-178 |
| VIII-18 | Melting point 235-237 |
| VIII-19 | Melting point 195-196 |
| VIII-20 | Melting point 264-266 |
| VIII-21 | Melting point 272-274 |
| VIII-22 | Melting point 265-268 |
| VIII-23 | Melting point 211-214 |
| VIII-24 | Melting point 224-226 |
| VIII-25 | Melting point 256-258 |
| VIII-26 | Melting point 242-244 |
| VIII-27 | Melting point 230-233 |
| VIII-28 | Melting point 242-244 |
| VIII-29 | Melting point 165-168 |
| VIII-30 | Melting point 213-215 |
| VIII-31 | Melting point 174-176 |
| VIII-32 | Melting point 176-178 |
| VIII-33 | Melting point 183-186 |
| VIII-34 | Melting point 177-180 |
| VIII-35 | Melting point 172-174 |
| VIII-36 | Melting point 231-233 |
| VIII-37 | Melting point 162-165 |
| VIII-38 | Melting point 203-206 |
| VIII-39 | Melting point 187-189 |
| VIII-40 | Melting point 254-256 |
| VIII-41 | Melting point 196-198 |
| VIII-42 | Melting point 196-198 |
| VIII-43 | Melting point 180-182 |

The $^1$H-NMR values of Intermediate Compound No. VIII-41 for the compound [I] of the present invention produced according to the Intermediate Production Examples described above, are shown below.

Compound No. VIII-41

(CDCl$_3$/TMS δ (ppm)): 7.17-7.30 (2H, m), 7.54-7.67 (3H, m), 9.07 (1H, s), 9.11 (1H, s), 9.24 (1H, s), 13.30 (1H, br)

Next, the methods for formulation will be described in detail by way of representative Formulation Examples. The compounds, the type of additives, and the mixing ratios can be varied in a wide range without being limited to these Formulation Examples. In the following descriptions, the unit "parts" means parts by weight.

Formulation Example 1

Wettable Powder Formulation

| | |
|---|---|
| Compound of Compound No. II-2 | 10 parts |
| Polyoxyethylene octyl phenyl ether | 0.5 parts |
| β-naphthalenesulfonic acid-formalin condensate sodium salt | 0.5 parts |
| Diatomaceous earth | 20 parts |
| Clay | 69 parts |

The above components were uniformly mixed and pulverized, and thereby a wettable powder formulation was obtained. Furthermore, wettable powder formulations could be obtained in the same manner by using the respective compounds described in Tables 1 to 66 in place of Compound No. II-2.

Formulation Example 2

Flowable Formulation

| | |
|---|---|
| Compound of Compound No. II-41 | 20 parts |
| Water | 69 parts |
| Polyoxyethylene styrenated phenyl ether sulfate | 4 parts |
| Ethylene glycol | 7 parts |

Silicone AF-118N (manufactured by Asahi Kasei Corp.) was added to the above components in an amount of 200 ppm relative to the total amount, and the mixture was mixed for 30 minutes in a high-speed agitator. The mixture was pulverized in a wet type pulverizer, and thus a flowable formulation was obtained. Furthermore, flowable formulations can be obtained in the same manner by using the respective compounds described in Tables 1 to 66 in place of Compound No. II-41.

Formulation Example 3

Emulsifiable Concentrate

| | |
|---|---|
| Compound of Compound No. III-118 | 30 parts |
| Equal amount mixture of xylene and isophorone | 60 parts |
| Polyoxyethylene sorbitan alkylate | 4 parts |
| Polyoxyethylene polyalkyl aryl ether | 4 parts |
| Alkylaryl sulfonate | 2 parts |

The above components were uniformly dissolved, and thus an emulsifiable concentrate was obtained. Furthermore, emulsifiable concentrates can be obtained in the same manner by using the respective compounds described in Tables 1 to 66 in place of Compound No. III-118.

Formulation Example 4

Granule Formulation

| | |
|---|---|
| Compound of Compound No. IV-41 | 10 parts |
| Mixture of talc and bentonite (1:3) | 80 parts |
| White carbon | 5 parts |
| Polyoxyethylene sorbitan alkylate | 2 parts |
| Polyoxyethylene polyalkyl aryl ether | 2 parts |
| Alkylaryl sulfonate | 1 part |

The above components were uniformly mixed and pulverized. Water was added to the resulting mixture in an amount equivalent to 10 parts, and the mixture was kneaded. The kneaded mixture was extruded through sieve holes having a diameter of 0.7 mm using an extrusion type granulator, dried, and then cut to a length of 0.5 to 1 mm. Thus, a granule formulation was obtained. Furthermore, granule formulations can be obtained in the same manner by using the respective compounds described in Tables 1 to 66 in place of Compound No. IV-41.

The compounds described in Tables 1 to 66 can be formulated into various similar formulations according to the methods described in Formulation Examples 1 to 4.

Next, the herbicidal activity of the compounds of the present invention will be described by way of Test Examples.

Test Example 1

Test for Herbicidal Effects in Paddy Field Soil Treatment 100-cm² plastic pots were filled with paddy field soil. After puddling and leveling, seeds of *Echinochloa oryzicola* Vasing, *Monochoria vaginalis* (Burm. f.) Presl var. *plantaginea* (Roxb.) Solms-Laub., and *Scirpus juncoides* Roxb. var. *ohwianus*. *T. Koyama* were sowed in the pots, and the soil was waterlogged to a water depth of 3 cm. On the next day, a wettable powder formulation prepared according to Formulation Example 1 was diluted with water, and the dilution was added dropwise onto the water surface. The amount of application was an amount equivalent to 1000 g of the active ingredient per hectare. Thereafter, the plants were grown in a greenhouse, and on the $21^{st}$ day after the treatment, the herbicidal effects were investigated according to the criteria described in Table 71.

TABLE 71

| Index No. | Herbicidal effects (degree of growth suppression) and phytotoxicity |
|---|---|
| 5 | Herbicidal effect of 90% or more suppression, phytotoxic |
| 4 | Herbicidal effect of equal to or greater than 70% and less than 90%, phytotoxic |
| 3 | Herbicidal effect of equal to or greater than 50% and less than 70%, phytotoxic |
| 2 | Herbicidal effect of equal to or greater than 30% and less than 50%, phytotoxic |
| 1 | Herbicidal effect of equal to or greater than 10% and less than 30%, phytotoxic |
| 0 | Herbicidal effect of equal to or greater than 0% and less than 10%, phytotoxic |

The results are presented in Tables 72 and 73.

In addition, comparative compound A, comparative compound B, comparative compound C, and comparative compound D in the tables represent Compound Nos. 70, 34, 32, and 31, respectively, as described in EP-283261. The structural formulas of these compounds are presented below.

[Chemical Formula 26]

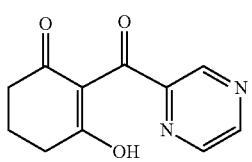

Comparative compound A

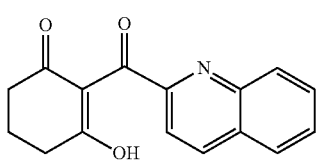

Comparative compound B

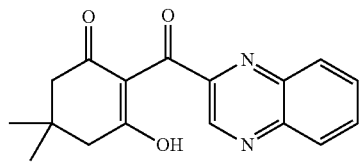

Comparative compound C

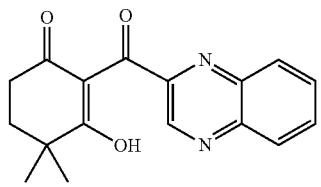

Comparative compound D

TABLE 72

| Compound No. | Echinochloa oryzicola | Monochoria vaginlis | Scirpus juncoides |
|---|---|---|---|
| I-2 | 5 | 5 | 5 |
| I-56 | 5 | 5 | 5 |
| I-157 | 5 | 4 | 3 |
| II-2 | 5 | 5 | 5 |
| II-3 | 5 | 5 | 5 |
| II-4 | 5 | 5 | 5 |
| II-15 | 5 | 5 | 5 |
| II-19 | 5 | 5 | 5 |
| II-24 | 5 | 5 | 5 |
| II-28 | 5 | 5 | 5 |
| II-29 | 5 | 5 | 5 |
| II-30 | 4 | 5 | 5 |
| II-37 | 5 | 5 | 5 |
| II-38 | 5 | 5 | 5 |
| II-39 | 5 | 5 | 5 |
| II-41 | 5 | 5 | 5 |
| II-43 | 5 | 5 | 5 |
| II-48 | 5 | 5 | 5 |
| II-52 | 5 | 5 | 5 |
| II-54 | 5 | 5 | 5 |
| II-55 | 5 | 5 | 5 |
| II-56 | 5 | 5 | 5 |
| II-58 | 5 | 5 | 5 |
| II-63 | 5 | 5 | 5 |
| II-92 | 5 | 5 | 5 |
| II-118 | 5 | 5 | 5 |
| II-121 | 5 | 5 | 5 |
| II-123 | 5 | 5 | 5 |
| II-126 | 3 | 5 | 4 |
| II-128 | 5 | 5 | 5 |
| II-131 | 5 | 5 | 5 |
| II-133 | 5 | 5 | 5 |
| II-136 | 5 | 5 | 5 |
| II-138 | 5 | 5 | 5 |
| II-141 | 5 | 5 | 5 |
| II-143 | 5 | 5 | 5 |
| II-434 | 5 | 5 | 5 |
| II-442 | 5 | 5 | 5 |

TABLE 73

| Compound No. | Echinochloa oryzicola | Monochoria vaginalis | Scirpus juncoides |
|---|---|---|---|
| III-41 | 4 | 4 | 4 |
| IV-41 | 5 | 5 | 5 |
| V-41 | 5 | 5 | 5 |
| Comparative compound A | 2 | 0 | 0 |
| Comparative compound B | 0 | 0 | 0 |

TABLE 73-continued

| Compound No. | Echinochloa oryzicola | Monochoria vaginalis | Scirpus juncoides |
|---|---|---|---|
| Comparative compound C | 1 | 2 | 1 |
| Comparative compound D | 1 | 4 | 2 |

Test Example 2

Test on Herbicidal Effects in Farmland Soil Treatment 80-cm² plastic pots were filled with farmland soil. Seeds of *Abutilon theophrasti medicus* and *Amaranthus retroflexus* were sowed in the pots, and soil was covered. A wettable powder formulation prepared according to Formulation Example 1 was diluted with water, and the dilution was uniformly sprayed on the soil surface with a small sprayer, in an amount equivalent to 1000 liters per hectare, such that 1000 g of the active ingredient was applied per hectare. Thereafter, the plants were grown in a greenhouse, and on the 21$^{st}$ day after the treatment, the herbicidal effects were investigated according to the criteria described in Table 71 shown above. The results are presented in the following Table 74.

TABLE 74

| Compound No. | Echinochloa crus-galli | Setaria viridis | Abutilon thophrasti | Amaranthus retroflexus |
|---|---|---|---|---|
| II-2 | 5 | 5 | 5 | 5 |
| II-4 | 5 | 4 | 5 | 5 |
| II-15 | 5 | 5 | 5 | 5 |
| II-19 | 4 | 4 | 5 | 5 |
| II-24 | 5 | 3 | 5 | 5 |
| II-41 | 5 | 5 | 5 | 5 |
| II-43 | 5 | 5 | 5 | 5 |
| II-48 | 5 | 5 | 4 | 5 |
| II-52 | 5 | 5 | 5 | 5 |
| II-54 | 5 | 5 | 5 | 5 |
| II-55 | 5 | 5 | 5 | 5 |
| II-56 | 5 | 5 | 5 | 5 |
| II-58 | 5 | 5 | 5 | 5 |
| II-63 | 4 | 3 | 5 | 5 |
| II-92 | 5 | 4 | 5 | 5 |
| II-118 | 5 | 5 | 5 | 5 |
| II-123 | 5 | 5 | 5 | 5 |
| II-128 | 5 | 5 | 4 | 5 |
| II-131 | 4 | 3 | 5 | 5 |
| II-133 | 5 | 5 | 5 | 5 |
| II-136 | 5 | 4 | 4 | 5 |
| II-141 | 3 | 4 | 5 | 3 |
| II-143 | 5 | 5 | 5 | 5 |
| IV-41 | 5 | 5 | 5 | 5 |
| V-41 | 5 | 4 | 5 | 4 |
| Comparative compound A | 5 | 1 | 1 | 0 |
| Comparative compound B | 3 | 0 | 2 | 2 |
| Comparative compound C | 2 | 0 | 0 | 3 |
| Comparative compound D | 2 | 0 | 0 | 3 |

Test Example 3

Test on Herbicidal Effects in Farmland Foliar Treatment 80-cm² plastic pots were filled with farmland soil. Seeds of *Echinochloa crus-galli* (L.) P. Beauv. var. *crus-galli*, *Abutilon theophrasti medicus*, and *Amaranthus retroflexus* were sowed in the pots, and the plants were grown for two weeks in a greenhouse. A wettable powder formulation prepared according to Formulation Example 1 was diluted with water, and the dilution was applied by foliar treatment by spraying with a small sprayer over the whole plant from the upper part, in an amount equivalent to 1000 liters per hectare, such that 1000 g of the active ingredient was applied per hectare. Thereafter, the plants were grown in a greenhouse, and on the 14$^{th}$ day after the treatment, the herbicidal effects were investigated according to the criteria described in Table 71 shown above. The results are presented in the following Table 75.

TABLE 75

| Compound No. | Echinochloa crus-galli | Setaria viridis | Abutilon theoprasti | Amaranthus retroflexus |
|---|---|---|---|---|
| I-56 | 3 | 3 | 5 | 5 |
| II-2 | 5 | 4 | 5 | 5 |
| II-3 | 5 | 4 | 5 | 5 |
| II-4 | 5 | 4 | 5 | 5 |
| II-15 | 5 | 5 | 5 | 5 |
| II-19 | 5 | 5 | 5 | 5 |
| II-28 | 4 | 3 | 5 | 5 |
| II-39 | 5 | 3 | 5 | 5 |
| II-41 | 5 | 5 | 5 | 5 |
| II-43 | 5 | 5 | 5 | 5 |
| II-48 | 5 | 5 | 5 | 5 |
| II-52 | 5 | 5 | 5 | 5 |
| II-54 | 5 | 5 | 5 | 5 |
| II-55 | 5 | 5 | 5 | 5 |
| II-56 | 5 | 5 | 5 | 5 |
| II-58 | 5 | 5 | 5 | 5 |
| II-63 | 5 | 5 | 5 | 5 |
| II-92 | 5 | 5 | 5 | 5 |
| II-118 | 5 | 5 | 5 | 5 |
| II-121 | 4 | 3 | 5 | 5 |
| II-123 | 5 | 5 | 5 | 5 |
| II-128 | 5 | 5 | 5 | 5 |
| II-131 | 4 | 4 | 5 | 5 |
| II-133 | 5 | 5 | 5 | 5 |
| II-136 | 5 | 4 | 5 | 5 |
| II-138 | 5 | 5 | 5 | 3 |
| II-141 | 3 | 4 | 5 | 4 |
| II-143 | 5 | 5 | 5 | 5 |
| IV-41 | 5 | 5 | 5 | 5 |
| V-41 | 5 | 4 | 5 | 5 |
| Comparative compound A | 0 | 0 | 2 | 1 |
| Comparative compound B | 0 | 0 | 5 | 1 |
| Comparative compound C | 0 | 0 | 4 | 0 |
| Comparative compound D | 0 | 0 | 4 | 1 |

From the results shown above, it was found that the compounds of the present invention have an excellent herbicidal activity.

INDUSTRIAL APPLICABILITY

The present invention provides novel compounds having an excellent herbicidal activity. These compounds are useful in the field of agrochemicals and the field of agriculture, and are highly industrially applicable.

The invention claimed is:
1. A 2-pyridone derivative represented by formula [I], or an agrochemically acceptable salt thereof:

[Chemical Formula 1]

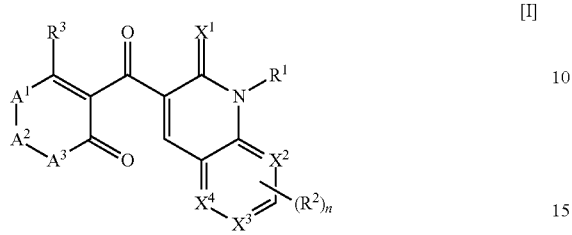

[I]

wherein $X^1$ represents an oxygen atom or a sulfur atom;
$X^2$, $X^3$, and $X^4$ each represent CH (the carbon atom may be substituted with $R^2$), or $N(O)_m$;
m represents an integer of 0 or 1;
$R^1$ represents a hydrogen atom; a $C_1$-$C_{12}$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; an amino-$C_1$-$C_6$ alkyl group; a nitro-$C_1$-$C_6$ alkyl group; a mono($C_1$-$C_6$ alkyl)amino-$C_1$-$C_6$ alkyl group; a di($C_1$-$C_6$ alkyl)amino-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a $C_1$-$C_6$ alkoxy-$C_1$-$C_6$ alkyl group; a hydroxy-$C_1$-$C_6$ alkyl group; a phenyl-$C_1$-$C_6$ alkoxy-$C_1$-$C_6$ alkyl group (the phenyl moiety of this group may be substituted with one $R^4$ or two to five identical or different $R^4$); a $C_1$-$C_6$ alkoxy-$C_1$-$C_6$ alkoxy-$C_1$-$C_6$ alkyl group; a $C_3$-$C_8$ cycloalkyloxy-$C_1$-$C_6$ alkyl group; a $C_3$-$C_8$ cycloalkyl-$C_1$-$C_6$ alkoxy-$C_1$-$C_6$ alkyl group; a phenyloxy-$C_1$-$C_6$ alkyl group (the phenyl moiety of this group may be substituted with one $R^4$ or two to five identical or different $R^4$); a heterocyclic-oxy-$C_1$-$C_6$ alkyl group in which the heterocyclic moiety has 2 to 10 carbon atoms and 1 to 5 heteroatoms selected from an oxygen atom, a sulfur atom, and a nitrogen atom (the heterocyclic moiety having 2 to 10 carbon atoms and having 1 to 5 heteroatoms selected from an oxygen atom, a sulfur atom, and a nitrogen atom in the group, may be substituted with one $R^5$ or two to five identical or different $R^5$); a phenylthio-$C_1$-$C_6$ alkyl group (the phenyl moiety of this group may be substituted with one $R^4$ or two to five identical or different $R^4$); a phenylsulfinyl-$C_1$-$C_6$ alkyl group (the phenyl moiety of this group may be substituted with one $R^4$ or two to five identical or different $R^4$), a phenylsulfonyl-$C_1$-$C_6$ alkyl group (the phenyl moiety of this group may be substituted with one $R^4$ or two to five identical or different $R^4$); a $C_1$-$C_6$ haloalkoxy-$C_1$-$C_6$ alkyl group; a heterocyclic-$C_1$-$C_6$ alkoxy-$C_1$-$C_6$ alkyl group in which the heterocyclic moiety has 2 to 10 carbon atoms and 1 to 5 heteroatoms selected from an oxygen atom, a sulfur atom, and a nitrogen atom (the heterocyclic moiety having 2 to 10 carbon atoms and having 1 to 5 heteroatoms selected from an oxygen atom, a sulfur atom, and a nitrogen atom in this group, may be substituted with one $R^5$ or two to five identical or different $R^5$); a $C_1$-$C_6$ alkylthio-$C_1$-$C_6$ alkoxy-$C_1$-$C_6$ alkyl group; a $C_1$-$C_6$ alkylsulfinyl-$C_1$-$C_6$ alkoxy-$C_1$-$C_6$ alkyl group; a $C_1$-$C_6$ alkylsulfonyl-$C_1$-$C_6$ alkoxy-$C_1$-$C_6$ alkyl group; a cyano-$C_1$-$C_6$ alkoxy-$C_1$-$C_6$ alkyl group; a cyano-$C_1$-$C_6$ alkyl group; a $C_1$-$C_6$ alkylcarbonyloxy-$C_1$-$C_6$ alkyl group; a $C_1$-$C_6$ acyl-$C_1$-$C_6$ alkyl group; a di($C_1$-$C_6$ alkoxy)-$C_1$-$C_6$ alkyl group; a $C_1$-$C_6$ alkoxycarbonyl-$C_1$-$C_6$ alkyl group; a $C_1$-$C_6$ alkoxyimino-$C_1$-$C_6$ alkyl group; a $C_1$-$C_6$ alkylideneaminooxy-$C_1$-$C_6$ alkyl group; a ($R^6R^7N$—$C$=$O$)—$C_1$-$C_6$ alkyl group; a $C_6$-$C_{10}$ aryl-$C_1$-$C_6$ alkyl group (the aryl moiety of this group may be substituted with one $R^4$ or two to five identical or different $R^4$); a heterocyclic-$C_1$-$C_6$ alkyl group in which the heterocyclic moiety has 2 to 10 carbon atoms and 1 to 5 heteroatoms selected from an oxygen atom, a sulfur atom, and a nitrogen atom (the heterocyclic moiety having 2 to 10 carbon atoms and 1 to 5 heteroatoms selected from an oxygen atom, a sulfur atom, and a nitrogen atom in this group, may be substituted with one $R^5$ or two to five identical or different $R^5$); an $NR^8R^9$ group; a $C_1$-$C_6$ alkoxy group; a $C_6$-$C_{10}$ aryl group (this group may be substituted with one $R^4$ or two to five identical or different $R^4$); or a heterocyclic group having 2 to 10 carbon atoms and 1 to 5 heteroatoms selected from an oxygen atom, a sulfur atom, and a nitrogen atom (this group may be substituted with one $R^5$ or two to five identical or different $R^5$);
$R^2$ represents a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_3$-$C_8$ cycloalkyl-$C_1$-$C_6$ alkyloxy group; a $C_2$-$C_6$ alkenyloxy group; a $C_2$-$C_6$ alkynyloxy group; a $C_1$-$C_6$ haloalkoxy group; a $C_1$-$C_6$ alkoxy-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl)amino group; a $C_1$-$C_6$ acylamino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; or a heterocyclic group having 2 to 10 carbon atoms and 1 to 5 heteroatoms selected from an oxygen atom, a sulfur atom, and a nitrogen atom (the heterocyclic moiety having 2 to 10 carbon atoms and 1 to 5 heteroatoms selected from an oxygen atom, a sulfur atom, and a nitrogen atom in this group, may be substituted with one $R^{10}$ or two to five identical or different $R^{10}$);

furthermore, two adjacent $R^2$ may be joined to form, together with the respective carbon atoms to which $R^2$ are directly bound, a 4- to 8-membered carbocyclic ring or a 4- to 8-membered heterocyclic ring having 1 to 4 heteroatoms selected from an oxygen atom, a sulfur atom, and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group, or an oxo group;

n represents an integer from 0 to 4 when $X^2$, $X^3$, and $X^4$ each represent CH (the relevant carbon atom may be substituted with $R^2$), that is, when $X^2$, $X^3$ and, $X^4$ each represent CH which may be substituted with substituent $R^2$;

$R^3$ represents a hydroxyl group; $O^-M^+$ (wherein $M^+$ represents an alkali metal cation or an ammonium cation); an amino group; a halogen atom; a $C_1$-$C_6$ alkylsulfonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; a $C_2$-$C_6$ alkenylthio group; a $C_2$-$C_6$ alkenylsulfinyl group; a $C_2$-$C_6$ alkenylsulfonyl group; a $C_2$-$C_6$ alkynylthio group; a $C_2$-$C_6$ alkynylsulfinyl group; a $C_2$-$C_6$ alkynylsulfonyl group; a $C_1$-$C_6$ alkylcarbonyloxy group; a $C_2$-$C_6$ alkenylcarbonyloxy group; a $C_2$-$C_6$ alkynylcarbonyloxy group; a phenoxy group (this group may be substituted with one $R^{10}$ or two to five identical or different $R^{10}$); a phenylthio group (this group may be substituted with one $R^{10}$ or two to five identical or different $R^{10}$); a phenylsulfinyl group (this group may be substituted with one $R^{10}$ or two to five identical or different $R^{10}$); a phenylsulfonyl group (this group may be substituted with one $R^{10}$ or two to five identical or different $R^{10}$); a phenylsulfonyloxy group (this group may be substituted with one $R^{10}$ or two to five identical or different $R^{10}$); a phenylcarbonyloxy group (this group may be substituted with one $R^{10}$ or two to five identical or different $R^{10}$); a 1,2,4-triazol-1-yl group; a 1,2,3-triazol-1-yl group; a 1,2,3-triazol-2-yl group; an imidazol-1-yl group; a pyrazol-1-yl group; a tetrazol-1-yl group; or a tetrazol-2-yl group;

$R^4$ represents a halogen atom; a hydroxyl group; a nitro group; a cyano group; a $C_1$-$C_6$ alkyl group; a $C_3$-$C_8$ cycloalkyl group; a $C_3$-$C_8$ cycloalkyl-$C_1$-$C_6$ alkyl group; a $C_2$-$C_6$ alkenyl group; a $C_2$-$C_6$ alkynyl group; a $C_1$-$C_6$ haloalkyl group; a $C_2$-$C_6$ haloalkenyl group; a $C_2$-$C_6$ haloalkynyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_3$-$C_8$ cycloalkyloxy group; a $C_2$-$C_6$ alkenyloxy group; a $C_2$-$C_6$ alkynyloxy group; a $C_1$-$C_6$ alkylcarbonyloxy group; a $C_1$-$C_6$ haloalkoxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a $C_1$-$C_6$ acylamino group; a mono($C_1$-$C_6$ alkyl)amino group; a di($C_1$-$C_6$ alkyl)amino group; a hydroxy-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; a cyano-$C_1$-$C_6$ alkyl group; a $C_1$-$C_6$ alkoxy-$C_1$-$C_6$ alkoxy group; a $C_3$-$C_8$ cycloalkyl-$C_1$-$C_6$ alkyloxy group; a $C_1$-$C_6$ haloalkoxy-$C_1$-$C_6$ alkoxy group; a cyano-$C_1$-$C_6$ alkoxy group; a $C_1$-$C_6$ acyl group; a $C_1$-$C_6$ alkoxyimino-$C_1$-$C_6$ alkyl group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl) aminocarbonyl group; a heterocyclic group having 2 to 10 carbon atoms and 1 to 5 heteroatoms selected from an oxygen atom, a sulfur atom, and a nitrogen atom (the heterocyclic moiety in this group, may be substituted with one $R^{10}$ or two to five identical or different $R^{10}$); or a heterocyclic-oxy group having 2 to 10 carbon atoms and 1 to 5 heteroatoms arbitrarily selected from an oxygen atom, a sulfur atom, and a nitrogen atom (the heterocyclic moiety having 2 to 10 carbon atoms and 1 to 5 heteroatoms selected from an oxygen atom, a sulfur atom, and a nitrogen atom in this group, may be substituted with one $R^{10}$ or two to five identical or different $R^{10}$);

furthermore, two adjacent $R^4$ may be joined to form, together with the respective carbon atoms to which $R^4$ are directly bound, a 4- to 8-membered carbocyclic ring or a 4- to 8-membered heterocyclic ring having 1 to 4 heteroatoms selected from an oxygen atom, a sulfur atom, and a nitrogen atom, while the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group, or an oxo group;

$R^5$ represents an oxo group; a thioxo group; a hydroxyl group; a halogen atom; a nitro group; a cyano group; a $C_1$-$C_6$ alkyl group; a $C_2$-$C_6$ alkenyl group; a $C_2$-$C_6$ alkynyl group; a $C_3$-$C_8$ cycloalkyl group; a $C_3$-$C_8$ cycloalkyl-$C_1$-$C_6$ alkyl group; a $C_1$-$C_6$ haloalkyl group; a $C_2$-$C_6$ haloalkenyl group; a $C_3$-$C_8$ halocycloalkyl group; a $C_3$-$C_8$ halocycloalkyl-$C_1$-$C_6$ alkyl group; a $C_1$-$C_6$ alkoxy group; a $C_2$-$C_6$ alkenyloxy group; a $C_2$-$C_6$ alkynyloxy group; a $C_3$-$C_8$ cycloalkyloxy group; a $C_3$-$C_8$ cycloalkyl-$C_1$-$C_6$ alkyloxy group; a $C_1$-$C_6$ haloalkoxy group; a $C_1$-$C_6$ alkoxy-$C_1$-$C_6$ alkoxy group; a $C_1$-$C_6$ haloalkoxy-$C_1$-$C_6$ alkoxy group; a cyano-$C_1$-$C_6$ alkoxy group; a $C_1$-$C_6$ alkylcarbonyloxy group; a $C_1$-$C_6$ alkylthio group; a $C_1$-$C_6$ alkylsulfinyl group; a $C_1$-$C_6$ alkylsulfonyl group; a $C_1$-$C_6$ haloalkylthio group; a $C_1$-$C_6$ haloalkylsulfinyl group; a $C_1$-$C_6$ haloalkylsulfonyl group; an amino group; a mono($C_1$-$C_6$ alkyl)amino group; a di($C_1$-$C_6$ alkyl)amino group; a $C_1$-$C_6$ acylamino group; a carboxyl group; a $C_1$-$C_6$ alkoxycarbonyl group; a carbamoyl group; a mono($C_1$-$C_6$ alkyl)aminocarbonyl group; a di($C_1$-$C_6$ alkyl)aminocarbonyl group; a $C_1$-$C_6$ acyl group; a $C_1$-$C_6$ alkoxyimino-$C_1$-$C_6$ alkyl group; a $C_1$-$C_6$ alkoxy-$C_1$-$C_6$ alkyl group; a $C_1$-$C_6$ alkylthio-$C_1$-$C_6$ alkyl group; a $C_1$-$C_6$ alkylsulfinyl-$C_1$-$C_6$ alkyl group; a $C_1$-$C_6$ alkylsulfonyl-$C_1$-$C_6$ alkyl group; a $C_1$-$C_6$ haloalkylthio-$C_1$-$C_6$ alkyl group; a $C_1$-$C_6$ haloalkylsulfinyl-$C_1$-$C_6$ alkyl group; a $C_1$-$C_6$ haloalkylsulfonyl-$C_1$-$C_6$ alkyl group; or a cyano-$C_1$-$C_6$ alkyl group;

furthermore, two adjacent $R^5$ may be joined to form, together with the respective carbon atoms to which $R^5$ are directly bound, a 4- to 8-membered carbocyclic ring or a 4- to 8-membered heterocyclic ring having 1 to 4 heteroatoms selected from an oxygen atom, a sulfur atom, and a nitrogen atom, and the ring thus formed may be substituted with a halogen atom, a cyano group, a nitro group, a $C_1$-$C_6$ alkyl group, a $C_1$-$C_6$ haloalkyl group, a $C_1$-$C_6$ alkoxy group, a $C_1$-$C_6$ haloalkoxy group, or an oxo group;

$R^6$ and $R^7$ each independently represent a $C_1$-$C_6$ alkyl group; or a phenyl-$C_1$-$C_6$ alkyloxycarbonyl group;

furthermore, $R^6$ and $R^7$ may be joined to form, together with the nitrogen atom to which these are bound, a 5- to 6-membered ring, while the ring thus formed may be interrupted by an oxygen atom in addition to the nitrogen atom to which $R^6$ and $R^7$ are bound;

$R^8$ and $R^9$ each independently represent a hydrogen atom; a $C_1$-$C_6$ alkyl group; a $NR^6R^7$ group; or a $C_1$-$C_6$ alkoxycarbonyl group;

furthermore, $R^8$ and $R^9$ may be joined to form, together with the nitrogen atom to which these are bound, a 5- to 6-membered ring, while the ring thus formed may be interrupted by a sulfur atom and/or an oxygen atom in addition to the nitrogen atom to which $R^8$ and $R^9$ are bound;

$R^{10}$ represents a halogen atom; a nitro group; a cyano group; a $C_1$-$C_6$ alkyl group; a $C_1$-$C_6$ haloalkyl group; a $C_1$-$C_6$ alkoxy group; or a $C_1$-$C_6$ haloalkoxy group;

$A^1$ represents $C(R^{11}R^{12})$;

$A^2$ represents $C(R^{13}R^{14})$, or $C=O$;

$A^3$ represents $C(R^{15}R^{16})$; and $R^{11}$, $R^{12}$, $R^{13}$, $R^{14}$, $R^{15}$, and $R^{16}$ each independently represent a hydrogen atom; or a $C_1$-$C_6$ alkyl group.

2. A herbicide comprising the 2-pyridone derivative or a salt thereof according to claim 1, as an active ingredient.

3. A method of treating soil and/or a plant, comprising treating the soil or plant with a herbicide of claim 2 wherein the herbicide provides a herbicidal effect.

\* \* \* \* \*